US007908087B2

(12) United States Patent
Sperling et al.

(10) Patent No.: US 7,908,087 B2
(45) Date of Patent: Mar. 15, 2011

(54) METHODS OF IDENTIFYING LATENT SPLICE SITES

(75) Inventors: Joseph Sperling, Jerusalem (IL); Ruth Sperling, Jerusalem (IL)

(73) Assignees: Yeda Research And Development Co. Ltd., Rehovot (IL); Yissum Research Development Company of the Hebrew University of Jerusalem, Jerusalem (IL)

( * ) Notice: Subject to any disclaimer, the term of this patent is extended or adjusted under 35 U.S.C. 154(b) by 620 days.

(21) Appl. No.: 10/505,884

(22) PCT Filed: Mar. 18, 2003

(86) PCT No.: PCT/IL03/00236
§ 371 (c)(1),
(2), (4) Date: Sep. 7, 2004

(87) PCT Pub. No.: WO03/078660
PCT Pub. Date: Sep. 25, 2003

(65) Prior Publication Data
US 2005/0221313 A1  Oct. 6, 2005

Related U.S. Application Data

(60) Provisional application No. 60/428,690, filed on Nov. 25, 2002, provisional application No. 60/364,591, filed on Mar. 18, 2002.

(51) Int. Cl.
*G01N 33/48* (2006.01)
(52) U.S. Cl. ........................................................ 702/19
(58) Field of Classification Search ..................... 702/19
See application file for complete search history.

(56) References Cited

FOREIGN PATENT DOCUMENTS

| EP | 0264166 | 4/1988 |
| WO | WO 98/38297 | 3/1998 |
| WO | WO 98/38298 | 3/1998 |
| WO | WO 98/38299 | 3/1998 |

OTHER PUBLICATIONS

Biotech Life Science Dicationary "locus" (1998) available at http://biotech.icmb.utexas.edu/search/dict-search2.html?bo1=AND &word=locus%20(pl.%20loci)&search_type=normal&def=.*
Burge et al. "Prediction of Complete Gene Structures in Human Genomic DNA," J. Mol. Biol. (1997) vol. 268, pp. 78-94.*
Kananura et al. "A Splice-Site Mutation in GABRG2 Associated with Childhood Absence Epilepsy and Febrile Convulsions," Arch. Neurol. (Jul. 2002) vol. 59, pp. 1137-1141.*
Cartegni et al. "Listening to Silence and Understanding Nonsense: Exonic Mutations That Affect Splicing", Nature Review Genetics, 3(4): 285-298, 2002.
Office Action Dated Oct. 12, 2008 From the Israeli Patent Office Re.: Application No. 163945 and Its Translation Into English.
Office Action Dated Feb. 1, 2010 From the Israel Patent Office Re.: Application No. 163945 and Its Translation Into English.
Louis et al. "Molecular Biology of Central Nervous System Tumors", http://brain.mgh.havard.edu/MolecularGenetics.htm, 2005.
Black "Protein Diversity From Alternative Slicing: A Challenge for Bioinformatics and Post-Genome Biology", Cell, vol. 103, pp. 367-370, 2000.
Brudno et al. "Computational Analysis of Candidate Intron Regulatory Elements for Tissue-Specific Alternative Pre-mRNA Splicing", Nucleic Acids Research, vol. 29(11):2338-2351, XP002248424, ISSN:0305-1048, 2001.
Lopez "Alternative Splicing of Pre-mRNA: Developmental Consequences and Mechanisms of Regulation", Annu. Rev. Genetics, 32: 279-305, 1998.
Ahn et al. "The Structural and Functional Diversity of Dystrophin", Nature Genetics, 3: 283-291, 1993.
Aoufouchi et al. "Nonsense Mutations Inhibit RNA Splicing in a Cell-Free System: Recognition of Mutant Codon Is Independent of Protein Synthesis", Cell, 85: 415-422, 1996.
Bach et al. "Molecular Analysis of Hurler Syndrome in Druze and Muslim Arab Patients in Israel: Multiple Allelic Mutations of the IDUA Gene in A Small Geographic Area", Am. J. Hum. Genet., 53: 330-338, 1993.
Banerji et al. "A Lymphocyte-Specific Cellular Enhancer Is Located Downstream of the Joining Region in Immunoglobulin Heavy Chain Genes", Cell, 33: 729-740, 1983.
Bedwell et al. "Suppression of A CFTR Premature Stop Mutation in A Bronchial Epithelial Cell Line", Nature Medicine, 3(11): 1280-1284, 1997.
Berget "Exon Recognition in Vertebrate Splicing", The Journal of Biological Chemistry, 270(6): 2411-2414, 1995.
Black "Finding Splice Sites Within A Wilderness of RNA", RNA, 1: 763-771, 1995.
Blencowe "Exonic Splicing Enhancers: Mechanism of Action, Diversity and Role in Human Genetic Diseases", Trends Biochem. Sci., 25: 106-110, 2000.
Buckbinder et al. "Gene Regulation by Temperature-Sensitive P53 Mutants: Identification of P53 Response Genes", Proc. Natl. Acad. Sci. USA, 9.1: 10640-10644, 1994.
Byrne et al. "Multiplex Gene Regulation: A Two-Tiered Approach to Transgene Regulation in Transgenic Mice", Proc. Natl. Acad. Sci. USA, 86: 5473-5477, 1989.
Calame et al. "Transcriptional Controlling Elements in the Immunoglobulin and T Cell Receptor Loci", Advances in Immunology, 43: 235-275, 1988.
Carter et al. "A Regulatory Mechanism That Detects Premature Nonsense Codons in T-Cell Receptor Transcripts In Vivo Is Reversed by Protein Synthesis Inhibitors In Vitro", The Journal of Biological Chemistry, 270(48): 28995-29003, 1995.
Charlet-B. et al. "Loss of the Muscle-Specific Chloride Channel in Type 1 Myotonic Dystrophy Due to Misregulated Alternative Splicing", Molecular Cell, 10: 45-53, 2002.

(Continued)

*Primary Examiner* — Jerry Lin

(57) ABSTRACT

A method of identifying latent splice sites, the method comprising identifying at least one intronic in-frame stop codon located upstream of a 5' splice site sequence being a latent splice site, thereby identifying latent splice sites.

3 Claims, 15 Drawing Sheets

OTHER PUBLICATIONS

Cole et al. "Human Monoclonal Antibodies", Molecular and Cellular Biochemistry, 62: 109-120, 1984.

Cote et al. "Generation of Human Monoclonal Antibodies Reactive With Cellular Antigens", Proc. Natl. Acad. Sci. USA, 80: 2026-2030, 1983.

Culbertson "RNA Surveillance: Unforeseen Consequences for Gene Expression, Inherited Genetic Disorders and Cancer", Trends in Genetics, 15(2); 74-80, 1999.

Dietz et al. "The Skipping of Constitutive Exons In Vivo Induced by Nonsense Mutations", Science, 259(5095): 680-683, 1993.

Dietz et al. "Maintenance of An Open Reading Frame as An Additional Level of Scrutiny During Splice Site Selection", Nature Genetics, 8: 183-188, 1994.

Dostie et al. "Nuclear Eukaryotic Initiation Factor 4E(eIF4E) Colocalizes With Splicing Factors in Speckles", The Journal of Cell Biology, 148: 239-247, 2000.

Dumas et al. "New Species of Human Tyrosine Hydroxylase mRNA Are Produced in Variable Amounts in Adrenal Medulla and Are Overexpressed in Progressive Supranuclear Palsy", Journal of Neurochemistry, 67: 19-25, 1996.

Edlund et al. "Cell-Specific Expression of the Rat Insulin Gene: Evidence for Role of Two Distinct 5$\wedge${\Prime}$ Flanking Elements", Science, 230(4728): 912-916, 1985.

Fairbrother et al. "Predictive Identification of Exonic Splicing Enhancers in Human Genes", Science, 297: 1007-1013, 2002.

Farnham et al. "Characterization of the 5' End of the Growth-Regulated Syrian Hamster CAD Gene[1]", Cell Growth & Differentiation, 1: 179-189, 1990.

Fodor et al. "Light-Directed, Spatially Addressable Parallel Chemical Synthesis", Science, 251(4995): 767-773, 1991.

Frischmeyer et al. "Nonsense-Mediated mRNA Decay in Health and Disease", Human Molecular Genetics, 8(10): 1893-1900, 1999.

Fu "The Superfamily of Arginine/Serine-Rich Splicing Factors", RNA, 1: 663-680, 1995.

Gersappe et al. "A Premature Termination Codon in Either Exon of Minute Virus of Mice P4 Promoter-Generated Pre-mRNA Can Inhibit Nuclear Splicing of the Intervening Intron in an Open Reading Frame-Dependent Manner", The Journal of Biological Chemistry, 274(32): 22452-22458, 1999.

Graveley "Sorting Out the Complexity of SR Protein Functions", RNA, 6: 1197-1211, 2000.

Green "Biochemical Mechanisms of Constitutive and Regulated Pre-mRNA Splicing", Annu. Rev. Cell Biol., 7: 559-599, 1991.

Grima et al. "A Single Human Gene Encoding Multiple Tyrosine Hydroxylases With Different Predicted Functional Characteristics", Nature, 326: 707-711, 1987.

Hammond et al. "Angiogenic Gene Therapy for Heart Disease: A Review of Animal Studies and Clinical Trials", Cardiovascular Research, 49: 561-567, 1987.

Hentze et al. "A Perfect Message: RNA Surveillance and Nonsense-Mediated Decay", Cell, 96: 307-310, 1999.

High "Gene Therapy: A 2001 Perspective", Haemophilia, 7(Suppl. 1): 23-27, 2001.

Howard et al. "Aminoglycoside Antibiotics Restore CFTR Function by Overcoming Premature Stop Mutations", Nature Medicine, 2(4): 467-469, 1996.

Iborra et al. "Coupled Transcription and Translation Within Nuclei of Mammalian Cells", Science, 293: 1139-1142, 2001.

International Human Genome Sequencing Consortium "Initial Sequenciong and Analysis of the Human Genome", Nature, 409: 860-921, 2001.

Isner "Myocardialgenetherapy", Nature, 415: 234-239, 2002.

Kohler et al. "Continuous Cultures of Fused Cells Secreting antibody of Predefined Specificity", Nature, 256: 495-497, 1975.

Kozbor et al. "Specific Immunoglobulin Production and Enhanced Tumorigenicity Following Ascites Growth of Human Hybridomas", Journal of Immunological Methods, 81: 31-42, 1985.

Krämer "The Structure and Function of Proteins Involved in Mammalian Pre-mRNA Splicing", Annu. Rev. Biochem., 65: 367-409, 1996.

Ladd et al. "The CELF Family of RNA Binding Proteins Is Implicated in Cell-Specific and Developmentally Regulated Alternative Splicing", Molecular and Cellular Biology, 21(4): 1285-1296, 2001.

Li et al. "Nonsense Surveillance in Lymphocytes?", Immunity, 8: 135-141, 1998.

Li et al. "T Cell Receptor (TCR) Mini-Gene mRNA Expression Regulated by Nonsense Codons: A Nuclear-Associated Translation-Like Mechanism", J. Exp. Med., 185(6): 985-992, 1997.

Liang et al. "Differential Display of Eukaryotic Messenger RNA by Means of the Polymerase Chain Reaction", Science, 257(5072): 967-970, 1992.

Lim et al. "A Computational Analysis of Sequence Features Involved in Recognition of Short Introns", Proc. Natl. Acad. Sci. USA, 98(20): 11193-11198, 2001.

Linnoila et al. "Peripheral Airway Cell Marker Expression in Non-Small Cell Lung Carcinoma", Am. J. Clin. Pathol., 97: 233-243, 1992.

Liu et al. "Exonic Splicing Enhancer Motif Recognized by Human SC35 Under Splicing Conditions", Molecular and Cellular Biology, 20(3): 1063-1071, 2000.

Liu et al. "A Mechanism for Exon Skipping Caused by Nonsense or Missense Mutations in BRCA1 and Other Genes", Nature Genetics, 27: 55-58, 2001.

Lozano et al. "Low Cytoplasmic mRNA Levels of Immunoglobulin κ Light Chain Genes Containing Nonsense Codons Correlate With Inefficient Splicing", The EMBO Journal, 13(19): 4617-4622, 1994.

Lund et al. "Proofreading and Aminoacylation of tRNAs Before Export From the Nucleus", Science, 282: 2082-2085, 1998.

Lykke-Anderson et al. "Human Upf Proteins Target an mRNA for Nonsense-Mediated Decay When Bound Downstream of a Termination Codon", Cell, 103: 1121-1131, 2000.

Lykke-Anderson et al. "Communication of the Position of Exon-Exon Junctions to the mRNA Surveillance Machinery by the Protein RNPS1", Science, 293(5536): 1836-1839, 2001.

Maquat "When Cells Stop Making Sense: Effects of Nonsense Codons on RNA Metabolism in Vertebrate Cells", RNA, 1: 453-465, 1995.

Maquat "NASty Effects on Fibrillin Pre-mRNA Splicing: Another Case of ESE Does It, But Proposals for Translation-Dependent Splice Site Choice Live on", Genes & Development, 16: 1743-1753, 2002.

Mendell et al. "Novel Upf2p Orthologues Suggest a Functional Link Between Translation Initiation and Nonsense Surveillance Complexes", Molecular and Cellular Biology, 20(23): 8944-8957, 2000.

Miriami et al. "Heat Shock Affects 5' Splice Site Selection, Cleavage and Ligation of CAD Pre-mRNA in Hamster Cells, But Not Its Packaging in InRNP Particles", Nucleic Acids Research, 22(15): 3084-3091, 1994.

Miriami et al. "Conservation of an Open-Reading Frame as an Element Affecting 5' Splice Site Selection", Journal of Structural Biology, 140: 116-122, 2002.

Misawa et al. "A Method to Identify cDNAs Based on Localization of Green Fluorescent Protein Fusion Products", Proc. Natl. Acad. Sci. USA, 97(7): 3062-3066, 2000.

Mount "A Catalogue of Splice Junctions Sequences", Nucleic Acids Research, 10(2): 459-472, 1982.

Mühlemann et al. "Precursor RNAs Harboring Nonsense Codons Accumulate Near the Site of Transcription", Molecular Cell, 8: 33-44, 2001.

Müller et al. "A Supraspliceosome Model for Large Nuclear Ribonucleoprotein Particles Based on Mass Determinations by Scanning Transmission Electron Microscopy", J. Mol. Biol., 283: 383-394, 1998.

Naeger et al. "Nonsense Mutations Inhibit Splicing of MVM RNA in Cis When They Interrupt the Reading Frame of Either Exon of the Final Spliced Product", Genes & Development, 6: 1107-1119, 1992.

Neufeld "Lysosomal Storage Diseases", Annu. Rev. Biochem., 60: 257-280, 1991.

Ohshima et al. "Signals for the Selection of a Splice Site in Pre-mRNA. Computer Analysis of Splice Junction Sequences and Like Sequences", J. Mol. Biol., 195: 247-259, 1987.

Orlandi et al. "Cloning Immunoglobulin Variable Domains for Expression by the Polymerase Chain Reaction", Proc. Natl. Acad. Sci. USA, 86: 3833-3837, 1989.

Padgett et al. "Structure of the Gene for CAD, the Multifunctional Protein That Initiates UMP Synthesis in Syrian Hamster Cells", Molecular and Cellular Biology, 2(3): 293-301, 1982.

Peri et al. "Tissue-Specific Expression of the Gene Coding for Human Clara Cell 10- kD Protein, a Phospholipase A2-Inhibitory Protein", The Journal of Clinical Investigation, 92: 2099-2109, 1993.

Pinkert et al. "An Albumin Enhancer Located 10 KB Upstream Functions Along With Its Promoter to Direct Efficient, Liver-Specific Expression in Transgenic Mice", Genes & Development, 1: 268-276, 1987.

Rajavel et al. "Nonsense-Mediated Decay of Human HEXA mRNA", Molecular and Cellular Biology, 21(16): 5512-5519, 2001.

Roscigno et al. "A Mutational Analysis of the Polypyrimidine Tract of Introns. Effects of Sequence Differences in Pyrimidine Tracts on Splicing", The Journal of Biological Chemistry, 268(15): 11222-11229, 1993.

Schaal et al. "Multiple Distinct Splicing Enhancers in the Protein-Coding Sequences of a Constitutively Spliced Pre-mRNA", Molecular and Cellular Biology, 19(1): 261-273, 1999.

Schena et al. "Quantitative Monitoring of Gene Expression Patterns With a Complementary DNA Microarray", Science, 270(5235): 467-470, 1995.

Schmucker et al. "Drosophila Dscam Is an Axon Guidance Receptor Exhibiting Extraordinary Molecular Diversity", Cell, 101: 671-684, 2000.

Scott et al. "Structure and Sequence of the Human α-L-Iduronidase Gene", Genomics, 13: 1311-1313, 1992.

Shapiro et al. "RNA Splice Junctions of Different Classes of Eukaryotes: Sequence Statistics and Functional Implications in Gene Expression", Nucleic Acids Research, 15(17): 7155-7174, 1987.

Sun et al. "A Mutated Human Homologue to Yeast Upf1 Protein Has a Dominant-Negative Effect on the Decay of Nonsense-Containing mRNAs in Mammalian Cells", Proc. Natl. Acad. Sci. USA, 95: 10009-10014, 1998.

Tacke et al. "Determinants of SR Protein Specificity", Current Opinion in Cell Biology, 11: 358-362, 1999.

Tomita et al. "Introns and Reading Frames: Correlation Between Splicing Sites and Their Codon Positions", Mol. Biol. Evol., 13(9): 1219-1223, 1996.

Tonkinson et al. "Antisense Oligodeoxynucleotides as Clinical Therapeutic Agents", Cancer Incvestigation, 14(1): 54-65, 1996.

Urlaub et al. "Nonsense Mutations in the Dihydrofolate Reductase Gene Affect RNA Processing", Molecular and Cellular Biology, 9(7): 2868-2880, 1989.

Valcárcel et al. "Post-Transcriptional Regulation: The Dawn of PTB", Current Biology, 7: R705-R708, 1997.

Velculescu et al. "Serial Analysis of Gene Expression", Science, 270(5235): 484-488, 1995.

Valentine et al. "The Association of Nonsense Mutation With Exon-Skipping in HPRT mRNA of Chinese Hamster Ovary Cells Results From an Artifact of RT-PCR", RNA, 3: 660-676, 1997.

Venter et al. "The Sequence of the Human Genome", Science, 291(5507): 1304-1351, 2001.

Verma "Genetherapy: Trials and Tribulations", Naturereviews Genetics, 1: 91-99, 2000.

Wang et al. "Regulation of Pre-mRNA Splicing in Metazoa", Current Opinion in Genetics & Development, 7: 205-211, 1997.

Welsh et al. "Arbitrarily Primed PCR Fingerprinting of RNA", Nucleic Acid Research, 20(19): 4965-4970, 1992.

Winoto et al. "A Novel, Inducible and T Cell-Specific Enhancer Located at the 3' End of the T Cell Receptor α Locus", The EMBO Journal, 8(3): 729-733, 1989.

Winter et al. "Man-Made Antibodies", Nature, 349: 293-299, 1991.

Wu et al. "Specific Interactions Between Proteins Implicated in Splice Site Selection and Regulated Alternative Splicing", Cell, 75: 1061-1070, 1993.

Zhang et al. "Intron Function in the Nonsense-Mediated Decay of β-Globin mRNA: Indications That Pre-mRNA Splicing in the Nucleus Can Influence mRNA Translation in the Cytoplasm", RNA, 4: 801-815, 1998.

Caceres et al. "Alternative Splicing: Multiple Control Mechanisms and Involvement in Human Disease", TRENDS in Genetics, vol. 18(4), 2002.

Ladd et al. "Finding Signals That Regulate Alternative Splicing in the Postgenomic Era", http://genomebiology.com/2002/3/II/reviews/0008.I, 2002.

Li et al. "Stop Codons Affect 5' Splice Site Selection by Surveillance of Splicing", Proc. Natl. Acad. Sci. USA, 99(8): 5277-5282, 2002.

Marshall et al. "Naturally Occurring Splicing Variants of the hMSH2 Gene Containing Nonsense Codons Identify Possible mRNA Instability Motifs Within the Gene Coding Region",Biochimica Et Biophysica Acta,vol. 1308(1):88-92,XP009013956, ISSN:0006-3002, Discussion,1996.

Harker et al. "Selective Use of an Alternative Stop Codon and Polydenylation Signal Within Intron Sequences Lead to a Truncated Topoisomerase IIa Messenger RNA and Protein in Human HL-60 Leukemia Cell Selected for Resistance to Mitoxantrone", Cancer Research, vol. 55, p. 4962-4971, XP001153550, Abstract, p. 4963, L.Col. Discussion,1995.

\* cited by examiner

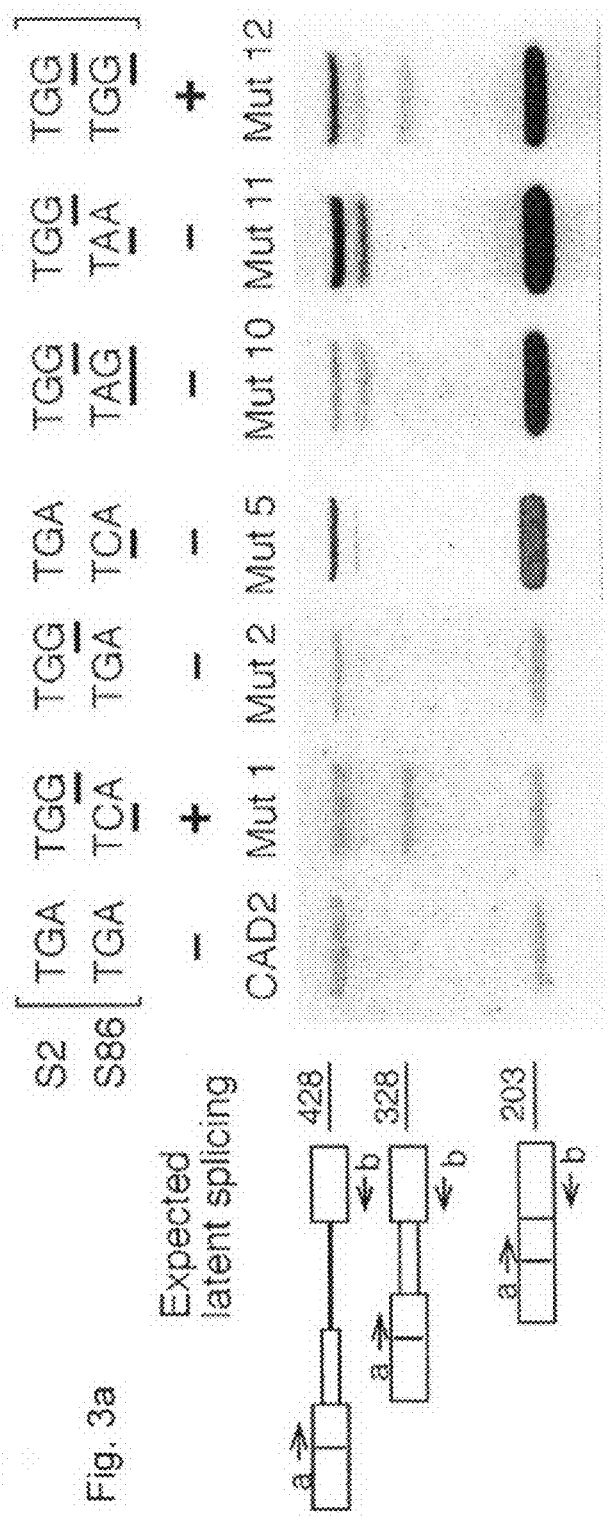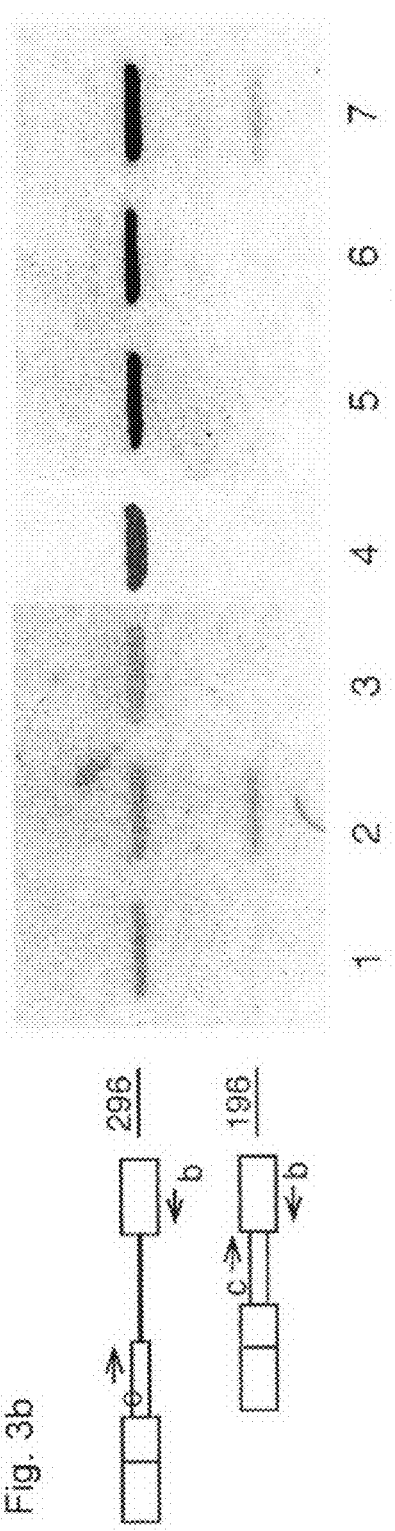
Fig. 3a
Fig. 3b

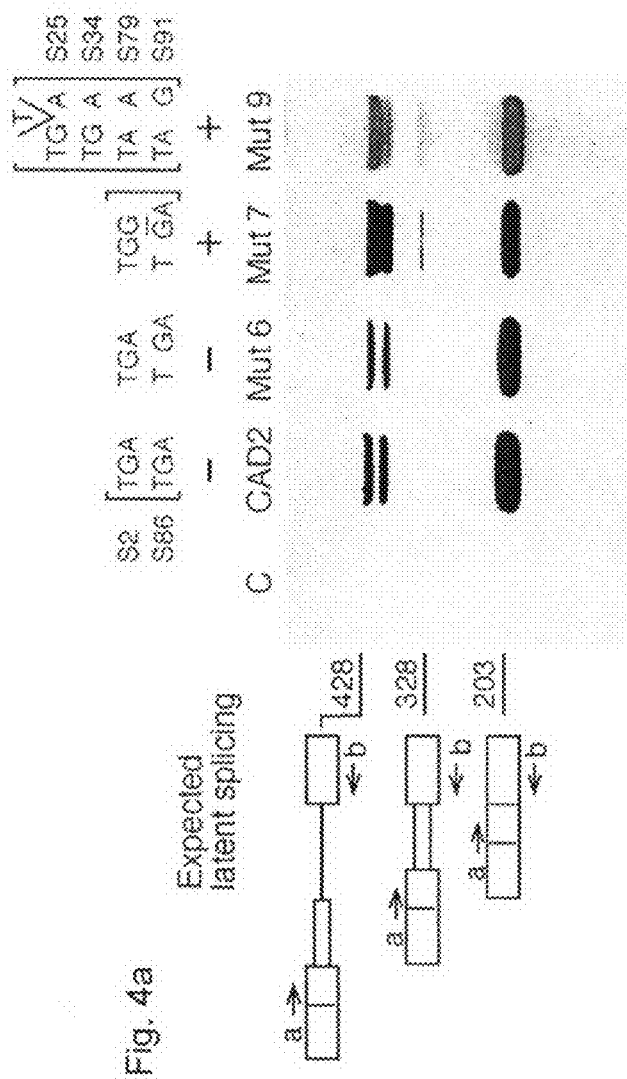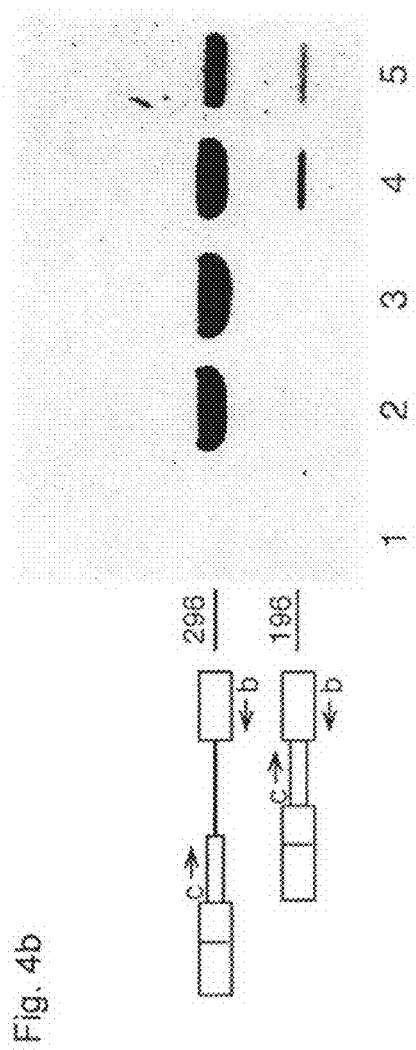
Fig. 4a
Fig. 4b

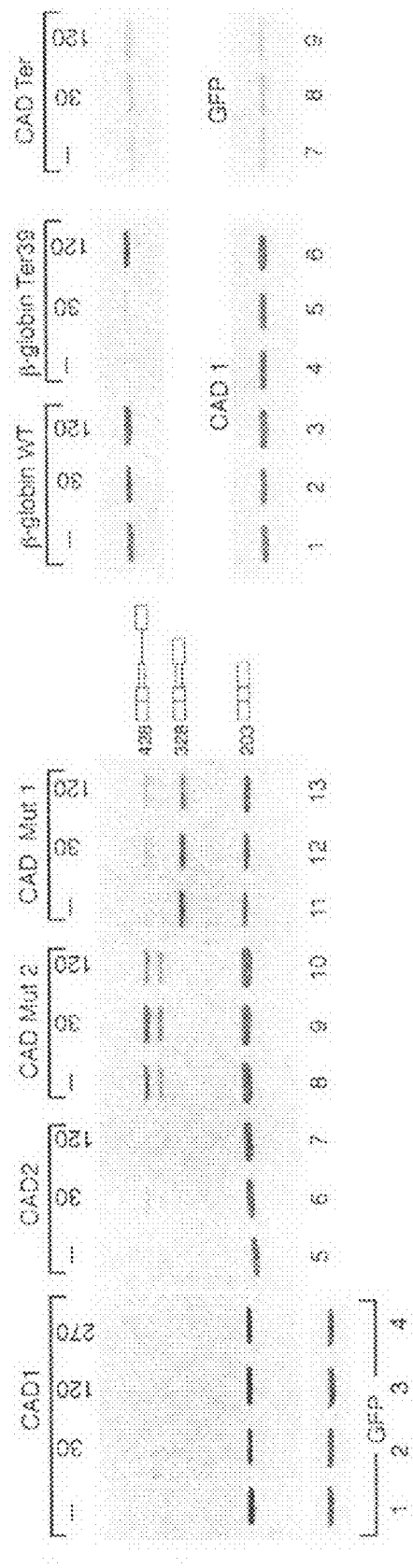

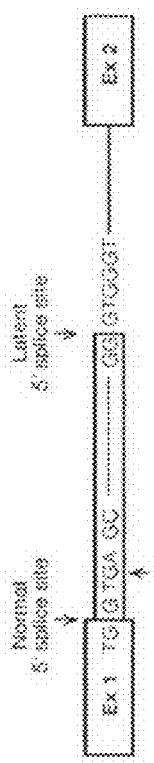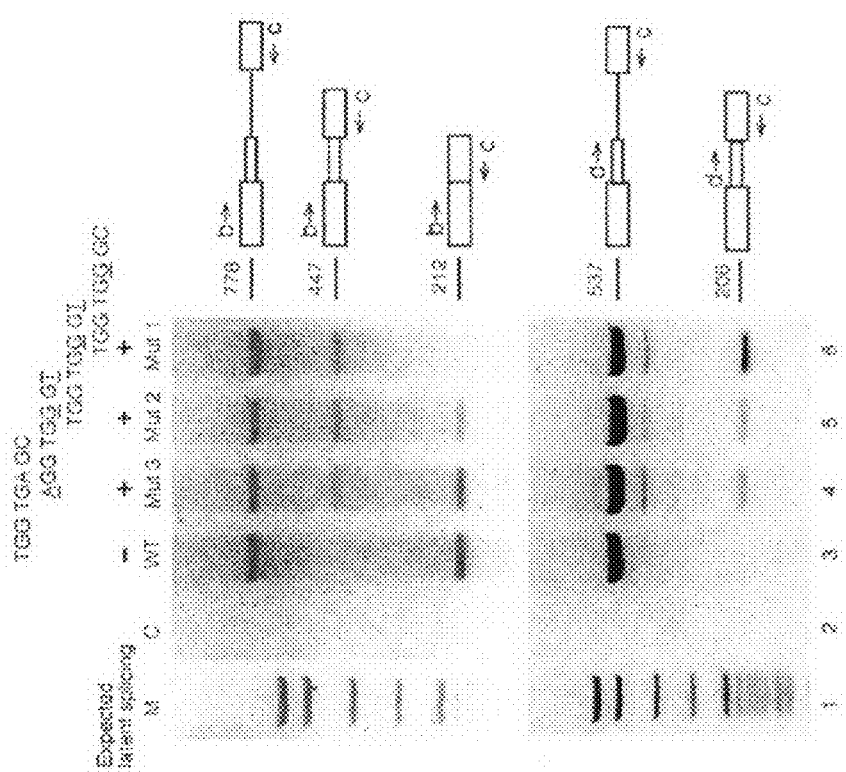
Fig. 6a
Fig. 6b
Fig. 6c

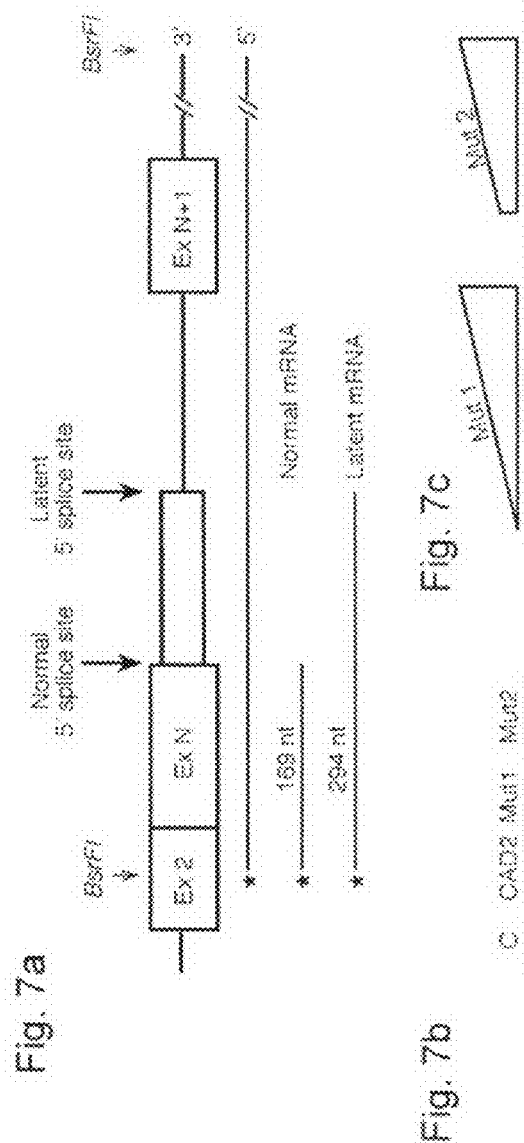
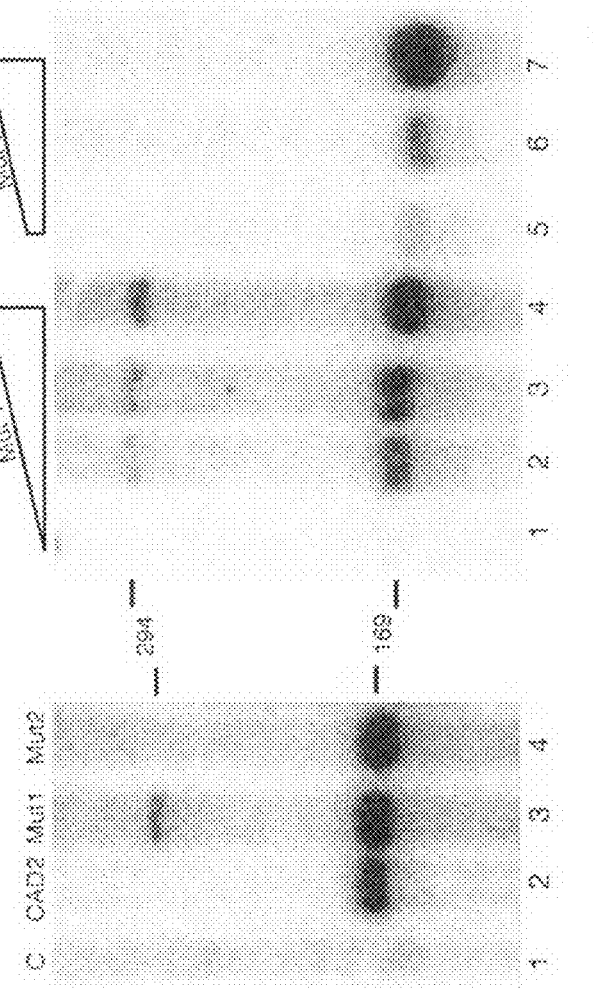
Fig. 7a
Fig. 7b
Fig. 7c

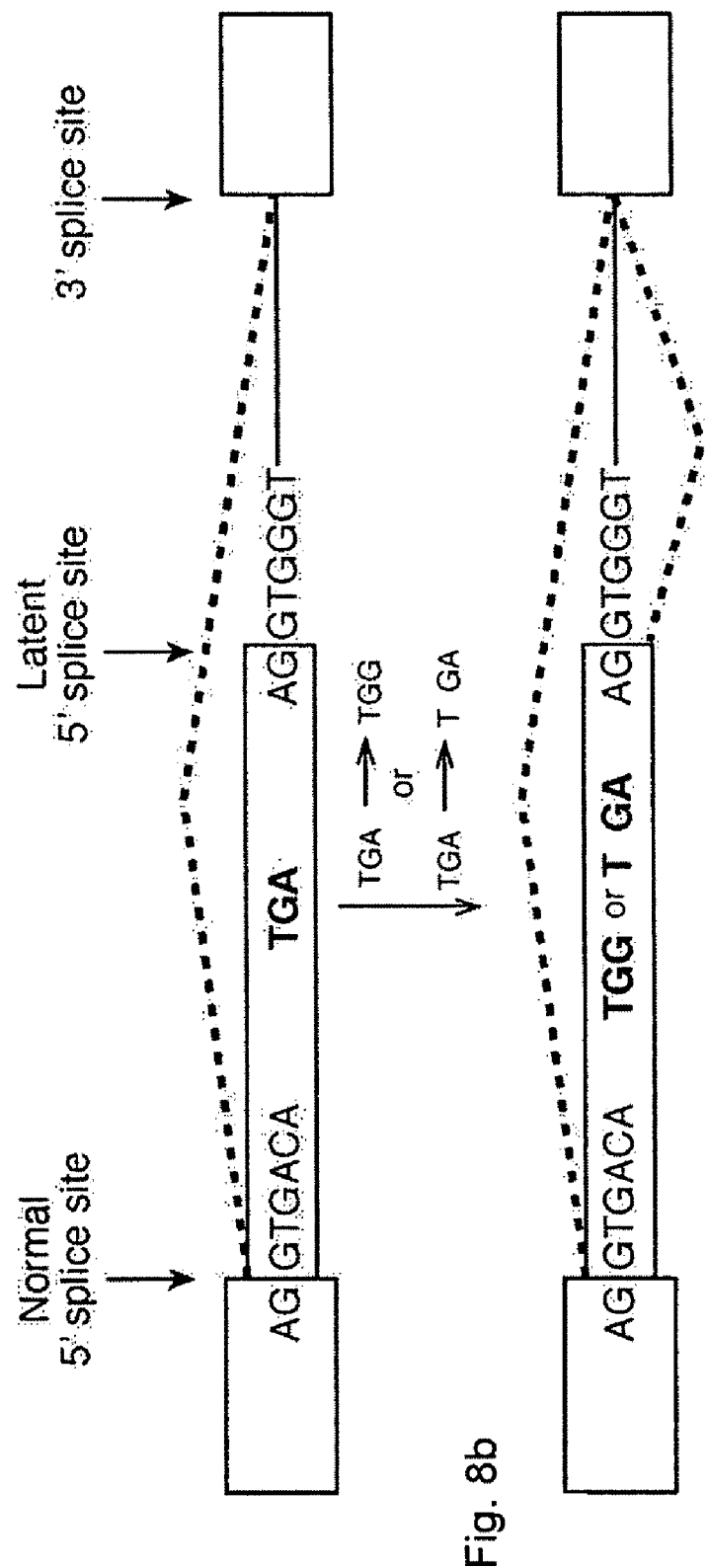

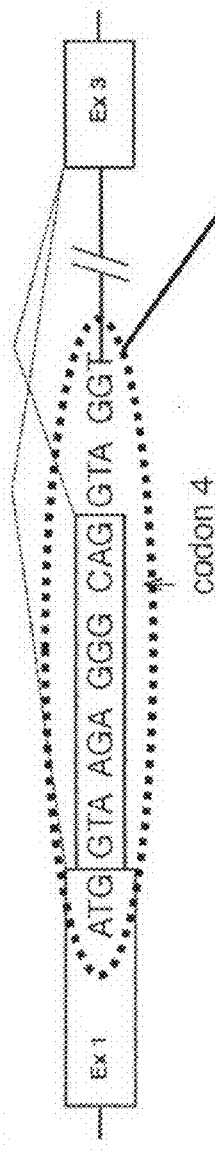
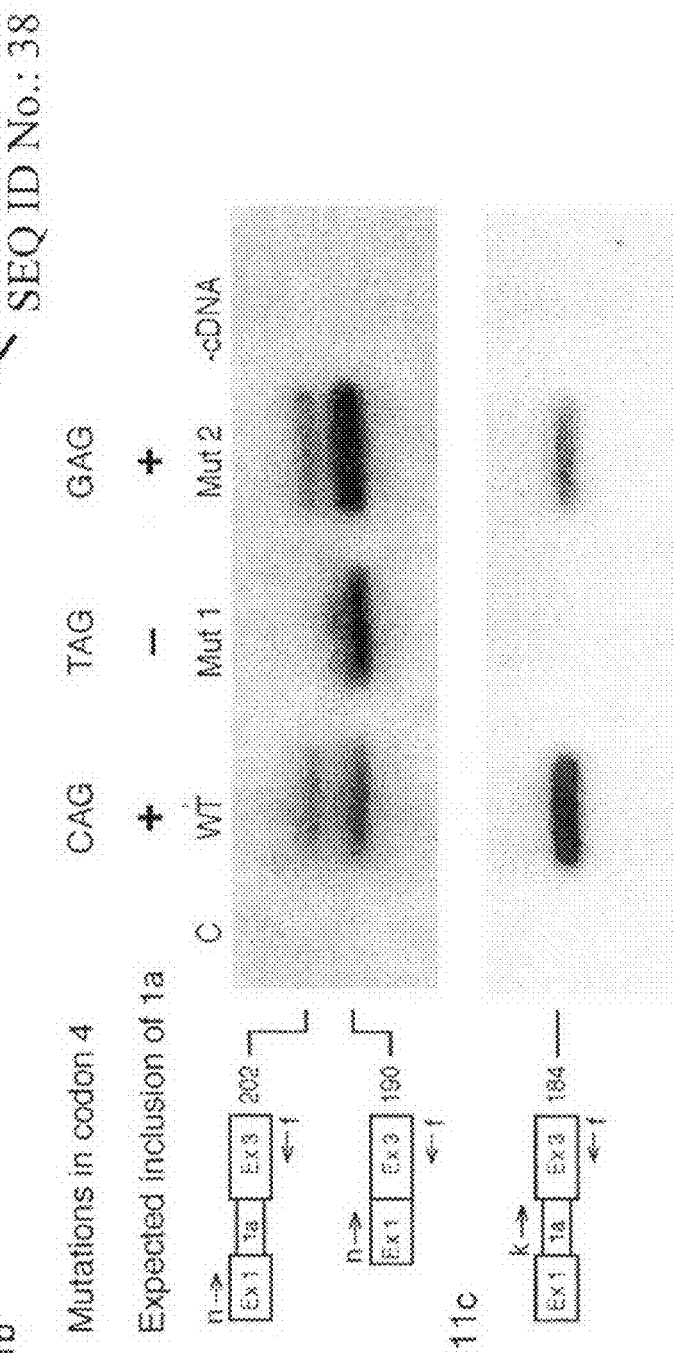
Fig. 11a
Fig. 11b
Fig. 11c

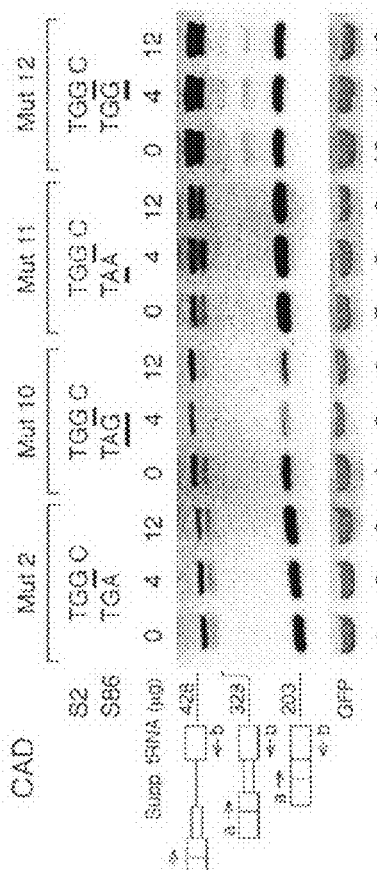
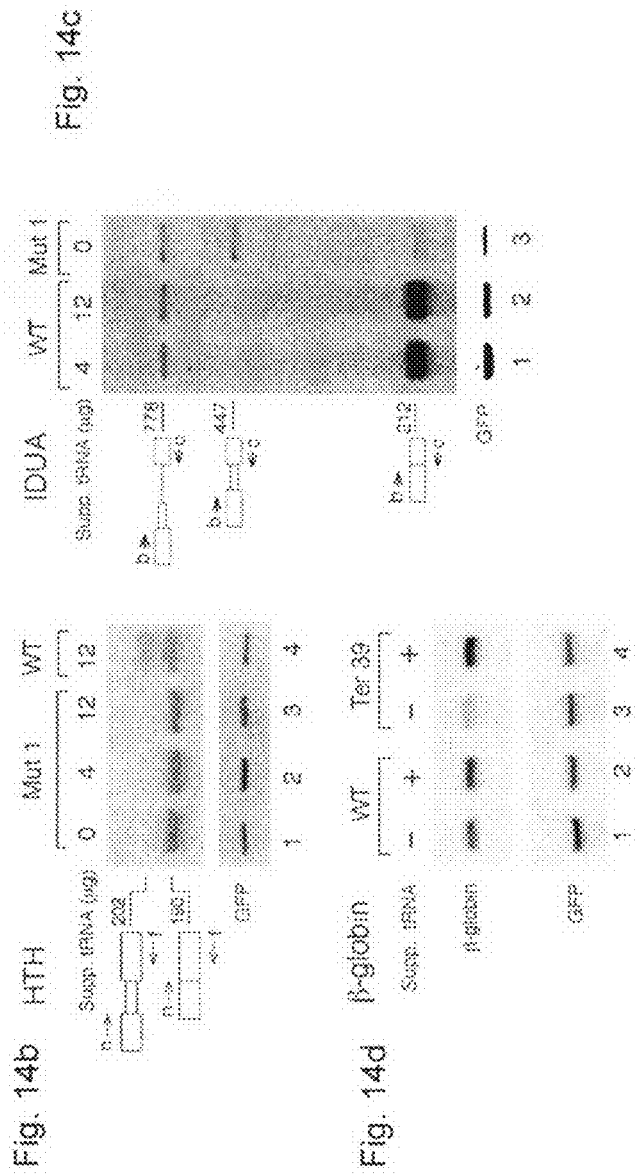
Fig. 14a
Fig. 14b
Fig. 14c
Fig. 14d

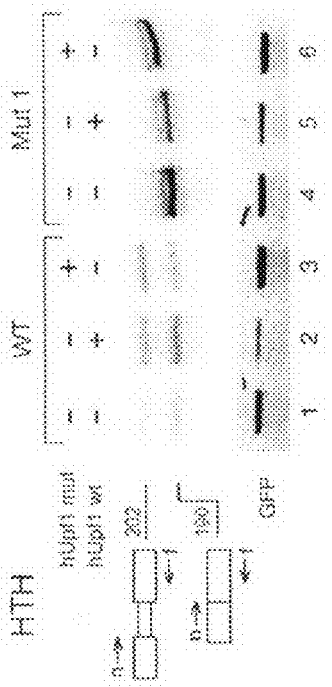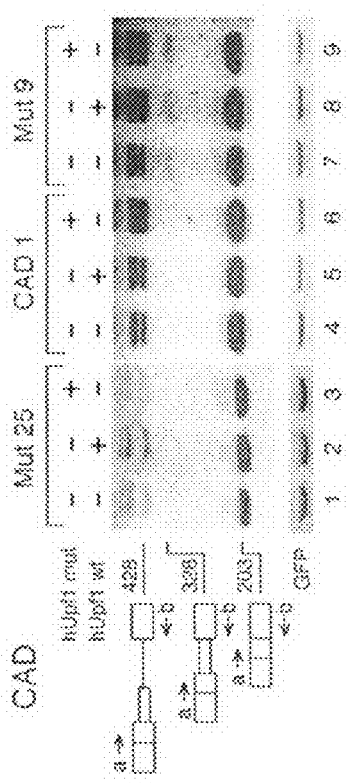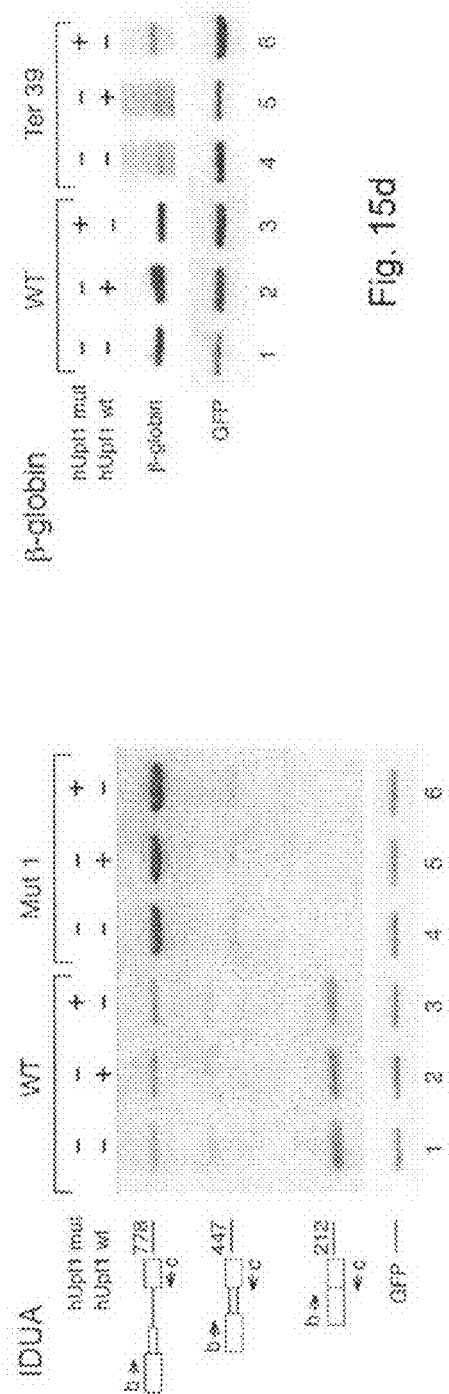
Fig. 15a
Fig. 15b
Fig. 15c
Fig. 15d

METHODS OF IDENTIFYING LATENT SPLICE SITES

RELATED APPLICATIONS:

This application is a National Phase Application of PCT/IL03/00236 having International Filing date of 18 Mar. 2003, which claims priority from U.S. Provisional Patent Application No. 60/364,591 filed 18 Mar. 2002 and U.S. Provisional Patent Application No. 60/428,690 filed 25 Nov. 2002.

FIELD AND BACKGROUND OF THE INVENTION

The present invention relates to methods of identifying gene expression products which result from alternative splicing and more particularly to methods of diagnosing and treating disorders associated with the expression of such gene products, such as cancer.

Alternative splicing, the process by which multiple messenger RNA (mRNA) isoforms are generated from a single pre-mRNA species is an important means of regulating gene expression. Alternative splicing plays a central role in numerous biological processes such as sexual differentiation in Drosophila and apoptosis in mammals [Lopez (1998) Ann. Rev. Genet. 32:279-305]. Aberrant splicing generates abnormal mRNAs which are either unstable or code for defective or deleterious protein isoforms which are frequently implicated in the development of human disease [Lopez (1998) Ann. Rev. Genet. 32:279-305; Charlet (2002) Mol. Cell 10:45-53].

The significance of alternative splicing is further extended in the post genomic era. On the basis of the initial drafts of the human genome sequence it was estimated that 30,000-40,000 genes comprise the human genome [International Human Genome Sequencing Consortium. Nature 2001 409:860-921; Venter (2001) Science 291:1304-1351]. Although final gene counts may be higher, there is a disparity between the relatively small number of human genes and the complexity of the human proteome, suggesting that alternative splicing is important in the generation of protein diversity. The most striking example of alternative splicing complexity known, is the single pre-mRNA for a Drosophlia axon guidance receptor gene, Down Syndrome cell-adhesion molecule (Dscam), which can be processed to generate potentially 38,016 different mature transcripts [Schmucker (2000) Cell 101:671-684].

The accuracy and efficiency of the gene splicing reaction is attributed mainly to a number of cis sequence elements and trans-acting factors which are required for splicing.

Cis Sequence Elements

Any constitutive or alternative splicing event requires the assembly of the basal splicing machinery in spliceosome complexes on consensus sequences present at all boundaries between introns and exons, herein after the 5' splice site (5'SS) and 3' splice site (3'SS). The spliceosome has two functions; to recognize and select splice sites and to catalyze the two sequential transesterification reactions, which remove the introns and join the two exons together. The efficiency with which the splicosome acts on an exon is determined by a balance of several features, including the strength of a splice site essentially conformity to consensus splice site sequences, exon size and the presence of auxiliary cis elements. Exons of ideal size, (i.e., 50-300 nucleotides) with well conserved splice site sequences are recognized efficiently by the splicing machinery and are constitutively included in the transcript, whereas suboptimal exons require auxilliary elements for recognition. Typically, auxiliary elements which regulate the usage of alternative splice sites share several common features; they are small and variable in sequence and mostly present in multiple copies. Although most of these elements are single stranded, secondary structures have been implicated in the function of a few elements. Despite high level of conservation auxiliary cis elements are degenerate, rendering identification thereof difficult. Interestingly, auxiliary cis elements can be both exonic and intronic. Intronic cis elements can lie upstream, downstream or flanking both sides of the regulated exon and can be positioned proximally or distal to the regulated exon, however in most cases they are located close to the exon. Notably, such cis elements can enhance or repress splice site selection. Thus, depending on the location of the auxiliary cis elements and the effect thereof on the recognition of alternative splice sites, the elements are referred to as exonic splicing enhancers or silencers or intronic splicing enhancers or silencers. Ladd and Cooper list intronic splicing enhancers and silencers identified to date [(2002) Gen. Biol. 3(11):1-16]. Exonic splicing enhancers and silencers are described in Fairbrother (2002) Science 297:1007-1013

It is suggested that many alternative splice sites are associated with both enhancers and silencers and that regulation thereof is often the result of a dynamic antagonism between proteins binding such elements (i.e., trans-acting factors)

Trans-Acting Splicing Factors

The SR family of proteins—The SR proteins, a group of highly conserved proteins in metazones, are required for constitutive splicing and also affect alternative splicing regulation. They have a modular structure consisting of one or two copies of an RNA-recognition motif (RRM) and a C-terminal domain rich in alternating serine and arginine residues (the RS domain). The RRMs determine RNA binding specificity, whereas the RS domain mediates protein-protein interactions that are thought to be essential for the recruitment of the splicing apparatus and for splice-site pairing [Fu (1995) RNA 1:663-680; Graveley (2000) RNA 6:1197-1211; Tacke (1999) Curr. Opin. Cell. Biol. 11:358-362; Wu (1993) Cell 75:1061-1070].

Another class of RS domain containing proteins involved in splicing are the RS-related proteins (SRrps). These proteins which oftentimes contain RRMs, include the U1-70K protein, both subunits of U2AF, SRm 160/300 (two SR-related nuclear matrix proteins of 160 and 300 kDa), as well as alternative splicing regulators such as Tra and Tra2 [Pu (1995) RNA 1:663-680; Graveley (2000) RNA 6:1197-1211]. SR family and SR-related proteins function in the recognition of exonic splicing enhancers (ESEs) leading to the activation of suboptimal adjacent 3' splice sites [Blenckowe (2000) Trends Biochem. Sci. 25:106-110].

Polypyrimidine tract binding proteins (PTB)—These RNA binding proteins, also termed hnRNPI, recognize the polypyrimidine tracts preceding 3' splice sties and have a role as negative regulators of splicing. PTB repress several neuron specific exons in non-neuronal cells, as well as smooth muscle-specific inclusion of alternatively spliced exons in the a-tropomyosin and a-actinin pre-mRNAs. PTB and U2AF bind competitively to the polypyrimidine and this competitive binding has been proposed as the basis for the negative regulatory effects of PTB. However, more complex mechanisms of regulation by PTB are also likely to operate since binding of PTB to sites on both sides of the neuronal specific N1 exon in the mouse c-src pre-mRNA is required for repression [Valcarcel (1997) Curr. Biol. 7:R705-R708]

The CELF protein family—This family of proteins are involved in cell-specific and developmentally regulated alternative splicing [Ladd (2001) Mol. Cell. Biol. 21:1285-1296]. These RNA binding proteins contain three RRNs and divergent linker domain of unknown function. Several members of the family exhibit tissue specific expression and others are more broadly expressed. CELF proteins bind to muscle specific enhancers (MSE) in the cardiac Troponin-T gene (cTNT) and promote inclusion of the developmentally regulated exon 5.

Despite significant development of the splicing research, the ability to accurately predict splicing patterns is still difficult especially in light of the observation that functional splice sites do not always match the consensus sequences well, while many cryptic sites in the genome match the consensus but are not normally recognized by the splicing machinery. For example, a key step in pre-mRNA splicing involves the recognition and selection of a consensus sequence at the 5' splice site (5'SS). Frequently, however, sequences which comply with the consensus are not selected for splicing [Green (1991) Annu. Rev. Biochem. 65:367-409]. These findings suggest that the sequence surrounding a splice site as well as the match thereof to the consensus, strongly affects the recognition of the splice site.

While reducing the present invention to practice the present inventors have uncovered that intronic in-frame stop codons located upstream to 5'SS sequence inactivate splicing from such splice sites. These findings enable to accurately and efficiently predict gene expression products in-silico.

SUMMARY OF THE INVENTION

According to one aspect of the present invention there is provided a method of identifying latent splice sites, the method comprising identifying at least one intronic in-frame stop codon located upstream of a 5' splice site sequence being a latent splice site, thereby identifying latent splice sites.

According to another aspect of the present invention there is provided a method of identifying a putative pathogenic gene, the method comprising identifying an in-frame stop codon in an intronic sequence of the gene, thereby identifying the putative pathogenic gene.

According to yet another aspect of the present invention there is provided a computer readable storage medium comprising data stored in a retrievable manner, the data including a plurality of genes each having an in-frame stop codon in an intron thereof.

According to further features in preferred embodiments of the invention described below, the data is as set forth in Table 6.

According to still another aspect of the present invention there is provided a method of uncovering genes associated with a pathogenic tissue, the method comprising: (a) identifying genes having an in-frame stop codon in an intronic sequence thereof; and (b) detecting a presence or absence of a truncated expression product resultant of the in-frame stop codon in a gene of the genes which is expressed in the pathogenic tissue, thereby uncovering genes associated with the pathogenic tissue.

According to an additional aspect of the present invention there is provided an oligonucleotide useful for detecting abnormally spliced nucleic acid sequences, the oligonucleotide comprising a nucleic acid sequence specifically hybridizable with a polynucleotide sequence including at least one in-frame stop codon located in an intronic sequence of a gene.

According to still further features in the described preferred embodiments the gene is selected from the group consisting of the genes set forth in Table 6.

According to yet an additional aspect of the present invention there is provided a kit useful for detecting abnormally spliced nucleic acid sequences, the kit comprising at least one oligonucleotide including a nucleic acid sequence specifically hybridizable with a polynucleotide sequence including at least one in-frame stop codon located in an intronic sequence of a gene and reagents for detecting the at least one oligonucleotide when hybridized to the polynucleotide sequence.

According to still further features in the described preferred embodiments the at least one oligonucleotide is labeled.

According to still further features in the described preferred embodiments the at least one oligonucleotide is attached to a solid substrate.

According to still further features in the described preferred embodiments the solid substrate is configured as a microarray and whereas the at least one oligonucleotide includes a plurality of oligonucleotides each being attached to the microarray in a regio-specific manner.

According to still an additional aspect of the present invention there is provided a method of determining association between a genetic marker and a pathology, the method comprising: (a) identifying a gene having an in-frame stop codon in an intronic sequence thereof; (b) generating a probe capable of specifically hybridizing with a truncated expression product of the gene resultant from the in-frame stop codon; (c) contacting normal and pathological biological samples with the probe; and (d) detecting a level of probe binding in the normal and the pathological biological samples, to thereby determine association between a gene and a pathology.

According to still further features in the described preferred embodiments the truncated expression product is an mRNA and whereas the detecting is effected using an oligonucleotide probe.

According to still further features in the described preferred embodiments the truncated expression product is a polypeptide and whereas the detecting is effected using an antibody probe.

According to a further aspect of the present invention there is provided a method of detecting a presence or absence of an abnormal cellular phenotype associated with a defective transcription machinery, the method comprising: (a) expressing within a cell a recombinant polynucleotide capable of transcribing at least two distinct mRNA transcripts, wherein one of the at least two distinct mRNA transcripts encodes a reporter molecule, whereas a transcript encoding the reporter molecule forms only in cells having the defective transcription machinery; and (b) detecting a presence or absence of the reporter molecule thereby detecting a presence or absence of the abnormal cellular phenotype associated with a defective transcription machinery.

According to still further features in the described preferred embodiments the reporter molecule is selected from the group consisting of a fluorescer, an enzyme and an epitope tag.

According to yet a further aspect of the present invention there is provided a recombinant polynucleotide comprising a nucleic acid sequence being capable of transcribing at least two distinct mRNA transcripts, wherein one of the at least two distinct mRNA transcripts encodes a reporter molecule, whereas a transcript encoding the reporter molecule forms only in cells having a defective transcription machinery.

According to still a further aspect of the present invention there is provided a method of killing cells having abnormal cellular phenotype associated with a defective transcription machinery, the method comprising expressing within the cells a recombinant polynucleotide capable of transcribing at least two distinct mRNA transcripts, wherein one of the at least two distinct mRNA transcripts encodes a peptide toxin, whereas a transcript encoding the peptide toxin forms only in cells having the defective transcription machinery, thereby killing cells having abnormal cellular phenotype associated with the defective transcription machinery.

According to still further features in the described preferred embodiments the peptide toxin is selected from the group consisting of Pseudomonas exotoxin, Diphtheria toxin, Cholera toxin, ricin, abrin, gelonin, pertussis toxin and Shigella toxin.

According to still a further aspect of the present invention there is provided a nucleic acid construct encoding the recombinant polynucleotide of claim 20.

According to still a further aspect of the present invention there is provided a method of treating a genetic disorder associated with a defective transcription machinery in a subject, the method comprising administering to the subject a therapeutically effective amount of a recombinant polynucleotide capable of transcribing at least two distinct mRNA transcripts, wherein one of the at least two distinct mRNA transcripts encodes a peptide toxin, whereas a transcript encoding the peptide toxin forms only in cells having the defective transcription machinery, thereby treating the genetic disorder associated with a defective transcription machinery.

According to still further features in the described preferred embodiments the peptide toxin is selected from the group consisting of Pseudomonas exotoxin, Diphtheria toxin, Cholera toxin, ricin, abrin, gelonin, pertussis toxin and Shigella toxin.

According to still a further aspect of the present invention there is provided a pharmaceutical composition comprising a recombinant polynucleotide capable of transcribing at least two distinct mRNA transcripts, wherein one of the at least two distinct mRNA transcripts encodes a peptide toxin, whereas a transcript encoding the peptide toxin forms only in cells having the defective transcription machinery, and a pharmaceutically acceptable carrier or diluent.

According to still further features in the described preferred embodiments the peptide toxin is selected from the group consisting of Pseudomonas exotoxin, Diphtheria toxin, Cholera toxin, ricin, abrin, gelonin, pertussis toxin and Shigella toxin.

According to still a further aspect of the present invention there is provided a method of treating a genetic disorder associated with abnormal splicing the method comprising fixing mutations associated with premature stop codons thereby treating genetic disorders associated with defective transcription machinery.

According to still further features in the described preferred embodiments the fixing is effected by gene nock-in and whereas the gene nock-in is directed at in-frame stop codons located at intronic sequences.

According to still a further aspect of the present invention there is provided a method of identifying agents which affect the activity of the transcription machinery, the method comprising: (a) expressing in a plurality of cells a recombinant polynucleotide capable of transcribing at least two distinct mRNA transcripts, wherein one of the at least two distinct mRNA transcripts encodes a reporter molecule, whereas a transcript encoding the reporter molecule forms only in cells having the defective transcription machinery; (b) exposing the plurality of cells expressing the recombinant polynucleotide to a plurality of agents; and (c) identifying an agent of the plurality of agents which alters expression of the reporter molecule to thereby identify agents which affect the activity of the transcription machinery.

According to still further features in the described preferred embodiments the agent up-regulates expression of the reporter molecule, to thereby identify agents which damage the transcription machinery.

According to still further features in the described preferred embodiments the agent down-regulates expression of the reporter molecule, to thereby identify agents which repair the transcription machinery.

The present invention successfully addresses the shortcomings of the presently known configurations by providing methods for accurately identifying gene expression products which result from alternative splicing and methods of identifying and treating disorders associated with such genes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3a-b are photomicrographs of RT-PCR analyses depicting suppression of latent splicing by all in-frame stop codon variants of the CAD pre-mRNA. RT-PCR analyses of CAD constructs were performed with primers a and b (FIG. 3a) and with primers c and b (FIG. 3b). Lettering and symbols are as in FIGS. 2b-c.

FIGS. 4a-b are photomicrographs of RT-PCR analyses depicting the activation of latent splicing in the CAD mini gene which includes mutations eliminating in-frame stop codons. S86 in CAD2 was frame shifted by an AT insertion at a distance of 53 nt downstream of the normal 5'SS (Mut 6 and Mut 7). All four stop codons in CAD1 (see FIG. 2b, lane 3) were mutated by a T insertion into S25, thus frame shifting the remaining three (Mut 9). C denotes Control, RNA from untransfected cells. RT-PCR analyses were performed with primers a and b (FIG. 4a) and with primers c and b (FIG. 4b). Lettering and symbols are as in FIGS. 2b-c.

FIGS. 5a-b are photomicrographs of RT-PCR analyses showing that abrogation of NMD does not Reveal Latent Splicing. FIG. 5a—Human 293T cells (lanes 1-13) were transfected with CAD mini gene constructs as indicated (lanes 1-4 are co-transfections with pEGFP-N3). 24 hours post-transfection the cultures were treated with cyclohexamide (CHX, 20 µg/ml) for the indicated time periods. RNA was analyzed by RT-PCR as in FIG. 2b (lettering and symbols are as in FIGS. 2b-c). FIG. 5b—Human 293T cells were co-transfected as indicated (β-globin WT, wild type β-globin; β-globin Ter39, a mutant construct expressing β-globin mRNA having a PTC at position 39; CAD Ter, a mutant construct expressing CAD mRNA having a PTC in exon N+1). Treatment with CHX was as in FIG. 5a. β-globin mRNA was revealed by RT-PCR. Mature CAD 1 and CAD Ter mRNAs were revealed as in FIG. 2b.

FIG. 6a is a schematic drawing of wild type IDUA mini genes (symbols are as in FIG. 2a; S denotes an intronic in-frame stop codon).

FIGS. 6b-c are photomicrographs of RT-PCR analyses showing that intronic latent 5' splice site is activated in IDUA mutant mini genes devoid of upstream in-frame stop codons. Gel electrophoretic analyses of RT-PCR DNA fragments obtained from IDUA mini genes. The sequences of the normal 5'SSs in the wild type and the mutant mini genes (mutations underlined) are indicated above each of the respective lanes. Bands corresponding to precursor and mature (normal and latent) IDUA fragments amplified with primers b+c (FIG. 6b) and primers d+c (FIG. 6c) are indicated by schematic drawings on the right (other symbols are as in FIGS. 2b-c). These assignments were confirmed by sequence analyses of the DNA fragments extracted from the gel. The additional minor band that appears just below the 539-nt band in lanes 4-6 of FIG. 6c was assigned to a heteroduplex between precursor and mature PCR amplified DNAs, as confirmed by sequence analyses of the DNA extracted from the gel, and by re-running it on a second gel. Lane 2, control with RNA from untransfected cells. Lane 1, molecular size markers, pBR322 cut with MspI.

FIGS. 7a-c illustrate the results of nuclease S1 mapping analysis which show that intronic latent 5' splice site is activated in CAD mutant mini genes devoid of upstream stop codons. FIG. 7a—is a map of the 972-bp BsrFI fragment probe and the expected 3' end labeled fragments protected by the normally spliced CAD RNA (169 nt) and by the latent RNA (294 nt). FIG. 7b—DNA fragments protected by CAD RNA expressed from CAD2 (lane 2), Mut 1 (lane 3), and Mut 2 (lane 4) constructs. A control of untransfected cells (lane 1) shows no protected DNA fragments of the above size. FIG. 7c—Nuclease S1 protection experiments were carried out with increasing amounts of input RNA expressed from Mut 1 (lanes 2-4) and from Mut 2 (lanes 5-7). Lane 1 is a control with no input RNA.

FIGS. 8a-b are schematic illustrations depicting the activation of latent splicing by abrogation of in-frame stop codons. Boxes—exon 1, exon 2; Narrow box—extension of exon 1 resulting from splicing at the latent 5' splice site; Solid line, intros. Expected splicing patterns are denoted by heavy dotted lines). Splicing at the latent 5' splice site of the in-frame stop codon-containing pre-mRNA (FIG. 8a—TGA) is suppressed. Nonsense to sense mutation of this stop codon by either point or frame shift mutation (FIG. 8b—TGA to TGG or T GA) results in activation of splicing from the downstream latent 5' splice site.

FIGS. 9a-c are schematic illustrations depicting splice site sequence patterns. The sequence pattern at the normal 5' splice sites for introns with internal 5' splice site consensus sequences (FIG. 9a) and for introns without internal 5' splice site consensus sequences (FIG. 9b), as well as the sequence pattern at the internal intronic 5' splice site consensus sequences (FIG. 9c), are represented as weight matrices. The sequence patterns were displayed by using the PICTOGRAM program http://genesDOTmitDOTedu/pictogramDOThtml; Lim and Burge (2001) Proc. Natl. Acad. Sci. USA 98:11193-11198]. The height of each letter is proportional to the frequency of the corresponding base at the given position, and bases are listed in descending order of frequency from top to bottom. The information content (IC in bits) relative to the background of the intron base composition is also shown.

FIG. 11a is a schematic illustration of the wild type HTH mini-gene (schematics as in FIG. 10) and a blowup of exons 1 and 1 a , showing the sequence (SEQ ID No.: 38)and reading frame of exon 1a, and the alternative splicing patterns (diagonal lines).

FIGS. 11b-c are photomicrographs showing that an alternative 5'SS in the first exon of the HTH gene is suppressed by the introduction of an upstream in-frame stop codon. FIG. 11b—is an RT-PCR analysis of HTH transcripts, expressed from wild type and mutant constructs. The sequence of codon 4 in the wild type and the mutant mini genes, and the expected occurrence of splicing at 5' splice site 1a (±), are indicated above each lane. Bands of RT-PCR fragments corresponding to the alternatively spliced HTH RNAs are indicated by schematic drawings, on the left. RT-PCR fragments were amplified with primers n+f, and revealed by Southern blotting using $^{32}$P-labeled antisense HTH RNA as a probe. FIG. 11c—are RT-PCR fragments of FIG. 11b as visualized by ethidium bromide staining.

FIGS. 14a-d are photomicrographs showing that suppressor tRNA is unable to activate latent splicing. Mini gene constructs of wild type and mutant of CAD (FIG. 14a), HTH (FIG. 14b) and IDUA (FIG. 14c) were each co-transfected with GFP and the respective cognate suppressor tRNA, and RT-PCR was performed. Control experiments using a wild type and β-globin Ter39 constructs showed that the cognate suppressor tRNA was able to abrogate NMD under the same conditions (FIG. 14d).

FIGS. 15a-d are photomicrographs showing that dominant negative mutant of hUpf1 is unable to activate latent splicing. Mini gene constructs of wild type and mutant of CAD (FIG. 15a), HTH (FIG. 15b) and IDUA (FIG. 15c) were each co-transfected with GFP and with either hUpf1 wild type or its dominant negative mutant construct as indicated, and analyzed by RT-PCR. The band at ~500 in FIG. 15c, lanes 1-3, is a heteroduplex, as confirmed by denaturing gel analysis. Control experiments with β-globin constructs showed that the dominant negative mutant of hUpf1 was able to abrogate NMD under the same conditions (FIG. 15d).

DESCRIPTION OF THE PREFERRED EMBODIMENTS

Figure 1:
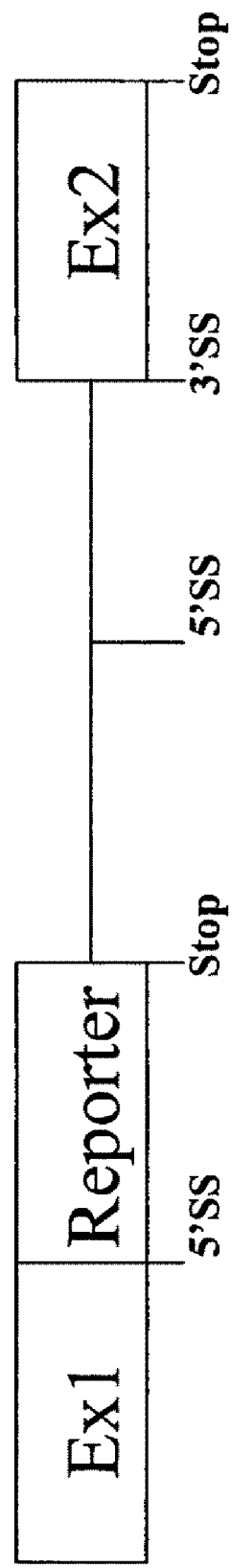
FIG. 1 is a schematic illustration of one configuration of the recombinant polynucleotide reporter of the present invention.

The present invention is of methods of identifying gene expression products, which can be used to identify pathogenic genes such as oncogenes. Specifically, the present invention can be used to diagnose and treat diseases associated with the expression of such pathogenic genes, such as cancer.

The principles and operation of the present may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Alternative splicing, the process by which multiple mRNA isoforms are generated from a single pre-mRNA species is an important means of regulating gene expression. The accuracy and efficiency of pre-mRNA splicing is governed by a number of trans-acting factors and cis acting sequence elements.

A key step in pre-mRNA splicing involves the recognition and selection of a consensus sequence AG/GTRAGT (wherein R denotes a purine and "/" denotes the splice junction, SEQ ID NO: 1) at the 5' splice site [5'SS, Black (1995) RNA 1:763-771; Kramer (1996) Annu. Rev. Biochem. 65:367-409; Burge (1999) in The RNA World, $2^{nd}$ edition, eds. Gesteland C B., Cech T R., and Atkins J F., (Cold Spring Harbor Press, Cold Spring Harbor, N.Y.)]. Frequently, however, 5'SS which comply with the consensus are not selected for splicing [i.e., 'latent 5'SS', Green (1 991) Annu. Rev. Biochem. 65:367-409], suggesting that the splicing machinery distinguishes between normal and latent 5'SSs. To date, parameters used for identifying latent 5'SSs are not known.

While reducing the present invention to practice the present inventors have uncovered that intronic in-frame stop codons located upstream to 5'SS sequence render the such splice site sequences latent.

As described hereinbelow and in the Examples section which follows the present inventors illustrate that elimination of in-frame stop codons located upstream of latent 5' splice sites activated splicing in the CAD and IDUA genes (GENEBANK Accession Nos. M31621.1 and AH002600.1, respectively, see Examples 1-4) and further that introduction of an in-frame stop codon between two adjacent alternative 5' splice sites which are normally used to express splice variants of the HTH gene (GENEBANK Accession No. D00269.1) abolished splicing from the downstream site (see Example. 6), substantiating the effect of intronic in-frame stop codons on latent splicing.

Thus, the findings presented herein provide, for the first time, guidelines which can be used to accurately predict gene expression products in-silico.

Thus, according to one aspect of the present invention there is provided a method of uncovering latent splice sites.

As used herein the phrase "latent splice sites" refers to intron splice sites from which splicing is suppressed under normal cellular conditions.

The method is effected by identifying at least one intronic in-frame stop codon located upstream of a 5' splice site sequence, wherein such 5' splice sequence is a latent splice site to thereby uncover latent splice sites.

As used herein an "intronic in-frame stop codon" refers to a stop codon such as UAA, UAG or UGA which is located in an intron sequence but maintains the open reading frame of the preceding upstream exon. The intronic in-frame stop codons of this aspect of the present invention are typically flanked by an upstream normal 5'SS and a downstream latent 5'SS. Methods of identifying an open reading frame are well known in the art.

Identification of intronic in-frame stop codons which are located upstream of 5'SSs can be effected manually or using suitable software applications such as operable on a PC machine. Such software applications are well known in the art. Examples include but are not limited to the Motif software of the GCG package (Genetics Computer Group, Wisconsin), Macvector (available from www.accelrvs.com/products/macvector/), DNASIS (available from Hitachi software engineering, Inc.), GeneMine (available from Molecular Application Group, Inc.), LaserGene (available from DNAStar Inc.) and Omiga (available from Oxford Molecular Group, Inc.).

Using the methodology of this aspect of the present invention, the present inventors uncovered that 95.8% of latent splice sites include at least one in-frame stop codon in the upstream intronic sequence (see Example 5 of the Examples section).

The hereinabove described methodology can be applied in a large scale to identify latent splice sites even at the level of a whole genome or transcriptom. Once genes including such latent splice sites are identified they can be stored in a database which can be generated by a suitable computing platform.

It is conceivable that 5'SS located downstream of intronic in-frame stop codons are rendered latent to avoid inclusion of stop codons in the reading frame of the expression product thereby leading to premature termination of the protein product (i.e., truncated proteins). Thus, the present invention suggests a general surveillance mechanism which role is to identify in-frame stop codons and suppress splicing (SOS) at latent downstream 5'SS such that the deleterious effects of premature termination codons (PTCs) in apparently wild-type transcripts are avoided.

Such a surveillance mechanism has been previously described for the nonsense mediated mRNA decay (NMD) pathway, which ensures the degradation of nonsense mRNAs [Frischmeyer and Dietz (1999) Hum. Mol. Genet. 8:1893-1900; Hentze and Kulozik (1999) Cell 96:307-310; Li and Wilkinson (1998) Immunity 8:135-141 and Maquat (2002) Genes Dev. 16:1743-1753]. However, in sharp contrast, the SOS mechanism of the present invention does not seem to involve ribosomes since it is not affected by either the protein synthesis inhibitor cyclohexamide (CHX) or the aminoglycoside antibiotic G-418, which allows stop codon read-through (see Examples 3-4 of the Examples section). Furthermore, latent splicing is not activated in the presence of a suppressor tRNA which also allow stop codon readthrough nor is it activated in the presence of a dominant negative mutant of the NMD gene, hUpf1 [GENBANK Accession No. U59323, Sun (1998) Proc. Natl. Acad. Sci. USA 95:10009-10014, see Example 6 of the Examples section]. These findings suggest that SOS has a different mechanism than NMD.

The nuclear scanning mechanism identified and characterized herein can be harnessed, for example to generate within cells, which are characterized by a defective nuclear scanning mechanism, alternative transcripts from a single coding sequence. Such alternative transcripts can exhibit distinct characteristics to be utilized in diagnostic and therapeutic applications.

Thus, according to another aspect of the present invention there is provided a method of detecting a presence or absence of an abnormal cellular phenotype which is associated with a defective transcription machinery.

As used herein the phrase "defective transcription machinery" refers to cellular mechanisms which ensure transcript quality. Examples include but are not limited to the nuclear scanning mechanism described hereinabove, the splicing machinery such as the SR proteins described hereinabove and the nonsense mediated mRNA decay (NMD) machinery.

The method is effected by expressing within a cell a recombinant polynucleotide capable of transcribing at least two mRNA transcripts, wherein one of the at least two distinct mRNA transcripts encodes a reporter molecule, which forms only in cells having the transcription machinery.

Once the recombinant polynucleotide is expressed, the presence or absence of the reporter molecule in the cell is detected to thereby detect the presence or absence of the abnormal cellular phenotype which is associated with the defective transcription machinery.

As used herein the phrase "recombinant polynucleotide" refers to a polynucleotide sequence which includes at least two otherwise separated nucleic acid sequence segments, generated using molecular biology techniques.

The recombinant polynucleotide of this aspect of the present invention can have numerous configurations. One representative configuration is illustrated in FIG. 1 wherein, the recombinant polynucleotide of this aspect of the present invention includes a first exon followed by an intron which includes an in-frame stop codon flanked by two 5'SSs and a downstream 3'SS and a second exon, which includes an in-frame stop codon. An in-frame intronic reporter molecule is positioned upstream of the in-frame intronic stop codon. Such a recombinant polynucleotide encodes under normal conditions an expression product, which includes exon 1 and exon 2 only. However, under pathological conditions (e.g., viral infection, exposure to mutagens and the like) a fusion protein including exon 1 followed by a down stream reporter molecule would be expressed.

It will be appreciated that the recombinant polynucleotides of this aspect of the present invention can also be used to identify agents, which affect the activity of the transcription machinery. The method of this aspect of the present invention is effected by exposing the cells which express the recombinant polynucleotides of the present invention to a plurality of agent and determining which agent is capable of altering the expression of the reporter molecule to thereby identify agents, which affect the activity of the transcription machinery. The method can identify agents which upregulate expression of the reporter molecule, thereby identifying agents which damage the transcription machinery. Alternatively the method can identify agents which down regulate expression of the reporter molecule in a transcription defective cell, thereby identifying agents which repair the transcription machinery, such agents can be used in numerous therapeutic applications.

Agents, which can be utilized according to the present invention include, can include small molecules, such as, for example, naturally occurring compounds (e.g., compounds derived from plant extracts, microbial broths, and the like) or synthetic organic or organometallic compounds; mutagenic agents can also include viruses and microorganisms such as bacteria and intracellular parasites.

Various growth conditions can also be used as agents of this aspect of the present invention. Conditions suitable for use as putative mutagens according to the present invention include, but are not limited to, temperature, humidity, atmospheric pressure, gas concentrations, growth media, contact surfaces, radiation exposure (such as, gamma radiation, UV radiation, X-radiation) and the presence or absence of other cells in a culture.

The reporter molecule of the present invention can be a polypeptide label which can be quantitated directly or indirectly. For example, a polypeptide label can be an enzyme which when in the presence of a suitable substrate generates chromogenic products. Such enzymes include but are not limited to alkaline phosphatase, β-galactosidase, β-D-glucoronidase (GUS) and the like. A polypeptide label can also be a fluorescer such as the polypeptides belonging to the green fluorescent protein family including the green fluorescent protein, the yellow fluorescent protein, the cyan fluorescent protein and the red fluorescent protein as well as their enhanced derivatives. In such case, the polypeptide label can be quantified via its fluorescence, which is generated upon the application of a suitable excitatory light. Alternatively, a polypeptide label can be an epitope tag, a fairly unique polypeptide sequence to which a specific antibody can bind without substantially cross reacting with other cellular epitopes. Such epitope tags include a Myc tag, a Flag tag, a His tag, a Leucine tag, an IgG tag, a streptavidin tag and the like. Further detail of polypeptide labels can be found in Misawa et al. (2000) Proc. Natl. Acad. Sci. USA 97:3062-3066

Alternatively the reporter molecule can be a nucleic acid molecule such as a reporter mRNA molecule. For example an amplifiable nucleic acid sequence can be used as a reporter molecule, provided that it is a unique sequence included only in the reporter segment of the recombinant polynucleotide (see for example U.S. Pat. No. 6,369,207).

As mentioned hereinabove the recombinant polynucleotide is expressed within a cell. The cell according to this aspect of the present invention is preferably a eukartyotic cell which includes a functional or dysfunctional transcription (e.g., splicing) machinery and which is readily propagatable in culture. Cells of this aspect of the present invention can be recovered from an abnormal tissue such as a tumor tissue or can be chemically or genetically (e.g., site directed mutagenesis) induced using laboratory techniques known in the art.

Typically, the recombinant polynucleotide of the present invention is expressed from a nucleic acid expression construct. Such an expression construct further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any available promoter can be used by the present methodology. In a preferred embodiment of the present invention, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The constructs of the present methodology preferably further include an appropriate selectable marker and/or an origin of replication. Preferably, the construct utilized is a shuttle vector, which can propagate both in *E. coli* (wherein the construct comprises an appropriate selectable marker and origin of replication) and be compatible for propagation in cells, or integration in a gene and a tissue of choice.

The construct according to the present invention can be, for example, a plasmid, a bacmid, a phagemid, a cosmid, a phage, a virus or an artificial chromosome.

Methods of introducing the recombinant polynucleotides of the present invention into eukaryotic cells are well known in the art. Examples include but are not limited to transfection, infection, conjugation, electroporation, calcium phosphate-precipitation, direct microinjection, liposome fusion and the like. Selection of a suitable introduction method is dependent upon the host cell and the nucleic acid construct used.

Since abnormal transcripts which exhibit nonsense mutations such as premature stop codons are normally identified by the nonsense-mediated mRNA decay (NMD) machinery which functions to degrade non-functional or deleterious transcripts, measures are taken to prevent the activation of such RNA degradation machinery, thereby allowing optimal accumulation of the expression products within the cell. Examples of NMD inhibitors include but are not limited to cyclohexamide.

Following expression, cells, which exhibit reporter activity are identified preferably by comparing these cells to similar cells, which were not introduced with the recombinant polynucleotide of the present invention. Methods of identifying such reporter activity are well known in the art. For example, in cases where a fluorescent reporter is used reporter activity is identified using a variety of microscopic visualization techniques which are well known in the art.

It will be appreciated that, once a cell with a defective transcription machinery is identified it can be used to uncover novel genes which constitute the transcription machinery such as genes which comprise the nuclear scanning mechanism. Identification of such genes can be effected using molecular biology techniques which are well known in the art. Examples include but are not limited to differential display technique [Liang and Pardee (1992) Science 257:967-70; Welsh et al. (1992) Nucleic Acids Res. 20:4965-70], subtractive cloning [Buckbinder (1994) Proc. Natl. Acad. Sci. USA 91:10640-10644] and serial analysis of gene expression (SAGE) [Valculescu et al. (1995) Science 270:484-8].

It is well known that defective transcription machinery, which results predominantly in immediate truncation, splicing abnormalities or altered reading frames producing grossly truncated proteins is directly correlated with the development of genetic diseases and cancer. For example, a nonsense mutation in exon 51 of the fibrillin 1 (FBN1) gene is associated with exon skipping and causes Marfan syndrome [Dietz (1993) Science 259:680-683], other examples include Duchenne muscular dystrophy, and Becker muscular dystrophy which are caused by mutations in the dystrophyn gene [DMD, Ahn (1993) Nature Genet. 3:283-291].

Thus, once cells which are characterized by defective transcription machinery, are identified they are preferably eliminated.

Thus, according to yet another aspect of the present invention there is provided a method of killing cells having abnormal cellular phenotype associated with a defective transcription machinery.

The method is effected by expressing within the cells a recombinant polynucleotide which is capable of transcribing at least two distinct mRNA transcripts, such as described hereinabove, however rather than a reporter molecule, a peptide toxin is formed only in cells with the defective transcription machinery to thereby kill such cells.

Examples of peptide toxins which can be used by the present methodology include but are not limited to cholera toxin, botulinum toxin, anthrax toxin, diphteria toxin, pertussis toxin, shigella toxin pseudomonas exo-toxin and the like (see U.S. Pat. Nos. 6,399,078, 6,221,397, 6,051,238 and 5,980,898).

The recombinant polynucleotides of the present invention can be used to diagnose and treat genetic disorders which are associated with a defective transcription machinery in a subject. Preferred individual subjects according to the present invention are mammals such as canines, felines, ovines, porcines, equines, bovines and humans.

The recombinant polynucleotides of the present invention can be provided to an individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the recombinant polynucleotide preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethyl-cellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p.1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)].

Preferred constructs for use in-vivo applications are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Preferred modes for in-vivo nucleic acid delivery protocols are provided in Somia and Verma (2000) Nature Reviews 1:91-99, Isner (2002) Myocardial gene therapy Nature 415: 234-239; High (2001) Gene therapy: a 2001 perspective. Haemophilia 7:23-27; and Hammond and McKirnan (2001) Angiogenic gene therapy for heart disease: a review of animal studies and clinical trials. 49:561-567.

Genetic disorders are frequently caused by mutations in normal cellular genes which control development, growth and differentiation. For example, the tumorigenic process involves an interplay between at least two classes of genes: oncogenes and tumor suppressor genes. Abnormal activation of oncogenes which promote cell proliferation and/or inactivation of tumor suppressor genes result in tumor formation or progression.

Despite remarkable advances in DNA technology and the completion of the first draft of the human genome, only very limited number of genes which control disease development and progression is currently known.

As is describes hereinabove the present inventors have uncovered a new class of genes which are characterized by an in-frame intronic stop codon. Expression of such genes can lead under special circumstances to the generation of truncated and potentially harmful protein products and thus can be considered as putative pathogenic genes.

Thus according to still another aspect of the present invention, there is provided a method of identifying putative pathogenic genes.

As used herein the phrase "pathogenic genes" refers to genes which abnormal expression thereof results in a genetic disease, such as proto-oncogenes and tumor suppressor genes.

The method according to this aspect o the present invention is effected by identifying an in-frame stop codon in an intronic sequence of a gene, thereby identifying the putative pathogenic genes.

The in-frame stop codons in intronic sequences of this aspect of the present invention may lead to truncated expression products, such as occurring in the absence of a functional nuclear scanning mechanism or a functional nonsense mediated mRNA decay machinery.

Identification of in-frame stop codons in intronic sequences is preferably effected on gene sequences which include introns, such as genomic DNA sequences, contigs or pre-mRNA sequences. Such sequences can be retrieved from nucleic acid sequence databases which are prepared from specific tissues or cell-lines or from whole organisms.

Identification of intron sequences may be effected based on pre-determined annotations, however since sequence annotations from publicly available databases is oftentimes unreliable, further validation of intron-exon boundaries is preferably effected based on intron exon conserved sequences, such as 5'SS, 3'SS, polypyrimidine tract and the like [Roscigno, R., F. et al., (1993) J. Biol. Chem. 268:11222-11229 and the Background section].

Once putative pathogenic gene sequences are identified they are preferably stored in a database which can be generated by a suitable computing platform.

Optionally, expression of truncated expression products resultant from such putative pathogenic genes is detected in a pathogenic tissue to uncover genes which are associated with a pathogenic tissue.

Identification of such truncated expression products may be effected using computer based techniques. For example, in-frame intronic stop codon can be identified in a database of expressed polynucleotide sequences, using computer dedicated software described hereinabove.

Such a database can be a pre-existing publicly available database [i.e., GENBANK database maintained by the National Center for Biotechnology Information (NCBI), part of the National Library of Medicine, and the TIGR database maintained by The Institute for Genomic Research] or private databases (i.e., the LifeSeq.™ and PathoSeq.™ databases available from Incyte Pharmaceuticals, Inc. of Palo Alto, Calif.).

Alternatively, the database can be generated from sequence libraries including, but not limited to, cDNA libraries, EST libraries, mRNA libraries and the like.

Construction and sequencing of a cDNA library is one approach for generating a database of expressed mRNA sequences. cDNA library construction is typically effected by tissue or cell sample preparation, RNA isolation, cDNA sequence construction and sequencing.

It will be appreciated that such cDNA libraries can be constructed from RNA isolated from whole organisms, tissues, tissue sections, or cell populations. Libraries are preferably constructed from a tissue reflecting a particular pathological or physiological state which is, for example, associated with genetic aberrations.

For example, libraries can be constructed from hematological malignancies including leukemia and lymphoma. Examples of such libraries include the human chronic myelogenous leukemia Creator™ Smart™ cDNA library and human acute myelogenous leukemia Creator™ Smart™ cDNA library (Cat. Nos. HL9507DD and HL9506DD, respectively Clontech Inc.).

Alternatively, identification of truncated expression products can be effected using well known molecular biology (e.g., hybridization assay such as northern blot, dot blot, RNase protection assay, RT-PCR and the like) and/or biochemical (i.e., protein gel electrophoresis, western blot and the like) techniques.

For example, antibodies or antibody fragments can be used to detect truncated expression products. For example, when an antibody is directed at a truncated polypeptide region a presence or absence of signal will be indicative of an intact protein (i.e., presence signal) or a truncated product thereof (i.e., absence signal).

Alternatively, antibodies directed at a region which is shared by the intact and truncated polypeptide product can be used to detect the truncation however additional parameters such as migration of the immunocomplex on an SDS-PAGE should be applied.

The use of immunological reagents for detecting particular proteins in samples using such reagents are described in current protocols in immunology, Coligan et al., Eds., John Wiley & Sons, New York (1995); Volume 2, Chapter 14 of current protocols in molecular biology, Ausubel et al., Eds., John Wiley & Sons, Inc. (1994); and Linnoila et al., A.J.C.P. 97(2): 235-243 (1992) and Peri et al., J. Clin. Invest. 92: 2099-2109 (1992).

Methods of generating antibodies (i.e., monoclonal and polyclonal) are well known in the art. Antibodies may be generated via any one of several methods known in the art, which methods can employ induction of in vivo production of antibody molecules, screening immunoglobulin libraries or panels of highly specific binding reagents as disclosed [Orlandi D. R. et al. (1989) Proc. Natl. Acad. Sci. 86:3833-3837, Winter G. et al. (1991) Nature 349:293-299] or generation of monoclonal antibody molecules by continuous cell lines in culture. These include but are not limited to, the hybridoma technique, the human B-cell hybridoma technique, and the Epstein-Bar-Virus (EBV)-hybridoma technique [Kohler G., et al. (1975) Nature 256:495-497, Kozbor D., et al. (1985) J. Immunol. Methods 81:31-42, Cote R. J. et al. (1983) Proc. Natl. Acad. Sci. 80:2026-2030, Cole S. P. et al. (1984) Mol. Cell. Biol. 62:109-120]; Antibody fragments can be obtained using methods well known in the art. (See for example, Harlow and Lane, Antibodies: A Laboratory Manual, Cold Spring Harbor Laboratory, New York, 1988, incorporated herein by reference).

Alternatively, an mRNA expression product including an in-frame intronic stop codon can be identified using an oligonucleotide which includes a nucleic acid sequence specifically hybridizable with the in-frame intronic stop codon.

To specifically hybridize with the in-frame intronic stop codon the oligonucleotide probe of the present invention is preferably designed to hybridize with the stop codon and sequences flanking thereof. For example, an oligonucleotide probe capable of specifically hybridizing with a truncated CAD expression product is set forth in SEQ ID NO: 31.

The oligonucleotides of the present invention can be of varying lengths such as between 10-100 base pairs and are preferably purine rich to increase hybridization stringency (i.e., purine content is higher than 50%).

In general, the oligonucleotides of the present invention may be generated by any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and as such is not further described herein.

Probes generated according to the teachings of the present invention can be used to determine an association between a genetic marker and a pathology.

First, a gene having an in-frame stop codon in an intronic sequence thereof is identified. Then, probes capable of specifically hybridizing with a truncated expression product of the gene resultant of the in-frame stop codon are generated, such as described hereinabove. Such probes are contacted with normal and pathological biological samples and a level of probe binding to these samples is determined to thereby determine association between a gene and a pathology.

For example, contacting of the oligonucleotide probes of the present invention with the biological sample is effected by stringent, moderate or mild hybridization (as used in any polynucleotide hybridization assay such as northern blot, dot blot, RNase protection assay, RT-PCR and the like). Wherein stringent hybridization is effected by a hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5 ° C. below the $T_m$, final wash solution of 3 M TMACl, 0.01 M sodium phosphate (pH 6.8), 1 mM EDTA (pH 7.6), 0.5% SDS at 1-1.5° C. below the $T_m$; moderate hybridization is effected by a hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$, final wash solution of 6×SSC, and final wash at 22° C.; whereas mild hybridization is effected by a hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 37° C., final wash solution of 6×SSC and final wash at 22° C.

Once markers of genetic disorders are identified, the probes of the present invention can be employed to determine predisposition of a subject to a genetic disorder.

Diagnostic probes prepared according to the teachings of the present invention can be attached to a solid substrate, which may consist of a particulate solid phase such as nylon filters, glass slides or silicon chips [Schena et al. (1995) Science 270:467-470].

In a particular embodiment, oligonucleotide probes prepared according to the teachings of the present invention can be attached to a solid substrate configured as a microarray. Microarrays are known in the art and consist of a surface to which probes that correspond in sequence to gene products (e.g., cDNAs, mRNAs, cRNAs, polypeptides, and fragments thereof), can be specifically hybridized or bound at a known position (regiospecificity).

Several methods for attaching the oligonucleotides to a microarray are known in the art including but not limited to glass-printing, described generally by Schena et al., 1995, Science 270:467-47, photolithographic techniques [Fodor et al. (1991) Science 251:767-773], inkjet printing, masking and the like. Methods of fabricating protein arrays are disclosed in U.S. Pat. No. 6,406,840.

Recombinant polynucleotides and probes generated according to the teachings of the present invention can be included in diagnostic or therapeutic kits. For example, oligonucleotides sets pertaining to specific disease related genes can be packaged in a one or more containers with appropriate buffers and preservatives along with suitable instructions for use and used for diagnosis or for directing therapeutic treatment.

Preferably, the containers include a label. Suitable containers include, for example, bottles, vials, syringes, and test tubes. The containers may be formed from a variety of materials such as glass or plastic.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Example 1

Latent Splicing in CAD pre-mRNA is Activated by Point Mutating in-frame Stop Codons The accuracy and efficiency of pre-mRNA splicing is multifactorial dependent, including trans-acting factors and cis-acting sequence elements. Currently known cis acting sequence elements include 5' and 3' splice sites, a branch point, a polypyrimidine tract and splicing enhancer and silencer sequence elements. A key step in pre-mRNA splicing involves the recognition and selection of a 5'SS consensus sequence such as the mammalian AG/GTRAGT sequence [SEQ ID NO: 1, where R denotes purine and "/" denotes the splice junction, Black (1995) RNA 1, 763-771; Krämer (1996) Annu. Rev. Biochem. 65, 367-409; Burge (1999) in The RNA World, second edition, eds. Gesteland, R. F., Cech, T. R. & Atkins, J. F. Cold Spring Harbor Laboratory Press, Cold Spring Harbor, N.Y. pp. 525-560].

Frequently, sequences that comply with the consensus are not selected for splicing [Green (1991) Annu. Rev. Cell. Biol. 7:559-599]. Such 5' consensus sequences are referred to as latent 5'SSs, splicing events in which such sites are utilized are referred to as 'latent splicing' and the resulting mRNA is referred to as latent RNA.

While reducing the present invention to practice the present inventors hypothesized that intronic stop codons located upstream to the latent site in the reading frame determined by the bona fide exons can silence splicing of the 5'SS.

To address this model, the in-frame intronic stop codons upstream of a 5'SS latent site in the multi-functional CAD (Carbamoyl-phosphate synthetase, Aspartate trans-carbamylase, Dihydroorotase, GENBANK Accession No. M31621.1) gene were manipulated.

Experimental Procedures

DNA and Plasmids

Ex1-Ex2 of the CAD constructs was derived from the CAD genomic plasmid p209 [Padgett, R. A., Wahl, G. M. & Stark, G. R. (1982) Mol. Cell. Biol. 2, 293-301], covering the 5' end of the gene [Farnham, P. J. & Kollmar, R. (1990) Cell Growth Differ. 1, 179-189] and containing EcoRI and SalI restriction sites. ExN-ExN+3 was a SalI—PstI fragment from the CAD genomic plasmid pGS [Burge (1999) in The RNA World, second edition, eds. Gesteland, R. F., Cech, T. R. & Atkins, J. F. Cold Spring Harbor Laboratory Press, Cold Spring Harbor, N.Y. pp. 525-560]. The Ex1-Ex2 fragment was inserted into the EcoRI—SalI site of pGS, and the EcoRI—SphI fragment of this plasmid was cloned into the respective sites of pcDNAI/Amp.

The three fragments used to construct CAD mutants (i.e., Muts 1-4) by the Power-Cloning technology (Gesher Advanced Biotechs, Israel, WO98/38297, WO98/38298 and WO98/38299) were as follows: (i) A 5601-bp Bpu11021 fragment cut from CAD2 and purified by gel electrophoresis; (ii) A 135-bp PCR fragment which harbored the mutation(s) generated by the PCR primers listed in Table 1, hereinbelow (mutated nucleotides are underlined):

TABLE 1

| Primer | Nucleotide Sequence | SEQ ID NO: | Mut1 | Mut2 | Mut3 | Mut4 |
|---|---|---|---|---|---|---|
| 1 | ATCAAGTGCACCAAACTCTTCGTGGAGGTGGCACAG | 2 | + | + | | |
| 2 | ATCAAGTGCACCAAACTCTTCGTGGAGGTGGGACAG | 3 | | | + | + |
| 3 | CACAAAGCTCCACCGCTAGCTCAGCCCTTATACG | 4 | | + | | + |
| 4 | CACAAAGCTCCACCGCTAGCTGAGCCCTTATACG | 5 | + | | + | |

Primers 1 and 2 include sequences, which flank the EarI site, and primers 3 and 4 include sequences which flank the "right" Bpu11021 site;

(iii) A 572 bp PCR fragment that includes sequences flanking the "left" Bpu11021 site at one end and sequences flanking the EarI site at the other end. The fragment was prepared by PCR amplification using the sense primer 5'-GCCTGCTCTCCAGCGCCCCGCTC-3' (SEQ ID NO: 6) and the antisense primer 5'-ACGAAGAGTTTGGTGCACTTGATG-3' (SEQ ID NO: 7).

PCR fragments were purified by gel electrophoresis.

Mutant 5 was generated by inserting a 856 nt XmaI-SphI fragment flanking the mutated downstream stop codon in Mut 1 into the respective site in the CAD2 construct. The remaining CAD mutant constructs were prepared by the QuickChange PCR-based mutagenesis method (Stratagene, Torrey Pines Road, La Jolla, Calif.).

For the frame-shift mutants, Mut 6 and Mut 7, the following primers were used to insert an AT dinucleotide (underlined) at a distance of 53 nt downstream of the normal 5' splice site in CAD2 and Mut 2 to generate Mut 6 and Mut 7, respectively: sense primer 5'-GGGGGGATGAGCGTGCATGCTGGGGTTGGGAG-3' (SEQ ID NO: 8) and antisense primer 5'-CTCCCAACCCCAGCATGCACGCTCATCCCCCC-3' (SEQ ID NO: 9). The TGA located 32 nt further downstream was thus frame shifted, and no new in-frame stop codons were generated.

To mutate the downstream TGA stop codon (S86) in Mut 2 the following primer pairs were used (mutated nucleotides are underlined):

```
Mut 10 (TGA: to TAG):
Sense primer
                                          (SEQ ID NO: 10)
5'-GCAGCGTATAAGGGCTAGGCTAGCGGTGGAGCT-3';
and Antisense primer
                                          (SEQ ID NO: 11)
5'-AGCTCCACCGCTAGCCTAGCCCTTATACGCTGC-3'.

Mut 11 (TGA to TAA):
Sense primer
                                          (SEQ ID NO: 12)
5'-GCAGCGTATAAGGGCTAAGCTAGCGGTGGAGCT-3';
and Antisense primer
                                          (SEQ ID NO: 13)
5'-AGCTCCACCGCTAGCTTAGCCCTTATACGCTGC-3'.

Mut 12 (TGA to TGG),
Sense primer
                                          (SEQ ID NO: 14)
5'-GCAGCGTATAAGGGCTGGGCTAGCGGTGGAGCT-3';
and Antisense primer
                                          (SEQ ID NO: 15)
5'-AGCTCCACCGCTAGCCCAGCCCTTATACGCTGC-3'.
```

To generate Mut 9, in which all four stop codons in CAD1 were mutated in a single step, the sense primer 5'-CGGGTGCAGGAGTGTACAGCTGTGAAGGGGGGA AGAGCGTGCGCTGGGG TTG-3' (SEQ ID NO: 16) and antisense primer 5'-CAACCCCAGCGCACGC TCTTCCCCCCTTCACAGCTGTACACTCCTGCACCC G-3' (SEQ ID NO: 17), were used. S25 was mutated by a T insertion at position 27 (boldface), thereby frame shifting S34, S79, and S91 (see FIGS. 2b and 5a). This insertion also shifted the TGA triplet at position 45 into the reading frame. This stop codon was eliminated by a T to A mutation (underlined).

Transfections—Syrian hamster SV28 fibroblast cells and human 293T cells were grown to 50% confluence in tissue culture plates as described [Miriami, E., Sperling, J. and Sperling, R. (1994) Nucleic Acids Res. 22, 3084-3091], and transiently transfected with the indicated DNA constructs (10 μg or 2 μg per 5×10$^6$ SV28 or 293T cells, respectively) using the calcium phosphate method [Kingston (1992) in Short protocols in molecular biology, eds. Ausubel, F. M., Brent, R., Kingston, R. E., Moore, D. D., Seidman, J. G., Smith, J. A. & Struhl, K. (John Wiley and Sons, NewYork), pp. 9.1-9.16]. Cells were harvested 24 or 48 hours following transfection and total cellular RNA was extracted with guanidinium thiocyanate as described [Miriami, E., Sperling, J. and Sperling, R. (1994) Nucleic Acids Res. 22, 3084-3091].

RT-PCR—Total RNA was treated with RNase-free DNase I (50 U/ml; Promega), and cDNA was synthesized from 1 μg of RNA with dT$_{15}$ primer using MMLV reverse transcriptase (Gibco BRL, Crewe UK). PCR reactions (20 μl) contained cDNA synthesized from 0.2 μg of total RNA, 10 pmole of each of the indicated primer pairs (listed in Table 2 hereinbelow), and 1.0 units of Taq DNA polymerase (Roche Molecular Diagnostics, Pleasanton Calif. USA). Amplification was carried out in a DNA Programmable Thermal Controller (PTC-100; MJ Research, Inc.) for 30 cycles, at annealing temperature of 63° C. (for primer pairs a+b) or 58° C. (for primer pair c+b). The amplified products were analyzed by electrophoresis in 2% agarose gels. The identity of the bands was confirmed by sequencing of the DNA extracted from a gel and purified with a commercial DNA purification kit (QIAGEN, Chatsworth, Calif. USA).

TABLE 2

| Primer identity | Primer Sequence | SEQ ID NO: |
|---|---|---|
| a sense | CTCAGATCCTGGTCGACGGC | 18 |
| a' sense | CTCAGATCCTGGGTCGACGGC | 19 |
| b antisense | CAGGGAGCCGCACCAGTTTC | 20 |
| c sense | CCGGGTGCAGGAGTGACAGC | 21 |
| c' sense | CCGGGTGCAGGAGTGTACAGC | 22 |

Note that primers a' and c' were used to amplify Mut 9.

For PCR analysis of β-globin RNA the following primers from exon 1 were used; Sense: 5' CCTGAAGTTCTCAG-GATCC 3' (SEQ ID NO: 23). Antisense: 5' AGGAGAAGTCTGCCGTTAC 3' (SEQ ID NO: 24).

Quantitative PCR—To ensure that PCR was performed under linear conditions, the following quantitative PCR protocol was used. For each transfection, cDNAs were synthesized from 1 μg, 0.33 μg, 0.1 μg, and 0.033 μg of total RNA. PCR amplification was performed with primer pair a+b using the reaction conditions as above. Amplification was carried out for 15, 20, 25 and 30 cycles, and the DNA from each reaction was analyzed by Southern blot hybridization using $^{32}$P-labeled Primer 6. The autoradiograms were quantified with MacBas 2.5 software.

S1 Nuclease Mapping—To verify the RT-PCR results, the RNAs expressed from CAD2, Mut 1, and Mut 2 constructs were analyzed by the independent S1 nuclease mapping method using a 3' end labeled 951-bp BsrFI fragment from CAD2. S1 nuclease mapping was carried out essentially as previously described [Miriami, E., Sperling, J. & Sperling, R. (1994) Nucleic Acids Res. 22, 3084-3091]. Probe labeling was effected by gel purifying the 951-bp BsrFI fragment from CAD2 and 3' end labeling with [α-$^{32}$P]dCTP and [α-$^{32}$P] dGTP using the Klenow fragment of DNA polymerase I.

Results

Figure 2A:
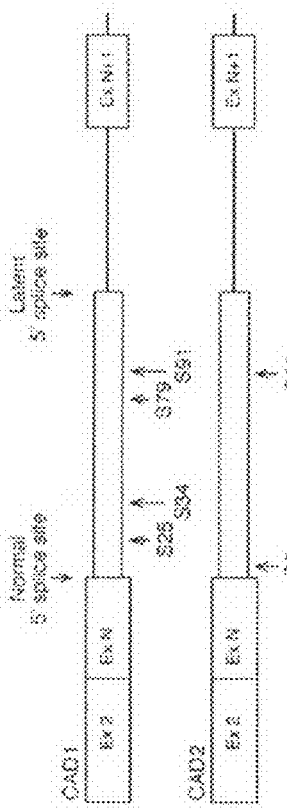
FIG. 2a is a schematic illustration depicting the structure of wild type CAD1 and CAD2 mini genes. Open boxes—exons; Heavy line—intron; narrow box -an intronic sequence included as a part of the exon in the latent RNA. The normal and latent 5'SSs and the in-frame stop codons therebetween are indicated. The S character designates the T nucleotide in a stop codon and the respective distance thereof from the normal 5'SS.

Latent splicing in CAD pre-mRNA is activated upon removal of in-frame stop codons—The wild type CAD chimeric mini gene containing the first two exons and the first intron of the CAD gene (Ex1-Ex2) fused in-frame to a downstream CAD subgenomic region composed of four exons and three introns (ExN-ExN+3) was inserted into pcDNAI/Amp expression vector (Invitrogen, The Netherlands). Two constructs, designated CAD1 and CAD2, were cloned. DNA sequencing confirmed an open reading frame in ExN of CAD1, and revealed four in-frame stop codons between the normal and the latent 5'SSs in the downstream intron (IntN). CAD2 included a single nucleotide deletion in the Ex2-ExN junction. DNA sequencing confirmed that ExN in this construct maintained an open reading frame, and revealed two in-frame stop codons in the same region of IntN (FIG. 2a).

The indicated mini gene constructs were transfected into Syrian hamster or 293T cells and the transiently expressed CAD RNAs were analyzed by RT-PCR.

Figure 2B:
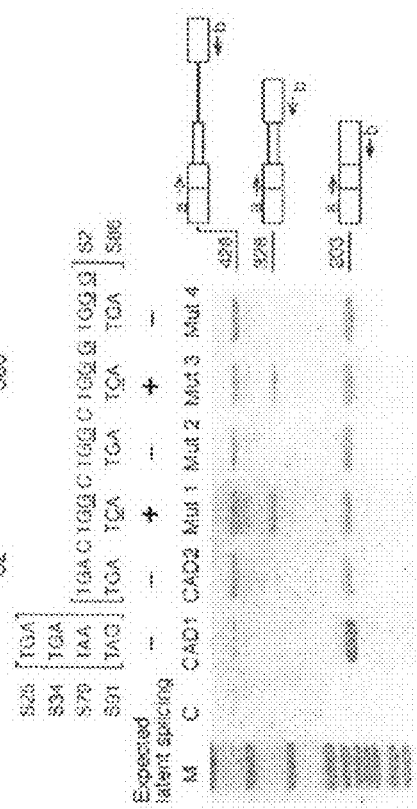
FIGS. 2b-c are photomicrographs of RT-PCR analyses depicting activation of latent splicing in CAD mutant mini genes devoid of upstream stop codons. Sequences including stop codons and mutations thereof (underlined nucleotides) are indicated above each of the respective lanes; – and + symbols indicate the expected occurrence of latent splicing. Bands corresponding to precursor and mature (i.e., normal and latent) CAD fragments amplified with primers a+b (FIG. 2b) and primers c+b (FIG. 2c) are indicated by schematic drawings on the right. These assignments were confirmed by sequence analyses of the DNA fragments extracted from the gel. Note an additional minor band, which is assigned to a heteroduplex between precursor and mature PCR amplified DNAs, occasionally appearing just below the 428 nt band in FIGS. 2b, 4b, and 5b, as confirmed by sequence analyses of the DNA extracted from the gel, and by re-running it on a second gel. Lane 2, control untransfected cells. Lane 1, molecular size markers pBR322 cut with MspI.

FIG. 2b shows the amplified PCR fragments produced from primer a (see Table 2), which spans the junction between exon 2 and exon N and primer b (see Table 2), which is complementary to a sequence within the downstream exon N+1.

Analysis of RNA from control untransfected cells, showed that endogenous CAD RNA was not amplified (FIG. 2b, lane 2). Transfection with a wild type CAD mini gene construct (i.e., CAD1), which contained four in-frame stop codons upstream of the latent site in intron N (FIG. 2a, upper scheme), gave rise to a 428-base pair (bp) DNA fragment representing the pre-mRNA and/or remnants of the mini gene DNA and a 203-bp fragment representing normally spliced CAD RNA (normal RNA, FIG. 2b, lane 3). CAD2, which contained two in-frame stop codons upstream of the latent site in intron N (FIG. 2a, lower scheme), gave similar results (FIG. 2b, lane 4). Notably, neither constructs gave rise to latent splicing. However, as predicted, elimination of all stop codons from both CAD1 and CAD2, allowed latent splicing in the respective mutants.

Thus, a construct in which both stop codons in CAD2 were mutated [S2: TGA to TGG, S86: TGA to TCA, Mut 1; FIG. 2b, lane 5] gave rise to a fragment of 328 bp which corresponded to an RNA species produced by a splicing event at the latent 5'SS. Mutating the upstream stop codon (S2) in CAD2, which is located within the normal 5'SS, increased the number of mismatches with the consensus at this site from two to three. However, the alteration in the splicing pattern could not be attributed to this change, since a construct in which both stop codons were mutated, but the normal 5'SS was strengthened by an additional C to G mutation, restoring the number of mismatches with the consensus to two (Mut 3; FIG. 2b, lane 7), gave rise to splicing at both the normal and latent sites. For control, a double mutation in the normal 5'SS alone was used. Such a construct which did not seem to perturb splicing from the normal splice site, was not sufficient to elicit latent splicing (Mut 4; FIG. 2b, lane 8). Furthermore, a construct in which only the stop codon included in the normal 5'SS (S2) was mutated, leaving the downstream stop codon (S86) unchanged, did not give rise to latent RNA but normal splicing was observed (Mut 2; FIG. 2b, lane 6).

Figure 2C:
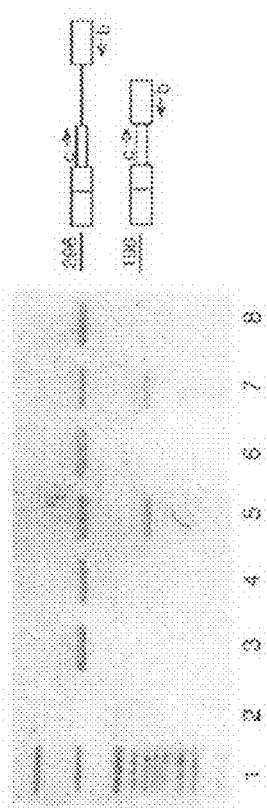

To exclude the possibility that latent splicing occurs in transcripts containing in-frame stop codons, but amplification thereof by PCR is suppressed by the high concentration of normally spliced RNA [Valentine (1997) RNA 3, 660-676], PCR amplification was performed using the intronic primer (Table 2, primer c) and primer b (Table 2, FIG. 2c). These primers were not expected to amplify the normally spliced RNA, so that suppression of amplification of the latent RNA was not expected to take place. However as shown in FIG. 2c, no PCR product arising from the latent RNA was observed in cells expressing the wild type constructs (FIG. 2c, lanes 3, 4), or in cells expressing constructs in which only S2 was mutated to a sense codon (FIG. 2c, lanes 6, 8). Mutating both stop codons to sense codons, however, gave rise to the latent RNA (FIG. 2c, lanes 5, 7), thereby substantiating the results shown in FIG. 2b.

To further demonstrate the null phenotype of latent splicing in stop-codon-containing constructs, quantitative RT-PCR analysis under linear conditions was employed. For each transfection, cDNAs were synthesized from 1 μg, 0.33 μg, 0.1 μg, and 0.033 μg of total RNA. PCR amplification was performed with primer pair a+b using the reaction conditions as above. Amplification was carried out for 15, 20, 25 and 30 cycles, and the DNA from each reaction was analyzed by Southern blot hybridization using $^{32}$P-labeled antisense primer (SEQ ID NO: 7). Thus, 30 fold serial dilutions of input RNA and 15 to 30 cycles of amplification displaying total amplification range of more than four orders of magnitude, assuming an average amplification of 1.5-fold per cycle, revealed latent splicing only in mutants lacking stop codons but not in WT or mutants containing stop codons (data not shown). Thus, latent nonsense RNA in quantities larger than 0.0076% of normally spliced RNA should have been detected by this analysis.

The RT-PCR results were confirmed by S1 nuclease mapping. FIG. 7b shows that splicing at the latent 5' splice site occurred only in cells expressing the double mutant construct (Mut 1, FIG. 7b lane 3) but not in cells expressing CAD2 (FIG. 7b lane 2) or Mut 2 (FIG. 7b lane 4). FIG. 3c confirms this result by showing that the 294 bp fragment, which represents splicing at the latent 5' splice site, could not be observed in Mut 2 RNA even when the highest concentration of input RNA was used (FIG. 7b lane 7). In comparison, the 294 bp fragment was detected already in the lowest amount of Mut 1 RNA (FIG. 7b lane 2). These results suggest that activation of splicing at an intronic latent 5' splice site occur upon elimination of upstream in-frame stop codons.

Example 2

Activation of Latent Splicing Cannot be Attributed to Interference with Splicing Control Elements The relative efficiencies of alternative splicing events may often be influenced by short enhancer sequences [Liu (2000) Mol. Cell. Biol. 20:1063-1071; Schaal (1999) Mol. Cell Biol. 19:261-273], as well as other splicing control elements that suppress or enhance splicing [Black (1995) RNA 1:763-771; Berget (1995) J. Biol. Chem. 270:2411-2414; Blencowe (2000) Trends. Biochem. Sci. 25:106-110; Wang (1997) Curr. Opin. Genet. Dev. 7:205-211]. The possibility that activation of latent splicing can be attributed to suppression of a splicing silencing element or to activation of a splicing enhancing element, was therefore addressed Results As shown in FIGS. 3a-b mutating either S2 (i.e., Mut2) or S86 (i.e., Mut5) alone did not give rise to latent splicing (Mut 2 and Mut 5; FIGS. 3a-b, lanes 3 and 4, respectively), while latent splicing was elicited only when both S2 and S86 were mutated (Mut 1; FIGS. 3a-b, lane 2). Furthermore, latent splicing was suppressed when the TGA stop codon in S86 of Mut 2 was mutated to either of the remaining stop codons TAG or TAA (Mut 10 and Mut 11; FIGS. 3a-b, lanes 5 and 6, respectively), while mutating S86 to the missense codon TGG elicited latent splicing (Mut 12; FIGS. 3a-b, lane 7).

Thus, the phenotypic behavior of mutants 10-12 supported the conclusion that the effect on latent splicing should be attributed to the reading context of the mutation in S86 rather than the mutation per se.

However, since splicing enhancer and silencer sequence elements are degenerate and location thereof is not precisely defined with respect to the splice junctions [Blencowe (2000) Trends Biochem. Sci. 25:106-110; Liu (2001) Nat. Genet. 27:55-58], frame shift mutation analysis was effected. A dinucleotide AT was inserted 53 nt downstream of the normal 5'SS, thereby frame shifting the S86 TGA located 33 nt further downstream. Frame shifting of S86 alone, leaving S2 unchanged, did not give rise to latent RNA but gave rise to normal RNA (Mut 6; FIGS. 4a-b, lane 3). On the other hand, a frame shift mutation of S86 together with a point mutation in S2 resulted in latent splicing (Mut 7; FIGS. 4a-b, lane 4). Likewise, a frame shift mutation in CAD1, eliminating all four stop codons upstream of the latent site, also gave rise to latent splicing (Mut 9; FIGS. 4a-b, lane 5). These results substantiate the significance of the reading context of putative stop codons, rather than the sequence in which they are embedded, in rendering a downstream 5'SS latent.

Example 3

Suppression of Latent Splicing is not Alleviated by Drugs that Abrogate Nonsense-Mediated mRNA Decay (NMD)

Messenger RNAs which contain premature translation termination codons (PTCs) lead to truncated proteins, which can be toxic to cells if they function in a dominant-negative or gain-of-function fashion [Li (1998) Immunity 8, 135-141; Hentze (1999) Cell 96, 307-310; Frischmeyer (1999) Hum. Mol. Genet. 8, 1893-1900.]. Numerous studies have shown that the nuclear and cytoplasmic abundance of many nonsense mRNAs expressed in mammalian cells is reduced. This was attributed to NMD, whereby the occurrence of PTCs activates a mechanism which rapidly degrades such aberrant mRNAs (Li Supra; Hentze Supra; Frischmeyer Supra; Maquat (1995) RNA 1:453-465].

In the reported cases of NMD, the levels of nonsense mRNAs were substantially reduced but remained detectable [1-30% of the normal message (Li Supra; Maquat Supra]. Interestingly, no PTC-containing CAD RNA was detected in cells expressing constructs harboring intronic in-frame stop codons upstream of the latent 5'SS, whether analyzed by RT-PCR or nuclease S1 mapping.

To exclude the possibility that latent splicing had occurred, but the resulting nonsense RNAs were subjected to rapid degradation by NMD to an extent that rendered them undetectable, the splicing pattern of CAD RNAs, expressed from several constructs, in cells treated with drugs [e.g., Cycloheximide (CHX), aminoglycoside antibiotic G-418] known to abrogate NMD was tested. Other protein synthesis inhibitors shown to efficiently reverse the down regulatory effects of PTCs in exons of the T-cell receptor-β and the β-globin mRNAs [Carter (1995) J. Biol. Chem. 270:28995-29003] and in the HEXA mRNA [Rajavel (2001) Mol. Cell Biol. 21:5512-5519] were tested as well.

Results

FIGS. 5a-b show that treatment with CHX does not alter CAD splicing patterns. Notably, latent splicing was not detected in cells expressing constructs including in-frame stop codons upstream of the latent 5'SS including CAD1 having four stop codons (FIG. 5a, lanes 1-4), CAD2 including two stop codons (FIG. 5a, lanes 5-7), Mut 2 having one stop codon (FIG. 5a, lanes 8-10), in the presence or absence of CHX. Latent splicing was, however, observed only when stop codons were absent (Mut 1) and was not affected by CHX (FIG. 5a, lanes 11-13).

The CHX experiments were performed under conditions in which NMD was eliminated in 293T cells, as shown in FIG. 5b. For this experiment 293T cells were co-transfected either with a wild type β-globin construct (WT, FIG. 5b, lanes 1-3), or with a PTC-containing β-globin construct (Ter 39) together with CAD1 as a control (FIG. 5b, lanes 4-6). FIG. 5b (lanes 1-3) shows that the expression of WT β-globin RNA did not change upon CHX treatment. However, the level of Ter 39 β-globin RNA was reduced significantly (FIG. 5b, lane 4), presumably due to NMD, and treatment with CHX reversed this effect (FIG. 5b, lanes 5 and 6).

To further exclude the possibility that an unusual rapid degradation by NMD may have accounted for the absence of transcripts spliced at the latent 5'SS in wild type CAD RNA, CAD RNA that contains a PTC in a bona fide exon (CAD Ter) was analyzed. If this interpretation were valid, the transcript expressed from CAD Ter should be undetectable as well. In contrast, FIG. 5b (lane 7, upper panel) shows that CAD Ter RNA was detected. Furthermore, the stability of this nonsense RNA increased by about 40% upon treatment with CHX (FIG. 5b, lanes 8 and 9, lower panel), as estimated by comparing to the co-expressed GFP RNA reference (lower panel).

Taken together, these results suggest that the absence of a signal for nonsense RNA should be attributed to the suppression of the latent 5'SS by the presence of upstream in-frame stop codons.

Example 4

Latent Splicing is Activated in the α-L-Iduronidase (IDUA) Gene by Mutating an in-frame Stop Codon Upstream of the Latent 5' Splice Site To generalize the role of in-frame intronic stop codons in latent splicing, RNA expressed from the human IDUA gene was analyzed [Neufeld (1991) Ann. Rev. Biochem. 60:257-280]. Sequence examination of this gene [Scott (1992) Genomics 13:1311-1313] revealed a latent site within the first intron, which is preceded by an in-frame stop codon (FIG. 6a). The effect of missense mutating this stop codon on latent splicing was addressed.

Experimental procedures
DNA and Plasmids

A plasmid carrying a 9 kb fragment from the 5' end of the IDUA gene [Bach (1993) Am. J. Hum. Genet. 53:330-338], was provided by Dr. Elizabeth Neufeld, Department of Biological Chemistry, UCLA. The wild type IDUA mini-gene was constructed by cloning an 893-bp PCR fragment comprising the first IDUA intron flanked by the first two exons into pcDNAI/Amp expression vector (Invitrogen, The Netherlands). Mutant IDUA mini genes were prepared by the Power-Cloning technology as described in Example 1, hereinabove. Cloning was confirmed by DNA sequence analyses.

A normal β-globin construct (pmCMV-Gl-Normal) and a construct expressing a PTC-containing β-globin mRNA [pmCMV-Gl-39Ter Zhang (1998) RNA 4:801-815] were provided by Dr. L. E. Maquat University of Rochester, Rochester, N.Y.

RT-PCR

IDUA cDNA was generated using a primer that is complementary to the fusion region of IDUA with the pcDNAI/Amp vector (5'-AGAGGGCCCTCTAGATGCATG CTGGTGGT-GACAAGCTCCAGCAGC-3', SEQ ID NO: 25). The following primers were used for PCR: sense primer b 5'-CGAG-CACGCGTGGCCATGCGT-3' (SEQ ID NO: 26); antisense primer c 5'-AGGACGTACTGGTCAGCCTGG-3' (SEQ ID NO: 27); sense primer d[+]5'-ACTGTGAGAGCTTCA-GAGACC-3' (SEQ ID NO: 28).

Analysis of IDUA RNA was carried out on total RNA, prepared 48 hr after transfection, by RT-PCR. For the preparation of IDUA cDNA a primer complementary to the fusion region of IDUA with the vector was used. PCR was effected as described for CAD (see Example 1) but with the addition of 5% DMSO, at an annealing temperature of 63° C. (primers b+c) or 59° C. (primers d+c).

Results

Chinese hamster ovary cells were transiently transfected with the wild type and mutant IDUA mini-genes, and the IDUA RNAs were analyzed by RT-PCR. As shown in FIGS. 6a-c, total RNA from control untransfected cells gave no PCR signal corresponding to JDUA RNA with either combination of primers (FIG. 6b and c, lane 2). PCR amplification with primers b and c of the RNA obtained from cells transfected with the wild type construct gave rise to the expected fragments representing IDUA pre-mRNA and normally spliced RNA (778 and 212 bp, respectively; FIG. 6b lane 3). Amplification of the same RNA with primers d and c gave rise only to a PCR product of 537 bp representing the pre-mRNA (FIG. 6c lane 3). Amplification with primers b and c of total RNA from cells transfected with the Mut 1 construct (FIG. 6b lane 6) gave rise to the expected 778 bp pre-mRNA PCR product and to a 447-bp PCR product representing latent RNA. This result was confirmed by the nested PCR experiment (FIG. 6c, lane 6), showing PCR products of 537 and 206 bp, representing the pre-mRNA and latent RNA, respectively.

Notably, the 212 bp fragment, which represents normally spliced IDUA RNA, was not detected in the Mut 1 IDUA RNA (FIG. 6b, lane 6), though trace amounts of this band were detected by radioactive PCR (not shown), suggesting that the TGA to TGG mutation in Mut 1 rendered the normal 5'SS almost inactive in splicing. This observation was attributed to the fact that the number of mismatches with the consensus of the normal 5'SS increased from two in the wild type to three in the mutant. Therefore analogous experiments with constructs in which further mutations that decreased the number of mismatches with the consensus were introduced (Mut 2, two mismatches; Mut 3, one mismatch) were effected. FIG. 6b (lanes 4, 5) shows that each one of these mutants gave rise to PCR products resulting from splicing at the normal 5'SS without impairing splicing from the latent 5'SS.

Finally, as observed in the CAD case, the null phenotype of latent splicing in IDUA gene constructs having an in-frame stop codon upstream of the latent 5'SS was maintained even after treatment with CHX and G-418 (not shown). Thus, it may be concluded that the absence of a signal for nonsense RNA should be attributed to the suppression of the latent 5'SS by the presence of upstream in-frame stop codons.

The identification of upstream in-frame stop codons, which activates latent splicing implies the existence of a nuclear surveillance mechanism that is functionally coupled to the splicing machine. By scanning the pre-mRNA, this mechanism detects the presence of in-frame stop codons and suppresses splicing at downstream potential 5'SSs, which could have led to the inclusion of PTCs in the mRNA. The hereinabove described results are consistent with studies that suggested a nuclear scanning mechanism. These include mutations in the DHFR gene [Urlaub (1989) Mol. Cell. Biol. 9:2868-2880] and several cases of human genetic diseases in which exons harboring PTCs were skipped (Bach Supra; Maquat (1995) Supra; Dietz (1993) Science 259:680-683; Dietz (1994) Nat. Genet. 8:183-188]. In the fibrillin gene, associated with Marfan syndrome, nonsense, but not missense, mutations were associated with skipping of exon 51 Dietz (1994) Supra]. These studies also include cases of intron retention [Naeger (1992) Genes Dev. 6:1107-1119; Lozano (1994) EMBO J. 13:4617-4622; Aoufouchi (1996) Cell 85:415-422; Gersappe (1999) J. Biol. Chem. 274:22452-22458; Muhlemann (2001) Mol. Cell 8:33-44]. In particular, nonsense mutations in the Igβ gene cause defective splicing of this pre-mRNA in a B cell in vitro system [Aoufouchi supra]. While the above studies dealt with the effect of mutations which generate exonic in-frame stop codons, the present study addresses the issue of nonsense RNA from the viewpoint of splice site selection and the role endogenous intronic stop codons play in this process.

The observation that a large number of protein-coding transcripts that contain nonsense mutations in their exons are spliced, despite the above-described is highly significant since such nonsense transcripts are characteristic of many genetic diseases [Culbertson (1999) Trends Genet. 15:74-80]. A clue to a possible answer lies in the sequence environment in which the stop codons are embedded. In the hereinabove described, the intronic in-frame stop codons are flanked by 5'SSs on both sides. In the absence of stop codons, two alternative exons can be defined by the exon definition process [Berget (1995) J. Biol. Chem. 270:2411-2414] and independently, or in a regulated fashion, enter the splicing pathway. The presence of an in-frame stop codon between the alternative 5'SSs apparently interferes with the exon definition involving the downstream one, thereby suppressing participation thereof in splicing. A different situation arises when a stop codon is located in a bona fide exon, where it is flanked by an upstream 3'SS and a downstream 5'SS, as is the case for most nonsense transcripts that are spliced and contain PTCs in their exons. It is possible that interference with the exon definition process has the alternative of choosing a further downstream 3'SS, thereby skipping the PTC-containing exon, alternatively it may result in intron retention. However, if no alternative splice choices that could eliminate the in-frame stop codon are available, such "ill-defined exons" might escape the surveillance mechanism and enter the splicing pathway. This would result in the production of PTC-containing mRNAs that can be subjected to the NMD pathway.

Such a surveillance mechanism is difficult to conceive mainly because it implies that the reading frame of mRNAs can be recognized at the level of pre-mRNA before splicing commences. The machine performing this role could involve intranuclear ribosomes. Support for such a view is the occurrence in the nucleus of charging of tRNA [Lund (1998) Science 282:2082-2085], translation initiation factors [Dostie (2000) J. Cell Biol. 148:239-247], and coupled transcription and translation [Iborra (2001) 293:1139-1142]. Alternatively, a yet unknown nuclear machine might perform this reading frame task. But even if a nuclear 'ribosome-like' machine, capable of reading nucleotide triplets was invoked [Li (1998) Supra; Frischmeyer (1999) Supra], it would be difficult to envisage its function on a pre-mRNA because the presence of introns whose length is not an integer multiple of three alter the reading frame. However, a supraspliceosome complex which serves as a frame onto which the pre-mRNA is folded to align exons about to be spliced, while introns are looped out of each of the respective spliceosomes [see FIG. 5 in Muller (1998) J. Mol. Biol. 283:383-394], allows exon sequences to be scanned consecutively even when introns are still part of the pre-mRNA, suggesting that the decision whether to splice or not is made at the level of the complex. Namely, splicing complexes in which a latent 5'SS is aligned with a 3'SS may be formed, but splicing does not take place because an in-frame stop codon is recognized upstream of that site in the context of the reading frame of the not-yet-formed mRNA. Such unproductive complexes may reassociate to form productive splicing complexes. When the stop codon is removed, the homologous complex is stable and is capable of entering the splicing pathway.

In summary, the suppression of splicing (SOS) mechanism proposed here acts to prevent the inclusion of PTCs in mRNAs rather than dealing with them after splicing by activating NMD. Despite this conceptual difference between NMD and SOS, it is plausible that independent or complementary nuclear and cytoplasmic mechanisms are required to alleviate the potentially toxic effect of in-frame stop codons.

Example 5

A Computerized Survey for Latent 5' Splice Sites in 446 Protein-Coding Human Genes Experimental Procedures Database—The data were derived from a non-redundant complete human gene sequences data base (http://wwwDOT-fruitflyDOTorg/seq_tooools/datasets/Human/coding_data/). The data were further filtered and 16 genes were excluded based on the criteria that they were described as pseudogenes or partial [Burge (1999) in The RNA World, second edition, eds. Gesteland, R. F., Cech, T. R. & Atkins, J. F. Cold Spring Harbor Laboratory Press, Cold Spring Harbor, N.Y. pp. 525-560]. After this filtering, the data set included 446 spliced genes.

Identification of 5' splice site signals—A program in C language was written to search for 5' splice site signals within the database. The criteria for the search for 5' splice site consensus sequences are detailed in the Results. Intronic in-frame stop codons refer to the reading frame of the preceding exon.

The identified 5' splice site consensus sequences were represented as weight matrices and presented in a logo representation produced by the PICTOGRAM program [http://genes-DOTmitDOTedu/pictogram.html Lim and Burge supra]. The representation of signals as a weight matrix allows also for the evaluation of its degree of conservation by computing information content thereof.

Results

As described hereinabove splicing at latent 5' splice sites could be activated upon removal of in-frame stop codons that are located between the normal and the latent sites [Li (2002) Proc. Natl. Acad. Sci. USA 99:5277-5282, FIGS. 8a-b]. This finding provided an experimental proof to the hypothesis that intronic in-frame stop codons play a role in the maintenance of an open reading frame in mRNAs by rendering downstream 5' splice sites as latent.

To generalize this hypothesis, the frequency of 5' splice site consensus sequences in protein-coding pre-mRNAs was addressed. Thus, a computer search for 5' splice site consensus sequences within a non-redundant complete human gene sequences from the GENBANK was performed. This data set includes 446 multi-exon genes having a total of 2,311 introns. The search algorithm allowed for a maximum of two mismatches in the consensus octanucleotide AG/GTRAGT (SEQ ID NO: 29), excluding the dinucleotide GT (underlined), which invariably appears at the 5' end of U2 introns [Burge supra; Mount (1982) Nucleic Acids Research 10:459-472; Ohshima (1987) J. Mol. Biol. 195:247-259; Shapiro (1987) Nucleic Acids Research 15:7155-7174]. The use of this criterion is justified because 85.5% of the normal 5' splice sites in this data set deviate from the consensus by no more than two nucleotides, thereby allowing each of most of the latent 5' splice sites to compete with the respective normal 5' splice site for a downstream 3' splice site. Of the 2,311 normal 5' splice sites, a total of 1,977 sites were picked up by this search. The remaining 334 normal 5' splice sites deviate from the consensus by three (305) or more (29) mismatches. As shown in Table 3, below, in addition to these 2,311 normal 5' splice sites, the search revealed 10,626 intronic 5' splice sites consensus sequences which are located within 1,601 introns, whereas 710 introns are devoid of internal 5' splice sites consensus sequences. It should be pointed out, that 5' splice site consensus sequences are significantly less abundant in exon sequences, as only 551 were scored in 429 of the 2,311 exons.

TABLE 3

Occurrence of 5' SS consensus sequences in 446 human genes

|  | Total | Sequences with consensus 5' SS[b] | Number of consensus 5' SS[a] | Sequences without consensus 5' SS[c] |
|---|---|---|---|---|
| Introns | 2,311 | 1,601 | 10,626 | 710 |
| Exons | 2,311[d] | 429 | 551 | 1,882 |

[a]Consensus 5' SSs, excluding the normal 5' SSs.
[b]Number of introns or exons that contain at least one consensus 5' SS.
[c]Number of introns or exons that do not contain consensus 5' SS.
[d]Last exons were excluded from this count.

Figures 9A, 9B, 9C:
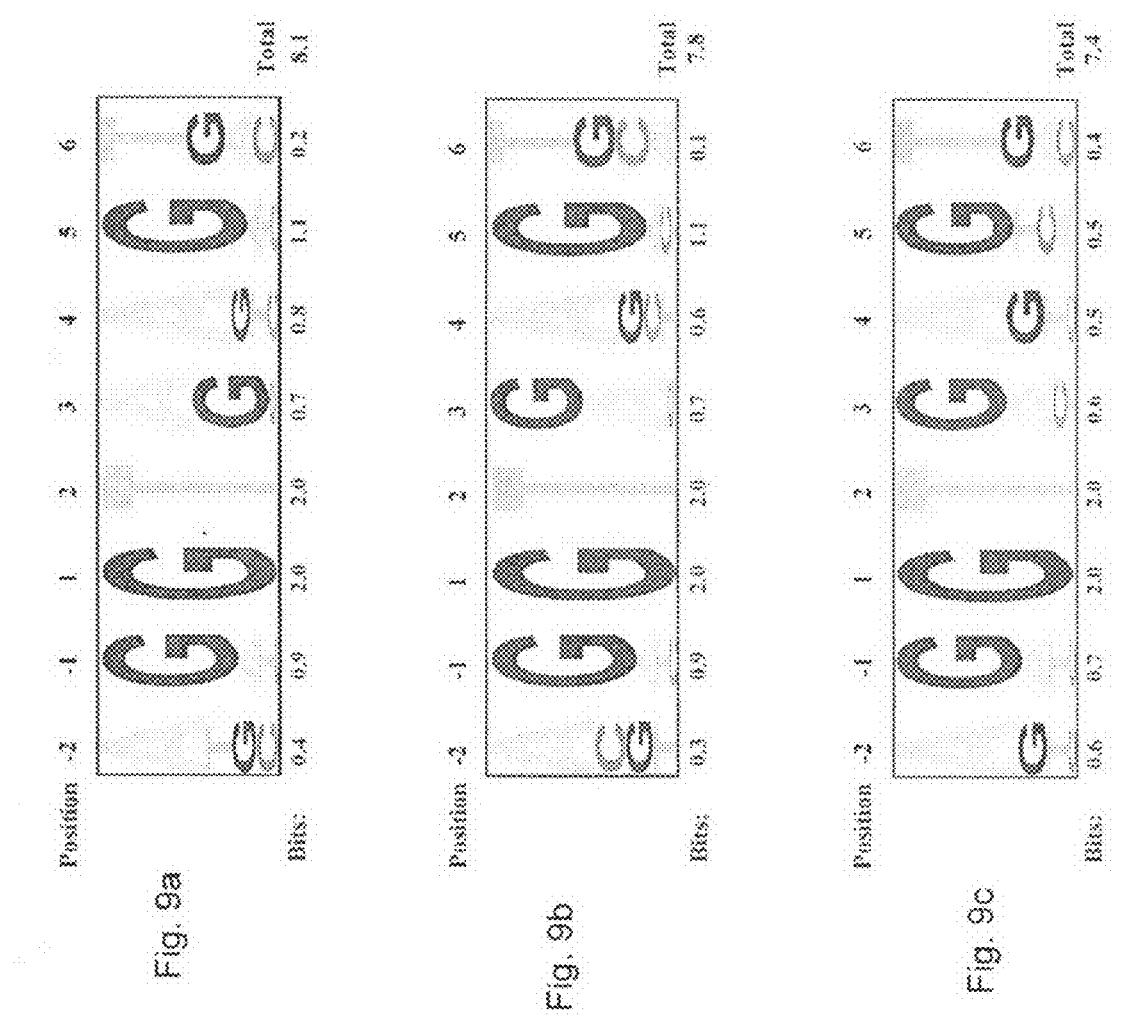

As shown in FIGS. 9a-c introns having internal 5' splice site consensus sequences do not differ from introns lacking such sites with respect to the weight matrices of their normal 5' splice sites (FIGS. 9a-b). To ascertain that these two matrices are not different, a $\chi^2$ test to compare the nucleotide distributions throughout the aligned positions was applied. The null hypothesis that these two weight matrices are different was rejected (p<0.005). A $\chi^2$ test to compare these two weight matrices and the weight matrix of the internal 5' splice site sequences (FIG. 9c) revealed that the nucleotide distributions throughout the aligned positions were not different, except at position +3 which exhibited a preference to G at the latent sites. Interestingly introns having internal 5' splice site consensus sequences do not differ from introns lacking such sites with respect to their phases (zero, one, or two, according to whether the first nucleotide in the given intron is the first, second or third in a coding triplet, respectively). Similarly to previous analysis [Tomita (1996) Mol. Biol. Evol. 13:1219-1223], introns from both groups were shown to have a preference to phase zero as shown in Table 4 below, whereas introns of phase two are less abundant. However, the introns with and without internal 5' splice site consensus sequences vary significantly with respect to the presence of stop codons, as described below.

TABLE 4

Percentage of intron phases

|  | Number of introns | Phase zero | one | two |
|---|---|---|---|---|
| With consensus 5' SS | 1,601 | 44.72 | 36.67 | 18.61 |
| Without consensus 5' SS | 710 | 46.62 | 35.35 | 18.03 |

To consider the possibility that the occurrence of in-frame stop codons upstream of internal 5' splice site consensus sequences is a significant general phenomenon, which may be involved in the prevention of splicing at such sites, the occurrences of in-frame stop codons upstream to all internal 5' splice site consensus sequences was scored (Table 5). Splicing at 136 internal 5' splice site consensus sequences lacking upstream in-frame stop codons, which are located in 105 introns, would not change the reading frame of the resulting mRNAs. These sites are thus potential candidates for alternative splicing, and have therefore been excluded from the statistical analysis described below. The remaining 1,496 introns contain 10,490 latent 5' splice sites—10,045 of which (95.8%) have at least one upstream in-frame stop codon.

TABLE 5

Occurrence of in-frame stop codons upstream of intronic 5' SS consensus sequences in 446 human genes

|  | Number of introns | Number of 5'SS |
|---|---|---|
| Introns with stop codons | 1,359[a] | 10,045[b] |
| Introns without stop codons | 137[c] | 445[d] |
| Total introns with latent 5' SSs | 1,496 | 10,490 |
| Introns with potential alternative 5' SSs | 105 | 136 |
| Total | 1,601 | 10,626 |

[a]Introns with in-frame stop codon upstream of the most 3' latent site.
[b]Latent 5' SSs with upstream in-frame stop codons.
[c]Introns without in-frame stop codon upstream of the most 3' latent site.
[d]Latent 5' SSs without upstream in-frame stop codons.

The possibility whether in introns having latent 5' splice sites, stop codons upstream of the latent sites occur more frequently than in introns lacking such sites, was addressed. A total of 1496 introns (of different lengths) that have latent 5' splice sites and 710 introns that do not were examined. If N is the length of an intron in nucleotides, its effective number of codons (L) is the integral part of N/3, (N−2)/3 or (N−1)/3 (according to the reading phase being zero, one or two, respectively). The number of in-frame stop codons in each intron of effective length L was scored, and their density was calculated. Then, estimates and standard errors of the density of stop codons were calculated for each group using ratio estimate techniques [Cochran (1953) Sampling Techniques Wiley, New York]. For introns having latent 5' splice sites, the estimate of the density of stop codons was 0.04840±0.00064 stop codons per effective number of codons, whereas for introns that do not have latent 5' splice sites, the estimate of the density was only 0.03382±0.00110. This difference is highly significant (P<0.001). If, for introns having latent 5' splice sites, only the upstream part (up to the most 3' latent site) is considered, the estimate of the density is 0.04883±0.00069, which makes the difference between the two types of introns even more pronounced.

A slightly different approach is to consider whether or not each intron has any stop codons at all. If stop codons are distributed independently, the probability that an intron, whose effective number of codons is L, will not have any stop codons is a negative exponential function $e^{-\beta L}$. For any given L, the probability of not having any stop codons is smaller, the larger β is. Out of 1496 introns that have latent 5' splice sites, 137 do not have any stop codons upstream of the most 3' latent site (Table 5); and out of 710 introns that do not have latent 5' splice sites, 167 introns do not have any stop codons. From the data, maximum likelihood estimates (MLE) of β was derived. For introns having latent 5' splice sites, the MLE of β was 0.04485±0.00007 (estimate±standard error), compared to only 0.03019±0.00006 for introns without latent 5' splice sites. This difference is highly significant (P<0.001).

Conclusions

In a survey of a database consisting of 446 human protein-coding-genes 10,490 latent 5' splice sites which are located within 1,496 introns were identified. The high abundance of latent 5' splice sites in the genome indicates that the splicing machine must frequently and efficiently discriminate between normal 5' splice sites and latent ones, and emphasizes the necessity for a mechanism that identifies such latent sites and renders them as latent. A suggested mechanism is provided in Example 4, hereinabove and in [Miriami et al. J. Struct. Biol. 140 (2002) 116-122].

Interestingly, of the 10,490 latent 5' splice sites scored hereinabove, 10,045 (95.8%) have at least one in-frame stop codon in the upstream intronic sequence. Subsequent statistical analyses of the data confirmed that in-frame stop codons are significantly over represented in introns that harbor latent 5' splice sites, in comparison to introns that lack such sites. Thus, a functional linkage between 5' splice site selection and the necessity to maintain an open reading frame in the mRNA is strongly implicated. Further, because the occurrence of intronic latent 5' splice sites, having upstream in-frame stop codons, appears to be widespread in the genome, a general mechanism is suggested. The suggested role of such mechanism is to identify in-frame stop codons and suppress splicing at latent downstream 5' splice sites so that the deleterious effects of including PTCs in apparently wild type transcripts is avoided. Such a mechanism is referred to as suppression of splicing (SOS). Clearly, not all parameters that control splice site selection are known, and the relative importance of those that have already been characterized cannot be assessed as yet. Nonetheless, the relevance of the SOS mechanism for accurate gene expression is highlighted by the fact that 413 genes out of the 446 genes in the data base examined here have at least one intron with latent 5' splice sites. Of these 413 genes, 404 (98%) have at least one intron with a latent 5' splice site whose usage for splicing would introduce an in-frame stop codon into the resultant mRNA.

Example 6

Alternative Splicing of HTH can be Regulated by SOS

The hereinabove described computational analysis and mutational experiments suggested a functional linkage between 5' splice site selection and the necessity to maintain an open reading frame in the mRNA. It was therefore suggested that such a linkage is mediated by a general mechanism termed suppression of splicing (SOS). To further substantiate this mechanism, in-frame stop codons were introduced in between two adjacent alternative 5'SS which are normally used to express splice variants of the human tyrosine hydroxylase (HTH, GENBANK Accession No. D00269.1) gene [Dumas (1996) J. Neurochem. 67:19-25; Grima (1987) Nature 326:707-711] and the effect of such mutations on repression of splicing was thereafter determined.

Experimental Procedures

Plasmids—Wild type HTH-a construct containing the first three exons and two introns of HTH cloned into pcDNA3/Amp was provided by Dr. Jacques Mallet, Salpêtrièr Hospital, Paris. The mutant HTH mini genes were prepared by the Power-Cloning technology described in Example 1. HTH primer 1: [+] 5'-TAC GAC TCA CTA TAG GGA GAC CCA AGC T-3' (SEQ ID NO: 32) and HTH primer 2: [−] 5'-CCT GGG CTC CGG TCC ACT GCG GCC GCC GGGCAC CTA CCT ACC CTC TTA CC-3' (SEQ ID NO:33) were used to prepare HTH Mut1. HTH primer 1 and HTH primer 3: [−] 5'-CCT GGG CTC CGG TCC ACT GCG GCC GCC GGGCAC CTA CCT CCC CTC TTA CC-3' (SEQ ID NO: 34) were used to generate hTH Mut2. The incorporation of the appropriate mutations and the preservation of the reading frame in all mutants were confirmed by DNA sequence analyses. CAD and IDUA wild type and mutant mini gene constructs were described by Li et al., Supra. CAD mutant 25 was prepared using the QuickChange PCR-based mutagenesis method (Stratagene). It was derived from CAD1 by a frameshift mutation that eliminated the 4 intronic in-frame stop codons, and introduced a new in-frame stop codon (S#45). All constructs were confirmed by DNA sequence analysis. A wild type (WT) hUpf1 construct and a construct expressing a dominant negative hUpf1 mutant [Lykke-Andersen (2000) Cell 103:1121-1131] were kindly provided by Dr. Jens Lykke Andersen (Yale University). Suppressor tRNA constructs [Li (1997) J. Exp. Med. 185:985-992] were kindly provided by Dr. Miles Wilkinson (University of Texas, Houston). A WT β-globin construct (pmCMV-Gl-Normal) and a construct expressing a PTC-containing β-globin mRNA [pmCMV-GI-39Ter were provided by Dr. Lynne E. Maquat (University of Rochester) Zhang (1998) RNA 4:801-815].

Cells and transfections—Human 293T cells were grown to 50% confluence in tissue culture plates as described by (44), and transiently co-transfected with the appropriate test DNA construct (2-10 µg per 5×106 293T cells) and pEGFP-N3 (Clontech) (1 µg per 5×106 293T cells) using the calcium phosphate method (Kingston, 1992). Treatment with CHX was as described hereinabove. Treatment with G-418 was effected for 18 hours with the indicated concentrations. The experiments with suppressor tRNAs were performed by co-transfection of the test DNA constructs with pEGFP-N3 and the cognate suppressor tRNA (4 or 12 µg per 5×106 293T cells). In the hUpf1 experiments, cells were co-transfected with the test DNA construct, pEGFP-N3 and the appropriate hUpf1 construct (8 µg per 5×106 293T cells). Cells were harvested 24 or 48 hours following transfection and total cellular RNA was prepared as previously described by (44).

RT-PCR analyses—Splicing products of CAD constructs were analyzed as described in Example 1. RT-PCR reactions of the IDUA RNA spliced products were done as described In Example 1, with the following changes: The primer used for the RT reaction was complementary to the SP6 promoter sequence of the plasmid (SP6 primer, SEQ ID NO: 30), and radioactive PCR was performed using 5' $^{32}$P-labeled primer c (see Table 2). IDUA PCR products were analyzed by running on 5% polyacrylamide/urea denaturing gels. RT of HTH RNA was performed with the SP6 primer followed by PCR, using primers: HTH primer n [+] 5'-AAGCAGGCAGAGGC-CCATCAT-3', SEQ ID NO: 35; HTH primer k [+] 5'-ATGG-TAAGAGGGCAG-3', SEQ ID NO: 36, and HTH primer f [−] 5'-AGAAGAGCAGGTTTAGCACGG-3', SEQ ID NO: 37). PCR was performed as previously described [Li (2002) supra], but at an annealing temperature of 58° C., in 3 mM MgCl$_2$ (primers n+f), or at an annealing temperature of 62° C. (primers k+f). Analysis of PCR products of primers n+f was done by running on a 10% polyacrylamide/urea denaturing gel, followed by Southern hybridization with a $^{32}$P-labeled anti-sense RNA probe. Analysis of PCR products of primers k+f was performed by running on a 2% agarose gel and staining with ethidium bromide.

Results

HTH encodes for a key enzyme in the synthesis of cathecolamines [Grima (1987) Nature 326:707-711], unlike the IDUA and CAD gene systems, HTH has two adjacent alternative 5'SS in the first intron thereof (FIG. 11a), both of which are used in normal tissues. Because these alternative 5'SS are 12 nucleotides apart, splicing from either site retains the same open reading frame in the expressed product. For this reason the HTH system was selected to examine the effect of in-frame stop codon insertion on suppression of splicing.

Point mutations were Inserted in the wild type HTH minigene construct (FIG. 11a) changing the CAG in codon 4 of exon 1a to TAG (HTH Mut 1) or to GAG (HTH Mut 2). Each of the three constructs was transfected into 293T cells, total RNA was prepared 24 hours following transfection, and subjected to RT-PCR using a primer in the first exon and a primer in exon 3 (primers n and f, respectively). The PCR products were resolved on denaturing gels and detected by Southern blotting.

As shown In FIG. 11b, the wild type construct (WT) underwent splicing from both 5' splice sites. Upon insertion of a stop codon between these sites (Mut 1), the product that includes exon 1a was not detected, while a sense mutation in codon 4 (CAG to GAG, Mut 2) retained the wild type phenotype. To demonstrate that the failure to detect the inclusion of exon 1a in HTH Mut 1 was not attributable to competition from the PCR product in which exon 1a was excluded, a second PCR was performed using primers that are specific to the exon 1a included RNA (primers k and f). As shown in FIG. 11c, even under these conditions, the inclusion of exon 1a was not detected in Mut 1, indicating that splicing from the downstream 5' splice site in Mut 1 was inactivated, as expected for a latent 5' splice site subjected to SOS.

Figure 10:
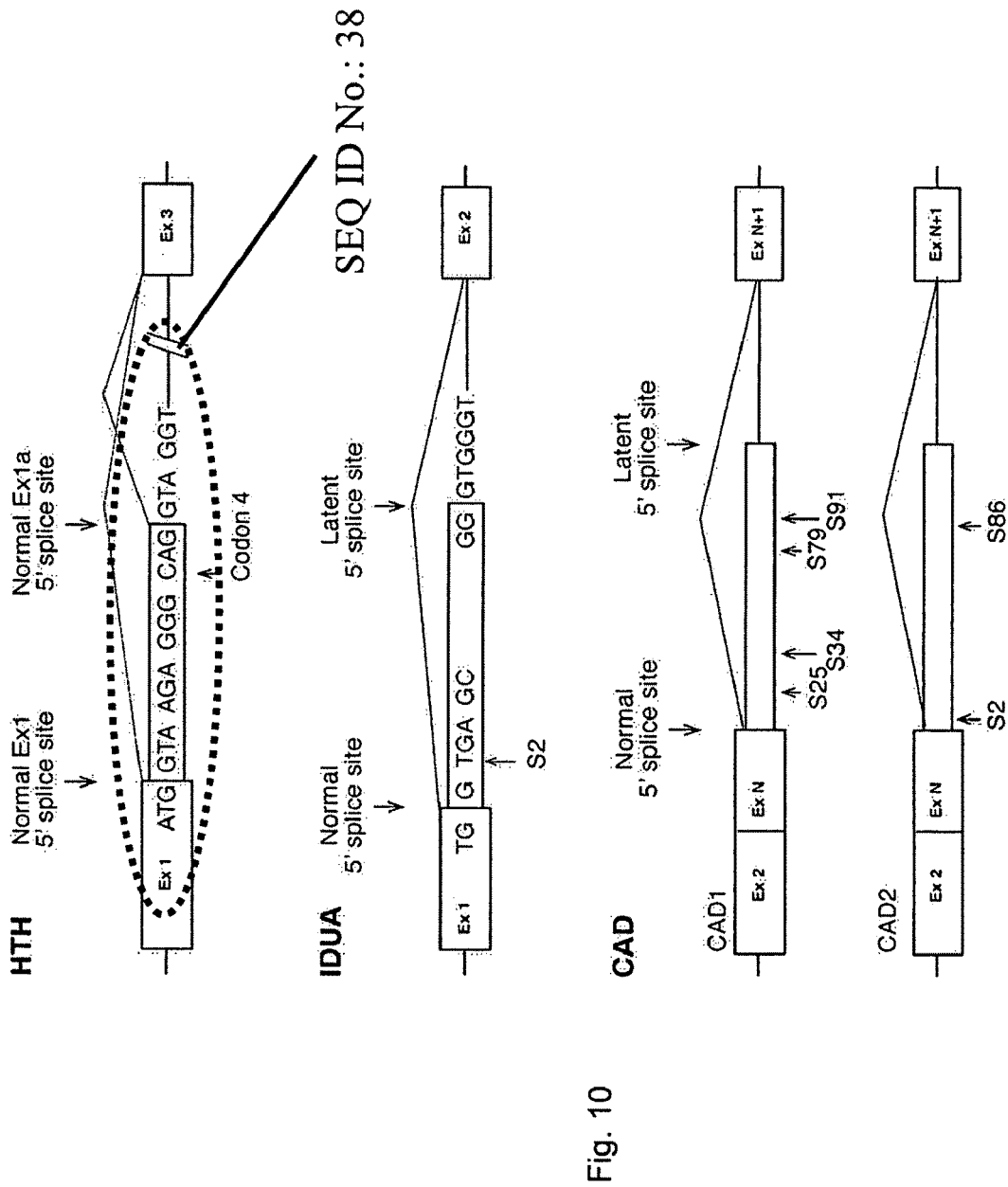
FIG. 10 is a schematic illustration showing wild type HTH (SEQ ID No.: 38), IDUA and CAD mini gene constructs. Open boxes—exons; Lines—introns; Narrow boxes—intronic sequence included as part of the exon in latent RNA; Diagonal lines—normal splicing patterns. The normal and latent 5' splice sites and the in-frame stop codons between them are indicated (S# designates the T nucleotide in a stop codon and its respective distance from the normal 5' splice site).
Figure 12A:
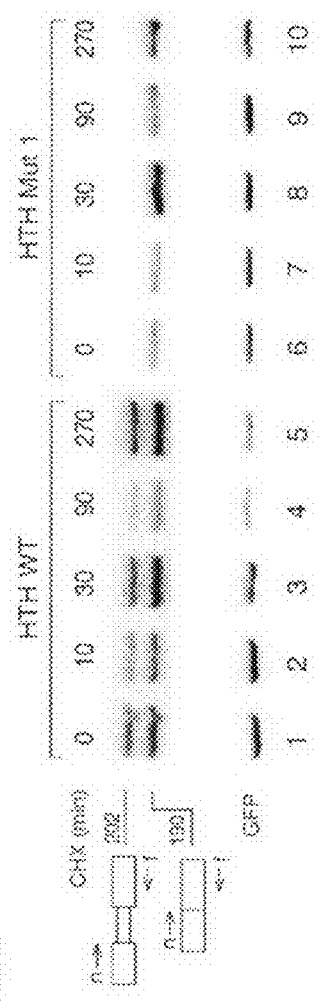
FIGS. 12a-b are photomicrographs showing that the presence of the translation inhibitor CHX does not effect latent splicing of HTH wild type or Mut 1 (FIG. 12a) and IDUA wild type or Mut 1 constructs (FIG. 12b) as indicated. Twenty-four hours post-transfection the cell cultures were treated with cycloheximide (CHX, 20 mg/ml, for the indicated lengths of time). RT-PCR was performed with primers n+f (FIG. 12a) or b+c (FIG. 12b).
Figure 12B:
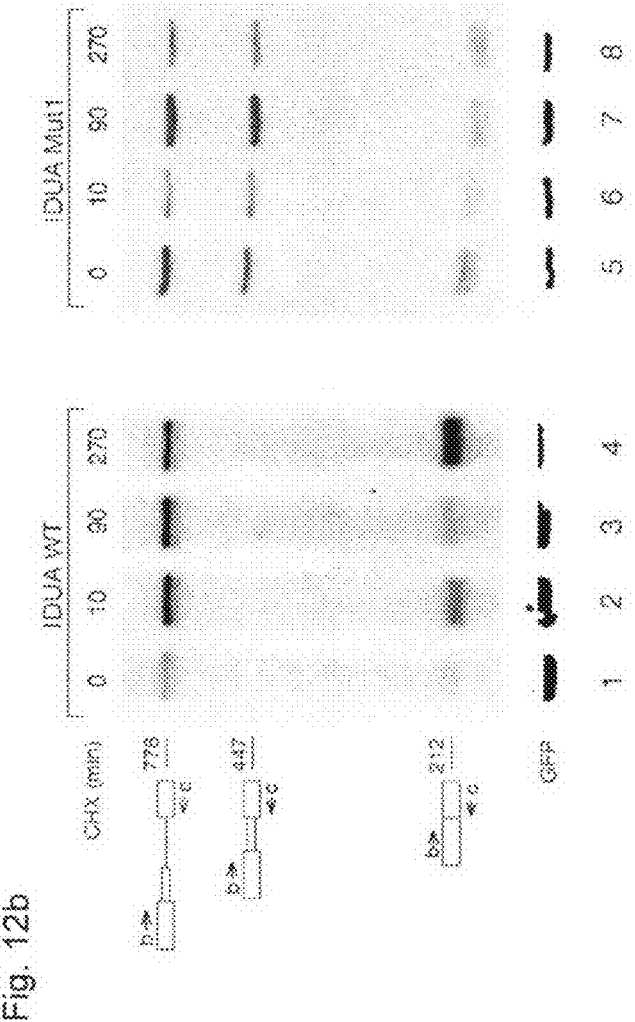

Latent splicing is not activated by CHX, an inhibitor of translation known to abrogate NMD—A possible interpretation of our results is that latent splicing normally occurs in pre-mRNAs derived from constructs harboring in-frame stop codons, but the presence of the stop codon sends the spliced transcript, which now harbors a pre-mature translation termination (PTC) codon, to the NMD pathway, where it is rapidly and efficiently degraded. To rule out this possibility, it was previously shown that the protein synthesis inhibitor cycloheximide (CHX), which had already been shown to efficiently reverse the down regulatory effects of PTCs in exons of the T cell receptor-b, the β-globin mRNAs [Carter et al., (1995) J. Biol. Chem. 270:28995-29003], and in the HEXA mRNA [Rajavel and Neufeld (2001) Mol. Cell Biol. 21:5512-5519], did not activate latent splicing in CAD constructs harboring in-frame stop codons between the normal and the latent sites [Li et al., (2002) supra]. Interestingly transcripts derived from HTH and IDUA mini genes behave similarly. Thus, treatment with CHX for up to 270 min of cells transfected with HTH Mut 1, which harbors an in-frame stop codon between the two alternative 5' splice sites, did not reveal latent splicing that includes exon 1a (FIG. 12a, lanes 6-10). As a control, the same treatment of cells transfected with wild type HTH, were shown to have virtually no effect on the levels of the exon 1a included-, and exon 1a excluded-splice variants that are normally expressed in wild type HTH (FIG. 12a, lanes 1-5). Similarly, FIG. 12b (lanes 1-4) shows that treatment with CHX did not reveal latent splicing in a wild type IDUA construct that harbors an in-frame stop codon downstream of a latent 5' splice site (FIG. 10). The control shows that when this stop codon was eliminated in IDUA Mut 1 (TGA to TGG mutation), latent splicing was activated but the level of the latent RNA was not affected by the drug (FIG. 12b, lanes 5-8). A β-globin RNA from cells transfected with pmCMV-GI-39Ter, which harbors a PTC within a bonafide exon [Zhang et al., (1998) RNA 4:801-815] was used as a control. The low level of nonsense β-globin RNA transcribed from this construct increased upon treatment with CHX, indicating that NMD was abrogated [Li et al., (2002) supra and data not shown].

Figure 13A:
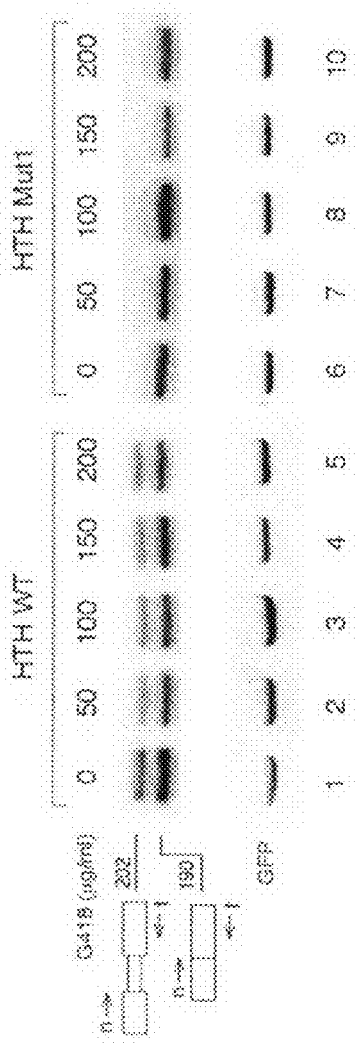
FIGS. 13a-b are photomicrographs showing that the presence of G418 does not effect latent splicing of HTH wild type or Mut 1 (FIG. 13a) and IDUA wild type or Mut 1 constructs (FIG. 13b) as indicated. Cells were treated for 18 hours with the Indicated concentrations of G418. RT-PCR was performed with primers n+f (FIG. 13a) or b+c (FIG. 13b).
Figure 13B:
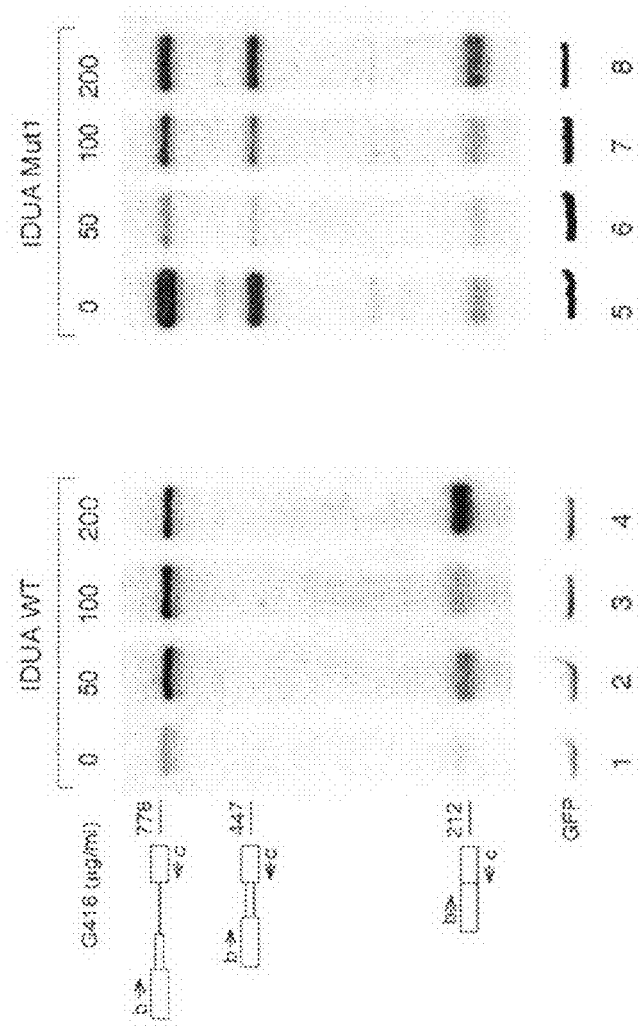

Latent splicing is not activated by G-418, a drug that enables translation read-through—To further show that the null phenotype of latent splicing is not due to NMD, the aminoglycoside antibiotic G-418 was used. This drug is known to abrogate NMD [Bedwell et al. (1997) Nat. Med. 3:1280-1284; Howard et al. (1996) Nat. Med. 2:467-469] by allowing translation read-through of PTC-containing RNAs. Thus, cells transfected with HTH or IDUA mini-genes were treated with different concentrations of G-418 for 18 hr. Here again, latent splicing was not detected in cells transfected with HTH Mut 1 (FIG. 13a, lanes 6-10), nor in cells transfected with IDUA WT (FIG. 13b, lanes 1-4) even at a G-418 concentration of 200 mg/ml, as expected for SOS in pre-mRNAs that harbor intronic in-frame stop codons. The negative controls show that the level of exon 1a inclusion in HTH WT (FIG. 13a, lanes 1-5) and the level of latent splicing in IDUA Mut 1 (FIG. 13b, lanes 5-8) were not significantly affected by the G-418 treatment.

Latent splicing is not affected by suppressor tRNA—Suppressor tRNAs enable translation read-through of nonsense mRNAs and were previously shown to be an effective means to abrogate NMD [Li et al. (1997) J. Exp. Med. 185:985-992]. To test whether suppressor tRNAs can reveal latent splicing, each of three different constructs of CAD mutants derived from CAD2 (FIG. 10, CAD), each having a different stop codon (S86) between the normal and the latent 5' splice sites (CAD Mut 2—TGA; CAD Mut 10—TAG; CAD Mut 11—TAA), were co-transfected with the cognate suppressor tRNA. As can be seen in FIG. 14a, no latent splicing was observed in RNAs arising from these transfections (lanes 1-9), while in transfection experiments using CAD Mut 12, in which the TGA stop codon at S86 was mutated to TGG (lanes 10-12), the expected latent splicing was observed but, was not affected by co-transfection with suppressor tRNA. Co-transfection experiments with the cognate suppressor tRNAs were also performed with HTH and IDUA constructs (FIGS. 14b and 14c, respectively). Here again, the null phenotype of latent splicing was maintained in cells transfected with either HTH Mut 1 (FIG. 14b, lanes 1-3) or IDUA WT (FIG. 14c, lanes 1-2) and the respective cognate suppressor tRNA, as expected for SOS in pre-mRNAs that harbor intronic in-frame stop codons upstream of a latent 5' splice site. As a control β-globin constructs was co-transfected with similar levels of the cognate suppressor tRNA. Transfection with wild type β-globin, with or without suppressor tRNA, gave rise to similar levels of β-globin RNA (FIG. 14d, lanes 1, 2). Transfection with β-globin 39Ter alone gave rise to a low level of the nonsense β-globin RNA (FIG. 14d, lane 3), which was up regulated to almost the wild type level by the suppressor tRNA due to abrogation of NMD (FIG. 14d, lane 4).

Latent splicing is not affected by a dominant negative mutant of hupf1—Human Upf1 is one of a number of proteins directly involved in the NMD pathway [Lykke-Andersen et al., (2000) Cell 103:1121-1131; Lykke-Andersen et al., (2001) Science 293:1836-1839; Mendell et al., (2000) Mol. Cell Biol. 20:8944-8957; Sun et al., (1998) Proc. Natl. Acad. Sci. USA 95:10009-10014]. A dominant negative mutant of hUpf1, in which an arginine at residue 844 was mutated to cysteine (R844C), was shown to abrogate NMD [Lykke-Andersen et al., (2000) supra; Sun et al., (1998) supra]. Therefore is was possible to test directly whether the absence of latent splicing could be attributable to NMD in co-transfection experiments with wild type and mutant hUpf1 constructs. For the CAD system a wild type construct CAD 1, which harbors four in-frame stop codons upstream of the latent 5' splice site (FIG. 10, CAD) was used along with two mutant constructs: (i) CAD Mut 25 was derived from CAD 1 by a T insertion at position 25, which frame-shifted the four in-frame stop codons and introduced a new one at position 45; and (ii) CAD Mut 9, which has no stop codons upstream of the latent 5' splice site (Li et al., 1997). FIG. 15a shows that the null phenotype of latent splicing in CAD Mut 25 and CAD1 (lanes 1 and 4, respectively) was not affected by co-transfection with either wild type hUpf1 (lanes 2 and 5, respectively) or by the dominant negative mutant of hUpf1 (lanes 3 and 6, respectively). Whereas the latent splicing observed in a control of CAD Mut 9 (lane 7) was not significantly affected in the presence of either hUpf1 constructs (lanes 8 and 9). HTH and IDUA were also tested to see if hUpf1 has an effect on them. HTH wild type (no in-frame stop codons) and Mut 1 (one in-frame stop codon) constructs were each co-transfected with either wild type or mutant hUpf1. As expected, neither hUpf1 constructs had any effect on the splicing of HTH wild type (FIG. 15b lanes 2 and 3). The dominant negative mutant of hUpf1 also had no effect on latent splicing, since it did not activate latent splicing in HTH Mut 1 (FIG. 15b, lane 6). The co-transfection of either IDUA wild type (one in-frame stop codon) and Mut 1 (no in-frame stop codons), with both hUpf1 constructs had no effect on the splicing pattern of both constructs (FIG. 15c), further showing that the dominant negative mutant of hUpf1 does not disrupt the SOS mechanism. As a positive control β-globin constructs were co-transfected with similar levels of the hUpf1 constructs. Transfection with β-globin 39Ter alone gave rise to a low level of the nonsense β-globin RNA (FIG. 15d, lane 4) relative to that of wild type β-globin RNA (FIG. 15d, lane 1). This level remained unchanged in co-transfection with wild type hUpf1 (FIG. 15d, lane 5), but was up regulated by the mutant hUpf1 (FIG. 15d, lane 6).

TABLE 6

Database of genes having putative latent splice sites
Each row includes the following information from left to right
<GENBANK Accession No.><Number of intron (IVS) which includes the latent site/s><The coordinate of the latent site/s in the intron (in nt, counted from the 5 end of the intron)><The position of the first stop codon (in nt, counted from the 5' end of the intron>.

| Accession No. | IVS No. | Latent Pos. | First Stop codon |
|---|---|---|---|
| HSCOMT2 | 2 | 168 | |
| HSCOMT2 | 2 | 228 | 106 |
| HSCOMT2 | 3 | 168 | 91 |
| HUMCYC1A | 1 | 464 | |
| HUMCYC1A | 1 | 528 | |
| HUMCYC1A | 1 | 554 | 313 |
| HUMCYC1A | 2 | 48 | 74 |
| HUMCYC1A | 6 | 21 | no-stop |
| HSU37106 | 1 | 13 | |
| HSU37106 | 1 | 24 | |
| HSU37106 | 1 | 116 | |
| HSU37106 | 1 | 162 | 187 |
| HSU37106 | 2 | 105 | 24 |
| HSGTRH | 1 | 116 | |
| HSGTRH | 1 | 296 | |
| HSGTRH | 1 | 603 | |
| HSGTRH | 1 | 608 | |
| HSGTRH | 1 | 935 | 31 |
| HSGTRH | 2 | 45 | |
| HSGTRH | 2 | 1582 | |
| HSGTRH | 2 | 1731 | |
| HSGTRH | 2 | 2109 | 7 |
| HUMGALK1A | 1 | 663 | |
| HUMGALK1A | 1 | 729 | 25 |
| HUMGALK1A | 2 | 315 | 33 |
| HUMGALK1A | 5 | 511 | |
| HUMGALK1A | 5 | 766 | |
| HUMGALK1A | 5 | 903 | |
| HUMGALK1A | 5 | 1199 | |
| HUMGALK1A | 5 | 1584 | |
| HUMGALK1A | 5 | 2361 | |
| HUMGALK1A | 5 | 2450 | |
| HUMGALK1A | 5 | 2458 | |
| HUMGALK1A | 5 | 2576 | |
| HUMGALK1A | 5 | 2669 | |
| HUMGALK1A | 5 | 2874 | |

TABLE 6-continued

Database of genes having putative latent splice sites
Each row includes the following information from left to right
<GENBANK Accession No.><Number of intron (IVS) which includes the latent site/s><The coordinate of the latent site/s in the intron (in nt, counted from the 5 end of the intron)><The position of the first stop codon (in nt, counted from the 5' end of the intron>.

| Accession No. | IVS No. | Latent Pos. | First Stop codon |
|---|---|---|---|
| HUMGALK1A | 5 | 2878 | |
| HUMGALK1A | 5 | 3538 | 168 |
| HSU01102 | 1 | 148 | |
| HSU01102 | 1 | 1002 | |
| HSU01102 | 1 | 1042 | |
| HSU01102 | 1 | 1274 | |
| HSU01102 | 1 | 1541 | |
| HSU01102 | 1 | 1899 | |
| HSU01102 | 1 | 2077 | |
| HSU01102 | 1 | 2430 | |
| HSU01102 | 1 | 2604 | 192 |
| HSU01102 | 2 | 714 | 163 |
| HSC1INHIB | 1 | 486 | |
| HSC1INHIB | 1 | 585 | |
| HSC1INHIB | 1 | 589 | |
| HSC1INHIB | 1 | 595 | |
| HSC1INHIB | 1 | 605 | |
| HSC1INHIB | 1 | 1189 | |
| HSC1INHIB | 1 | 1202 | 82 |
| HSC1INHIB | 2 | 26 | |
| HSC1INHIB | 2 | 274 | |
| HSC1INHIB | 2 | 359 | |
| HSC1INHIB | 2 | 615 | |
| HSC1INHIB | 2 | 806 | |
| HSC1INHIB | 2 | 1077 | |
| HSC1INHIB | 2 | 1122 | |
| HSC1INHIB | 2 | 1233 | |
| HSC1INHIB | 2 | 1389 | |
| HSC1INHIB | 2 | 1420 | 213 |
| HSC1INHIB | 3 | 131 | |
| HSC1INHIB | 3 | 156 | |
| HSC1INHIB | 3 | 359 | |
| HSC1INHIB | 3 | 371 | |
| HSC1INHIB | 3 | 667 | |
| HSC1INHIB | 3 | 687 | |
| HSC1INHIB | 3 | 833 | |
| HSC1INHIB | 3 | 851 | |
| HSC1INHIB | 3 | 1104 | |
| HSC1INHIB | 3 | 1160 | |
| HSC1INHIB | 3 | 1455 | |
| HSC1INHIB | 3 | 1750 | |
| HSC1INHIB | 3 | 1768 | |
| HSC1INHIB | 3 | 1840 | |
| HSC1INHIB | 3 | 2118 | |
| HSC1INHIB | 3 | 2155 | |
| HSC1INHIB | 3 | 2159 | |
| HSC1INHIB | 3 | 2601 | |
| HSC1INHIB | 3 | 2699 | |
| HSC1INHIB | 3 | 2969 | |
| HSC1INHIB | 3 | 2999 | |
| HSC1INHIB | 3 | 3228 | |
| HSC1INHIB | 3 | 3337 | |
| HSC1INHIB | 3 | 3735 | 42 |
| HSC1INHIB | 5 | 251 | |
| HSC1INHIB | 5 | 339 | |
| HSC1INHIB | 5 | 413 | |
| HSC1INHIB | 5 | 1416 | |
| HSC1INHIB | 5 | 1717 | |
| HSC1INHIB | 5 | 1840 | |
| HSC1INHIB | 5 | 1845 | |
| HSC1INHIB | 5 | 1858 | |
| HSC1INHIB | 5 | 2106 | |
| HSC1INHIB | 5 | 2440 | |
| HSC1INHIB | 5 | 2502 | |
| HSC1INHIB | 5 | 2802 | |
| HSC1INHIB | 5 | 2816 | |
| HSC1INHIB | 5 | 3047 | |
| HSC1INHIB | 5 | 3494 | |
| HSC1INHIB | 5 | 3747 | |
| HSC1INHIB | 5 | 3776 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSC1INHIB | 5 | 3809 | |
| HSC1INHIB | 5 | 4570 | |
| HSC1INHIB | 5 | 4659 | |
| HSC1INHIB | 5 | 4710 | 10 |
| HSC1INHIB | 6 | 135 | |
| HSC1INHIB | 6 | 190 | |
| HSC1INHIB | 6 | 323 | |
| HSC1INHIB | 6 | 332 | |
| HSC1INHIB | 6 | 907 | |
| HSC1INHIB | 6 | 1086 | |
| HSC1INHIB | 6 | 1267 | |
| HSC1INHIB | 6 | 1422 | |
| HSC1INHIB | 6 | 1693 | 69 |
| HSCST4 | 1 | 160 | |
| HSCST4 | 1 | 263 | |
| HSCST4 | 1 | 601 | |
| HSCST4 | 1 | 852 | |
| HSCST4 | 1 | 1128 | |
| HSCST4 | 1 | 1219 | |
| HSCST4 | 1 | 1223 | |
| HSCST4 | 1 | 1687 | 145 |
| HSCST4 | 2 | 12 | |
| HSCST4 | 2 | 53 | |
| HSCST4 | 2 | 67 | |
| HSCST4 | 2 | 183 | |
| HSCST4 | 2 | 361 | |
| HSCST4 | 2 | 385 | |
| HSCST4 | 2 | 411 | |
| HSCST4 | 2 | 423 | |
| HSCST4 | 2 | 445 | |
| HSCST4 | 2 | 1029 | |
| HSCST4 | 2 | 1104 | 10 |
| HUMA1ATP | 1 | 549 | |
| HUMA1ATP | 1 | 567 | |
| HUMA1ATP | 1 | 696 | |
| HUMA1ATP | 1 | 1284 | |
| HUMA1ATP | 1 | 1332 | 21 |
| HUMA1ATP | 2 | 210 | |
| HUMA1ATP | 2 | 218 | |
| HUMA1ATP | 2 | 531 | |
| HUMA1ATP | 2 | 569 | |
| HUMA1ATP | 2 | 966 | |
| HUMA1ATP | 2 | 1149 | |
| HUMA1ATP | 2 | 1192 | 2 |
| HUMA1ATP | 3 | 483 | |
| HUMA1ATP | 3 | 760 | 13 |
| HSINT2 | 1 | 1635 | |
| HSINT2 | 1 | 2040 | |
| HSINT2 | 1 | 2125 | |
| HSINT2 | 1 | 2171 | 384 |
| HSINT2 | 2 | 17 | |
| HSINT2 | 2 | 240 | |
| HSINT2 | 2 | 309 | |
| HSINT2 | 2 | 4050 | |
| HSINT2 | 2 | 4981 | |
| HSINT2 | 2 | 5118 | |
| HSINT2 | 2 | 5423 | |
| HSINT2 | 2 | 5506 | 31 |
| HUMRBPA | 2 | 4 | |
| HUMRBPA | 2 | 451 | |
| HUMRBPA | 2 | 698 | |
| HUMRBPA | 2 | 982 | 34 |
| HUMRBPA | 3 | 105 | |
| HUMRBPA | 3 | 184 | |
| HUMRBPA | 3 | 352 | |
| HUMRBPA | 3 | 719 | |
| HUMRBPA | 3 | 919 | |
| HUMRBPA | 3 | 1074 | |
| HUMRBPA | 3 | 1102 | |
| HUMRBPA | 3 | 1367 | |
| HUMRBPA | 3 | 1388 | |
| HUMRBPA | 3 | 1665 | |
| HUMRBPA | 3 | 1704 | 156 |
| HUMRBPA | 4 | 98 | |
| HUMRBPA | 4 | 116 | |
| HUMRBPA | 4 | 1320 | |
| HUMRBPA | 4 | 1598 | |
| HUMRBPA | 4 | 1660 | |
| HUMRBPA | 4 | 1715 | |
| HUMRBPA | 4 | 1798 | |
| HUMRBPA | 4 | 1984 | |
| HUMRBPA | 4 | 2074 | |
| HUMRBPA | 4 | 2553 | |
| HUMRBPA | 4 | 2596 | |
| HUMRBPA | 4 | 2691 | 217 |
| HUMRBPA | 5 | 611 | |
| HUMRBPA | 5 | 888 | 124 |
| HUMHSKPQZ7 | 1 | 417 | 2 |
| HUMHSKPQZ7 | 3 | 151 | 90 |
| HUMHSKPQZ7 | 4 | 128 | |
| HUMHSKPQZ7 | 4 | 182 | |
| HUMHSKPQZ7 | 4 | 210 | |
| HUMHSKPQZ7 | 4 | 281 | |
| HUMHSKPQZ7 | 4 | 480 | 2 |
| HSLH01 | 1 | 129 | |
| HSLH01 | 1 | 223 | 76 |
| HSBGPG | 2 | 5 | |
| HUMGAD45A | 1 | 371 | 2 |
| HUMGAD45A | 3 | 84 | |
| HUMGAD45A | 3 | 88 | |
| HUMGAD45A | 3 | 234 | |
| HUMGAD45A | 3 | 521 | |
| HUMGAD45A | 3 | 525 | |
| HUMGAD45A | 3 | 548 | |
| HUMGAD45A | 3 | 750 | |
| HUMGAD45A | 3 | 781 | |
| HUMGAD45A | 3 | 826 | |
| HUMGAD45A | 3 | 883 | 70 |
| HSU50871 | 1 | 129 | |
| HSU50871 | 1 | 263 | |
| HSU50871 | 1 | 319 | |
| HSU50871 | 1 | 379 | |
| HSU50871 | 1 | 1174 | 217 |
| HSU50871 | 2 | 31 | |
| HSU50871 | 2 | 260 | |
| HSU50871 | 2 | 304 | |
| HSU50871 | 2 | 441 | |
| HSU50871 | 2 | 717 | |
| HSU50871 | 2 | 762 | |
| HSU50871 | 2 | 852 | |
| HSU50871 | 2 | 1074 | |
| HSU50871 | 2 | 1267 | |
| HSU50871 | 2 | 1273 | |
| HSU50871 | 2 | 1300 | |
| HSU50871 | 2 | 1419 | |
| HSU50871 | 2 | 1557 | 2 |
| HSU50871 | 3 | 331 | |
| HSU50871 | 3 | 861 | |
| HSU50871 | 3 | 936 | |
| HSU50871 | 3 | 983 | |
| HSU50871 | 3 | 1240 | |
| HSU50871 | 3 | 1456 | |
| HSU50871 | 3 | 1706 | |
| HSU50871 | 3 | 1731 | |
| HSU50871 | 3 | 1938 | 70 |
| HSU50871 | 4 | 533 | |
| HSU50871 | 4 | 570 | 2 |
| HSU50871 | 5 | 3 | |
| HSU50871 | 5 | 327 | |
| HSU50871 | 5 | 586 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSU50871 | 5 | 590 | 87 |
| HSU50871 | 6 | 714 | 6 |
| HSU50871 | 7 | 118 | |
| HSU50871 | 7 | 219 | 126 |
| HSU50871 | 8 | 231 | |
| HSU50871 | 8 | 382 | |
| HSU50871 | 8 | 405 | |
| HSU50871 | 8 | 706 | |
| HSU50871 | 8 | 796 | |
| HSU50871 | 8 | 818 | |
| HSU50871 | 8 | 848 | |
| HSU50871 | 8 | 1538 | |
| HSU50871 | 8 | 1722 | |
| HSU50871 | 8 | 1944 | |
| HSU50871 | 8 | 2048 | 183 |
| HSU50871 | 9 | 173 | |
| HSU50871 | 9 | 189 | |
| HSU50871 | 9 | 225 | |
| HSU50871 | 9 | 317 | |
| HSU50871 | 9 | 1095 | |
| HSU50871 | 9 | 1100 | |
| HSU50871 | 9 | 1114 | 85 |
| D84344S3 | 1 | 49 | 19 |
| D84344S3 | 2 | 26 | 159 |
| D84344S3 | 3 | 43 | |
| D84344S3 | 3 | 106 | 56 |
| AF001689 | 1 | 396 | 12 |
| AF001689 | 2 | 48 | |
| AF001689 | 2 | 248 | |
| AF001689 | 2 | 405 | |
| AF001689 | 2 | 761 | |
| AF001689 | 2 | 835 | 77 |
| AF001689 | 3 | 385 | 83 |
| HSU31929 | 1 | 117 | |
| HSU31929 | 1 | 231 | |
| HSU31929 | 1 | 753 | |
| HSU31929 | 1 | 776 | |
| HSU31929 | 1 | 787 | |
| HSU31929 | 1 | 1499 | |
| HSU31929 | 1 | 1729 | |
| HSU31929 | 1 | 2395 | |
| HSU31929 | 1 | 2869 | |
| HSU31929 | 1 | 3020 | |
| HSU31929 | 1 | 3191 | |
| HSU31929 | 1 | 3345 | 120 |
| HSU65896 | 1 | 88 | 132 |
| HSU65896 | 2 | 379 | |
| HSU65896 | 2 | 445 | |
| HSU65896 | 2 | 487 | |
| HSU65896 | 2 | 819 | |
| HSU65896 | 2 | 843 | |
| HSU65896 | 2 | 916 | |
| HSU65896 | 2 | 1183 | |
| HSU65896 | 2 | 1320 | 273 |
| HSU65896 | 3 | 61 | |
| HSU65896 | 3 | 202 | 24 |
| HSU65896 | 4 | 115 | |
| HSU65896 | 4 | 130 | |
| HSU65896 | 4 | 231 | |
| HSU65896 | 4 | 355 | |
| HSU65896 | 4 | 468 | |
| HSU65896 | 4 | 494 | |
| HSU65896 | 4 | 1035 | |
| HSU65896 | 4 | 1077 | |
| HSU65896 | 4 | 1433 | |
| HSU65896 | 4 | 1515 | |
| HSU65896 | 4 | 1540 | |
| HSU65896 | 4 | 1756 | 59 |
| HSU65896 | 6 | 49 | |
| HSU65896 | 6 | 264 | |
| HSU65896 | 6 | 695 | 2 |
| HSU65896 | 7 | 261 | |
| HSU65896 | 7 | 292 | |
| HSU65896 | 7 | 310 | 12 |
| HSU65896 | 8 | 111 | 40 |
| HSU65896 | 9 | 144 | |
| HSU65896 | 9 | 202 | |
| HSU65896 | 9 | 342 | 82 |
| HSU65896 | 10 | 184 | |
| HSU65896 | 10 | 232 | |
| HSU65896 | 10 | 385 | |
| HSU65896 | 10 | 389 | 32 |
| HSU65896 | 11 | 11 | |
| HSU65896 | 11 | 123 | |
| HSU65896 | 11 | 149 | 96 |
| HSU65896 | 12 | 81 | |
| HSU65896 | 12 | 283 | 16 |
| HSU65896 | 14 | 48 | |
| HSU65896 | 14 | 113 | |
| HSU65896 | 14 | 348 | 2 |
| HSSHBG | 6 | 466 | |
| HSSHBG | 6 | 553 | |
| HSSHBG | 6 | 604 | |
| HSSHBG | 6 | 661 | 106 |
| HUMDEF5A | 1 | 350 | |
| HUMDEF5A | 1 | 467 | |
| HUMDEF5A | 1 | 624 | |
| HUMDEF5A | 1 | 708 | |
| HUMDEF5A | 1 | 727 | |
| HUMDEF5A | 1 | 751 | 93 |
| HSU60477 | 1 | 48 | |
| HSU60477 | 1 | 72 | |
| HSU60477 | 1 | 243 | |
| HSU60477 | 1 | 1442 | 75 |
| HSU60477 | 2 | 782 | |
| HSU60477 | 2 | 833 | |
| HSU60477 | 2 | 905 | |
| HSU60477 | 2 | 1284 | |
| HSU60477 | 2 | 1794 | |
| HSU60477 | 2 | 1899 | 39 |
| AF034632 | 1 | 294 | |
| AF034632 | 1 | 509 | |
| AF034632 | 1 | 661 | 219 |
| HUMHPRTB | 1 | 196 | |
| HUMHPRTB | 1 | 397 | |
| HUMHPRTB | 1 | 607 | |
| HUMHPRTB | 1 | 1098 | |
| HUMHPRTB | 1 | 1272 | |
| HUMHPRTB | 1 | 1732 | |
| HUMHPRTB | 1 | 1794 | |
| HUMHPRTB | 1 | 2078 | |
| HUMHPRTB | 1 | 2556 | |
| HUMHPRTB | 1 | 2645 | |
| HUMHPRTB | 1 | 2665 | |
| HUMHPRTB | 1 | 2703 | |
| HUMHPRTB | 1 | 2767 | |
| HUMHPRTB | 1 | 2810 | |
| HUMHPRTB | 1 | 3292 | |
| HUMHPRTB | 1 | 3745 | |
| HUMHPRTB | 1 | 4063 | |
| HUMHPRTB | 1 | 4104 | |
| HUMHPRTB | 1 | 4506 | |
| HUMHPRTB | 1 | 4842 | |
| HUMHPRTB | 1 | 5107 | |
| HUMHPRTB | 1 | 5246 | |
| HUMHPRTB | 1 | 5319 | |
| HUMHPRTB | 1 | 5395 | |
| HUMHPRTB | 1 | 5399 | |
| HUMHPRTB | 1 | 5722 | |
| HUMHPRTB | 1 | 5850 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMHPRTB | 1 | 5866 | |
| HUMHPRTB | 1 | 5978 | |
| HUMHPRTB | 1 | 6133 | |
| HUMHPRTB | 1 | 6198 | |
| HUMHPRTB | 1 | 6296 | |
| HUMHPRTB | 1 | 6365 | |
| HUMHPRTB | 1 | 6542 | |
| HUMHPRTB | 1 | 6591 | |
| HUMHPRTB | 1 | 6839 | |
| HUMHPRTB | 1 | 6948 | |
| HUMHPRTB | 1 | 7091 | |
| HUMHPRTB | 1 | 7226 | |
| HUMHPRTB | 1 | 7402 | |
| HUMHPRTB | 1 | 7845 | |
| HUMHPRTB | 1 | 7906 | |
| HUMHPRTB | 1 | 8145 | |
| HUMHPRTB | 1 | 8204 | |
| HUMHPRTB | 1 | 8884 | |
| HUMHPRTB | 1 | 9070 | |
| HUMHPRTB | 1 | 9074 | |
| HUMHPRTB | 1 | 9359 | |
| HUMHPRTB | 1 | 9381 | |
| HUMHPRTB | 1 | 9543 | |
| HUMHPRTB | 1 | 9636 | |
| HUMHPRTB | 1 | 10277 | |
| HUMHPRTB | 1 | 10289 | |
| HUMHPRTB | 1 | 10311 | |
| HUMHPRTB | 1 | 10371 | |
| HUMHPRTB | 1 | 10987 | |
| HUMHPRTB | 1 | 11221 | |
| HUMHPRTB | 1 | 11323 | |
| HUMHPRTB | 1 | 11403 | |
| HUMHPRTB | 1 | 11535 | |
| HUMHPRTB | 1 | 11731 | |
| HUMHPRTB | 1 | 11774 | |
| HUMHPRTB | 1 | 12470 | |
| HUMHPRTB | 1 | 12705 | |
| HUMHPRTB | 1 | 12995 | 400 |
| HUMHPRTB | 2 | 3 | |
| HUMHPRTB | 2 | 320 | |
| HUMHPRTB | 2 | 1097 | |
| HUMHPRTB | 2 | 1277 | |
| HUMHPRTB | 2 | 1517 | |
| HUMHPRTB | 2 | 1558 | |
| HUMHPRTB | 2 | 1625 | |
| HUMHPRTB | 2 | 1653 | 2 |
| HUMHPRTB | 3 | 201 | |
| HUMHPRTB | 3 | 356 | |
| HUMHPRTB | 3 | 474 | |
| HUMHPRTB | 3 | 676 | |
| HUMHPRTB | 3 | 923 | |
| HUMHPRTB | 3 | 1098 | |
| HUMHPRTB | 3 | 1572 | |
| HUMHPRTB | 3 | 1839 | |
| HUMHPRTB | 3 | 1932 | |
| HUMHPRTB | 3 | 2409 | |
| HUMHPRTB | 3 | 2452 | |
| HUMHPRTB | 3 | 2655 | |
| HUMHPRTB | 3 | 2753 | |
| HUMHPRTB | 3 | 2796 | |
| HUMHPRTB | 3 | 2992 | |
| HUMHPRTB | 3 | 3019 | |
| HUMHPRTB | 3 | 3553 | |
| HUMHPRTB | 3 | 3606 | |
| HUMHPRTB | 3 | 3830 | |
| HUMHPRTB | 3 | 3838 | |
| HUMHPRTB | 3 | 4384 | |
| HUMHPRTB | 3 | 4455 | |
| HUMHPRTB | 3 | 4633 | |
| HUMHPRTB | 3 | 4820 | |
| HUMHPRTB | 3 | 4840 | |
| HUMHPRTB | 3 | 5222 | |
| HUMHPRTB | 3 | 5671 | |
| HUMHPRTB | 3 | 5940 | |
| HUMHPRTB | 3 | 6029 | |
| HUMHPRTB | 3 | 6244 | |
| HUMHPRTB | 3 | 6376 | |
| HUMHPRTB | 3 | 6435 | |
| HUMHPRTB | 3 | 6669 | |
| HUMHPRTB | 3 | 7210 | |
| HUMHPRTB | 3 | 7594 | |
| HUMHPRTB | 3 | 8076 | |
| HUMHPRTB | 3 | 8367 | |
| HUMHPRTB | 3 | 8372 | |
| HUMHPRTB | 3 | 8529 | |
| HUMHPRTB | 3 | 8534 | |
| HUMHPRTB | 3 | 8864 | |
| HUMHPRTB | 3 | 8913 | |
| HUMHPRTB | 3 | 9009 | |
| HUMHPRTB | 3 | 9233 | |
| HUMHPRTB | 3 | 9354 | |
| HUMHPRTB | 3 | 10148 | |
| HUMHPRTB | 3 | 11059 | 19 |
| HUMHPRTB | 4 | 135 | |
| HUMHPRTB | 4 | 312 | |
| HUMHPRTB | 4 | 322 | |
| HUMHPRTB | 4 | 385 | |
| HUMHPRTB | 4 | 480 | |
| HUMHPRTB | 4 | 489 | |
| HUMHPRTB | 4 | 567 | |
| HUMHPRTB | 4 | 787 | |
| HUMHPRTB | 4 | 1037 | |
| HUMHPRTB | 4 | 1348 | |
| HUMHPRTB | 4 | 1564 | |
| HUMHPRTB | 4 | 1708 | |
| HUMHPRTB | 4 | 2106 | |
| HUMHPRTB | 4 | 2384 | |
| HUMHPRTB | 4 | 2639 | |
| HUMHPRTB | 4 | 2788 | |
| HUMHPRTB | 4 | 3051 | |
| HUMHPRTB | 4 | 3120 | |
| HUMHPRTB | 4 | 3133 | |
| HUMHPRTB | 4 | 3244 | |
| HUMHPRTB | 4 | 3258 | |
| HUMHPRTB | 4 | 3431 | |
| HUMHPRTB | 4 | 3589 | 85 |
| HUMHPRTB | 5 | 66 | |
| HUMHPRTB | 5 | 1299 | |
| HUMHPRTB | 5 | 1668 | |
| HUMHPRTB | 5 | 1714 | |
| HUMHPRTB | 5 | 1718 | |
| HUMHPRTB | 5 | 1730 | |
| HUMHPRTB | 5 | 3188 | 25 |
| HUMHPRTB | 6 | 51 | |
| HUMHPRTB | 6 | 308 | |
| HUMHPRTB | 6 | 565 | |
| HUMHPRTB | 6 | 789 | |
| HUMHPRTB | 6 | 818 | |
| HUMHPRTB | 6 | 898 | |
| HUMHPRTB | 6 | 962 | |
| HUMHPRTB | 6 | 1261 | |
| HUMHPRTB | 6 | 1373 | |
| HUMHPRTB | 6 | 1429 | |
| HUMHPRTB | 6 | 1517 | |
| HUMHPRTB | 6 | 1699 | |
| HUMHPRTB | 6 | 1914 | |
| HUMHPRTB | 6 | 2579 | |
| HUMHPRTB | 6 | 2965 | |
| HUMHPRTB | 6 | 3104 | |
| HUMHPRTB | 6 | 3200 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMHPRTB | 6 | 3228 | |
| HUMHPRTB | 6 | 3256 | |
| HUMHPRTB | 6 | 3335 | |
| HUMHPRTB | 6 | 3980 | |
| HUMHPRTB | 6 | 4120 | |
| HUMHPRTB | 6 | 4136 | |
| HUMHPRTB | 6 | 4382 | |
| HUMHPRTB | 6 | 4568 | |
| HUMHPRTB | 6 | 4665 | |
| HUMHPRTB | 6 | 4725 | 8 |
| HUMHPRTB | 7 | 3 | 6 |
| HUMHPRTB | 8 | 3 | |
| HUMHPRTB | 8 | 265 | |
| HUMHPRTB | 8 | 580 | |
| HUMHPRTB | 8 | 660 | |
| HUMHPRTB | 8 | 904 | |
| HUMHPRTB | 8 | 1317 | 94 |
| HSCKBG | 3 | 299 | 246 |
| HSCKBG | 4 | 189 | |
| HSCKBG | 4 | 257 | |
| HSCKBG | 4 | 262 | 197 |
| HSCKBG | 5 | 45 | |
| AF010238 | 1 | 500 | |
| AF010238 | 1 | 839 | |
| AF010238 | 1 | 900 | |
| AF010238 | 1 | 1682 | |
| AF010238 | 1 | 1700 | |
| AF010238 | 1 | 2633 | |
| AF010238 | 1 | 2723 | |
| AF010238 | 1 | 2766 | |
| AF010238 | 1 | 2783 | |
| AF010238 | 1 | 2798 | |
| AF010238 | 1 | 3031 | |
| AF010238 | 1 | 3105 | |
| AF010238 | 1 | 3109 | |
| AF010238 | 1 | 3664 | |
| AF010238 | 1 | 3930 | |
| AF010238 | 1 | 3947 | |
| AF010238 | 1 | 4274 | 105 |
| AF010238 | 2 | 39 | |
| AF010238 | 2 | 250 | |
| AF010238 | 2 | 719 | |
| AF010238 | 2 | 829 | |
| AF010238 | 2 | 871 | |
| AF010238 | 2 | 964 | |
| AF010238 | 2 | 1274 | |
| AF010238 | 2 | 1363 | |
| AF010238 | 2 | 1436 | |
| AF010238 | 2 | 1525 | |
| AF010238 | 2 | 1589 | |
| AF010238 | 2 | 1628 | |
| AF010238 | 2 | 2146 | |
| AF010238 | 2 | 2179 | |
| AF010238 | 2 | 2944 | |
| AF010238 | 2 | 3047 | |
| AF010238 | 2 | 3069 | 42 |
| HUMBHSD | 1 | 20 | |
| HUMBHSD | 1 | 48 | |
| HUMBHSD | 1 | 479 | |
| HUMBHSD | 1 | 497 | |
| HUMBHSD | 1 | 501 | |
| HUMBHSD | 1 | 651 | |
| HUMBHSD | 1 | 1564 | |
| HUMBHSD | 1 | 2455 | |
| HUMBHSD | 1 | 2548 | |
| HUMBHSD | 1 | 2644 | |
| HUMBHSD | 1 | 2802 | |
| HUMBHSD | 1 | 2862 | |
| HUMBHSD | 1 | 3178 | 6 |
| HUMBHSD | 2 | 30 | |
| HUMBHSD | 2 | 199 | |
| HUMBHSD | 2 | 222 | |
| HUMBHSD | 2 | 226 | |
| HUMBHSD | 2 | 234 | |
| HUMBHSD | 2 | 523 | |
| HUMBHSD | 2 | 1138 | |
| HUMBHSD | 2 | 1486 | |
| HUMBHSD | 2 | 1704 | |
| HUMBHSD | 2 | 1717 | |
| HUMBHSD | 2 | 1968 | 87 |
| HSREP10 | 1 | 406 | |
| HSREP10 | 1 | 750 | 409 |
| HSREP10 | 2 | 23 | |
| HSREP10 | 3 | 162 | |
| HSREP10 | 3 | 344 | |
| HSREP10 | 3 | 405 | |
| HSREP10 | 3 | 706 | |
| HSREP10 | 3 | 909 | |
| HSREP10 | 3 | 941 | |
| HSREP10 | 3 | 1031 | |
| HSREP10 | 3 | 1400 | |
| HSREP10 | 3 | 1549 | |
| HSREP10 | 3 | 1627 | |
| HSREP10 | 3 | 1657 | |
| HSREP10 | 3 | 1945 | |
| HSREP10 | 3 | 2387 | |
| HSREP10 | 3 | 2580 | |
| HSREP10 | 3 | 2584 | |
| HSREP10 | 3 | 2681 | |
| HSREP10 | 3 | 3547 | |
| HSREP10 | 3 | 3921 | |
| HSREP10 | 3 | 3963 | |
| HSREP10 | 3 | 4211 | |
| HSREP10 | 3 | 4611 | |
| HSREP10 | 3 | 4676 | |
| HSREP10 | 3 | 4798 | 51 |
| HUMIL5 | 1 | 40 | 43 |
| HUMIL5 | 2 | 40 | |
| HUMIL5 | 2 | 279 | |
| HUMIL5 | 2 | 450 | |
| HUMIL5 | 2 | 743 | |
| HUMIL5 | 2 | 858 | 7 |
| HUMBFXIII | 1 | 390 | |
| HUMBFXIII | 1 | 512 | |
| HUMBFXIII | 1 | 595 | |
| HUMBFXIII | 1 | 713 | |
| HUMBFXIII | 1 | 1163 | |
| HUMBFXIII | 1 | 1588 | |
| HUMBFXIII | 1 | 1711 | |
| HUMBFXIII | 1 | 1715 | |
| HUMBFXIII | 1 | 1780 | |
| HUMBFXIII | 1 | 2076 | |
| HUMBFXIII | 1 | 2566 | |
| HUMBFXIII | 1 | 2646 | |
| HUMBFXIII | 1 | 3340 | |
| HUMBFXIII | 1 | 3471 | |
| HUMBFXIII | 1 | 3501 | |
| HUMBFXIII | 1 | 3974 | 15 |
| HUMBFXIII | 2 | 274 | |
| HUMBFXIII | 2 | 495 | |
| HUMBFXIII | 2 | 574 | 72 |
| HUMBFXIII | 3 | 155 | |
| HUMBFXIII | 3 | 391 | |
| HUMBFXIII | 3 | 538 | |
| HUMBFXIII | 3 | 662 | 18 |
| HUMBFXIII | 4 | 282 | 150 |
| HUMBFXIII | 5 | 532 | |
| HUMBFXIII | 5 | 819 | |
| HUMBFXIII | 5 | 889 | |
| HUMBFXIII | 5 | 1234 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMBFXIII | 5 | 1371 | |
| HUMBFXIII | 5 | 1672 | |
| HUMBFXIII | 5 | 1841 | |
| HUMBFXIII | 5 | 2044 | |
| HUMBFXIII | 5 | 2083 | |
| HUMBFXIII | 5 | 2205 | |
| HUMBFXIII | 5 | 2245 | |
| HUMBFXIII | 5 | 2764 | 60 |
| HUMBFXIII | 6 | 56 | 3 |
| HUMBFXIII | 7 | 155 | |
| HUMBFXIII | 7 | 279 | |
| HUMBFXIII | 7 | 328 | |
| HUMBFXIII | 7 | 434 | |
| HUMBFXIII | 7 | 675 | |
| HUMBFXIII | 7 | 918 | 30 |
| HUMBFXIII | 8 | 42 | |
| HUMBFXIII | 8 | 593 | |
| HUMBFXIII | 8 | 704 | |
| HUMBFXIII | 8 | 774 | |
| HUMBFXIII | 8 | 911 | |
| HUMBFXIII | 8 | 1266 | |
| HUMBFXIII | 8 | 1629 | |
| HUMBFXIII | 8 | 2124 | |
| HUMBFXIII | 8 | 2488 | |
| HUMBFXIII | 8 | 2508 | 45 |
| HUMBFXIII | 9 | 169 | |
| HUMBFXIII | 9 | 1477 | |
| HUMBFXIII | 9 | 1626 | 36 |
| HUMBFXIII | 10 | 225 | |
| HUMBFXIII | 10 | 262 | |
| HUMBFXIII | 10 | 1149 | |
| HUMBFXIII | 10 | 1843 | |
| HUMBFXIII | 10 | 1903 | |
| HUMBFXIII | 10 | 2393 | |
| HUMBFXIII | 10 | 2450 | |
| HUMBFXIII | 10 | 2519 | |
| HUMBFXIII | 10 | 2594 | |
| HUMBFXIII | 10 | 2661 | |
| HUMBFXIII | 10 | 2856 | |
| HUMBFXIII | 10 | 2897 | |
| HUMBFXIII | 10 | 3800 | |
| HUMBFXIII | 10 | 3826 | |
| HUMBFXIII | 10 | 4198 | |
| HUMBFXIII | 10 | 4233 | |
| HUMBFXIII | 10 | 4250 | |
| HUMBFXIII | 10 | 4269 | |
| HUMBFXIII | 10 | 4560 | |
| HUMBFXIII | 10 | 4640 | |
| HUMBFXIII | 10 | 4675 | |
| HUMBFXIII | 10 | 5706 | |
| HUMBFXIII | 10 | 5830 | |
| HUMBFXIII | 10 | 6747 | |
| HUMBFXIII | 10 | 6949 | |
| HUMBFXIII | 10 | 6987 | |
| HUMBFXIII | 10 | 7804 | |
| HUMBFXIII | 10 | 7993 | |
| HUMBFXIII | 10 | 8129 | |
| HUMBFXIII | 10 | 8131 | |
| HUMBFXIII | 10 | 8527 | |
| HUMBFXIII | 10 | 9085 | |
| HUMBFXIII | 10 | 9089 | |
| HUMBFXIII | 10 | 9112 | |
| HUMBFXIII | 10 | 9439 | |
| HUMBFXIII | 10 | 9483 | 12 |
| HUMBFXIII | 11 | 711 | |
| HUMBFXIII | 11 | 885 | |
| HUMBFXIII | 11 | 975 | 2 |
| HUMSAP01 | 1 | 7 | |
| HUMSAP01 | 1 | 33 | |
| HUMSAP01 | 1 | 85 | 36 |
| HUMCRYABA | 1 | 103 | |
| HUMCRYABA | 1 | 618 | |
| HUMCRYABA | 1 | 690 | 118 |
| HUMCRYABA | 2 | 423 | |
| HUMCRYABA | 2 | 1300 | 49 |
| HUMROD1X | 1 | 241 | 2 |
| HUMPRF1A | 1 | 146 | |
| HUMPRF1A | 1 | 226 | |
| HUMPRF1A | 1 | 275 | |
| HUMPRF1A | 1 | 999 | 2 |
| HS2OXOC | 1 | 356 | 2 |
| HS2OXOC | 5 | 24 | 2 |
| HS2OXOC | 6 | 52 | |
| HS2OXOC | 6 | 68 | 88 |
| HUMAPOA4A | 2 | 279 | |
| HUMAPOA4A | 2 | 339 | |
| HUMAPOA4A | 2 | 531 | |
| HUMAPOA4A | 2 | 539 | 2 |
| HSODF2 | 1 | 121 | 2 |
| HSN10C3 | 1 | 252 | |
| HSN10C3 | 1 | 694 | |
| HSN10C3 | 1 | 945 | |
| HSN10C3 | 1 | 974 | |
| HSN10C3 | 1 | 1873 | |
| HSN10C3 | 1 | 2078 | |
| HSN10C3 | 1 | 2420 | |
| HSN10C3 | 1 | 2525 | |
| HSN10C3 | 1 | 2889 | |
| HSN10C3 | 1 | 3024 | |
| HSN10C3 | 1 | 3047 | |
| HSN10C3 | 1 | 3722 | |
| HSN10C3 | 1 | 3808 | |
| HSN10C3 | 1 | 4320 | |
| HSN10C3 | 1 | 4555 | |
| HSN10C3 | 1 | 4992 | |
| HSN10C3 | 1 | 5235 | |
| HSN10C3 | 1 | 5432 | |
| HSN10C3 | 1 | 6369 | |
| HSN10C3 | 1 | 6634 | |
| HSN10C3 | 1 | 7031 | |
| HSN10C3 | 1 | 7386 | |
| HSN10C3 | 1 | 7682 | 463 |
| HSN10C3 | 2 | 304 | |
| HSN10C3 | 2 | 766 | |
| HSN10C3 | 2 | 1562 | |
| HSN10C3 | 2 | 1655 | |
| HSN10C3 | 2 | 2212 | 363 |
| HSN10C3 | 3 | 259 | |
| HSN10C3 | 3 | 540 | 36 |
| HSN10C3 | 4 | 38 | |
| HSN10C3 | 4 | 100 | |
| HSN10C3 | 4 | 209 | |
| HSN10C3 | 4 | 264 | |
| HSN10C3 | 4 | 523 | 73 |
| HSN10C3 | 5 | 782 | |
| HSN10C3 | 5 | 925 | |
| HSN10C3 | 5 | 1140 | |
| HSN10C3 | 5 | 1792 | |
| HSN10C3 | 5 | 1819 | |
| HSN10C3 | 5 | 1987 | |
| HSN10C3 | 5 | 2249 | |
| HSN10C3 | 5 | 2256 | |
| HSN10C3 | 5 | 2444 | |
| HSN10C3 | 5 | 2582 | |
| HSN10C3 | 5 | 2744 | |
| HSN10C3 | 5 | 2758 | |
| HSN10C3 | 5 | 2879 | |
| HSN10C3 | 5 | 2893 | |
| HSN10C3 | 5 | 3153 | |
| HSN10C3 | 5 | 3205 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSN10C3 | 5 | 3274 | |
| HSN10C3 | 5 | 3278 | |
| HSN10C3 | 5 | 3433 | |
| HSN10C3 | 5 | 3747 | |
| HSN10C3 | 5 | 3872 | |
| HSN10C3 | 5 | 3991 | |
| HSN10C3 | 5 | 4078 | |
| HSN10C3 | 5 | 4171 | 69 |
| HSU46692 | 1 | 361 | |
| HSU46692 | 1 | 684 | 43 |
| HSU46692 | 2 | 203 | |
| HSU46692 | 2 | 282 | 82 |
| HSPROPG | 1 | 7 | |
| HSPROPG | 2 | 398 | |
| HSPROPG | 2 | 937 | |
| HSPROPG | 2 | 1022 | |
| HSPROPG | 2 | 1048 | |
| HSPROPG | 2 | 1117 | |
| HSPROPG | 2 | 1226 | 113 |
| HSPROPG | 3 | 129 | |
| HSPROPG | 3 | 134 | |
| HSPROPG | 3 | 143 | |
| HSPROPG | 3 | 267 | |
| HSPROPG | 3 | 273 | |
| HSPROPG | 3 | 323 | 102 |
| HSPROPG | 8 | 99 | |
| HSPROPG | 8 | 546 | |
| HSPROPG | 8 | 604 | |
| HSPROPG | 8 | 919 | |
| HSPROPG | 8 | 1092 | |
| HSPROPG | 8 | 1219 | 2 |
| HSHCC1GEN | 1 | 193 | |
| HSHCC1GEN | 1 | 616 | |
| HSHCC1GEN | 1 | 818 | |
| HSHCC1GEN | 1 | 822 | |
| HSHCC1GEN | 1 | 880 | |
| HSHCC1GEN | 1 | 1523 | |
| HSHCC1GEN | 1 | 1528 | |
| HSHCC1GEN | 1 | 1897 | 135 |
| HSHCC1GEN | 2 | 105 | |
| HSHCC1GEN | 2 | 354 | |
| HSHCC1GEN | 2 | 359 | 2 |
| HUMNKG5PRO | 1 | 376 | |
| HUMNKG5PRO | 1 | 452 | |
| HUMNKG5PRO | 1 | 525 | |
| HUMNKG5PRO | 1 | 652 | 63 |
| HUMNKG5PRO | 2 | 67 | |
| HUMNKG5PRO | 2 | 98 | |
| HUMNKG5PRO | 2 | 171 | |
| HUMNKG5PRO | 2 | 364 | 70 |
| HUMNKG5PRO | 3 | 133 | |
| HUMNKG5PRO | 3 | 199 | |
| HUMNKG5PRO | 3 | 624 | |
| HUMNKG5PRO | 3 | 1119 | 58 |
| HUMNKG5PRO | 4 | 11 | |
| HUMNKG5PRO | 4 | 182 | |
| HUMNKG5PRO | 4 | 603 | |
| HUMNKG5PRO | 4 | 768 | |
| HUMNKG5PRO | 4 | 787 | 33 |
| HSG17G | 1 | 434 | 2 |
| HSG17G | 2 | 90 | 84 |
| HSG17G | 3 | 18 | |
| HSG17G | 4 | 103 | 65 |
| HSG17G | 5 | 62 | 88 |
| HSG17G | 6 | 100 | 24 |
| HUMIGERA | 1 | 82 | |
| HUMIGERA | 1 | 258 | 6 |
| HUMIGERA | 2 | 375 | |
| HUMIGERA | 2 | 776 | 93 |
| HUMIGERA | 3 | 35 | |
| HUMIGERA | 3 | 71 | |
| HUMIGERA | 3 | 191 | |
| HUMIGERA | 3 | 203 | |
| HUMIGERA | 3 | 577 | |
| HUMIGERA | 3 | 964 | |
| HUMIGERA | 3 | 1147 | |
| HUMIGERA | 3 | 1337 | |
| HUMIGERA | 3 | 1421 | |
| HUMIGERA | 3 | 1686 | 54 |
| HUMIGERA | 4 | 453 | |
| HUMIGERA | 4 | 950 | |
| HUMIGERA | 4 | 1112 | |
| HUMIGERA | 4 | 1193 | 81 |
| HUMGAPDHG | 1 | 129 | |
| HUMGAPDHG | 1 | 282 | |
| HUMGAPDHG | 1 | 486 | |
| HUMGAPDHG | 1 | 607 | |
| HUMGAPDHG | 1 | 620 | |
| HUMGAPDHG | 1 | 661 | |
| HUMGAPDHG | 1 | 1330 | |
| HUMGAPDHG | 1 | 1526 | 2 |
| HUMGAPDHG | 2 | 13 | 16 |
| HUMGAPDHG | 6 | 130 | 4 |
| HSGLUCG2 | 1 | 951 | |
| HSGLUCG2 | 1 | 1340 | |
| HSGLUCG2 | 1 | 1517 | 5 |
| HSGLUCG2 | 2 | 406 | |
| HSGLUCG2 | 2 | 951 | |
| HSGLUCG2 | 2 | 1022 | |
| HSGLUCG2 | 2 | 1082 | |
| HSGLUCG2 | 2 | 1387 | |
| HSGLUCG2 | 2 | 1617 | 2 |
| HSGLUCG2 | 3 | 109 | |
| HSGLUCG2 | 3 | 542 | |
| HSGLUCG2 | 3 | 1226 | 2 |
| HSGLUCG2 | 4 | 332 | 2 |
| HSU20499 | 1 | 3 | 6 |
| HSU20499 | 2 | 20 | 75 |
| HSU20499 | 3 | 499 | |
| HSU20499 | 3 | 835 | |
| HSU20499 | 3 | 927 | |
| HSU20499 | 3 | 1056 | |
| HSU20499 | 3 | 1093 | |
| HSU20499 | 3 | 1107 | 133 |
| HSU20499 | 5 | 441 | 31 |
| HSHSC70 | 1 | 67 | |
| HSHSC70 | 1 | 203 | |
| HSHSC70 | 1 | 242 | 63 |
| HSHSC70 | 2 | 4 | |
| HSHSC70 | 2 | 149 | |
| HSHSC70 | 2 | 278 | 139 |
| HSHSC70 | 4 | 44 | 57 |
| HSHSC70 | 6 | 58 | |
| HSHSC70 | 6 | 106 | 75 |
| HSRSGCG | 2 | 384 | |
| HSRSGCG | 2 | 836 | |
| HSRSGCG | 2 | 892 | |
| HSRSGCG | 2 | 946 | |
| HSRSGCG | 2 | 1796 | |
| HSRSGCG | 2 | 1812 | |
| HSRSGCG | 2 | 1819 | |
| HSRSGCG | 2 | 1823 | |
| HSRSGCG | 2 | 1880 | |
| HSRSGCG | 2 | 1960 | 127 |
| HSRSGCG | 4 | 16 | |
| HSRSGCG | 4 | 27 | |
| HSRSGCG | 4 | 111 | |
| HSRSGCG | 4 | 260 | 2 |
| HSRSGCG | 5 | 203 | 43 |
| HSRSGCG | 6 | 227 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSRSGCG | 6 | 307 | |
| HSRSGCG | 6 | 466 | |
| HSRSGCG | 6 | 809 | |
| HSRSGCG | 6 | 953 | |
| HSRSGCG | 6 | 1237 | 148 |
| HSRSGCG | 7 | 79 | |
| HSRSGCG | 7 | 156 | |
| HSRSGCG | 7 | 289 | |
| HSRSGCG | 7 | 589 | |
| HSRSGCG | 7 | 634 | |
| HSRSGCG | 7 | 775 | 82 |
| HSRSGCG | 9 | 443 | 168 |
| HSRSGCG | 10 | 384 | 78 |
| HSRSGCG | 11 | 257 | 133 |
| HSRSGCG | 12 | 67 | 92 |
| HSRSGCG | 13 | 190 | 28 |
| HSRSGCG | 15 | 27 | |
| HSRSGCG | 15 | 47 | |
| HSMB1GENE | 1 | 207 | |
| HSMB1GENE | 1 | 225 | |
| HSMB1GENE | 1 | 422 | |
| HSMB1GENE | 1 | 949 | 34 |
| HSMB1GENE | 2 | 372 | |
| HSMB1GENE | 2 | 537 | |
| HSMB1GENE | 2 | 569 | |
| HSMB1GENE | 2 | 693 | |
| HSMB1GENE | 2 | 879 | |
| HSMB1GENE | 2 | 1007 | |
| HSMB1GENE | 2 | 1141 | |
| HSMB1GENE | 2 | 1362 | |
| HSMB1GENE | 2 | 1497 | |
| HSMB1GENE | 2 | 1994 | |
| HSMB1GENE | 2 | 2049 | |
| HSMB1GENE | 2 | 2140 | |
| HSMB1GENE | 2 | 2261 | |
| HSMB1GENE | 2 | 2341 | |
| HSMB1GENE | 2 | 3107 | |
| HSMB1GENE | 2 | 3165 | |
| HSMB1GENE | 2 | 3320 | 45 |
| HUMHSP27X | 1 | 650 | 195 |
| HUMHSP27X | 2 | 22 | |
| HUMHSP27X | 2 | 26 | |
| HUMHSP27X | 2 | 76 | 2 |
| AF042001 | 1 | 642 | 36 |
| AF042001 | 2 | 280 | |
| AF042001 | 2 | 419 | |
| AF042001 | 2 | 661 | |
| AF042001 | 2 | 748 | |
| AF042001 | 2 | 818 | 87 |
| HUMSTATH2 | 1 | 557 | |
| HUMSTATH2 | 1 | 681 | |
| HUMSTATH2 | 1 | 760 | |
| HUMSTATH2 | 1 | 786 | |
| HUMSTATH2 | 1 | 843 | 94 |
| HUMSTATH2 | 3 | 144 | |
| HUMSTATH2 | 3 | 349 | |
| HUMSTATH2 | 3 | 455 | |
| HUMSTATH2 | 3 | 727 | |
| HUMSTATH2 | 3 | 854 | |
| HUMSTATH2 | 3 | 951 | 13 |
| HSFGFR4G | 1 | 13 | |
| HSFGFR4G | 1 | 246 | |
| HSFGFR4G | 1 | 263 | |
| HSFGFR4G | 1 | 299 | |
| HSFGFR4G | 1 | 425 | |
| HSFGFR4G | 1 | 625 | 225 |
| HSFGFR4G | 4 | 178 | 94 |
| HSFGFR4G | 5 | 112 | |
| HSFGFR4G | 5 | 120 | |
| HSFGFR4G | 5 | 143 | |
| HSFGFR4G | 5 | 382 | 147 |
| HSFGFR4G | 7 | 75 | |
| HSFGFR4G | 7 | 198 | 282 |
| HSFGFR4G | 10 | 161 | |
| HSFGFR4G | 10 | 324 | |
| HSFGFR4G | 10 | 393 | |
| HSFGFR4G | 10 | 470 | |
| HSFGFR4G | 10 | 1018 | 48 |
| HSFGFR4G | 12 | 234 | |
| HSFGFR4G | 12 | 274 | 4 |
| HSFGFR4G | 14 | 160 | 2 |
| HSFGFR4G | 15 | 70 | 2 |
| HUMCD79B | 1 | 391 | 171 |
| HUMCD79B | 2 | 317 | |
| HUMCD79B | 2 | 344 | |
| HUMCD79B | 2 | 711 | 6 |
| HUMCD79B | 3 | 10 | 30 |
| HUMCD79B | 5 | 39 | |
| HUMHOX4A | 1 | 353 | |
| HUMHOX4A | 1 | 480 | |
| HUMHOX4A | 1 | 484 | |
| HUMHOX4A | 1 | 680 | |
| HUMHOX4A | 1 | 902 | |
| HUMHOX4A | 1 | 1566 | |
| HUMHOX4A | 1 | 1649 | |
| HUMHOX4A | 1 | 1662 | |
| HUMHOX4A | 1 | 1682 | |
| HUMHOX4A | 1 | 1686 | |
| HUMHOX4A | 1 | 1690 | |
| HUMHOX4A | 1 | 1753 | 135 |
| HSCPH70 | 1 | 54 | |
| HSCPH70 | 1 | 822 | |
| HSCPH70 | 1 | 994 | |
| HSCPH70 | 1 | 1206 | |
| HSCPH70 | 1 | 1321 | |
| HSCPH70 | 1 | 1470 | |
| HSCPH70 | 1 | 1945 | |
| HSCPH70 | 1 | 1967 | |
| HSCPH70 | 1 | 2032 | |
| HSCPH70 | 1 | 2101 | |
| HSCPH70 | 1 | 2165 | |
| HSCPH70 | 1 | 2169 | |
| HSCPH70 | 1 | 2324 | 64 |
| HSCPH70 | 2 | 78 | 15 |
| HSCPH70 | 4 | 449 | |
| HSCPH70 | 4 | 1263 | 2 |
| HSALADG | 1 | 103 | |
| HSALADG | 1 | 395 | |
| HSALADG | 1 | 965 | 2 |
| HSALADG | 3 | 72 | |
| HSALADG | 3 | 169 | |
| HSALADG | 3 | 208 | |
| HSALADG | 3 | 405 | 22 |
| HSALADG | 6 | 137 | |
| HSALADG | 6 | 151 | 109 |
| HSALADG | 9 | 9 | |
| HSALADG | 10 | 280 | |
| HSALADG | 10 | 553 | 45 |
| HUMIDS | 2 | 25 | |
| HUMIDS | 2 | 209 | |
| HUMIDS | 2 | 337 | |
| HUMIDS | 2 | 510 | 340 |
| HUMIDS | 3 | 360 | |
| HUMIDS | 3 | 438 | |
| HUMIDS | 3 | 848 | |
| HUMIDS | 3 | 1236 | |
| HUMIDS | 3 | 1291 | |
| HUMIDS | 3 | 1801 | |
| HUMIDS | 3 | 1895 | |
| HUMIDS | 3 | 1982 | 120 |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMIDS | 4 | 140 | |
| HUMIDS | 4 | 201 | |
| HUMIDS | 4 | 605 | |
| HUMIDS | 4 | 619 | |
| HUMIDS | 4 | 826 | |
| HUMIDS | 4 | 933 | |
| HUMIDS | 4 | 1848 | |
| HUMIDS | 4 | 2123 | 10 |
| HUMIDS | 5 | 79 | |
| HUMIDS | 5 | 179 | |
| HUMIDS | 5 | 277 | |
| HUMIDS | 5 | 407 | |
| HUMIDS | 5 | 634 | |
| HUMIDS | 5 | 1074 | |
| HUMIDS | 5 | 1087 | |
| HUMIDS | 5 | 1195 | |
| HUMIDS | 5 | 1304 | |
| HUMIDS | 5 | 1439 | 37 |
| HUMIDS | 6 | 53 | |
| HUMIDS | 6 | 117 | |
| HUMIDS | 6 | 159 | |
| HUMIDS | 6 | 246 | |
| HUMIDS | 6 | 272 | |
| HUMIDS | 6 | 322 | |
| HUMIDS | 6 | 886 | |
| HUMIDS | 6 | 1029 | |
| HUMIDS | 6 | 1288 | |
| HUMIDS | 6 | 1310 | |
| HUMIDS | 6 | 1334 | |
| HUMIDS | 6 | 1549 | |
| HUMIDS | 6 | 1553 | |
| HUMIDS | 6 | 2080 | |
| HUMIDS | 6 | 2454 | |
| HUMIDS | 6 | 2477 | |
| HUMIDS | 6 | 3239 | |
| HUMIDS | 6 | 3964 | |
| HUMIDS | 6 | 4121 | |
| HUMIDS | 6 | 4570 | |
| HUMIDS | 6 | 4660 | |
| HUMIDS | 6 | 4797 | |
| HUMIDS | 6 | 4807 | |
| HUMIDS | 6 | 4854 | |
| HUMIDS | 6 | 5328 | |
| HUMIDS | 6 | 5362 | |
| HUMIDS | 6 | 5629 | 13 |
| HUMIDS | 7 | 21 | |
| HUMIDS | 7 | 88 | |
| HUMIDS | 7 | 198 | |
| HUMIDS | 7 | 204 | |
| HUMIDS | 7 | 818 | |
| HUMIDS | 7 | 964 | |
| HUMIDS | 7 | 978 | |
| HUMIDS | 7 | 1361 | |
| HUMIDS | 7 | 2250 | |
| HUMIDS | 7 | 2455 | |
| HUMIDS | 7 | 2672 | |
| HUMIDS | 7 | 2809 | |
| HUMIDS | 7 | 2931 | |
| HUMIDS | 7 | 3067 | |
| HUMIDS | 7 | 3077 | |
| HUMIDS | 7 | 3096 | 24 |
| HUMIDS | 8 | 268 | |
| HUMIDS | 8 | 478 | |
| HUMIDS | 8 | 775 | |
| HUMIDS | 8 | 1230 | |
| HUMIDS | 8 | 1981 | |
| HUMIDS | 8 | 2042 | |
| HUMIDS | 8 | 2355 | |
| HUMIDS | 8 | 2371 | |
| HUMIDS | 8 | 2661 | |
| HUMIDS | 8 | 2760 | |
| HUMIDS | 8 | 2995 | |
| HUMIDS | 8 | 3040 | |
| HUMIDS | 8 | 3100 | |
| HUMIDS | 8 | 3255 | |
| HUMIDS | 8 | 3267 | |
| HUMIDS | 8 | 3540 | 78 |
| HSU82083 | 1 | 1173 | |
| HSU82083 | 1 | 1783 | |
| HSU82083 | 1 | 2190 | 106 |
| HSU82083 | 2 | 251 | |
| HSU82083 | 2 | 255 | |
| HSU82083 | 2 | 263 | 282 |
| HSU82083 | 3 | 566 | 200 |
| HSU82083 | 4 | 296 | |
| HSU82083 | 4 | 676 | |
| HSU82083 | 4 | 696 | |
| HSU82083 | 4 | 884 | |
| HSU82083 | 4 | 910 | |
| HSU82083 | 4 | 1101 | |
| HSU82083 | 4 | 1146 | 129 |
| HSU82083 | 5 | 18 | |
| HSU82083 | 5 | 45 | 21 |
| HSU82083 | 6 | 94 | |
| HSU82083 | 6 | 444 | |
| HSU82083 | 6 | 930 | |
| HSU82083 | 6 | 944 | |
| HSU82083 | 6 | 1016 | |
| HSU82083 | 6 | 1550 | 30 |
| HSU82083 | 8 | 118 | |
| HSU82083 | 8 | 216 | |
| HSU82083 | 8 | 703 | |
| HSU82083 | 8 | 822 | |
| HSU82083 | 8 | 1655 | |
| HSU82083 | 8 | 2271 | |
| HSU82083 | 8 | 2327 | |
| HSU82083 | 8 | 2338 | |
| HSU82083 | 8 | 2477 | 10 |
| HSU82083 | 9 | 403 | |
| HSU82083 | 9 | 445 | |
| HSU82083 | 9 | 806 | |
| HSU82083 | 9 | 973 | 322 |
| HUM17BHSDI | 1 | 9 | 12 |
| HUM17BHSDI | 4 | 208 | |
| HUM17BHSDI | 4 | 213 | 2 |
| HUMTDGF1A | 1 | 275 | |
| HUMTDGF1A | 1 | 407 | |
| HUMTDGF1A | 1 | 495 | |
| HUMTDGF1A | 1 | 845 | |
| HUMTDGF1A | 1 | 853 | |
| HUMTDGF1A | 1 | 906 | 20 |
| HUMTDGF1A | 3 | 133 | 165 |
| HUMTDGF1A | 5 | 713 | |
| HUMTDGF1A | 5 | 816 | |
| HUMTDGF1A | 5 | 838 | |
| HUMTDGF1A | 5 | 955 | |
| HUMTDGF1A | 5 | 957 | 99 |
| HSALDCG | 1 | 21 | |
| HSALDCG | 1 | 32 | 24 |
| HSALDCG | 4 | 19 | 22 |
| HSALDCG | 7 | 19 | |
| HSCTAS | 1 | 62 | |
| HSCTAS | 1 | 101 | |
| HSCTAS | 1 | 785 | |
| HSCTAS | 1 | 1129 | |
| HSCTAS | 1 | 1342 | |
| HSCTAS | 1 | 1626 | |
| HSCTAS | 1 | 1748 | 6 |
| HSCTAS | 2 | 42 | 2 |
| HSCTAS | 3 | 3 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSCTAS | 3 | 91 | |
| HSCTAS | 3 | 379 | |
| HSCTAS | 3 | 490 | |
| HSCTAS | 3 | 517 | |
| HSCTAS | 3 | 529 | |
| HSCTAS | 3 | 666 | |
| HSCTAS | 3 | 801 | |
| HSCTAS | 3 | 864 | 94 |
| HSCTAS | 4 | 12 | |
| HSCTAS | 4 | 20 | |
| HSCTAS | 4 | 387 | |
| HSCTAS | 4 | 811 | |
| HSCTAS | 4 | 1503 | |
| HSCTAS | 4 | 2122 | 2 |
| HSCTAS | 6 | 92 | |
| HSCTAS | 6 | 632 | |
| HSCTAS | 6 | 639 | |
| HSCTAS | 6 | 781 | |
| HSCTAS | 6 | 788 | |
| HSCTAS | 6 | 1806 | |
| HSCTAS | 6 | 1810 | 31 |
| HSCTAS | 7 | 242 | |
| HSCTAS | 7 | 342 | 156 |
| HSU27266 | 1 | 9 | 6 |
| HSU27266 | 2 | 85 | |
| HSU27266 | 2 | 185 | |
| HSU27266 | 2 | 189 | |
| HSU27266 | 2 | 193 | |
| HSU27266 | 2 | 249 | |
| HSU27266 | 2 | 275 | |
| HSU27266 | 2 | 563 | 201 |
| HSU27266 | 3 | 564 | |
| HSU27266 | 3 | 632 | |
| HSU27266 | 3 | 684 | |
| HSU27266 | 3 | 1089 | 177 |
| HSU27266 | 4 | 149 | |
| HSU27266 | 4 | 175 | |
| HSU27266 | 4 | 318 | 313 |
| HSU27266 | 6 | 353 | |
| HSU27266 | 6 | 551 | |
| HSU27266 | 6 | 564 | |
| HSU27266 | 6 | 576 | 124 |
| HSU27266 | 7 | 263 | |
| HSU27266 | 7 | 306 | 186 |
| HSU27266 | 8 | 42 | 145 |
| HSU27266 | 9 | 96 | 30 |
| HSU89387 | 1 | 261 | |
| HSU89387 | 1 | 390 | |
| HSU89387 | 1 | 419 | |
| HSU89387 | 1 | 1073 | |
| HSU89387 | 1 | 1208 | |
| HSU89387 | 1 | 1252 | |
| HSU89387 | 1 | 1482 | |
| HSU89387 | 1 | 1695 | |
| HSU89387 | 1 | 1983 | |
| HSU89387 | 1 | 2026 | |
| HSU89387 | 1 | 2412 | |
| HSU89387 | 1 | 2594 | |
| HSU89387 | 1 | 2768 | |
| HSU89387 | 1 | 2869 | |
| HSU89387 | 1 | 3186 | |
| HSU89387 | 1 | 3763 | |
| HSU89387 | 1 | 4124 | |
| HSU89387 | 1 | 4166 | |
| HSU89387 | 1 | 4199 | |
| HSU89387 | 1 | 4203 | |
| HSU89387 | 1 | 4219 | |
| HSU89387 | 1 | 4223 | |
| HSU89387 | 1 | 4663 | 90 |
| HSU89387 | 2 | 386 | |
| HSU89387 | 2 | 522 | |
| HSU89387 | 2 | 534 | |
| HSU89387 | 2 | 580 | |
| HSU89387 | 2 | 674 | |
| HSU89387 | 2 | 718 | |
| HSU89387 | 2 | 1144 | |
| HSU89387 | 2 | 1212 | |
| HSU89387 | 2 | 2056 | |
| HSU89387 | 2 | 2097 | 2 |
| HSU89387 | 3 | 58 | |
| HSU89387 | 3 | 535 | |
| HSU89387 | 3 | 641 | |
| HSU89387 | 3 | 1088 | |
| HSU89387 | 3 | 1304 | |
| HSU89387 | 3 | 1316 | |
| HSU89387 | 3 | 1457 | |
| HSU89387 | 3 | 1545 | |
| HSU89387 | 3 | 1700 | |
| HSU89387 | 3 | 1770 | |
| HSU89387 | 3 | 1842 | |
| HSU89387 | 3 | 2105 | |
| HSU89387 | 3 | 2214 | |
| HSU89387 | 3 | 2303 | 38 |
| HSAPOA2 | 1 | 191 | |
| HSAPOA2 | 1 | 207 | 51 |
| HSFBRGG | 4 | 72 | |
| HSFBRGG | 4 | 415 | |
| HSFBRGG | 4 | 539 | |
| HSFBRGG | 4 | 793 | |
| HSFBRGG | 4 | 935 | |
| HSFBRGG | 4 | 939 | |
| HSFBRGG | 4 | 1072 | |
| HSFBRGG | 4 | 1151 | 2 |
| HSFBRGG | 5 | 38 | |
| HSFBRGG | 5 | 59 | |
| HSFBRGG | 5 | 184 | 6 |
| HSFBRGG | 6 | 124 | |
| HSFBRGG | 6 | 357 | |
| HSFBRGG | 6 | 696 | |
| HSFBRGG | 6 | 843 | 82 |
| HSFBRGG | 7 | 164 | |
| HSFBRGG | 7 | 1126 | |
| HSFBRGG | 7 | 1231 | 35 |
| HSFBRGG | 8 | 397 | |
| HSFBRGG | 8 | 435 | |
| HSFBRGG | 8 | 1426 | |
| HSFBRGG | 8 | 1539 | |
| HSFBRGG | 8 | 1589 | 36 |
| HSFBRGG | 9 | 433 | 61 |
| HSPACAP | 1 | 1863 | 2 |
| HSPACAP | 2 | 234 | 2 |
| HSPACAP | 3 | 37 | |
| HSPACAP | 3 | 73 | |
| HSPACAP | 3 | 95 | |
| HSPACAP | 3 | 725 | |
| HSPACAP | 3 | 801 | 2 |
| HUMDS | 1 | 30 | |
| HUMDS | 1 | 431 | 289 |
| HUMDS | 2 | 54 | |
| HUMDS | 2 | 365 | |
| HUMDS | 2 | 453 | |
| HUMDS | 2 | 802 | |
| HUMDS | 2 | 1249 | |
| HUMDS | 2 | 1424 | |
| HUMDS | 2 | 1727 | |
| HUMDS | 2 | 1755 | |
| HUMDS | 2 | 2106 | |
| HUMDS | 2 | 2143 | |
| HUMDS | 2 | 2174 | |
| HUMDS | 2 | 2477 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMDS | 2 | 2672 | |
| HUMDS | 2 | 2872 | 57 |
| HUMDS | 3 | 111 | |
| HUMDS | 3 | 224 | |
| HUMDS | 3 | 306 | |
| HUMDS | 3 | 491 | |
| HUMDS | 3 | 1093 | |
| HUMDS | 3 | 1342 | |
| HUMDS | 3 | 1638 | |
| HUMDS | 3 | 1778 | |
| HUMDS | 3 | 2371 | |
| HUMDS | 3 | 2431 | |
| HUMDS | 3 | 2463 | |
| HUMDS | 3 | 2531 | |
| HUMDS | 3 | 2828 | |
| HUMDS | 3 | 2909 | |
| HUMDS | 3 | 2971 | |
| HUMDS | 3 | 3126 | |
| HUMDS | 3 | 3156 | |
| HUMDS | 3 | 3233 | |
| HUMDS | 3 | 3376 | |
| HUMDS | 3 | 3407 | |
| HUMDS | 3 | 3438 | 2 |
| HUMDS | 5 | 119 | |
| HUMDS | 5 | 257 | 9 |
| HUMDS | 6 | 405 | |
| HUMDS | 6 | 541 | |
| HUMDS | 6 | 558 | |
| HUMDS | 6 | 645 | |
| HUMDS | 6 | 856 | 49 |
| HUMDS | 7 | 1016 | |
| HUMDS | 7 | 1339 | |
| HUMDS | 7 | 1383 | 57 |
| HUMDS | 9 | 245 | |
| HUMDS | 9 | 320 | |
| HUMDS | 9 | 682 | 10 |
| HUMDS | 10 | 108 | |
| HUMDS | 10 | 674 | |
| HUMDS | 10 | 761 | |
| HUMDS | 10 | 901 | |
| HUMDS | 10 | 1108 | |
| HUMDS | 10 | 1201 | |
| HUMDS | 10 | 1257 | |
| HUMDS | 10 | 1802 | |
| HUMDS | 10 | 2126 | |
| HUMDS | 10 | 2779 | |
| HUMDS | 10 | 3843 | |
| HUMDS | 10 | 3933 | 2 |
| HUMDS | 11 | 38 | |
| HUMDS | 11 | 42 | |
| HUMDS | 11 | 558 | |
| HUMDS | 11 | 1257 | 171 |
| HUMDS | 12 | 16 | 88 |
| HUMDS | 13 | 173 | |
| HUMDS | 13 | 494 | |
| HUMDS | 13 | 640 | 7 |
| HUMDS | 14 | 354 | |
| HUMDS | 14 | 802 | 43 |
| HSU48795 | 2 | 24 | 46 |
| HSU48795 | 3 | 542 | 130 |
| HSU19816 | 1 | 3 | |
| HSU19816 | 1 | 45 | |
| HSU19816 | 1 | 425 | 6 |
| HSODCG | 1 | 130 | |
| HSODCG | 1 | 233 | |
| HSODCG | 1 | 240 | |
| HSODCG | 1 | 252 | 10 |
| HSODCG | 6 | 404 | |
| HSODCG | 6 | 1002 | 7 |
| HSODCG | 9 | 3 | |
| HSODCG | 9 | 161 | |
| HSODCG | 9 | 221 | |
| HSODCG | 9 | 266 | |
| HSODCG | 9 | 437 | |
| HSODCG | 9 | 475 | |
| HSODCG | 9 | 573 | |
| HSODCG | 9 | 599 | 2 |
| HSU29895 | 2 | 270 | |
| HSU29895 | 2 | 387 | 34 |
| HSU29895 | 4 | 128 | 109 |
| HSU29895 | 5 | 121 | |
| HSU29895 | 6 | 1020 | |
| HSU29895 | 6 | 1112 | 121 |
| HSU29895 | 7 | 529 | |
| HSU29895 | 7 | 571 | |
| HSU29895 | 7 | 848 | |
| HSU29895 | 7 | 1416 | |
| HSU29895 | 7 | 1599 | |
| HSU29895 | 7 | 1841 | |
| HSU29895 | 7 | 1955 | |
| HSU29895 | 7 | 2084 | |
| HSU29895 | 7 | 2476 | |
| HSU29895 | 7 | 2561 | |
| HSU29895 | 7 | 2761 | |
| HSU29895 | 7 | 3087 | |
| HSU29895 | 7 | 3105 | |
| HSU29895 | 7 | 3182 | |
| HSU29895 | 7 | 3410 | |
| HSU29895 | 7 | 3492 | |
| HSU29895 | 7 | 3658 | |
| HSU29895 | 7 | 3708 | |
| HSU29895 | 7 | 4282 | |
| HSU29895 | 7 | 4286 | |
| HSU29895 | 7 | 4422 | 46 |
| HSU29895 | 8 | 21 | |
| HSU29895 | 8 | 84 | |
| HSU29895 | 8 | 352 | 2 |
| HSU29895 | 9 | 143 | |
| HSU29895 | 9 | 161 | |
| HSU29895 | 9 | 310 | |
| HSU29895 | 9 | 455 | |
| HSU29895 | 9 | 645 | |
| HSU29895 | 9 | 1089 | |
| HSU29895 | 9 | 1230 | |
| HSU29895 | 9 | 1480 | |
| HSU29895 | 9 | 1525 | 2 |
| HSU29895 | 10 | 69 | 58 |
| HSU29895 | 11 | 413 | |
| HSU29895 | 11 | 920 | |
| HSU29895 | 11 | 1123 | |
| HSU29895 | 11 | 1524 | |
| HSU29895 | 11 | 1587 | |
| HSU29895 | 11 | 1744 | |
| HSU29895 | 11 | 1902 | |
| HSU29895 | 11 | 2567 | |
| HSU29895 | 11 | 2571 | |
| HSU29895 | 11 | 2585 | |
| HSU29895 | 11 | 2829 | 247 |
| HSU29895 | 12 | 268 | |
| HSU29895 | 12 | 364 | |
| HSU29895 | 12 | 445 | |
| HSU29895 | 12 | 454 | |
| HSU29895 | 12 | 730 | |
| HSU29895 | 12 | 985 | |
| HSU29895 | 12 | 1034 | |
| HSU29895 | 12 | 1048 | |
| HSU29895 | 12 | 1194 | |
| HSU29895 | 12 | 1222 | |
| HSU29895 | 12 | 1328 | |
| HSU29895 | 12 | 1470 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSU29895 | 12 | 1776 | |
| HSU29895 | 12 | 1792 | |
| HSU29895 | 12 | 2092 | |
| HSU29895 | 12 | 2309 | |
| HSU29895 | 12 | 2726 | |
| HSU29895 | 12 | 2863 | |
| HSU29895 | 12 | 2890 | |
| HSU29895 | 12 | 3169 | |
| HSU29895 | 12 | 3529 | |
| HSU29895 | 12 | 3553 | 157 |
| HUMCD19A | 2 | 124 | 123 |
| HUMCD19A | 3 | 68 | 63 |
| HUMCD19A | 4 | 242 | |
| HUMCD19A | 4 | 407 | |
| HUMCD19A | 4 | 669 | |
| HUMCD19A | 4 | 943 | |
| HUMCD19A | 4 | 1760 | |
| HUMCD19A | 4 | 1885 | 69 |
| HUMCD19A | 5 | 275 | 54 |
| D88010 | 2 | 72 | 157 |
| D88010 | 3 | 329 | |
| D88010 | 3 | 505 | |
| D88010 | 3 | 720 | |
| D88010 | 3 | 1124 | |
| D88010 | 3 | 1158 | |
| D88010 | 3 | 1523 | 21 |
| D88010 | 4 | 209 | 7 |
| D88010 | 5 | 291 | 2 |
| HUMRPS6B | 1 | 3 | |
| HUMRPS6B | 1 | 39 | |
| HUMRPS6B | 1 | 424 | 22 |
| HUMRPS6B | 2 | 23 | |
| HUMRPS6B | 2 | 54 | |
| HUMRPS6B | 2 | 108 | |
| HUMRPS6B | 2 | 483 | 136 |
| HUMRPS6B | 4 | 37 | |
| HUMRPS6B | 4 | 270 | |
| HUMRPS6B | 4 | 754 | |
| HUMRPS6B | 4 | 865 | 75 |
| D89060 | 2 | 811 | |
| D89060 | 2 | 819 | |
| D89060 | 2 | 889 | |
| D89060 | 2 | 1352 | |
| D89060 | 2 | 1371 | |
| D89060 | 2 | 1472 | |
| D89060 | 2 | 1507 | |
| D89060 | 2 | 1729 | |
| D89060 | 2 | 1911 | |
| D89060 | 2 | 2120 | |
| D89060 | 2 | 2131 | |
| D89060 | 2 | 2161 | |
| D89060 | 2 | 2341 | |
| D89060 | 2 | 2549 | |
| D89060 | 2 | 2553 | |
| D89060 | 2 | 2625 | |
| D89060 | 2 | 2713 | |
| D89060 | 2 | 2812 | |
| D89060 | 2 | 3135 | |
| D89060 | 2 | 3144 | |
| D89060 | 2 | 4349 | |
| D89060 | 2 | 4401 | |
| D89060 | 2 | 4595 | 183 |
| D89060 | 3 | 299 | 210 |
| D89060 | 5 | 3 | |
| D89060 | 5 | 97 | |
| D89060 | 5 | 348 | |
| D89060 | 5 | 420 | |
| D89060 | 5 | 428 | |
| D89060 | 5 | 551 | 2 |
| D89060 | 6 | 133 | 19 |
| D89060 | 7 | 408 | 2 |
| D89060 | 8 | 144 | |
| D89060 | 8 | 205 | |
| D89060 | 8 | 292 | 49 |
| D89060 | 10 | 9 | |
| HSU95012 | 1 | 306 | |
| HSU95012 | 1 | 631 | |
| HSU95012 | 1 | 787 | 136 |
| HSINT1G | 1 | 3 | 2 |
| HSINT1G | 2 | 494 | 204 |
| HSINT1G | 3 | 71 | |
| HSINT1G | 3 | 169 | |
| HSINT1G | 3 | 410 | 64 |
| HSU25816 | 1 | 15 | |
| HSU25816 | 1 | 56 | 18 |
| HSU25816 | 3 | 18 | 2 |
| HSCKIIBE | 1 | 803 | 283 |
| HSCKIIBE | 2 | 366 | |
| HSCKIIBE | 2 | 452 | |
| HSCKIIBE | 2 | 465 | 102 |
| HSCKIIBE | 4 | 93 | |
| HSCKIIBE | 4 | 98 | 9 |
| HSCKIIBE | 5 | 244 | |
| HSCKIIBE | 5 | 252 | |
| HSCKIIBE | 5 | 264 | 2 |
| HUMEMBPA | 1 | 292 | |
| HUMEMBPA | 1 | 492 | 54 |
| HUMEMBPA | 2 | 25 | |
| HUMEMBPA | 2 | 139 | |
| HUMEMBPA | 2 | 246 | 91 |
| HUMEMBPA | 3 | 224 | |
| HUMEMBPA | 3 | 325 | 13 |
| HUMEMBPA | 4 | 4 | |
| HUMTS1 | 1 | 179 | |
| HUMTS1 | 1 | 221 | |
| HUMTS1 | 1 | 794 | |
| HUMTS1 | 1 | 862 | |
| HUMTS1 | 1 | 1184 | 96 |
| HUMTS1 | 2 | 23 | |
| HUMTS1 | 2 | 84 | |
| HUMTS1 | 2 | 143 | |
| HUMTS1 | 2 | 217 | |
| HUMTS1 | 2 | 509 | |
| HUMTS1 | 2 | 688 | |
| HUMTS1 | 2 | 923 | |
| HUMTS1 | 2 | 950 | |
| HUMTS1 | 2 | 1069 | |
| HUMTS1 | 2 | 1639 | |
| HUMTS1 | 2 | 1850 | |
| HUMTS1 | 2 | 2053 | |
| HUMTS1 | 2 | 2345 | 127 |
| HUMTS1 | 3 | 248 | |
| HUMTS1 | 3 | 315 | |
| HUMTS1 | 3 | 946 | |
| HUMTS1 | 3 | 1470 | |
| HUMTS1 | 3 | 1912 | |
| HUMTS1 | 3 | 1924 | |
| HUMTS1 | 3 | 1949 | |
| HUMTS1 | 3 | 2235 | |
| HUMTS1 | 3 | 2654 | |
| HUMTS1 | 3 | 2830 | |
| HUMTS1 | 3 | 2975 | |
| HUMTS1 | 3 | 3370 | |
| HUMTS1 | 3 | 3623 | |
| HUMTS1 | 3 | 3825 | |
| HUMTS1 | 3 | 4258 | |
| HUMTS1 | 3 | 4941 | |
| HUMTS1 | 3 | 4955 | |
| HUMTS1 | 3 | 4994 | |
| HUMTS1 | 3 | 5346 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMTS1 | 3 | 5708 | |
| HUMTS1 | 3 | 5740 | |
| HUMTS1 | 3 | 5777 | |
| HUMTS1 | 3 | 6001 | |
| HUMTS1 | 3 | 6180 | |
| HUMTS1 | 3 | 6235 | 72 |
| HUMTS1 | 4 | 633 | |
| HUMTS1 | 4 | 717 | |
| HUMTS1 | 4 | 956 | 3 |
| HUMTS1 | 5 | 18 | |
| HUMTS1 | 5 | 115 | |
| HUMTS1 | 5 | 119 | 58 |
| HUMTS1 | 6 | 66 | |
| HUMTS1 | 6 | 146 | |
| HUMTS1 | 6 | 452 | |
| HUMTS1 | 6 | 742 | |
| HUMTS1 | 6 | 811 | |
| HUMTS1 | 6 | 870 | 43 |
| HSNFLG | 1 | 158 | |
| HSNFLG | 1 | 498 | 103 |
| HSNFLG | 2 | 348 | 2 |
| HSNFLG | 3 | 61 | |
| HSNFLG | 3 | 172 | |
| HSNFLG | 3 | 221 | 57 |
| HSU19906 | 1 | 564 | |
| HSU19906 | 1 | 1005 | |
| HSU19906 | 1 | 1057 | |
| HSU19906 | 1 | 1318 | |
| HSU19906 | 1 | 1477 | |
| HSU19906 | 1 | 1513 | 102 |
| AF016052 | 2 | 1317 | |
| AF016052 | 2 | 1340 | |
| AF016052 | 2 | 1655 | 33 |
| HSU61537 | 1 | 162 | |
| HSU61537 | 1 | 387 | |
| HSU61537 | 1 | 1445 | 5 |
| HSU61537 | 2 | 44 | |
| HSU61537 | 2 | 446 | |
| HSU61537 | 2 | 949 | |
| HSU61537 | 2 | 1086 | |
| HSU61537 | 2 | 1229 | |
| HSU61537 | 2 | 1274 | |
| HSU61537 | 2 | 1416 | |
| HSU61537 | 2 | 1511 | |
| HSU61537 | 2 | 1687 | |
| HSU61537 | 2 | 1698 | |
| HSU61537 | 2 | 2054 | |
| HSU61537 | 2 | 2266 | |
| HSU61537 | 2 | 2298 | |
| HSU61537 | 2 | 2319 | |
| HSU61537 | 2 | 2627 | |
| HSU61537 | 2 | 2908 | |
| HSU61537 | 2 | 3556 | |
| HSU61537 | 2 | 3808 | |
| HSU61537 | 2 | 3988 | |
| HSU61537 | 2 | 4081 | |
| HSU61537 | 2 | 4453 | |
| HSU61537 | 2 | 4470 | 85 |
| HUMATPSAS | 1 | 290 | |
| HUMATPSAS | 1 | 333 | |
| HUMATPSAS | 1 | 378 | |
| HUMATPSAS | 1 | 439 | |
| HUMATPSAS | 1 | 502 | |
| HUMATPSAS | 1 | 882 | |
| HUMATPSAS | 1 | 1064 | |
| HUMATPSAS | 1 | 1267 | |
| HUMATPSAS | 1 | 1403 | |
| HUMATPSAS | 1 | 1883 | |
| HUMATPSAS | 1 | 2028 | |
| HUMATPSAS | 1 | 2189 | |
| HUMATPSAS | 1 | 2276 | |
| HUMATPSAS | 1 | 2409 | |
| HUMATPSAS | 1 | 2592 | |
| HUMATPSAS | 1 | 2894 | |
| HUMATPSAS | 1 | 2951 | 328 |
| HUMATPSAS | 2 | 72 | |
| HUMATPSAS | 2 | 275 | |
| HUMATPSAS | 2 | 341 | |
| HUMATPSAS | 2 | 841 | |
| HUMATPSAS | 2 | 867 | |
| HUMATPSAS | 2 | 1040 | |
| HUMATPSAS | 2 | 1175 | |
| HUMATPSAS | 2 | 1323 | |
| HUMATPSAS | 2 | 1999 | |
| HUMATPSAS | 2 | 3098 | 36 |
| HUMATPSAS | 3 | 382 | |
| HUMATPSAS | 3 | 440 | |
| HUMATPSAS | 3 | 724 | |
| HUMATPSAS | 3 | 963 | |
| HUMATPSAS | 3 | 994 | |
| HUMATPSAS | 3 | 1196 | |
| HUMATPSAS | 3 | 1566 | 37 |
| HUMATPSAS | 5 | 75 | |
| HUMATPSAS | 5 | 183 | |
| HUMATPSAS | 5 | 291 | |
| HUMATPSAS | 5 | 309 | |
| HUMATPSAS | 5 | 526 | 2 |
| HUMATPSAS | 6 | 132 | |
| HUMATPSAS | 6 | 353 | |
| HUMATPSAS | 6 | 446 | |
| HUMATPSAS | 6 | 526 | |
| HUMATPSAS | 6 | 547 | 36 |
| HUMATPSAS | 8 | 370 | 10 |
| HUMATPSAS | 10 | 304 | |
| HUMATPSAS | 10 | 397 | |
| HUMATPSAS | 10 | 440 | |
| HUMATPSAS | 10 | 950 | |
| HUMATPSAS | 10 | 952 | |
| HUMATPSAS | 10 | 1109 | |
| HUMATPSAS | 10 | 1319 | |
| HUMATPSAS | 10 | 1378 | 162 |
| HUMATPSAS | 11 | 104 | |
| HSU23853 | 2 | 121 | |
| HSU23853 | 2 | 220 | |
| HSU23853 | 2 | 230 | |
| HSU23853 | 2 | 265 | 61 |
| HSLCATG | 1 | 269 | |
| HSLCATG | 1 | 360 | |
| HSLCATG | 1 | 598 | |
| HSLCATG | 1 | 637 | |
| HSLCATG | 1 | 644 | |
| HSLCATG | 1 | 680 | 21 |
| HSLCATG | 5 | 34 | |
| HSLCATG | 5 | 230 | |
| HSLCATG | 5 | 1141 | |
| HSLCATG | 5 | 1318 | |
| HSLCATG | 5 | 1625 | 21 |
| D63789 | 1 | 47 | |
| D63789 | 1 | 225 | |
| D63789 | 1 | 235 | |
| D63789 | 1 | 403 | |
| D63789 | 1 | 510 | |
| D63789 | 1 | 765 | |
| D63789 | 1 | 855 | |
| D63789 | 1 | 1748 | 21 |
| D63789 | 2 | 29 | |
| D63789 | 2 | 87 | |
| D63789 | 2 | 91 | 2 |
| HUMCD7AA | 3 | 241 | |
| HUMCD7AA | 3 | 243 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMCD7AA | 3 | 270 | |
| HUMCD7AA | 3 | 346 | 52 |
| HSMTIXG | 1 | 120 | 69 |
| HSMTIXG | 2 | 155 | |
| HSMTIXG | 2 | 324 | |
| HSMTIXG | 2 | 535 | |
| HSMTIXG | 2 | 677 | 45 |
| HSPCK1 | 1 | 410 | |
| HSPCK1 | 1 | 414 | |
| HSPCK1 | 1 | 566 | |
| HSPCK1 | 1 | 844 | 2 |
| HSPCK1 | 2 | 324 | |
| HSPCK1 | 2 | 663 | |
| HSPCK1 | 2 | 936 | |
| HSPCK1 | 2 | 998 | 2 |
| HSPCK1 | 4 | 235 | 183 |
| HSPCK1 | 5 | 10 | 13 |
| HSPCK1 | 6 | 193 | 63 |
| HSPCK1 | 7 | 17 | |
| HSPCK1 | 7 | 539 | |
| HSPCK1 | 7 | 614 | |
| HSPCK1 | 7 | 1494 | |
| HSPCK1 | 7 | 1715 | |
| HSPCK1 | 7 | 1779 | |
| HSPCK1 | 7 | 1797 | |
| HSPCK1 | 7 | 1879 | |
| HSPCK1 | 7 | 1916 | |
| HSPCK1 | 7 | 2246 | |
| HSPCK1 | 7 | 2473 | |
| HSPCK1 | 7 | 2477 | 90 |
| HSPCK1 | 8 | 120 | 51 |
| AF036329 | 2 | 8 | |
| AF036329 | 2 | 363 | |
| AF036329 | 2 | 411 | |
| AF036329 | 2 | 543 | |
| AF036329 | 2 | 562 | 106 |
| HUMANT1 | 1 | 628 | 379 |
| HUMANT1 | 2 | 136 | |
| HUMANT1 | 2 | 404 | 87 |
| HUMANT1 | 3 | 230 | |
| HUMANT1 | 3 | 602 | 108 |
| HUMETMAGA | 1 | 13 | |
| HUMETMAGA | 1 | 97 | 162 |
| D85429 | 1 | 547 | |
| D85429 | 1 | 815 | |
| D85429 | 1 | 854 | 303 |
| D85429 | 2 | 11 | |
| D85429 | 2 | 84 | |
| D85429 | 2 | 91 | 28 |
| HUMCKMT | 1 | 39 | |
| HUMCKMT | 1 | 54 | |
| HUMCKMT | 1 | 66 | |
| HUMCKMT | 1 | 538 | 2 |
| HUMCKMT | 3 | 118 | |
| HUMCKMT | 3 | 193 | 121 |
| HUMCKMT | 6 | 27 | |
| HUMCKMT | 6 | 72 | |
| HUMCKMT | 6 | 285 | |
| HUMCKMT | 6 | 315 | |
| HUMCKMT | 6 | 320 | |
| HUMCKMT | 6 | 418 | |
| HUMCKMT | 6 | 871 | |
| HUMCKMT | 6 | 890 | |
| HUMCKMT | 6 | 966 | 40 |
| HUMCKMT | 7 | 28 | |
| HUMCKMT | 7 | 42 | |
| HUMCKMT | 7 | 275 | |
| HUMCKMT | 7 | 443 | 31 |
| HUMCKMT | 8 | 60 | |
| HUMCKMT | 8 | 139 | 10 |
| HUMADPRF02 | 1 | 278 | 180 |
| HUMADPRF02 | 2 | 147 | 60 |
| HUMADPRF02 | 3 | 286 | |
| HUMADPRF02 | 3 | 382 | 109 |
| HSHNRNPA | 1 | 53 | |
| HSHNRNPA | 1 | 271 | 7 |
| HSHNRNPA | 5 | 29 | 15 |
| HSHNRNPA | 7 | 57 | |
| HSHNRNPA | 7 | 203 | |
| HSHNRNPA | 7 | 359 | |
| HSHNRNPA | 7 | 732 | |
| HSHNRNPA | 7 | 903 | 21 |
| HSHNRNPA | 8 | 12 | 15 |
| HUMATPGG | 4 | 202 | |
| HUMATPGG | 4 | 227 | |
| HUMATPGG | 4 | 259 | |
| HUMATPGG | 4 | 347 | |
| HUMATPGG | 4 | 490 | |
| HUMATPGG | 4 | 1013 | |
| HUMATPGG | 4 | 1386 | |
| HUMATPGG | 4 | 1436 | 100 |
| HUMATPGG | 7 | 319 | |
| HUMATPGG | 7 | 574 | 229 |
| HUMATPGG | 8 | 72 | 57 |
| HUMATPGG | 11 | 31 | |
| HUMATPGG | 11 | 428 | |
| HUMATPGG | 11 | 451 | |
| HUMATPGG | 11 | 466 | 189 |
| HUMATPGG | 12 | 1005 | |
| HUMATPGG | 12 | 1072 | 31 |
| HUMATPGG | 16 | 163 | |
| HUMATPGG | 16 | 215 | |
| HUMATPGG | 16 | 287 | |
| HUMATPGG | 16 | 433 | |
| HUMATPGG | 16 | 598 | |
| HUMATPGG | 16 | 670 | 130 |
| HUMATPGG | 17 | 29 | 156 |
| HUMATPGG | 18 | 1061 | 94 |
| HUMTPALBU | 1 | 264 | 184 |
| HUMTPALBU | 2 | 86 | |
| HUMTPALBU | 2 | 156 | |
| HUMTPALBU | 2 | 291 | 2 |
| HUMTPALBU | 3 | 190 | |
| HUMTPALBU | 3 | 199 | 168 |
| HUMTPALBU | 4 | 355 | |
| HUMTPALBU | 4 | 430 | 129 |
| HSCRTRGN | 1 | 279 | |
| HSCRTRGN | 1 | 316 | |
| HSCRTRGN | 1 | 730 | 687 |
| HSCRTRGN | 2 | 269 | |
| HSCRTRGN | 2 | 509 | 78 |
| HSCRTRGN | 3 | 231 | |
| HSCRTRGN | 3 | 236 | 2 |
| HSCRTRGN | 4 | 83 | 397 |
| HSCRTRGN | 11 | 15 | |
| HSCRTRGN | 12 | 144 | 40 |
| HSARS81S | 1 | 367 | |
| HSARS81S | 1 | 372 | 36 |
| HSARS81S | 2 | 104 | |
| HSARS81S | 2 | 206 | |
| HSARS81S | 2 | 436 | |
| HSARS81S | 2 | 441 | 336 |
| HUMPAIA | 1 | 23 | |
| HUMPAIA | 1 | 347 | |
| HUMPAIA | 1 | 899 | |
| HUMPAIA | 1 | 1075 | |
| HUMPAIA | 1 | 1250 | 267 |
| HUMPAIA | 2 | 266 | |
| HUMPAIA | 2 | 608 | |
| HUMPAIA | 2 | 925 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMPAIA | 2 | 937 | 102 |
| HUMPAIA | 3 | 420 | |
| HUMPAIA | 3 | 438 | |
| HUMPAIA | 3 | 510 | |
| HUMPAIA | 3 | 925 | |
| HUMPAIA | 3 | 998 | |
| HUMPAIA | 3 | 1081 | |
| HUMPAIA | 3 | 1105 | |
| HUMPAIA | 3 | 1114 | |
| HUMPAIA | 3 | 1529 | 138 |
| HUMPAIA | 4 | 285 | |
| HUMPAIA | 4 | 616 | |
| HUMPAIA | 4 | 692 | |
| HUMPAIA | 4 | 710 | |
| HUMPAIA | 4 | 893 | |
| HUMPAIA | 4 | 907 | |
| HUMPAIA | 4 | 1077 | |
| HUMPAIA | 4 | 1531 | 2 |
| HUMPAIA | 6 | 14 | |
| HUMPAIA | 6 | 346 | |
| HUMPAIA | 6 | 360 | |
| HUMPAIA | 6 | 737 | |
| HUMPAIA | 6 | 1035 | 234 |
| HUMDKERB | 1 | 174 | |
| HUMDKERB | 1 | 323 | |
| HUMDKERB | 1 | 558 | |
| HUMDKERB | 1 | 685 | |
| HUMDKERB | 1 | 1735 | |
| HUMDKERB | 1 | 1988 | |
| HUMDKERB | 1 | 2249 | |
| HUMDKERB | 1 | 2386 | |
| HUMDKERB | 1 | 2412 | 283 |
| HUMDKERB | 2 | 463 | |
| HUMDKERB | 2 | 608 | 2 |
| HUMDKERB | 3 | 160 | |
| HUMDKERB | 3 | 164 | |
| HUMDKERB | 3 | 276 | |
| HUMDKERB | 3 | 296 | |
| HUMDKERB | 3 | 302 | 85 |
| HUMDKERB | 4 | 190 | |
| HUMDKERB | 4 | 271 | 124 |
| HUMDKERB | 5 | 45 | |
| HUMDKERB | 5 | 203 | |
| HUMDKERB | 5 | 223 | |
| HUMDKERB | 5 | 284 | 58 |
| HUMDKERB | 7 | 231 | |
| HUMDKERB | 7 | 253 | 99 |
| HSBSF2 | 1 | 61 | |
| HSBSF2 | 2 | 281 | |
| HSBSF2 | 2 | 501 | |
| HSBSF2 | 2 | 601 | |
| HSBSF2 | 2 | 653 | |
| HSBSF2 | 2 | 862 | |
| HSBSF2 | 2 | 1017 | 79 |
| HSBSF2 | 3 | 98 | |
| HSBSF2 | 3 | 102 | |
| HSBSF2 | 3 | 122 | |
| HSBSF2 | 3 | 181 | |
| HSBSF2 | 3 | 207 | |
| HSBSF2 | 3 | 587 | 253 |
| HSBSF2 | 4 | 3 | |
| HSBSF2 | 4 | 233 | |
| HSBSF2 | 4 | 715 | |
| HSBSF2 | 4 | 825 | |
| HSBSF2 | 4 | 841 | |
| HSBSF2 | 4 | 903 | |
| HSBSF2 | 4 | 1113 | |
| HSBSF2 | 4 | 1341 | 109 |
| HUMHBA1 | 1 | 44 | |
| HUMHBA1 | 1 | 48 | 2 |
| HSGMCSFG | 1 | 3 | 43 |
| HSGMCSFG | 2 | 53 | |
| HSGMCSFG | 2 | 401 | |
| HSGMCSFG | 2 | 435 | |
| HSGMCSFG | 2 | 518 | 22 |
| HSGMCSFG | 3 | 260 | |
| HSGMCSFG | 3 | 267 | |
| HSGMCSFG | 3 | 643 | |
| HSGMCSFG | 3 | 672 | |
| HSGMCSFG | 3 | 680 | 43 |
| HUMTKRA | 2 | 465 | |
| HUMTKRA | 2 | 499 | |
| HUMTKRA | 2 | 562 | |
| HUMTKRA | 2 | 973 | |
| HUMTKRA | 2 | 1018 | |
| HUMTKRA | 2 | 1036 | |
| HUMTKRA | 2 | 1304 | |
| HUMTKRA | 2 | 1381 | 2 |
| HUMTKRA | 3 | 130 | |
| HUMTKRA | 3 | 194 | |
| HUMTKRA | 3 | 911 | |
| HUMTKRA | 3 | 915 | |
| HUMTKRA | 3 | 1013 | |
| HUMTKRA | 3 | 1301 | |
| HUMTKRA | 3 | 1326 | |
| HUMTKRA | 3 | 1477 | |
| HUMTKRA | 3 | 2035 | |
| HUMTKRA | 3 | 2073 | 62 |
| HUMTKRA | 4 | 430 | |
| HUMTKRA | 4 | 752 | |
| HUMTKRA | 4 | 827 | |
| HUMTKRA | 4 | 1007 | |
| HUMTKRA | 4 | 1156 | |
| HUMTKRA | 4 | 1160 | |
| HUMTKRA | 4 | 1256 | |
| HUMTKRA | 4 | 1463 | |
| HUMTKRA | 4 | 1553 | |
| HUMTKRA | 4 | 1733 | |
| HUMTKRA | 4 | 1825 | |
| HUMTKRA | 4 | 2187 | |
| HUMTKRA | 4 | 2593 | |
| HUMTKRA | 4 | 2729 | |
| HUMTKRA | 4 | 2842 | |
| HUMTKRA | 4 | 3165 | |
| HUMTKRA | 4 | 3250 | |
| HUMTKRA | 4 | 3412 | |
| HUMTKRA | 4 | 3633 | |
| HUMTKRA | 4 | 4306 | |
| HUMTKRA | 4 | 4420 | |
| HUMTKRA | 4 | 4478 | |
| HUMTKRA | 4 | 4757 | |
| HUMTKRA | 4 | 4761 | |
| HUMTKRA | 4 | 4773 | |
| HUMTKRA | 4 | 5276 | |
| HUMTKRA | 4 | 5281 | |
| HUMTKRA | 4 | 5341 | |
| HUMTKRA | 4 | 5523 | |
| HUMTKRA | 4 | 5540 | |
| HUMTKRA | 4 | 5729 | 121 |
| HUMTKRA | 5 | 185 | |
| HUMTKRA | 5 | 250 | |
| HUMTKRA | 5 | 315 | 34 |
| HSU46920 | 1 | 217 | |
| HSU46920 | 1 | 611 | |
| HSU46920 | 1 | 756 | 115 |
| HSU46920 | 2 | 19 | |
| HSU46920 | 2 | 29 | 57 |
| HSU46920 | 3 | 3 | |
| HSU46920 | 3 | 100 | |
| HSU46920 | 3 | 708 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSU46920 | 3 | 918 | 31 |
| HSU46920 | 5 | 70 | 28 |
| HUMSEMI | 1 | 12 | |
| HUMSEMI | 1 | 181 | 15 |
| HUMADAG | 1 | 436 | |
| HUMADAG | 1 | 456 | |
| HUMADAG | 1 | 558 | |
| HUMADAG | 1 | 752 | |
| HUMADAG | 1 | 833 | |
| HUMADAG | 1 | 835 | |
| HUMADAG | 1 | 984 | |
| HUMADAG | 1 | 1076 | |
| HUMADAG | 1 | 1166 | |
| HUMADAG | 1 | 1202 | |
| HUMADAG | 1 | 1213 | |
| HUMADAG | 1 | 1276 | |
| HUMADAG | 1 | 1507 | |
| HUMADAG | 1 | 1592 | |
| HUMADAG | 1 | 2091 | |
| HUMADAG | 1 | 2127 | |
| HUMADAG | 1 | 3119 | |
| HUMADAG | 1 | 3503 | |
| HUMADAG | 1 | 3873 | |
| HUMADAG | 1 | 3915 | |
| HUMADAG | 1 | 4220 | |
| HUMADAG | 1 | 4356 | |
| HUMADAG | 1 | 5027 | |
| HUMADAG | 1 | 5464 | |
| HUMADAG | 1 | 6032 | |
| HUMADAG | 1 | 6074 | |
| HUMADAG | 1 | 6178 | |
| HUMADAG | 1 | 6912 | |
| HUMADAG | 1 | 7125 | |
| HUMADAG | 1 | 7503 | |
| HUMADAG | 1 | 7624 | |
| HUMADAG | 1 | 7698 | |
| HUMADAG | 1 | 7760 | |
| HUMADAG | 1 | 8007 | |
| HUMADAG | 1 | 8370 | |
| HUMADAG | 1 | 8433 | |
| HUMADAG | 1 | 9122 | |
| HUMADAG | 1 | 9351 | |
| HUMADAG | 1 | 9393 | |
| HUMADAG | 1 | 9438 | |
| HUMADAG | 1 | 9456 | |
| HUMADAG | 1 | 9770 | |
| HUMADAG | 1 | 10385 | |
| HUMADAG | 1 | 10684 | |
| HUMADAG | 1 | 10768 | |
| HUMADAG | 1 | 10825 | |
| HUMADAG | 1 | 10911 | |
| HUMADAG | 1 | 11004 | |
| HUMADAG | 1 | 11330 | |
| HUMADAG | 1 | 11596 | |
| HUMADAG | 1 | 11792 | |
| HUMADAG | 1 | 11810 | |
| HUMADAG | 1 | 11890 | |
| HUMADAG | 1 | 12043 | |
| HUMADAG | 1 | 12960 | |
| HUMADAG | 1 | 13002 | |
| HUMADAG | 1 | 13096 | |
| HUMADAG | 1 | 13140 | |
| HUMADAG | 1 | 13310 | |
| HUMADAG | 1 | 13336 | |
| HUMADAG | 1 | 13785 | |
| HUMADAG | 1 | 14400 | |
| HUMADAG | 1 | 14417 | |
| HUMADAG | 1 | 15113 | 223 |
| HUMADAG | 2 | 236 | |
| HUMADAG | 2 | 288 | |
| HUMADAG | 2 | 411 | |
| HUMADAG | 2 | 647 | |
| HUMADAG | 2 | 952 | |
| HUMADAG | 2 | 1483 | |
| HUMADAG | 2 | 1619 | |
| HUMADAG | 2 | 1713 | |
| HUMADAG | 2 | 1821 | |
| HUMADAG | 2 | 3052 | |
| HUMADAG | 2 | 3299 | |
| HUMADAG | 2 | 3442 | |
| HUMADAG | 2 | 3454 | |
| HUMADAG | 2 | 3819 | |
| HUMADAG | 2 | 4431 | |
| HUMADAG | 2 | 4515 | |
| HUMADAG | 2 | 4793 | |
| HUMADAG | 2 | 4931 | |
| HUMADAG | 2 | 5352 | |
| HUMADAG | 2 | 5459 | |
| HUMADAG | 2 | 5960 | |
| HUMADAG | 2 | 6239 | |
| HUMADAG | 2 | 6759 | 2 |
| HUMADAG | 3 | 135 | |
| HUMADAG | 3 | 181 | |
| HUMADAG | 3 | 738 | |
| HUMADAG | 3 | 1180 | |
| HUMADAG | 3 | 1615 | |
| HUMADAG | 3 | 1631 | |
| HUMADAG | 3 | 1894 | |
| HUMADAG | 3 | 2244 | |
| HUMADAG | 3 | 2342 | 2 |
| HUMADAG | 4 | 366 | |
| HUMADAG | 4 | 651 | 2 |
| HUMADAG | 5 | 257 | |
| HUMADAG | 5 | 826 | |
| HUMADAG | 5 | 920 | |
| HUMADAG | 5 | 1175 | 6 |
| HUMADAG | 6 | 37 | |
| HUMADAG | 6 | 110 | |
| HUMADAG | 6 | 339 | |
| HUMADAG | 6 | 938 | 40 |
| HUMADAG | 9 | 426 | |
| HUMADAG | 9 | 709 | |
| HUMADAG | 9 | 1035 | |
| HUMADAG | 9 | 1391 | 2 |
| HUMADAG | 10 | 93 | |
| HUMADAG | 10 | 257 | |
| HUMADAG | 10 | 349 | 28 |
| HUMBNPA | 1 | 181 | |
| HUMBNPA | 1 | 192 | 94 |
| HUMBNPA | 2 | 457 | |
| HUMBNPA | 2 | 476 | 99 |
| AF015954 | 1 | 198 | 154 |
| AF015954 | 2 | 268 | |
| AF015954 | 2 | 422 | |
| AF015954 | 2 | 501 | |
| AF015954 | 2 | 1027 | 51 |
| AF015954 | 3 | 518 | 24 |
| HUMAZCDI | 1 | 210 | 39 |
| HUMAZCDI | 2 | 85 | |
| HUMAZCDI | 2 | 89 | |
| HUMAZCDI | 2 | 574 | 2 |
| HUMAZCDI | 3 | 168 | |
| HUMAZCDI | 3 | 230 | |
| HUMAZCDI | 3 | 278 | |
| HUMAZCDI | 3 | 283 | |
| HUMAZCDI | 3 | 323 | |
| HUMAZCDI | 3 | 339 | |
| HUMAZCDI | 3 | 671 | 22 |
| HUMAZCDI | 4 | 339 | 43 |
| HSU37022 | 1 | 55 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSU37022 | 1 | 135 | 2 |
| HSU37022 | 2 | 26 | |
| HSU37022 | 2 | 67 | 22 |
| HSU37022 | 6 | 227 | |
| HSU37022 | 6 | 245 | 55 |
| HSACTH | 1 | 148 | |
| HSACTH | 1 | 434 | |
| HSACTH | 1 | 642 | |
| HSACTH | 1 | 765 | |
| HSACTH | 1 | 1142 | |
| HSACTH | 1 | 1225 | |
| HSACTH | 1 | 1344 | |
| HSACTH | 1 | 1860 | |
| HSACTH | 1 | 1880 | |
| HSACTH | 1 | 2450 | |
| HSACTH | 1 | 2623 | |
| HSACTH | 1 | 2714 | 13 |
| HSIL05 | 2 | 93 | |
| HSIL05 | 2 | 400 | |
| HSIL05 | 2 | 581 | |
| HSIL05 | 2 | 585 | |
| HSIL05 | 2 | 622 | |
| HSIL05 | 2 | 840 | |
| HSIL05 | 2 | 918 | |
| HSIL05 | 2 | 1185 | |
| HSIL05 | 2 | 1567 | |
| HSIL05 | 2 | 1932 | |
| HSIL05 | 2 | 2077 | |
| HSIL05 | 2 | 2109 | 34 |
| HSIL05 | 3 | 111 | |
| HSIL05 | 3 | 281 | |
| HSIL05 | 3 | 581 | |
| HSIL05 | 3 | 702 | |
| HSIL05 | 3 | 1295 | |
| HSIL05 | 3 | 1733 | |
| HSIL05 | 3 | 1753 | |
| HSIL05 | 3 | 1815 | 79 |
| HSGCAP2 | 1 | 154 | |
| HSGCAP2 | 1 | 256 | |
| HSGCAP2 | 1 | 357 | |
| HSGCAP2 | 1 | 685 | |
| HSGCAP2 | 1 | 776 | |
| HSGCAP2 | 1 | 898 | 31 |
| HSGCAP2 | 2 | 110 | |
| HSGCAP2 | 2 | 161 | |
| HSGCAP2 | 2 | 477 | 78 |
| HSNFM | 1 | 420 | 322 |
| HSNFM | 2 | 15 | |
| HSNFM | 2 | 746 | |
| HSNFM | 2 | 896 | |
| HSNFM | 2 | 1075 | |
| HSNFM | 2 | 1096 | |
| HSNFM | 2 | 1173 | |
| HSNFM | 2 | 1221 | |
| HSNFM | 2 | 1241 | 149 |
| HUMCOL2A1Z | 1 | 406 | |
| HUMCOL2A1Z | 1 | 888 | |
| HUMCOL2A1Z | 1 | 920 | |
| HUMCOL2A1Z | 1 | 1054 | |
| HUMCOL2A1Z | 1 | 1828 | |
| HUMCOL2A1Z | 1 | 2302 | |
| HUMCOL2A1Z | 1 | 2808 | |
| HUMCOL2A1Z | 1 | 3328 | |
| HUMCOL2A1Z | 1 | 3586 | |
| HUMCOL2A1Z | 1 | 3808 | |
| HUMCOL2A1Z | 1 | 3871 | |
| HUMCOL2A1Z | 1 | 3894 | 255 |
| HUMCOL2A1Z | 2 | 256 | |
| HUMCOL2A1Z | 2 | 412 | |
| HUMCOL2A1Z | 2 | 695 | |
| HUMCOL2A1Z | 2 | 745 | |
| HUMCOL2A1Z | 2 | 829 | |
| HUMCOL2A1Z | 2 | 911 | |
| HUMCOL2A1Z | 2 | 963 | |
| HUMCOL2A1Z | 2 | 1075 | |
| HUMCOL2A1Z | 2 | 1412 | |
| HUMCOL2A1Z | 2 | 1437 | 30 |
| HUMCOL2A1Z | 7 | 275 | |
| HUMCOL2A1Z | 7 | 428 | |
| HUMCOL2A1Z | 7 | 833 | |
| HUMCOL2A1Z | 7 | 853 | 55 |
| HUMCOL2A1Z | 10 | 349 | 43 |
| HUMCOL2A1Z | 11 | 57 | |
| HUMCOL2A1Z | 11 | 98 | |
| HUMCOL2A1Z | 11 | 481 | |
| HUMCOL2A1Z | 11 | 554 | |
| HUMCOL2A1Z | 11 | 650 | 16 |
| HUMCOL2A1Z | 12 | 85 | 37 |
| HUMCOL2A1Z | 13 | 12 | |
| HUMCOL2A1Z | 13 | 64 | |
| HUMCOL2A1Z | 15 | 272 | |
| HUMCOL2A1Z | 15 | 512 | 112 |
| HUMCOL2A1Z | 16 | 55 | |
| HUMCOL2A1Z | 16 | 237 | |
| HUMCOL2A1Z | 16 | 373 | |
| HUMCOL2A1Z | 16 | 519 | |
| HUMCOL2A1Z | 16 | 573 | |
| HUMCOL2A1Z | 16 | 649 | |
| HUMCOL2A1Z | 16 | 1956 | |
| HUMCOL2A1Z | 16 | 2565 | |
| HUMCOL2A1Z | 16 | 2627 | |
| HUMCOL2A1Z | 16 | 2705 | 10 |
| HUMCOL2A1Z | 17 | 23 | 43 |
| HUMCOL2A1Z | 18 | 190 | |
| HUMCOL2A1Z | 18 | 702 | |
| HUMCOL2A1Z | 18 | 794 | |
| HUMCOL2A1Z | 18 | 1121 | |
| HUMCOL2A1Z | 18 | 1280 | |
| HUMCOL2A1Z | 18 | 1460 | 103 |
| HUMCOL2A1Z | 19 | 244 | 58 |
| HUMCOL2A1Z | 22 | 483 | 46 |
| HUMCOL2A1Z | 23 | 4 | |
| HUMCOL2A1Z | 23 | 281 | |
| HUMCOL2A1Z | 23 | 285 | 7 |
| HUMCOL2A1Z | 27 | 149 | 85 |
| HUMCOL2A1Z | 28 | 268 | 25 |
| HUMCOL2A1Z | 29 | 93 | 112 |
| HUMCOL2A1Z | 30 | 3 | 241 |
| HUMCOL2A1Z | 33 | 3 | 52 |
| HUMCOL2A1Z | 35 | 3 | |
| HUMCOL2A1Z | 35 | 162 | 43 |
| HUMCOL2A1Z | 37 | 199 | |
| HUMCOL2A1Z | 37 | 325 | 202 |
| HUMCOL2A1Z | 40 | 143 | 226 |
| HUMCOL2A1Z | 41 | 503 | |
| HUMCOL2A1Z | 41 | 569 | |
| HUMCOL2A1Z | 41 | 706 | 100 |
| HUMCOL2A1Z | 42 | 45 | 79 |
| HUMCOL2A1Z | 43 | 105 | |
| HUMCOL2A1Z | 44 | 48 | |
| HUMCOL2A1Z | 44 | 215 | |
| HUMCOL2A1Z | 44 | 239 | |
| HUMCOL2A1Z | 44 | 243 | |
| HUMCOL2A1Z | 44 | 306 | |
| HUMCOL2A1Z | 45 | 60 | |
| HUMCOL2A1Z | 47 | 66 | |
| HUMCOL2A1Z | 51 | 192 | 195 |
| HUMCOL2A1Z | 52 | 163 | 19 |
| HUMCOL2A1Z | 53 | 153 | 58 |
| HUMCYPIIE | 1 | 50 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMCYPIIE | 1 | 54 | |
| HUMCYPIIE | 1 | 631 | |
| HUMCYPIIE | 1 | 837 | 232 |
| HUMCYPIIE | 2 | 351 | |
| HUMCYPIIE | 2 | 909 | |
| HUMCYPIIE | 2 | 1956 | |
| HUMCYPIIE | 2 | 2494 | |
| HUMCYPIIE | 2 | 2575 | |
| HUMCYPIIE | 2 | 2654 | 96 |
| HUMCYPIIE | 3 | 119 | |
| HUMCYPIIE | 3 | 197 | |
| HUMCYPIIE | 3 | 321 | 192 |
| HUMCYPIIE | 5 | 614 | |
| HUMCYPIIE | 5 | 718 | |
| HUMCYPIIE | 5 | 815 | 148 |
| HUMCYPIIE | 6 | 7 | |
| HUMCYPIIE | 6 | 119 | |
| HUMCYPIIE | 6 | 335 | |
| HUMCYPIIE | 6 | 363 | |
| HUMCYPIIE | 6 | 423 | |
| HUMCYPIIE | 6 | 539 | |
| HUMCYPIIE | 6 | 560 | |
| HUMCYPIIE | 6 | 609 | |
| HUMCYPIIE | 6 | 614 | |
| HUMCYPIIE | 6 | 783 | |
| HUMCYPIIE | 6 | 1093 | |
| HUMCYPIIE | 6 | 1222 | |
| HUMCYPIIE | 6 | 1544 | |
| HUMCYPIIE | 6 | 2224 | |
| HUMCYPIIE | 6 | 2498 | |
| HUMCYPIIE | 6 | 2558 | |
| HUMCYPIIE | 6 | 2606 | |
| HUMCYPIIE | 6 | 2638 | |
| HUMCYPIIE | 6 | 2642 | |
| HUMCYPIIE | 6 | 2729 | 102 |
| HUMCYPIIE | 8 | 217 | |
| HUMCYPIIE | 8 | 416 | |
| HUMCYPIIE | 8 | 755 | 96 |
| HSAPC3A | 2 | 67 | |
| HSAPC3A | 2 | 650 | |
| HSAPC3A | 2 | 961 | |
| HSAPC3A | 2 | 1146 | |
| HSAPC3A | 2 | 1194 | |
| HSAPC3A | 2 | 1336 | |
| HSAPC3A | 2 | 1391 | |
| HSAPC3A | 2 | 1599 | 245 |
| HUMRETBLAS | 1 | 1277 | |
| HUMRETBLAS | 1 | 1921 | |
| HUMRETBLAS | 1 | 2256 | |
| HUMRETBLAS | 1 | 2490 | |
| HUMRETBLAS | 1 | 2604 | |
| HUMRETBLAS | 1 | 2778 | |
| HUMRETBLAS | 1 | 3162 | 2 |
| HUMRETBLAS | 2 | 220 | |
| HUMRETBLAS | 2 | 707 | |
| HUMRETBLAS | 2 | 809 | |
| HUMRETBLAS | 2 | 846 | |
| HUMRETBLAS | 2 | 1019 | |
| HUMRETBLAS | 2 | 1031 | |
| HUMRETBLAS | 2 | 1143 | |
| HUMRETBLAS | 2 | 1696 | |
| HUMRETBLAS | 2 | 1936 | |
| HUMRETBLAS | 2 | 2609 | |
| HUMRETBLAS | 2 | 2646 | |
| HUMRETBLAS | 2 | 2945 | |
| HUMRETBLAS | 2 | 2949 | |
| HUMRETBLAS | 2 | 3497 | |
| HUMRETBLAS | 2 | 3561 | |
| HUMRETBLAS | 2 | 3585 | |
| HUMRETBLAS | 2 | 3730 | |
| HUMRETBLAS | 2 | 3974 | |
| HUMRETBLAS | 2 | 4138 | |
| HUMRETBLAS | 2 | 4655 | |
| HUMRETBLAS | 2 | 5883 | |
| HUMRETBLAS | 2 | 6153 | |
| HUMRETBLAS | 2 | 6487 | |
| HUMRETBLAS | 2 | 6724 | |
| HUMRETBLAS | 2 | 6792 | |
| HUMRETBLAS | 2 | 7066 | |
| HUMRETBLAS | 2 | 7165 | |
| HUMRETBLAS | 2 | 7183 | |
| HUMRETBLAS | 2 | 7897 | |
| HUMRETBLAS | 2 | 8168 | |
| HUMRETBLAS | 2 | 8283 | |
| HUMRETBLAS | 2 | 9972 | |
| HUMRETBLAS | 2 | 10761 | |
| HUMRETBLAS | 2 | 11041 | |
| HUMRETBLAS | 2 | 13180 | |
| HUMRETBLAS | 2 | 14204 | |
| HUMRETBLAS | 2 | 14917 | |
| HUMRETBLAS | 2 | 15908 | |
| HUMRETBLAS | 2 | 15976 | |
| HUMRETBLAS | 2 | 16006 | |
| HUMRETBLAS | 2 | 16123 | |
| HUMRETBLAS | 2 | 16521 | |
| HUMRETBLAS | 2 | 17013 | |
| HUMRETBLAS | 2 | 17017 | |
| HUMRETBLAS | 2 | 17180 | |
| HUMRETBLAS | 2 | 17581 | |
| HUMRETBLAS | 2 | 17765 | |
| HUMRETBLAS | 2 | 18342 | |
| HUMRETBLAS | 2 | 18423 | |
| HUMRETBLAS | 2 | 19003 | |
| HUMRETBLAS | 2 | 19044 | |
| HUMRETBLAS | 2 | 19102 | |
| HUMRETBLAS | 2 | 19480 | |
| HUMRETBLAS | 2 | 19489 | |
| HUMRETBLAS | 2 | 19658 | |
| HUMRETBLAS | 2 | 19992 | |
| HUMRETBLAS | 2 | 20247 | |
| HUMRETBLAS | 2 | 21202 | |
| HUMRETBLAS | 2 | 21495 | |
| HUMRETBLAS | 2 | 21846 | |
| HUMRETBLAS | 2 | 21917 | |
| HUMRETBLAS | 2 | 21985 | |
| HUMRETBLAS | 2 | 22024 | |
| HUMRETBLAS | 2 | 22296 | |
| HUMRETBLAS | 2 | 23257 | |
| HUMRETBLAS | 2 | 23410 | |
| HUMRETBLAS | 2 | 23945 | |
| HUMRETBLAS | 2 | 24185 | |
| HUMRETBLAS | 2 | 24197 | |
| HUMRETBLAS | 2 | 24205 | |
| HUMRETBLAS | 2 | 24312 | |
| HUMRETBLAS | 2 | 24474 | |
| HUMRETBLAS | 2 | 24552 | |
| HUMRETBLAS | 2 | 24607 | |
| HUMRETBLAS | 2 | 24751 | |
| HUMRETBLAS | 2 | 25020 | |
| HUMRETBLAS | 2 | 25271 | |
| HUMRETBLAS | 2 | 25531 | |
| HUMRETBLAS | 2 | 25535 | |
| HUMRETBLAS | 2 | 25775 | |
| HUMRETBLAS | 2 | 26039 | |
| HUMRETBLAS | 2 | 26183 | |
| HUMRETBLAS | 2 | 26187 | |
| HUMRETBLAS | 2 | 26250 | |
| HUMRETBLAS | 2 | 26804 | |
| HUMRETBLAS | 2 | 26961 | |
| HUMRETBLAS | 2 | 26989 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMRETBLAS | 2 | 27301 | |
| HUMRETBLAS | 2 | 27773 | |
| HUMRETBLAS | 2 | 28172 | |
| HUMRETBLAS | 2 | 28296 | |
| HUMRETBLAS | 2 | 28867 | |
| HUMRETBLAS | 2 | 28986 | |
| HUMRETBLAS | 2 | 29035 | |
| HUMRETBLAS | 2 | 29435 | |
| HUMRETBLAS | 2 | 29833 | |
| HUMRETBLAS | 2 | 30212 | |
| HUMRETBLAS | 2 | 30585 | |
| HUMRETBLAS | 2 | 30920 | |
| HEMRETBLAS | 2 | 30925 | |
| HUMRETBLAS | 2 | 31139 | |
| HUMRETBLAS | 2 | 31253 | |
| HUMRETBLAS | 2 | 31331 | |
| HUMRETBLAS | 2 | 31339 | |
| HUMRETBLAS | 2 | 31965 | |
| HUMRETBLAS | 2 | 32186 | |
| HUMRETBLAS | 2 | 32190 | |
| HUMRETBLAS | 2 | 33074 | |
| HUMRETBLAS | 2 | 33124 | |
| HUMRETBLAS | 2 | 33128 | 76 |
| HUMRETBLAS | 3 | 357 | 49 |
| HUMRETBLAS | 3 | 365 | |
| HUMRETBLAS | 3 | 486 | |
| HUMRETBLAS | 3 | 642 | |
| HUMRETBLAS | 3 | 1313 | |
| HUMRETBLAS | 3 | 1386 | |
| HUMRETBLAS | 3 | 1596 | |
| HUMRETBLAS | 3 | 1658 | |
| HUMRETBLAS | 3 | 1754 | |
| HUMRETBLAS | 3 | 1759 | |
| HUMRETBLAS | 3 | 1831 | |
| HUMRETBLAS | 3 | 1943 | |
| HUMRETBLAS | 3 | 2174 | |
| HUMRETBLAS | 3 | 2193 | |
| HUMRETBLAS | 3 | 2224 | |
| HUMRETBLAS | 3 | 2326 | 2 |
| HUMRETBLAS | 4 | 90 | |
| HUMRETBLAS | 4 | 94 | |
| HUMRETBLAS | 4 | 1172 | |
| HUMRETBLAS | 4 | 1976 | |
| HUMRETBLAS | 4 | 1988 | |
| HUMRETBLAS | 4 | 2167 | |
| HUMRETBLAS | 4 | 2361 | |
| HUMRETBLAS | 4 | 2450 | 2 |
| HUMRETBLAS | 5 | 79 | |
| HUMRETBLAS | 5 | 569 | |
| HUMRETBLAS | 5 | 693 | |
| HUMRETBLAS | 5 | 708 | |
| HUMRETBLAS | 5 | 980 | 2 |
| HUMRETBLAS | 6 | 651 | |
| HUMRETBLAS | 6 | 922 | |
| HUMRETBLAS | 6 | 1343 | |
| HUMRETBLAS | 6 | 1518 | |
| HUMRETBLAS | 6 | 1605 | |
| HUMRETBLAS | 6 | 1791 | |
| HUMRETBLAS | 6 | 2350 | |
| HUMRETBLAS | 6 | 2745 | |
| HUMRETBLAS | 6 | 2787 | |
| HUMRETBLAS | 6 | 2880 | |
| HUMRETBLAS | 6 | 3117 | |
| HUMRETBLAS | 6 | 3550 | |
| HUMRETBLAS | 6 | 3635 | |
| HUMRETBLAS | 6 | 3958 | |
| HUMRETBLAS | 6 | 3969 | |
| HUMRETBLAS | 6 | 4776 | |
| HUMRETBLAS | 6 | 6337 | |
| HUMRETBLAS | 6 | 6445 | |
| HUMRETBLAS | 6 | 6539 | |
| HUMRETBLAS | 6 | 6560 | |
| HUMRETBLAS | 6 | 6577 | |
| HUMRETBLAS | 6 | 6915 | |
| HUMRETBLAS | 6 | 6978 | |
| HUMRETBLAS | 6 | 7194 | |
| HUMRETBLAS | 6 | 7523 | |
| HUMRETBLAS | 6 | 7649 | |
| HUMRETBLAS | 6 | 8712 | |
| HUMRETBLAS | 6 | 8745 | |
| HUMRETBLAS | 6 | 8906 | |
| HUMRETBLAS | 6 | 9339 | |
| HUMRETBLAS | 6 | 9448 | |
| HUMRETBLAS | 6 | 10060 | |
| HUMRETBLAS | 6 | 10183 | 27 |
| HUMRETBLAS | 7 | 136 | |
| HUMRETBLAS | 7 | 612 | |
| HUMRETBLAS | 7 | 718 | |
| HUMRETBLAS | 7 | 1129 | |
| HUMRETBLAS | 7 | 1195 | |
| HUMRETBLAS | 7 | 1278 | |
| HUMRETBLAS | 7 | 1756 | 60 |
| HUMRETBLAS | 8 | 47 | |
| HUMRETBLAS | 8 | 272 | |
| HUMRETBLAS | 8 | 1561 | |
| HUMRETBLAS | 8 | 1647 | |
| HUMRETBLAS | 8 | 1722 | 7 |
| HUMRETBLAS | 9 | 332 | |
| HUMRETBLAS | 9 | 582 | |
| HUMRETBLAS | 9 | 993 | |
| HUMRETBLAS | 9 | 998 | |
| HUMRETBLAS | 9 | 1109 | |
| HUMRETBLAS | 9 | 1364 | |
| HUMRETBLAS | 9 | 1385 | |
| HUMRETBLAS | 9 | 1689 | |
| HUMRETBLAS | 9 | 1918 | |
| HUMRETBLAS | 9 | 1932 | |
| HUMRETBLAS | 9 | 2016 | 7 |
| HUMRETBLAS | 10 | 57 | |
| HUMRETBLAS | 10 | 188 | |
| HUMRETBLAS | 10 | 274 | |
| HUMRETBLAS | 10 | 895 | 20 |
| HUMRETBLAS | 11 | 99 | |
| HUMRETBLAS | 11 | 124 | |
| HUMRETBLAS | 11 | 187 | |
| HUMRETBLAS | 11 | 267 | |
| HUMRETBLAS | 11 | 866 | |
| HUMRETBLAS | 11 | 1424 | |
| HUMRETBLAS | 11 | 1605 | |
| HUMRETBLAS | 11 | 2015 | |
| HUMRETBLAS | 11 | 2604 | |
| HUMRETBLAS | 11 | 2686 | |
| HUMRETBLAS | 11 | 3250 | |
| HUMRETBLAS | 11 | 3269 | |
| HUMRETBLAS | 11 | 3331 | |
| HUMRETBLAS | 11 | 3360 | |
| HUMRETBLAS | 11 | 3821 | |
| HUMRETBLAS | 11 | 4330 | |
| HUMRETBLAS | 11 | 4638 | 20 |
| HUMRETBLAS | 12 | 1023 | |
| HUMRETBLAS | 12 | 1800 | |
| HUMRETBLAS | 12 | 2320 | |
| HUMRETBLAS | 12 | 2775 | |
| HUMRETBLAS | 12 | 3114 | 13 |
| HUMRETBLAS | 13 | 156 | |
| HUMRETBLAS | 13 | 335 | |
| HUMRETBLAS | 13 | 415 | |
| HUMRETBLAS | 13 | 864 | |
| HUMRETBLAS | 13 | 923 | |
| HUMRETBLAS | 13 | 1020 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMRETBLAS | 13 | 1036 | |
| HUMRETBLAS | 13 | 1729 | |
| HUMRETBLAS | 13 | 1904 | |
| HUMRETBLAS | 13 | 1986 | |
| HUMRETBLAS | 13 | 2109 | |
| HUMRETBLAS | 13 | 2259 | |
| HUMRETBLAS | 13 | 2316 | |
| HUMRETBLAS | 13 | 2323 | 7 |
| HUMRETBLAS | 14 | 79 | 7 |
| HUMRETBLAS | 15 | 44 | 2 |
| HUMRETBLAS | 16 | 53 | |
| HUMRETBLAS | 16 | 137 | |
| HUMRETBLAS | 16 | 254 | 21 |
| HUMRETBLAS | 17 | 67 | |
| HUMRETBLAS | 17 | 307 | |
| HUMRETBLAS | 17 | 1432 | |
| HUMRETBLAS | 17 | 1535 | |
| HUMRETBLAS | 17 | 2037 | |
| HUMRETBLAS | 17 | 2061 | |
| HUMRETBLAS | 17 | 2311 | |
| HUMRETBLAS | 17 | 2343 | |
| HUMRETBLAS | 17 | 2436 | |
| HUMRETBLAS | 17 | 3060 | |
| HUMRETBLAS | 17 | 3582 | |
| HUMRETBLAS | 17 | 3664 | |
| HUMRETBLAS | 17 | 3792 | |
| HUMRETBLAS | 17 | 3819 | |
| HUMRETBLAS | 17 | 3929 | |
| HUMRETBLAS | 17 | 4058 | |
| HUMRETBLAS | 17 | 4071 | |
| HUMRETBLAS | 17 | 4487 | |
| HUMRETBLAS | 17 | 4529 | |
| HUMRETBLAS | 17 | 4619 | |
| HUMRETBLAS | 17 | 4655 | |
| HUMRETBLAS | 17 | 4982 | |
| HUMRETBLAS | 17 | 5135 | |
| HUMRETBLAS | 17 | 5165 | |
| HUMRETBLAS | 17 | 5335 | |
| HUMRETBLAS | 17 | 5425 | |
| HUMRETBLAS | 17 | 5606 | |
| HUMRETBLAS | 17 | 5688 | |
| HUMRETBLAS | 17 | 6102 | |
| HUMRETBLAS | 17 | 6253 | |
| HUMRETBLAS | 17 | 6269 | |
| HUMRETBLAS | 17 | 6332 | |
| HUMRETBLAS | 17 | 6902 | |
| HUMRETBLAS | 17 | 6912 | |
| HUMRETBLAS | 17 | 6949 | |
| HUMRETBLAS | 17 | 7045 | |
| HUMRETBLAS | 17 | 7086 | |
| HUMRETBLAS | 17 | 7485 | |
| HUMRETBLAS | 17 | 7579 | |
| HUMRETBLAS | 17 | 7791 | |
| HUMRETBLAS | 17 | 8011 | |
| HUMRETBLAS | 17 | 8057 | |
| HUMRETBLAS | 17 | 8221 | |
| HUMRETBLAS | 17 | 8476 | |
| HUMRETBLAS | 17 | 8565 | |
| HUMRETBLAS | 17 | 9018 | |
| HUMRETBLAS | 17 | 9192 | |
| HUMRETBLAS | 17 | 9408 | |
| HUMRETBLAS | 17 | 9507 | |
| HUMRETBLAS | 17 | 10891 | |
| HUMRETBLAS | 17 | 11063 | |
| HUMRETBLAS | 17 | 11272 | |
| HUMRETBLAS | 17 | 11349 | |
| HUMRETBLAS | 17 | 12127 | |
| HUMRETBLAS | 17 | 12325 | |
| HUMRETBLAS | 17 | 12563 | |
| HUMRETBLAS | 17 | 12587 | |
| HUMRETBLAS | 17 | 13099 | |
| HUMRETBLAS | 17 | 13457 | |
| HUMRETBLAS | 17 | 13550 | |
| HUMRETBLAS | 17 | 13804 | |
| HUMRETBLAS | 17 | 13947 | |
| HUMRETBLAS | 17 | 14025 | |
| HUMRETBLAS | 17 | 15362 | |
| HUMRETBLAS | 17 | 16441 | |
| HUMRETBLAS | 17 | 16550 | |
| HUMRETBLAS | 17 | 16884 | |
| HUMRETBLAS | 17 | 17146 | |
| HUMRETBLAS | 17 | 17336 | |
| HUMRETBLAS | 17 | 17371 | |
| HUMRETBLAS | 17 | 17563 | |
| HUMRETBLAS | 17 | 17664 | |
| HUMRETBLAS | 17 | 17692 | |
| HUMRETBLAS | 17 | 17703 | |
| HUMRETBLAS | 17 | 17802 | |
| HUMRETBLAS | 17 | 18045 | |
| HUMRETBLAS | 17 | 18149 | |
| HUMRETBLAS | 17 | 18246 | |
| HUMRETBLAS | 17 | 18323 | |
| HUMRETBLAS | 17 | 18615 | |
| HUMRETBLAS | 17 | 18722 | |
| HUMRETBLAS | 17 | 18755 | |
| HUMRETBLAS | 17 | 18997 | |
| HUMRETBLAS | 17 | 19061 | |
| HUMRETBLAS | 17 | 19199 | |
| HUMRETBLAS | 17 | 19622 | |
| HUMRETBLAS | 17 | 20232 | |
| HUMRETBLAS | 17 | 20251 | |
| HUMRETBLAS | 17 | 21055 | |
| HUMRETBLAS | 17 | 21065 | |
| HUMRETBLAS | 17 | 21291 | |
| HUMRETBLAS | 17 | 21315 | |
| HUMRETBLAS | 17 | 22295 | |
| HUMRETBLAS | 17 | 22871 | |
| HUMRETBLAS | 17 | 22906 | |
| HUMRETBLAS | 17 | 23344 | |
| HUMRETBLAS | 17 | 23423 | |
| HUMRETBLAS | 17 | 24384 | |
| HUMRETBLAS | 17 | 24591 | |
| HUMRETBLAS | 17 | 24659 | |
| HUMRETBLAS | 17 | 24663 | |
| HUMRETBLAS | 17 | 24667 | |
| HUMRETBLAS | 17 | 24671 | |
| HUMRETBLAS | 17 | 24682 | |
| HUMRETBLAS | 17 | 24719 | |
| HUMRETBLAS | 17 | 24746 | |
| HUMRETBLAS | 17 | 24758 | |
| HUMRETBLAS | 17 | 24793 | |
| HUMRETBLAS | 17 | 25164 | |
| HUMRETBLAS | 17 | 25280 | |
| HUMRETBLAS | 17 | 25365 | |
| HUMRETBLAS | 17 | 25673 | |
| HUMRETBLAS | 17 | 25848 | |
| HUMRETBLAS | 17 | 25871 | |
| HUMRETBLAS | 17 | 25911 | |
| HUMRETBLAS | 17 | 25941 | |
| HUMRETBLAS | 17 | 26193 | |
| HUMRETBLAS | 17 | 26272 | |
| HUMRETBLAS | 17 | 26848 | |
| HUMRETBLAS | 17 | 27069 | |
| HUMRETBLAS | 17 | 27589 | |
| HUMRETBLAS | 17 | 27651 | |
| HUMRETBLAS | 17 | 28395 | |
| HUMRETBLAS | 17 | 28581 | |
| HUMRETBLAS | 17 | 28884 | |
| HUMRETBLAS | 17 | 28926 | |
| HUMRETBLAS | 17 | 28957 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMRETBLAS | 17 | 29117 | |
| HUMRETBLAS | 17 | 29536 | |
| HUMRETBLAS | 17 | 29652 | |
| HUMRETBLAS | 17 | 29905 | |
| HUMRETBLAS | 17 | 29966 | |
| HUMRETBLAS | 17 | 30699 | |
| HUMRETBLAS | 17 | 30796 | |
| HUMRETBLAS | 17 | 31538 | |
| HUMRETBLAS | 17 | 32006 | |
| HUMRETBLAS | 17 | 32657 | |
| HUMRETBLAS | 17 | 32937 | |
| HUMRETBLAS | 17 | 32948 | |
| HUMRETBLAS | 17 | 32964 | |
| HUMRETBLAS | 17 | 33133 | |
| HUMRETBLAS | 17 | 33403 | |
| HUMRETBLAS | 17 | 33407 | |
| HUMRETBLAS | 17 | 34210 | |
| HUMRETBLAS | 17 | 34454 | |
| HUMRETBLAS | 17 | 34496 | |
| HUMRETBLAS | 17 | 34573 | |
| HUMRETBLAS | 17 | 34733 | |
| HUMRETBLAS | 17 | 34737 | |
| HUMRETBLAS | 17 | 35316 | |
| HUMRETBLAS | 17 | 35630 | |
| HUMRETBLAS | 17 | 35724 | |
| HUMRETBLAS | 17 | 35977 | |
| HUMRETBLAS | 17 | 36175 | |
| HUMRETBLAS | 17 | 36822 | |
| HUMRETBLAS | 17 | 37378 | |
| HUMRETBLAS | 17 | 38065 | |
| HUMRETBLAS | 17 | 39487 | |
| HUMRETBLAS | 17 | 39912 | |
| HUMRETBLAS | 17 | 40220 | |
| HUMRETBLAS | 17 | 41552 | |
| HUMRETBLAS | 17 | 41595 | |
| HUMRETBLAS | 17 | 41658 | |
| HUMRETBLAS | 17 | 42232 | |
| HUMRETBLAS | 17 | 42553 | |
| HUMRETBLAS | 17 | 42806 | |
| HUMRETBLAS | 17 | 42868 | |
| HUMRETBLAS | 17 | 43053 | |
| HUMRETBLAS | 17 | 43358 | |
| HUMRETBLAS | 17 | 43431 | |
| HUMRETBLAS | 17 | 43973 | |
| HUMRETBLAS | 17 | 43983 | |
| HUMRETBLAS | 17 | 44065 | |
| HUMRETBLAS | 17 | 44102 | |
| HUMRETBLAS | 17 | 44139 | |
| HUMRETBLAS | 17 | 44440 | |
| HUMRETBLAS | 17 | 44548 | |
| HUMRETBLAS | 17 | 44989 | |
| HUMRETBLAS | 17 | 45259 | |
| HUMRETBLAS | 17 | 45337 | |
| HUMRETBLAS | 17 | 45427 | |
| HUMRETBLAS | 17 | 45670 | |
| HUMRETBLAS | 17 | 45723 | |
| HUMRETBLAS | 17 | 45776 | |
| HUMRETBLAS | 17 | 45829 | |
| HUMRETBLAS | 17 | 45882 | |
| HUMRETBLAS | 17 | 45935 | |
| HUMRETBLAS | 17 | 45988 | |
| HUMRETBLAS | 17 | 46041 | |
| HUMRETBLAS | 17 | 46094 | |
| HUMRETBLAS | 17 | 46147 | |
| HUMRETBLAS | 17 | 46200 | |
| HUMRETBLAS | 17 | 46253 | |
| HUMRETBLAS | 17 | 46306 | |
| HUMRETBLAS | 17 | 46359 | |
| HUMRETBLAS | 17 | 46412 | |
| HUMRETBLAS | 17 | 46465 | |
| HUMRETBLAS | 17 | 46518 | |
| HUMRETBLAS | 17 | 46571 | |
| HUMRETBLAS | 17 | 46624 | |
| HUMRETBLAS | 17 | 46677 | |
| HUMRETBLAS | 17 | 46730 | |
| HUMRETBLAS | 17 | 46783 | |
| HUMRETBLAS | 17 | 46836 | |
| HUMRETBLAS | 17 | 46889 | |
| HUMRETBLAS | 17 | 46942 | |
| HUMRETBLAS | 17 | 46995 | |
| HUMRETBLAS | 17 | 47048 | |
| HUMRETBLAS | 17 | 47101 | |
| HUMRETBLAS | 17 | 47154 | |
| HUMRETBLAS | 17 | 47207 | |
| HUMRETBLAS | 17 | 47288 | |
| HUMRETBLAS | 17 | 47981 | |
| HUMRETBLAS | 17 | 48051 | |
| HUMRETBLAS | 17 | 49244 | |
| HUMRETBLAS | 17 | 49258 | |
| HUMRETBLAS | 17 | 49456 | |
| HUMRETBLAS | 17 | 49898 | |
| HUMRETBLAS | 17 | 50222 | |
| HUMRETBLAS | 17 | 50404 | |
| HUMRETBLAS | 17 | 50670 | |
| HUMRETBLAS | 17 | 51079 | |
| HUMRETBLAS | 17 | 51295 | |
| HUMRETBLAS | 17 | 51806 | |
| HUMRETBLAS | 17 | 51873 | |
| HUMRETBLAS | 17 | 51912 | |
| HUMRETBLAS | 17 | 51999 | |
| HUMRETBLAS | 17 | 52439 | |
| HUMRETBLAS | 17 | 53170 | |
| HUMRETBLAS | 17 | 53542 | |
| HUMRETBLAS | 17 | 53918 | |
| HUMRETBLAS | 17 | 54653 | |
| HUMRETBLAS | 17 | 54847 | |
| HUMRETBLAS | 17 | 54855 | |
| HUMRETBLAS | 17 | 54880 | |
| HUMRETBLAS | 17 | 55456 | |
| HUMRETBLAS | 17 | 55783 | |
| HUMRETBLAS | 17 | 55787 | |
| HUMRETBLAS | 17 | 56379 | |
| HUMRETBLAS | 17 | 57385 | |
| HUMRETBLAS | 17 | 57607 | |
| HUMRETBLAS | 17 | 57819 | |
| HUMRETBLAS | 17 | 58140 | |
| HUMRETBLAS | 17 | 59298 | |
| HUMRETBLAS | 17 | 59458 | |
| HUMRETBLAS | 17 | 60528 | |
| HUMRETBLAS | 17 | 60801 | |
| HUMRETBLAS | 17 | 61241 | |
| HUMRETBLAS | 17 | 61354 | |
| HUMRETBLAS | 17 | 61393 | |
| HUMRETBLAS | 17 | 61636 | |
| HUMRETBLAS | 17 | 62274 | |
| HUMRETBLAS | 17 | 62450 | |
| HUMRETBLAS | 17 | 63013 | |
| HUMRETBLAS | 17 | 63331 | |
| HUMRETBLAS | 17 | 63336 | |
| HUMRETBLAS | 17 | 63694 | |
| HUMRETBLAS | 17 | 64495 | |
| HUMRETBLAS | 17 | 64607 | |
| HUMRETBLAS | 17 | 64825 | |
| HUMRETBLAS | 17 | 64918 | |
| HUMRETBLAS | 17 | 65116 | |
| HUMRETBLAS | 17 | 65273 | |
| HUMRETBLAS | 17 | 65363 | |
| HUMRETBLAS | 17 | 65380 | |
| HUMRETBLAS | 17 | 65639 | |
| HUMRETBLAS | 17 | 65780 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMRETBLAS | 17 | 66225 | |
| HUMRETBLAS | 17 | 66646 | |
| HUMRETBLAS | 17 | 66688 | |
| HUMRETBLAS | 17 | 66813 | |
| HUMRETBLAS | 17 | 67190 | |
| HUMRETBLAS | 17 | 68155 | |
| HUMRETBLAS | 17 | 68496 | |
| HUMRETBLAS | 17 | 69173 | |
| HUMRETBLAS | 17 | 69199 | |
| HUMRETBLAS | 17 | 69414 | |
| HUMRETBLAS | 17 | 69503 | |
| HUMRETBLAS | 17 | 69830 | |
| HUMRETBLAS | 17 | 70242 | |
| HUMRETBLAS | 17 | 70284 | |
| HUMRETBLAS | 17 | 70734 | |
| HUMRETBLAS | 17 | 70768 | |
| HUMRETBLAS | 17 | 71524 | |
| HUMRETBLAS | 17 | 71757 | |
| HUMRETBLAS | 17 | 72006 | |
| HUMRETBLAS | 17 | 72136 | |
| HUMRETBLAS | 17 | 72163 | |
| HUMRETBLAS | 17 | 72386 | |
| HUMRETBLAS | 17 | 72456 | |
| HUMRETBLAS | 17 | 72811 | |
| HUMRETBLAS | 17 | 72892 | |
| HUMRETBLAS | 17 | 73276 | |
| HUMRETBLAS | 17 | 73360 | |
| HUMRETBLAS | 17 | 73364 | |
| HUMRETBLAS | 17 | 73379 | |
| HUMRETBLAS | 17 | 73620 | |
| HUMRETBLAS | 17 | 73624 | |
| HUMRETBLAS | 17 | 74082 | |
| HUMRETBLAS | 17 | 74632 | |
| HUMRETBLAS | 17 | 74903 | |
| HUMRETBLAS | 17 | 75271 | |
| HUMRETBLAS | 17 | 75331 | |
| HUMRETBLAS | 17 | 75452 | |
| HUMRETBLAS | 17 | 75782 | |
| HUMRETBLAS | 17 | 76408 | |
| HUMRETBLAS | 17 | 76669 | |
| HUMRETBLAS | 17 | 76720 | |
| HUMRETBLAS | 17 | 77115 | |
| HUMRETBLAS | 17 | 77285 | |
| HUMRETBLAS | 17 | 78028 | |
| HUMRETBLAS | 17 | 78433 | |
| HUMRETBLAS | 17 | 78475 | |
| HUMRETBLAS | 17 | 78917 | |
| HUMRETBLAS | 17 | 78951 | 10 |
| HUMRETBLAS | 20 | 234 | |
| HUMRETBLAS | 20 | 366 | |
| HUMRETBLAS | 20 | 438 | |
| HUMRETBLAS | 20 | 817 | |
| HUMRETBLAS | 20 | 888 | |
| HUMRETBLAS | 20 | 978 | |
| HUMRETBLAS | 20 | 983 | |
| HUMRETBLAS | 20 | 1062 | |
| HUMRETBLAS | 20 | 1160 | |
| HUMRETBLAS | 20 | 1660 | |
| HUMRETBLAS | 20 | 1905 | |
| HUMRETBLAS | 20 | 2135 | |
| HUMRETBLAS | 20 | 2520 | |
| HUMRETBLAS | 20 | 2702 | |
| HUMRETBLAS | 20 | 2937 | |
| HUMRETBLAS | 20 | 3192 | |
| HUMRETBLAS | 20 | 3511 | |
| HUMRETBLAS | 20 | 3648 | |
| HUMRETBLAS | 20 | 3664 | |
| HUMRETBLAS | 20 | 3692 | 382 |
| HUMRETBLAS | 21 | 3 | |
| HUMRETBLAS | 21 | 16 | |
| HUMRETBLAS | 21 | 57 | |
| HUMRETBLAS | 21 | 118 | |
| HUMRETBLAS | 21 | 184 | |
| HUMRETBLAS | 21 | 258 | |
| HUMRETBLAS | 21 | 478 | |
| HUMRETBLAS | 21 | 992 | |
| HUMRETBLAS | 21 | 1111 | 16 |
| HUMRETBLAS | 23 | 250 | |
| HUMRETBLAS | 23 | 644 | |
| HUMRETBLAS | 23 | 867 | |
| HUMRETBLAS | 23 | 4625 | |
| HUMRETBLAS | 23 | 5629 | |
| HUMRETBLAS | 23 | 5748 | |
| HUMRETBLAS | 23 | 5982 | |
| HUMRETBLAS | 23 | 6107 | |
| HUMRETBLAS | 23 | 6149 | |
| HUMRETBLAS | 23 | 6290 | |
| HUMRETBLAS | 23 | 6385 | |
| HUMRETBLAS | 23 | 6432 | |
| HUMRETBLAS | 23 | 6961 | |
| HUMRETBLAS | 23 | 7155 | |
| HUMRETBLAS | 23 | 7815 | |
| HUMRETBLAS | 23 | 7891 | 17 |
| HUMRETBLAS | 24 | 38 | |
| HUMRETBLAS | 24 | 275 | |
| HUMRETBLAS | 24 | 666 | |
| HUMRETBLAS | 24 | 1072 | |
| HUMRETBLAS | 24 | 1076 | |
| HUMRETBLAS | 24 | 1164 | |
| HUMRETBLAS | 24 | 1759 | |
| HUMRETBLAS | 24 | 2302 | |
| HUMRETBLAS | 24 | 2316 | |
| HUMRETBLAS | 24 | 2365 | |
| HUMRETBLAS | 24 | 2379 | |
| HUMRETBLAS | 24 | 2416 | |
| HUMRETBLAS | 24 | 2841 | |
| HUMRETBLAS | 24 | 3000 | |
| HUMRETBLAS | 24 | 3059 | |
| HUMRETBLAS | 24 | 3125 | 19 |
| HUMRETBLAS | 25 | 367 | |
| HUMRETBLAS | 25 | 420 | 2 |
| HUMRETBLAS | 26 | 101 | |
| HUMRETBLAS | 26 | 136 | |
| HUMRETBLAS | 26 | 186 | |
| HUMRETBLAS | 26 | 531 | |
| HUMRETBLAS | 26 | 653 | |
| HUMRETBLAS | 26 | 665 | |
| HUMRETBLAS | 26 | 1591 | |
| HUMRETBLAS | 26 | 1727 | |
| HUMRETBLAS | 26 | 2122 | 24 |
| HSHLADZA | 2 | 377 | 66 |
| HSHLADZA | 4 | 59 | |
| HSHLADZA | 4 | 134 | |
| HSHLADZA | 4 | 139 | |
| HSHLADZA | 4 | 164 | 197 |
| HUMTBGA | 1 | 222 | |
| HUMTBGA | 1 | 289 | |
| HUMTBGA | 1 | 294 | |
| HUMTBGA | 1 | 527 | |
| HUMTBGA | 1 | 533 | |
| HUMTBGA | 1 | 571 | |
| HUMTBGA | 1 | 937 | 30 |
| HUMTBGA | 2 | 30 | |
| HUMTBGA | 2 | 48 | |
| HUMTBGA | 2 | 361 | |
| HUMTBGA | 2 | 575 | |
| HUMTBGA | 2 | 694 | 2 |
| HUMTBGA | 3 | 165 | |
| HUMTBGA | 3 | 241 | |
| HUMTBGA | 3 | 250 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMTBGA | 3 | 272 | |
| HUMTBGA | 3 | 296 | |
| HUMTBGA | 3 | 332 | 7 |
| HSAT3 | 1 | 8 | |
| HSAT3 | 1 | 178 | |
| HSAT3 | 1 | 1289 | |
| HSAT3 | 1 | 1578 | |
| HSAT3 | 1 | 1627 | |
| HSAT3 | 1 | 2199 | 2 |
| HSAT3 | 2 | 1110 | |
| HSAT3 | 2 | 1511 | |
| HSAT3 | 2 | 1666 | |
| HSAT3 | 2 | 1783 | |
| HSAT3 | 2 | 1999 | |
| HSAT3 | 2 | 2435 | 148 |
| HSAT3 | 3 | 585 | |
| HSAT3 | 3 | 751 | |
| HSAT3 | 3 | 819 | |
| HSAT3 | 3 | 874 | 22 |
| HSAT3 | 4 | 128 | |
| HSAT3 | 4 | 141 | 175 |
| HSAT3 | 5 | 232 | |
| HSAT3 | 5 | 532 | |
| HSAT3 | 5 | 741 | |
| HSAT3 | 5 | 1011 | |
| HSAT3 | 5 | 1142 | |
| HSAT3 | 5 | 1413 | |
| HSAT3 | 5 | 1785 | |
| HSAT3 | 5 | 1827 | |
| HSAT3 | 5 | 1901 | 48 |
| HSAT3 | 6 | 546 | |
| HSAT3 | 6 | 901 | |
| HSAT3 | 6 | 918 | |
| HSAT3 | 6 | 1452 | |
| HSAT3 | 6 | 2153 | |
| HSAT3 | 6 | 2317 | |
| HSAT3 | 6 | 2432 | |
| HSAT3 | 6 | 2634 | |
| HSAT3 | 6 | 2654 | |
| HSAT3 | 6 | 2821 | 25 |
| HUMCACY | 1 | 78 | 109 |
| HSUPA | 1 | 302 | 19 |
| HSUPA | 3 | 90 | |
| HSUPA | 3 | 95 | |
| HSUPA | 3 | 169 | |
| HSUPA | 3 | 174 | |
| HSUPA | 3 | 314 | |
| HSUPA | 3 | 545 | 93 |
| HSUPA | 4 | 4 | 2 |
| HSUPA | 5 | 27 | |
| HSUPA | 5 | 86 | 12 |
| HSUPA | 7 | 526 | 33 |
| HSUPA | 8 | 94 | |
| HSUPA | 8 | 171 | |
| HSUPA | 8 | 201 | 6 |
| HSUPA | 9 | 249 | |
| HSUPA | 9 | 266 | |
| HSUPA | 9 | 309 | |
| HSUPA | 9 | 355 | |
| HSUPA | 9 | 398 | |
| HSUPA | 9 | 704 | |
| HSUPA | 9 | 785 | 73 |
| HUMCNP | 1 | 291 | |
| HSU29953 | 1 | 382 | |
| HSU29953 | 1 | 424 | |
| HSU29953 | 1 | 651 | |
| HSU29953 | 1 | 728 | |
| HSU29953 | 1 | 1110 | |
| HSU29953 | 1 | 1205 | |
| HSU29953 | 1 | 1221 | |
| HSU29953 | 1 | 1696 | |
| HSU29953 | 1 | 2051 | |
| HSU29953 | 1 | 2093 | |
| HSU29953 | 1 | 2125 | |
| HSU29953 | 1 | 2203 | |
| HSU29953 | 1 | 2434 | 190 |
| HSU29953 | 2 | 310 | |
| HSU29953 | 2 | 328 | 72 |
| HSU29953 | 3 | 331 | 270 |
| HSU29953 | 4 | 1567 | |
| HSU29953 | 4 | 1887 | |
| HSU29953 | 4 | 2220 | |
| HSU29953 | 4 | 2401 | |
| HSU29953 | 4 | 2535 | |
| HSU29953 | 4 | 2663 | |
| HSU29953 | 4 | 2665 | 48 |
| HSU29953 | 5 | 133 | |
| HSU29953 | 5 | 228 | |
| HSU29953 | 5 | 568 | |
| HSU29953 | 5 | 779 | |
| HSU29953 | 5 | 894 | |
| HSU29953 | 5 | 1118 | 79 |
| HSU29953 | 6 | 26 | 126 |
| HUMAFP | 2 | 48 | |
| HUMAFP | 2 | 371 | |
| HUMAFP | 2 | 411 | |
| HUMAFP | 2 | 594 | |
| HUMAFP | 2 | 923 | 2 |
| HUMAFP | 3 | 170 | |
| HUMAFP | 3 | 371 | |
| HUMAFP | 3 | 472 | |
| HUMAFP | 3 | 613 | |
| HUMAFP | 3 | 722 | |
| HUMAFP | 3 | 976 | |
| HUMAFP | 3 | 1189 | |
| HUMAFP | 3 | 1230 | |
| HUMAFP | 3 | 1270 | |
| HUMAFP | 3 | 1402 | |
| HUMAFP | 3 | 1408 | |
| HUMAFP | 3 | 1460 | |
| HUMAFP | 3 | 1603 | |
| HUMAFP | 3 | 1637 | |
| HUMAFP | 3 | 1785 | |
| HUMAFP | 3 | 1798 | |
| HUMAFP | 3 | 2247 | 10 |
| HUMAFP | 4 | 18 | |
| HUMAFP | 4 | 144 | |
| HUMAFP | 4 | 168 | |
| HUMAFP | 4 | 537 | |
| HUMAFP | 4 | 983 | |
| HUMAFP | 4 | 1079 | |
| HUMAFP | 4 | 1448 | 2 |
| HUMAFP | 5 | 215 | |
| HUMAFP | 5 | 291 | |
| HUMAFP | 5 | 403 | |
| HUMAFP | 5 | 694 | |
| HUMAFP | 5 | 874 | 43 |
| HUMAFP | 6 | 28 | |
| HUMAFP | 6 | 180 | |
| HUMAFP | 6 | 602 | 2 |
| HUMAFP | 7 | 115 | |
| HUMAFP | 7 | 579 | |
| HUMAFP | 7 | 595 | |
| HUMAFP | 7 | 975 | |
| HUMAFP | 7 | 1280 | |
| HUMAFP | 7 | 1360 | |
| HUMAFP | 7 | 1368 | |
| HUMAFP | 7 | 1397 | |
| HUMAFP | 7 | 1700 | |
| HUMAFP | 7 | 1860 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMAFP | 7 | 2075 | 19 |
| HUMAFP | 8 | 107 | |
| HUMAFP | 8 | 644 | |
| HUMAFP | 8 | 859 | |
| HUMAFP | 8 | 943 | |
| HUMAFP | 8 | 1161 | |
| HUMAFP | 8 | 1309 | 2 |
| HUMAFP | 11 | 279 | |
| HUMAFP | 11 | 1089 | |
| HUMAFP | 11 | 1224 | |
| HUMAFP | 11 | 1228 | |
| HUMAFP | 11 | 1241 | |
| HUMAFP | 11 | 1352 | |
| HUMAFP | 11 | 1360 | |
| HUMAFP | 11 | 1470 | 55 |
| HUMAFP | 12 | 614 | |
| HUMAFP | 12 | 723 | |
| HUMAFP | 12 | 1005 | |
| HUMAFP | 12 | 1014 | 2 |
| HUMAFP | 13 | 258 | |
| HUMAFP | 13 | 280 | |
| HUMAFP | 13 | 865 | |
| HSRODPDE | 1 | 98 | |
| HSRODPDE | 1 | 276 | |
| HSRODPDE | 1 | 499 | |
| HSRODPDE | 1 | 638 | |
| HSRODPDE | 1 | 670 | |
| HSRODPDE | 1 | 795 | |
| HSRODPDE | 1 | 1107 | 2 |
| HSRODPDE | 2 | 215 | 114 |
| HUMINCP | 1 | 252 | |
| HUMINCP | 1 | 1045 | |
| HUMINCP | 1 | 1213 | |
| HUMINCP | 1 | 1459 | 97 |
| HUMINCP | 2 | 45 | |
| HUMINCP | 2 | 85 | |
| HUMINCP | 2 | 101 | |
| HUMINCP | 2 | 105 | |
| HUMINCP | 2 | 173 | |
| HUMINCP | 2 | 195 | |
| HUMINCP | 2 | 229 | |
| HUMINCP | 2 | 315 | |
| HUMINCP | 2 | 337 | |
| HUMINCP | 2 | 355 | |
| HUMINCP | 2 | 421 | |
| HUMINCP | 2 | 920 | |
| HUMINCP | 2 | 995 | |
| HUMINCP | 2 | 999 | 10 |
| AF005058 | 1 | 161 | |
| AF005058 | 1 | 199 | |
| AF005058 | 1 | 299 | |
| AF005058 | 1 | 496 | |
| AF005058 | 1 | 516 | |
| AF005058 | 1 | 767 | |
| AF005058 | 1 | 853 | |
| AF005058 | 1 | 1847 | |
| AF005058 | 1 | 2100 | 202 |
| HUMIFNRF1A | 1 | 108 | |
| HUMIFNRF1A | 1 | 199 | |
| HUMIFNRF1A | 1 | 546 | |
| HUMIFNRF1A | 1 | 647 | |
| HUMIFNRF1A | 1 | 1018 | |
| HUMIFNRF1A | 1 | 1347 | 37 |
| HUMIFNRF1A | 2 | 211 | |
| HUMIFNRF1A | 2 | 698 | 90 |
| HUMIFNRF1A | 3 | 54 | |
| HUMIFNRF1A | 4 | 47 | 85 |
| HUMIFNRF1A | 5 | 34 | |
| HUMIFNRF1A | 6 | 199 | |
| HUMIFNRF1A | 6 | 280 | |
| HUMIFNRF1A | 6 | 397 | |
| HUMIFNRF1A | 6 | 482 | 159 |
| HUMIFNRF1A | 7 | 180 | |
| HUMIFNRF1A | 7 | 239 | |
| HUMIFNRF1A | 7 | 431 | |
| HUMIFNRF1A | 7 | 498 | |
| HUMIFNRF1A | 7 | 516 | |
| HUMIFNRF1A | 7 | 1106 | 34 |
| HUMGCAPB | 1 | 69 | |
| HUMGCAPB | 1 | 148 | |
| HUMGCAPB | 1 | 717 | |
| HUMGCAPB | 1 | 794 | |
| HUMGCAPB | 1 | 805 | |
| HUMGCAPB | 1 | 856 | |
| HUMGCAPB | 1 | 1186 | |
| HUMGCAPB | 1 | 1269 | 58 |
| HUMGCAPB | 3 | 68 | |
| HUMGCAPB | 3 | 84 | 75 |
| S73906 | 1 | 78 | 2 |
| S73906 | 2 | 41 | 2 |
| HSB3A | 1 | 3 | |
| HSB3A | 1 | 96 | |
| HSB3A | 1 | 241 | |
| HSB3A | 1 | 779 | |
| HSB3A | 1 | 811 | |
| HSB3A | 1 | 826 | 2 |
| HSCYCLA | 1 | 28 | |
| HSCYCLA | 1 | 136 | 58 |
| HSCYCLA | 2 | 32 | |
| HSCYCLA | 2 | 102 | |
| HSCYCLA | 2 | 139 | |
| HSCYCLA | 2 | 375 | |
| HSCYCLA | 2 | 547 | |
| HSCYCLA | 2 | 624 | 9 |
| HSCYCLA | 4 | 351 | |
| HSCYCLA | 4 | 369 | 2 |
| HSCYCLA | 5 | 26 | |
| HSCYCLA | 5 | 50 | |
| HSCYCLA | 5 | 389 | 7 |
| HSCYCLA | 6 | 158 | |
| HSCYCLA | 6 | 248 | |
| HSCYCLA | 6 | 411 | |
| HSCYCLA | 6 | 571 | 37 |
| HSCYCLA | 7 | 198 | |
| HSCYCLA | 7 | 314 | 2 |
| HUMHCF2 | 1 | 54 | |
| HUMHCF2 | 1 | 352 | |
| HUMHCF2 | 1 | 440 | |
| HUMHCF2 | 1 | 873 | |
| HUMHCF2 | 1 | 1183 | |
| HUMHCF2 | 1 | 1559 | |
| HUMHCF2 | 1 | 2072 | |
| HUMHCF2 | 1 | 2641 | |
| HUMHCF2 | 1 | 3205 | |
| HUMHCF2 | 1 | 3509 | |
| HUMHCF2 | 1 | 3710 | 66 |
| HUMHCF2 | 2 | 618 | |
| HUMHCF2 | 2 | 700 | |
| HUMHCF2 | 2 | 1160 | |
| HUMHCF2 | 2 | 1171 | |
| HUMHCF2 | 2 | 1303 | 161 |
| HUMHCF2 | 3 | 233 | 154 |
| AC004130 | 1 | 89 | |
| AC004130 | 1 | 808 | |
| AC004130 | 1 | 846 | |
| AC004130 | 1 | 1195 | |
| AC004130 | 1 | 1888 | |
| AC004130 | 1 | 2516 | |
| AC004130 | 1 | 3881 | |
| AC004130 | 1 | 4602 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| AC004130 | 1 | 4628 | |
| AC004130 | 1 | 5040 | |
| AC004130 | 1 | 5646 | |
| AC004130 | 1 | 5787 | |
| AC004130 | 1 | 6004 | |
| AC004130 | 1 | 6037 | |
| AC004130 | 1 | 6078 | |
| AC004130 | 1 | 6118 | |
| AC004130 | 1 | 6197 | |
| AC004130 | 1 | 6230 | |
| AC004130 | 1 | 6461 | |
| AC004130 | 1 | 7028 | |
| AC004130 | 1 | 7044 | |
| AC004130 | 1 | 7363 | |
| AC004130 | 1 | 7434 | |
| AC004130 | 1 | 7469 | |
| AC004130 | 1 | 7473 | |
| AC004130 | 1 | 7862 | |
| AC004130 | 1 | 8377 | |
| AC004130 | 1 | 8534 | |
| AC004130 | 1 | 8538 | |
| AC004130 | 1 | 8740 | |
| AC004130 | 1 | 8819 | |
| AC004130 | 1 | 9501 | |
| AC004130 | 1 | 9940 | |
| AC004130 | 1 | 10090 | |
| AC004130 | 1 | 10246 | |
| AC004130 | 1 | 10310 | |
| AC004130 | 1 | 10536 | |
| AC004130 | 1 | 11002 | |
| AC004130 | 1 | 11032 | |
| AC004130 | 1 | 11464 | |
| AC004130 | 1 | 11636 | |
| AC004130 | 1 | 11828 | |
| AC004130 | 1 | 11950 | |
| AC004130 | 1 | 11974 | |
| AC004130 | 1 | 12145 | |
| AC004130 | 1 | 13149 | |
| AC004130 | 1 | 13356 | |
| AC004130 | 1 | 13504 | |
| AC004130 | 1 | 13576 | |
| AC004130 | 1 | 13688 | |
| AC004130 | 1 | 13845 | |
| AC004130 | 1 | 13964 | |
| AC004130 | 1 | 14076 | |
| AC004130 | 1 | 14082 | |
| AC004130 | 1 | 14112 | |
| AC004130 | 1 | 14126 | |
| AC004130 | 1 | 14189 | |
| AC004130 | 1 | 14282 | |
| AC004130 | 1 | 14561 | |
| AC004130 | 1 | 14587 | |
| AC004130 | 1 | 14704 | |
| AC004130 | 1 | 14794 | |
| AC004130 | 1 | 14932 | |
| AC004130 | 1 | 15027 | |
| AC004130 | 1 | 15071 | |
| AC004130 | 1 | 15276 | |
| AC004130 | 1 | 15423 | |
| AC004130 | 1 | 15430 | |
| AC004130 | 1 | 15443 | |
| AC004130 | 1 | 15590 | |
| AC004130 | 1 | 15676 | |
| AC004130 | 1 | 15807 | |
| AC004130 | 1 | 15856 | |
| AC004130 | 1 | 16032 | |
| AC004130 | 1 | 16214 | |
| AC004130 | 1 | 16337 | |
| AC004130 | 1 | 16699 | |
| AC004130 | 1 | 16708 | |
| AC004130 | 1 | 16733 | |
| AC004130 | 1 | 17257 | |
| AC004130 | 1 | 17399 | |
| AC004130 | 1 | 17411 | |
| AC004130 | 1 | 17682 | |
| AC004130 | 1 | 17973 | |
| AC004130 | 1 | 18127 | |
| AC004130 | 1 | 18449 | |
| AC004130 | 1 | 18629 | |
| AC004130 | 1 | 19443 | |
| AC004130 | 1 | 19531 | |
| AC004130 | 1 | 19695 | |
| AC004130 | 1 | 19837 | |
| AC004130 | 1 | 20380 | |
| AC004130 | 1 | 21567 | |
| AC004130 | 1 | 21571 | |
| AC004130 | 1 | 21784 | |
| AC004130 | 1 | 22419 | |
| AC004130 | 1 | 22535 | |
| AC004130 | 1 | 22563 | |
| AC004130 | 1 | 22906 | |
| AC004130 | 1 | 23300 | |
| AC004130 | 1 | 23524 | |
| AC004130 | 1 | 24337 | |
| AC004130 | 1 | 24442 | |
| AC004130 | 1 | 25052 | |
| AC004130 | 1 | 25569 | |
| AC004130 | 1 | 25775 | |
| AC004130 | 1 | 25787 | |
| AC004130 | 1 | 26174 | |
| AC004130 | 1 | 26306 | |
| AC004130 | 1 | 26496 | |
| AC004130 | 1 | 26704 | |
| AC004130 | 1 | 26819 | |
| AC004130 | 1 | 27422 | |
| AC004130 | 1 | 27698 | |
| AC004130 | 1 | 27710 | |
| AC004130 | 1 | 28103 | |
| AC004130 | 1 | 28171 | |
| AC004130 | 1 | 28540 | |
| AC004130 | 1 | 28645 | |
| AC004130 | 1 | 28767 | |
| AC004130 | 1 | 28885 | |
| AC004130 | 1 | 29390 | |
| AC004130 | 1 | 29440 | |
| AC004130 | 1 | 29790 | |
| AC004130 | 1 | 30250 | |
| AC004130 | 1 | 30526 | |
| AC004130 | 1 | 30953 | |
| AC004130 | 1 | 31020 | |
| AC004130 | 1 | 31256 | |
| AC004130 | 1 | 31506 | 159 |
| AC004130 | 2 | 83 | |
| AC004130 | 2 | 206 | |
| AC004130 | 2 | 850 | |
| AC004130 | 2 | 1505 | |
| AC004130 | 2 | 2097 | |
| AC004130 | 2 | 2105 | |
| AC004130 | 2 | 2197 | |
| AC004130 | 2 | 2371 | |
| AC004130 | 2 | 2760 | |
| AC004130 | 2 | 2828 | |
| AC004130 | 2 | 2908 | |
| AC004130 | 2 | 3239 | 34 |
| AC004130 | 3 | 251 | |
| AC004130 | 3 | 348 | |
| AC004130 | 3 | 359 | |
| AC004130 | 3 | 1064 | |
| AC004130 | 3 | 1076 | |
| AC004130 | 3 | 1639 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| AC004130 | 3 | 1812 | |
| AC004130 | 3 | 1887 | |
| AC004130 | 3 | 2022 | |
| AC004130 | 3 | 2094 | |
| AC004130 | 3 | 2192 | |
| AC004130 | 3 | 2409 | |
| AC004130 | 3 | 3524 | |
| AC004130 | 3 | 3662 | |
| AC004130 | 3 | 3779 | |
| AC004130 | 3 | 3928 | |
| AC004130 | 3 | 4475 | |
| AC004130 | 3 | 4489 | |
| AC004130 | 3 | 5022 | |
| AC004130 | 3 | 5191 | |
| AC004130 | 3 | 5234 | |
| AC004130 | 3 | 5435 | |
| AC004130 | 3 | 5501 | |
| AC004130 | 3 | 5583 | |
| AC004130 | 3 | 5587 | |
| AC004130 | 3 | 6002 | |
| AC004130 | 3 | 6789 | |
| AC004130 | 3 | 7131 | |
| AC004130 | 3 | 7205 | |
| AC004130 | 3 | 7254 | |
| AC004130 | 3 | 7457 | |
| AC004130 | 3 | 7597 | |
| AC004130 | 3 | 7681 | |
| AC004130 | 3 | 7880 | |
| AC004130 | 3 | 7889 | |
| AC004130 | 3 | 8105 | |
| AC004130 | 3 | 8148 | |
| AC004130 | 3 | 8158 | |
| AC004130 | 3 | 8392 | |
| AC004130 | 3 | 8749 | |
| AC004130 | 3 | 8850 | |
| AC004130 | 3 | 9305 | |
| AC004130 | 3 | 10658 | |
| AC004130 | 3 | 10768 | |
| AC004130 | 3 | 11106 | |
| AC004130 | 3 | 11787 | 18 |
| AC004130 | 4 | 125 | |
| AC004130 | 4 | 130 | |
| AC004130 | 4 | 266 | |
| AC004130 | 4 | 464 | |
| AC004130 | 4 | 499 | |
| AC004130 | 4 | 833 | 32 |
| AC004130 | 5 | 140 | |
| AC004130 | 5 | 153 | |
| AC004130 | 5 | 832 | 16 |
| AC004130 | 6 | 284 | |
| AC004130 | 6 | 544 | |
| AC004130 | 6 | 907 | |
| AC004130 | 6 | 911 | |
| AC004130 | 6 | 1247 | |
| AC004130 | 6 | 1399 | |
| AC004130 | 6 | 2130 | |
| AC004130 | 6 | 2523 | |
| AC004130 | 6 | 2699 | |
| AC004130 | 6 | 3332 | |
| AC004130 | 6 | 3384 | |
| AC004130 | 6 | 4036 | |
| AC004130 | 6 | 4153 | |
| AC004130 | 6 | 4213 | |
| AC004130 | 6 | 4964 | |
| AC004130 | 6 | 5118 | |
| AC004130 | 6 | 5469 | |
| AC004130 | 6 | 6663 | |
| AC004130 | 6 | 6804 | |
| AC004130 | 6 | 6871 | |
| AC004130 | 6 | 7564 | |
| AC004130 | 6 | 7653 | |
| AC004130 | 6 | 7730 | |
| AC004130 | 6 | 8940 | |
| AC004130 | 6 | 9167 | |
| AC004130 | 6 | 9414 | |
| AC004130 | 6 | 9426 | 13 |
| AC004130 | 7 | 42 | |
| AC004130 | 7 | 186 | |
| AC004130 | 7 | 450 | |
| AC004130 | 7 | 553 | |
| AC004130 | 7 | 1039 | |
| AC004130 | 7 | 1150 | |
| AC004130 | 7 | 1254 | |
| AC004130 | 7 | 1354 | |
| AC004130 | 7 | 2730 | 7 |
| AC004130 | 8 | 365 | |
| AC004130 | 8 | 754 | |
| AC004130 | 8 | 757 | |
| AC004130 | 8 | 889 | |
| AC004130 | 8 | 1225 | |
| AC004130 | 8 | 1237 | |
| AC004130 | 8 | 1551 | |
| AC004130 | 8 | 1865 | |
| AC004130 | 8 | 2341 | |
| AC004130 | 8 | 2475 | |
| AC004130 | 8 | 3069 | |
| AC004130 | 8 | 3174 | |
| AC004130 | 8 | 3847 | 13 |
| AC004130 | 9 | 3 | |
| AC004130 | 9 | 215 | |
| AC004130 | 9 | 381 | |
| AC004130 | 9 | 520 | |
| AC004130 | 9 | 724 | |
| AC004130 | 9 | 1627 | |
| AC004130 | 9 | 1632 | |
| AC004130 | 9 | 2126 | |
| AC004130 | 9 | 2261 | |
| AC004130 | 9 | 2688 | 37 |
| AC004130 | 10 | 166 | |
| AC004130 | 10 | 358 | |
| AC004130 | 10 | 701 | |
| AC004130 | 10 | 1349 | |
| AC004130 | 10 | 1680 | |
| AC004130 | 10 | 1961 | |
| AC004130 | 10 | 2101 | |
| AC004130 | 10 | 2189 | |
| AC004130 | 10 | 2455 | 90 |
| AC004130 | 11 | 326 | |
| AC004130 | 11 | 858 | |
| AC004130 | 11 | 998 | |
| AC004130 | 11 | 1022 | 164 |
| AC004130 | 12 | 165 | |
| AC004130 | 12 | 455 | |
| AC004130 | 12 | 998 | |
| AC004130 | 12 | 1245 | |
| AC004130 | 12 | 1250 | |
| AC004130 | 12 | 1921 | |
| AC004130 | 12 | 2025 | |
| AC004130 | 12 | 2476 | |
| AC004130 | 12 | 2502 | |
| AC004130 | 12 | 2786 | |
| AC004130 | 12 | 3189 | |
| AC004130 | 12 | 3300 | 42 |
| HSIFNG | 1 | 386 | |
| HSIFNG | 1 | 457 | |
| HSIFNG | 1 | 474 | |
| HSIFNG | 1 | 592 | 16 |
| HSIFNG | 3 | 154 | |
| HSIFNG | 3 | 188 | |
| HSIFNG | 3 | 237 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSIFNG | 3 | 266 | |
| HSIFNG | 3 | 270 | |
| HSIFNG | 3 | 401 | |
| HSIFNG | 3 | 1037 | |
| HSIFNG | 3 | 1455 | |
| HSIFNG | 3 | 1514 | |
| HSIFNG | 3 | 1820 | |
| HSIFNG | 3 | 2102 | |
| HSIFNG | 3 | 2253 | |
| HSIFNG | 3 | 2287 | |
| HSIFNG | 3 | 2306 | 121 |
| HUMNUCLEO | 1 | 172 | |
| HUMNUCLEO | 1 | 445 | |
| HUMNUCLEO | 1 | 691 | |
| HUMNUCLEO | 1 | 827 | 31 |
| HUMNUCLEO | 2 | 98 | |
| HUMNUCLEO | 2 | 177 | |
| HUMNUCLEO | 2 | 848 | |
| HUMNUCLEO | 2 | 937 | 61 |
| HUMNUCLEO | 3 | 41 | |
| HUMNUCLEO | 3 | 232 | |
| HUMNUCLEO | 3 | 473 | |
| HUMNUCLEO | 3 | 517 | |
| HUMNUCLEO | 3 | 653 | 18 |
| HUMNUCLEO | 6 | 112 | |
| HUMNUCLEO | 6 | 346 | |
| HUMNUCLEO | 6 | 506 | |
| HUMNUCLEO | 6 | 531 | |
| HUMNUCLEO | 6 | 806 | 2 |
| HUMNUCLEO | 7 | 3 | |
| HUMNUCLEO | 7 | 163 | |
| HUMNUCLEO | 7 | 191 | |
| HUMNUCLEO | 7 | 521 | 6 |
| HUMNUCLEO | 8 | 19 | |
| HUMNUCLEO | 8 | 111 | |
| HUMNUCLEO | 8 | 165 | |
| HUMNUCLEO | 8 | 234 | |
| HUMNUCLEO | 8 | 261 | |
| HUMNUCLEO | 8 | 308 | |
| HUMNUCLEO | 8 | 398 | 59 |
| HUMNUCLEO | 9 | 106 | |
| HUMNUCLEO | 9 | 110 | |
| HUMNUCLEO | 9 | 267 | |
| HUMNUCLEO | 9 | 319 | |
| HUMNUCLEO | 9 | 356 | 54 |
| HUMNUCLEO | 10 | 60 | |
| HUMNUCLEO | 10 | 200 | 2 |
| HUMNUCLEO | 12 | 14 | |
| HUMNUCLEO | 12 | 180 | |
| HUMNUCLEO | 12 | 347 | 2 |
| HSP53G | 3 | 486 | |
| HSP53G | 3 | 655 | 100 |
| HSP53G | 5 | 62 | |
| HSP53G | 5 | 129 | 37 |
| HSP53G | 6 | 288 | 227 |
| HSP53G | 8 | 309 | |
| HSP53G | 8 | 332 | |
| HSP53G | 8 | 1235 | |
| HSP53G | 8 | 1408 | |
| HSP53G | 8 | 1534 | |
| HSP53G | 8 | 1829 | |
| HSP53G | 8 | 1856 | |
| HSP53G | 8 | 2008 | |
| HSP53G | 8 | 2091 | |
| HSP53G | 8 | 2418 | |
| HSP53G | 8 | 2682 | 115 |
| HSP53G | 9 | 364 | |
| HSP53G | 9 | 405 | |
| HSP53G | 9 | 633 | |
| HSP53G | 9 | 718 | 2 |
| AF039307 | 1 | 311 | |
| AF039307 | 1 | 364 | |
| AF039307 | 1 | 1030 | 51 |
| HSMYBPC3 | 1 | 187 | |
| HSMYBPC3 | 1 | 193 | |
| HSMYBPC3 | 1 | 204 | |
| HSMYBPC3 | 1 | 865 | |
| HSMYBPC3 | 1 | 1006 | 81 |
| HSMYBPC3 | 2 | 83 | |
| HSMYBPC3 | 2 | 433 | |
| HSMYBPC3 | 2 | 577 | 24 |
| HSMYBPC3 | 3 | 81 | |
| HSMYBPC3 | 3 | 127 | |
| HSMYBPC3 | 3 | 143 | 39 |
| HSMYBPC3 | 5 | 47 | |
| HSMYBPC3 | 5 | 420 | |
| HSMYBPC3 | 5 | 529 | |
| HSMYBPC3 | 5 | 1040 | 100 |
| HSMYBPC3 | 6 | 292 | |
| HSMYBPC3 | 6 | 373 | 105 |
| HSMYBPC3 | 7 | 106 | |
| HSMYBPC3 | 7 | 146 | 2 |
| HSMYBPC3 | 9 | 32 | 2 |
| HSMYBPC3 | 10 | 41 | |
| HSMYBPC3 | 10 | 84 | |
| HSMYBPC3 | 10 | 125 | 2 |
| HSMYBPC3 | 12 | 73 | |
| HSMYBPC3 | 12 | 110 | |
| HSMYBPC3 | 12 | 232 | |
| HSMYBPC3 | 12 | 789 | |
| HSMYBPC3 | 12 | 1206 | |
| HSMYBPC3 | 12 | 1298 | 3 |
| HSMYBPC3 | 13 | 34 | 86 |
| HSMYBPC3 | 17 | 167 | |
| HSMYBPC3 | 17 | 208 | 24 |
| HSMYBPC3 | 18 | 16 | |
| HSMYBPC3 | 18 | 654 | |
| HSMYBPC3 | 18 | 701 | 2 |
| HSMYBPC3 | 19 | 20 | 18 |
| HSMYBPC3 | 20 | 236 | |
| HSMYBPC3 | 20 | 750 | |
| HSMYBPC3 | 20 | 780 | |
| HSMYBPC3 | 20 | 806 | |
| HSMYBPC3 | 20 | 826 | |
| HSMYBPC3 | 20 | 840 | |
| HSMYBPC3 | 20 | 897 | |
| HSMYBPC3 | 20 | 947 | 18 |
| HSMYBPC3 | 21 | 40 | |
| HSMYBPC3 | 21 | 146 | 34 |
| HSMYBPC3 | 22 | 14 | |
| HSMYBPC3 | 22 | 104 | |
| HSMYBPC3 | 22 | 428 | 307 |
| HSMYBPC3 | 23 | 297 | |
| HSMYBPC3 | 23 | 435 | |
| HSMYBPC3 | 23 | 636 | |
| HSMYBPC3 | 23 | 699 | 300 |
| HSMYBPC3 | 24 | 24 | |
| HSMYBPC3 | 25 | 728 | |
| HSMYBPC3 | 25 | 984 | 45 |
| HSMYBPC3 | 26 | 300 | |
| HSMYBPC3 | 26 | 472 | 75 |
| HSMYBPC3 | 27 | 66 | |
| HSMYBPC3 | 27 | 247 | |
| HSMYBPC3 | 27 | 319 | |
| HSMYBPC3 | 27 | 500 | |
| HSMYBPC3 | 27 | 581 | |
| HSMYBPC3 | 27 | 831 | 219 |
| HSMHCPU15 | 1 | 81 | |
| HSMHCPU15 | 1 | 852 | |
| HSMHCPU15 | 1 | 1382 | 196 |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSMHCPU15 | 2 | 148 | |
| HSMHCPU15 | 2 | 427 | |
| HSMHCPU15 | 2 | 763 | |
| HSMHCPU15 | 2 | 780 | |
| HSMHCPU15 | 2 | 860 | |
| HSMHCPU15 | 2 | 1029 | 2 |
| HSMHCPU15 | 3 | 272 | |
| HSMHCPU15 | 3 | 397 | 20 |
| HSMHCPU15 | 5 | 495 | |
| HSMHCPU15 | 5 | 523 | |
| HSMHCPU15 | 5 | 797 | 63 |
| HUMMHCD8A | 2 | 503 | 246 |
| HUMMHCD8A | 4 | 239 | |
| HUMMHCD8A | 4 | 343 | |
| HUMMHCD8A | 4 | 370 | 60 |
| HUMMHCD8A | 5 | 572 | |
| HUMMHCD8A | 5 | 1250 | |
| HUMMHCD8A | 5 | 2154 | |
| HUMMHCD8A | 5 | 2208 | |
| HUMMHCD8A | 5 | 2405 | 2 |
| HUMPALC | 1 | 58 | |
| HUMPALC | 1 | 225 | |
| HUMPALC | 1 | 528 | 34 |
| HUMPALC | 2 | 288 | |
| HUMPALC | 2 | 292 | |
| HUMPALC | 2 | 360 | |
| HUMPALC | 2 | 1623 | |
| HUMPALC | 2 | 2005 | 2 |
| HUMPALC | 3 | 105 | |
| HUMPALC | 3 | 418 | |
| HUMPALC | 3 | 574 | |
| HUMPALC | 3 | 821 | |
| HUMPALC | 3 | 1521 | |
| HUMPALC | 3 | 1632 | |
| HUMPALC | 3 | 1931 | |
| HUMPALC | 3 | 2023 | |
| HUMPALC | 3 | 2065 | |
| HUMPALC | 3 | 2154 | |
| HUMPALC | 3 | 2246 | |
| HUMPALC | 3 | 3239 | |
| HUMPALC | 3 | 3248 | 115 |
| HSRA36 | 2 | 415 | |
| HSRA36 | 2 | 833 | |
| HSRA36 | 2 | 878 | |
| HSRA36 | 2 | 894 | |
| HSRA36 | 2 | 1166 | |
| HSRA36 | 2 | 1434 | |
| HSRA36 | 2 | 1519 | |
| HSRA36 | 2 | 1548 | |
| HSRA36 | 2 | 2639 | |
| HSRA36 | 2 | 2915 | |
| HSRA36 | 2 | 3060 | |
| HSRA36 | 2 | 3108 | |
| HSRA36 | 2 | 3298 | 7 |
| HSRA36 | 3 | 82 | |
| HSRA36 | 3 | 270 | |
| HSRA36 | 3 | 702 | |
| HSRA36 | 3 | 930 | |
| HSRA36 | 3 | 963 | |
| HSRA36 | 3 | 1208 | |
| HSRA36 | 3 | 1235 | |
| HSRA36 | 3 | 1435 | |
| HSRA36 | 3 | 1476 | |
| HSRA36 | 3 | 1641 | |
| HSRA36 | 3 | 1937 | |
| HSRA36 | 3 | 1985 | 186 |
| HSFOLA | 1 | 154 | |
| HSFOLA | 1 | 181 | |
| HSFOLA | 1 | 285 | |
| HSFOLA | 1 | 289 | |
| HSFOLA | 1 | 316 | |
| HSFOLA | 1 | 421 | |
| HSFOLA | 1 | 734 | |
| HSFOLA | 1 | 768 | |
| HSFOLA | 1 | 875 | |
| HSFOLA | 1 | 888 | |
| HSFOLA | 1 | 1071 | |
| HSFOLA | 1 | 1210 | |
| HSFOLA | 1 | 1807 | |
| HSFOLA | 1 | 1833 | 139 |
| HSFOLA | 3 | 5 | |
| HSFOLA | 3 | 40 | 12 |
| HUMIL9RA | 1 | 344 | |
| HUMIL9RA | 1 | 514 | |
| HUMIL9RA | 1 | 926 | |
| HUMIL9RA | 1 | 1103 | |
| HUMIL9RA | 1 | 1463 | |
| HUMIL9RA | 1 | 1596 | |
| HUMIL9RA | 1 | 1663 | |
| HUMIL9RA | 1 | 2110 | |
| HUMIL9RA | 1 | 2201 | |
| HUMIL9RA | 1 | 2409 | |
| HUMIL9RA | 1 | 2521 | |
| HUMIL9RA | 1 | 2538 | |
| HUMIL9RA | 1 | 2857 | |
| HUMIL9RA | 1 | 2895 | |
| HUMIL9RA | 1 | 3205 | |
| HUMIL9RA | 1 | 3450 | |
| HUMIL9RA | 1 | 3550 | |
| HUMIL9RA | 1 | 3720 | |
| HUMIL9RA | 1 | 4129 | |
| HUMIL9RA | 1 | 4327 | |
| HUMIL9RA | 1 | 4341 | |
| HUMIL9RA | 1 | 4983 | |
| HUMIL9RA | 1 | 5009 | |
| HUMIL9RA | 1 | 5019 | 42 |
| HUMIL9RA | 2 | 29 | |
| HUMIL9RA | 2 | 259 | |
| HUMIL9RA | 2 | 324 | 27 |
| HUMIL9RA | 3 | 39 | 2 |
| HUMIL9RA | 4 | 85 | |
| HUMIL9RA | 4 | 97 | |
| HUMIL9RA | 4 | 438 | 15 |
| HUMIL9RA | 5 | 122 | |
| HUMIL9RA | 5 | 169 | |
| HUMIL9RA | 5 | 188 | |
| HUMIL9RA | 5 | 227 | |
| HUMIL9RA | 5 | 239 | |
| HUMIL9RA | 5 | 263 | |
| HUMIL9RA | 5 | 311 | |
| HUMIL9RA | 5 | 325 | |
| HUMIL9RA | 5 | 350 | |
| HUMIL9RA | 5 | 392 | |
| HUMIL9RA | 5 | 401 | |
| HUMIL9RA | 5 | 531 | |
| HUMIL9RA | 5 | 537 | |
| HUMIL9RA | 5 | 568 | |
| HUMIL9RA | 5 | 577 | |
| HUMIL9RA | 5 | 603 | |
| HUMIL9RA | 5 | 641 | 58 |
| HUMIL9RA | 6 | 151 | |
| HUMIL9RA | 6 | 421 | |
| HUMIL9RA | 6 | 463 | |
| HUMIL9RA | 6 | 537 | 141 |
| HUMIL9RA | 7 | 3 | |
| HUMIL9RA | 7 | 54 | |
| HUMIL9RA | 7 | 92 | |
| HUMIL9RA | 7 | 103 | |
| HUMIL9RA | 7 | 525 | |
| HUMIL9RA | 7 | 808 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMIL9RA | 7 | 842 | |
| HUMIL9RA | 7 | 873 | |
| HUMIL9RA | 7 | 914 | |
| HUMIL9RA | 7 | 933 | |
| HUMIL9RA | 7 | 1233 | 2 |
| HUMIL9RA | 8 | 247 | |
| HUMIL9RA | 8 | 332 | |
| HUMIL9RA | 8 | 366 | |
| HUMIL9RA | 8 | 617 | |
| HUMIL9RA | 8 | 900 | |
| HUMIL9RA | 8 | 943 | |
| HUMIL9RA | 8 | 1040 | |
| HUMIL9RA | 8 | 1060 | |
| HUMIL9RA | 8 | 1352 | |
| HUMIL9RA | 8 | 1548 | |
| HUMIL9RA | 8 | 1680 | 79 |
| HUMRCP | 1 | 722 | |
| HUMRCP | 1 | 780 | |
| HUMRCP | 1 | 1034 | |
| HUMRCP | 1 | 1340 | |
| HUMRCP | 1 | 1381 | |
| HUMRCP | 1 | 1474 | |
| HUMRCP | 1 | 1562 | |
| HUMRCP | 1 | 1603 | |
| HUMRCP | 1 | 1811 | |
| HUMRCP | 1 | 2160 | |
| HUMRCP | 1 | 2295 | |
| HUMRCP | 1 | 2302 | |
| HUMRCP | 1 | 2322 | |
| HUMRCP | 1 | 2878 | |
| HUMRCP | 1 | 3193 | |
| HUMRCP | 1 | 3322 | |
| HUMRCP | 1 | 3352 | |
| HUMRCP | 1 | 3411 | |
| HUMRCP | 1 | 3848 | |
| HUMRCP | 1 | 3870 | |
| HUMRCP | 1 | 4658 | |
| HUMRCP | 1 | 5225 | |
| HUMRCP | 1 | 5555 | |
| HUMRCP | 1 | 5797 | |
| HUMRCP | 1 | 5839 | |
| HUMRCP | 1 | 6056 | |
| HUMRCP | 1 | 6162 | |
| HUMRCP | 1 | 6723 | |
| HUMRCP | 1 | 6804 | |
| HUMRCP | 1 | 7143 | |
| HUMRCP | 1 | 7428 | |
| HUMRCP | 1 | 7499 | |
| HUMRCP | 1 | 7605 | |
| HUMRCP | 1 | 7947 | |
| HUMRCP | 1 | 8782 | |
| HUMRCP | 1 | 8858 | |
| HUMRCP | 1 | 8967 | |
| HUMRCP | 1 | 8971 | |
| HUMRCP | 1 | 9491 | |
| HUMRCP | 1 | 9688 | |
| HUMRCP | 1 | 10042 | |
| HUMRCP | 1 | 10103 | |
| HUMRCP | 1 | 10233 | |
| HUMRCP | 1 | 11203 | |
| HUMRCP | 1 | 11776 | |
| HUMRCP | 1 | 12158 | |
| HUMRCP | 1 | 12235 | 262 |
| HUMRCP | 2 | 8 | |
| HUMRCP | 2 | 304 | |
| HUMRCP | 2 | 406 | |
| HUMRCP | 2 | 493 | |
| HUMRCP | 2 | 962 | |
| HUMRCP | 2 | 1063 | |
| HUMRCP | 2 | 1135 | |
| HUMRCP | 2 | 1982 | |
| HUMRCP | 2 | 1999 | |
| HUMRCP | 2 | 2198 | |
| HUMRCP | 2 | 2534 | 111 |
| HUMRCP | 3 | 93 | |
| HUMRCP | 3 | 197 | |
| HUMRCP | 3 | 268 | |
| HUMRCP | 3 | 313 | |
| HUMRCP | 3 | 630 | |
| HUMRCP | 3 | 752 | |
| HUMRCP | 3 | 1766 | |
| HUMRCP | 3 | 1802 | |
| HUMRCP | 3 | 1970 | 172 |
| HUMRCP | 4 | 340 | |
| HUMRCP | 4 | 593 | |
| HUMRCP | 4 | 711 | |
| HUMRCP | 4 | 1465 | |
| HUMRCP | 4 | 2022 | |
| HUMRCP | 4 | 2097 | |
| HUMRCP | 4 | 2137 | |
| HUMRCP | 4 | 2227 | |
| HUMRCP | 4 | 2408 | |
| HUMRCP | 4 | 2489 | |
| HUMRCP | 4 | 2840 | 30 |
| HSN44A4 | 1 | 414 | |
| HSN44A4 | 1 | 667 | |
| HSN44A4 | 1 | 678 | |
| HSN44A4 | 1 | 1005 | |
| HSN44A4 | 1 | 1253 | |
| HSN44A4 | 1 | 1262 | |
| HSN44A4 | 1 | 1313 | |
| HSN44A4 | 1 | 1397 | |
| HSN44A4 | 1 | 1455 | |
| HSN44A4 | 1 | 1697 | |
| HSN44A4 | 1 | 1813 | |
| HSN44A4 | 1 | 2168 | |
| HSN44A4 | 1 | 2331 | |
| HSN44A4 | 1 | 2390 | |
| HSN44A4 | 1 | 2534 | |
| HSN44A4 | 1 | 2665 | |
| HSN44A4 | 1 | 2975 | |
| HSN44A4 | 1 | 2993 | |
| HSN44A4 | 1 | 3111 | |
| HSN44A4 | 1 | 3515 | |
| HSN44A4 | 1 | 3556 | |
| HSN44A4 | 1 | 4017 | |
| HSN44A4 | 1 | 4073 | |
| HSN44A4 | 1 | 4272 | |
| HSN44A4 | 1 | 4933 | |
| HSN44A4 | 1 | 5064 | |
| HSN44A4 | 1 | 5602 | |
| HSN44A4 | 1 | 5908 | |
| HSN44A4 | 1 | 6351 | |
| HSN44A4 | 1 | 6530 | |
| HSN44A4 | 1 | 6534 | |
| HSN44A4 | 1 | 6789 | |
| HSN44A4 | 1 | 6824 | |
| HSN44A4 | 1 | 6852 | |
| HSN44A4 | 1 | 6872 | |
| HSN44A4 | 1 | 6930 | |
| HSN44A4 | 1 | 6983 | |
| HSN44A4 | 1 | 7091 | |
| HSN44A4 | 1 | 7360 | |
| HSN44A4 | 1 | 7801 | |
| HSN44A4 | 1 | 7998 | |
| HSN44A4 | 1 | 8629 | |
| HSN44A4 | 1 | 8746 | |
| HSN44A4 | 1 | 8750 | |
| HSN44A4 | 1 | 8869 | |
| HSN44A4 | 1 | 8892 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSN44A4 | 1 | 8994 | |
| HSN44A4 | 1 | 9301 | |
| HSN44A4 | 1 | 9769 | |
| HSN44A4 | 1 | 10278 | |
| HSN44A4 | 1 | 10282 | |
| HSN44A4 | 1 | 11035 | 277 |
| HUMDODDA | 2 | 43 | |
| HUMDODDA | 2 | 610 | |
| HUMDODDA | 2 | 683 | |
| HUMDODDA | 2 | 767 | |
| HUMDODDA | 2 | 1194 | |
| HUMDODDA | 2 | 1336 | |
| HUMDODDA | 2 | 1505 | |
| HUMDODDA | 2 | 1663 | |
| HUMDODDA | 2 | 1776 | |
| HUMDODDA | 2 | 1792 | |
| HUMDODDA | 2 | 2064 | |
| HUMDODDA | 2 | 2325 | |
| HUMDODDA | 2 | 2693 | |
| HUMDODDA | 2 | 2871 | |
| HUMDODDA | 2 | 2897 | |
| HUMDODDA | 2 | 2909 | |
| HUMDODDA | 2 | 3137 | |
| HUMDODDA | 2 | 3158 | |
| HUMDODDA | 2 | 3270 | |
| HUMDODDA | 2 | 3274 | |
| HUMDODDA | 2 | 3323 | |
| HUMDODDA | 2 | 3621 | |
| HUMDODDA | 2 | 3637 | |
| HUMDODDA | 2 | 3973 | |
| HUMDODDA | 2 | 4156 | |
| HUMDODDA | 2 | 4246 | |
| HUMDODDA | 2 | 4392 | |
| HUMDODDA | 2 | 4506 | |
| HUMDODDA | 2 | 4520 | |
| HUMDODDA | 2 | 4716 | |
| HUMDODDA | 2 | 5193 | |
| HUMDODDA | 2 | 5660 | |
| HUMDODDA | 2 | 5948 | |
| HUMDODDA | 2 | 6070 | |
| HUMDODDA | 2 | 6457 | |
| HUMDODDA | 2 | 7019 | |
| HUMDODDA | 2 | 7092 | |
| HUMDODDA | 2 | 7538 | |
| HUMDODDA | 2 | 7671 | |
| HUMDODDA | 2 | 8209 | |
| HUMDODDA | 2 | 8255 | |
| HUMDODDA | 2 | 8841 | |
| HUMDODDA | 2 | 8876 | |
| HUMDODDA | 2 | 8965 | |
| HUMDODDA | 2 | 9116 | |
| HUMDODDA | 2 | 9164 | |
| HUMDODDA | 2 | 9168 | |
| HUMDODDA | 2 | 9262 | |
| HUMDODDA | 2 | 9670 | |
| HUMDODDA | 2 | 9677 | |
| HUMDODDA | 2 | 9770 | |
| HUMDODDA | 2 | 10083 | |
| HUMDODDA | 2 | 10776 | |
| HUMDODDA | 2 | 10915 | |
| HUMDODDA | 2 | 10990 | |
| HUMDODDA | 2 | 11076 | |
| HUMDODDA | 2 | 11287 | |
| HUMDODDA | 2 | 12601 | |
| HUMDODDA | 2 | 12898 | |
| HUMDODDA | 2 | 12902 | |
| HUMDODDA | 2 | 13364 | |
| HUMDODDA | 2 | 13454 | |
| HUMDODDA | 2 | 13818 | |
| HUMDODDA | 2 | 14002 | |
| HUMDODDA | 2 | 14414 | |
| HUMDODDA | 2 | 14424 | |
| HUMDODDA | 2 | 14489 | |
| HUMDODDA | 2 | 14977 | |
| HUMDODDA | 2 | 15070 | |
| HUMDODDA | 2 | 15201 | |
| HUMDODDA | 2 | 15266 | |
| HUMDODDA | 2 | 15280 | |
| HUMDODDA | 2 | 15687 | |
| HUMDODDA | 2 | 16753 | |
| HUMDODDA | 2 | 16794 | |
| HUMDODDA | 2 | 16858 | |
| HUMDODDA | 2 | 17030 | |
| HUMDODDA | 2 | 17146 | |
| HUMDODDA | 2 | 17378 | |
| HUMDODDA | 2 | 17765 | |
| HUMDODDA | 2 | 18167 | |
| HUMDODDA | 2 | 18424 | |
| HUMDODDA | 2 | 18626 | |
| HUMDODDA | 2 | 18733 | |
| HUMDODDA | 2 | 18880 | |
| HUMDODDA | 2 | 19272 | |
| HUMDODDA | 2 | 19364 | |
| HUMDODDA | 2 | 20096 | 30 |
| HUMDODDA | 3 | 348 | |
| HUMDODDA | 3 | 750 | |
| HUMDODDA | 3 | 1254 | |
| HUMDODDA | 3 | 1318 | 54 |
| HUMDODDA | 4 | 105 | |
| HUMDODDA | 4 | 234 | |
| HUMDODDA | 4 | 308 | |
| HUMDODDA | 4 | 623 | |
| HUMDODDA | 4 | 740 | |
| HUMDODDA | 4 | 847 | |
| HUMDODDA | 4 | 1100 | |
| HUMDODDA | 4 | 1443 | 2 |
| HSU79415 | 1 | 274 | |
| HSU79415 | 1 | 526 | |
| HSU79415 | 1 | 621 | |
| HSU79415 | 1 | 804 | |
| HSU79415 | 1 | 1046 | |
| HSU79415 | 1 | 1149 | |
| HSU79415 | 1 | 1271 | |
| HSU79415 | 1 | 1323 | |
| HSU79415 | 1 | 1327 | |
| HSU79415 | 1 | 1624 | 87 |
| HSU53874 | 1 | 173 | |
| HSU53874 | 2 | 48 | 2 |
| HSU53874 | 3 | 306 | |
| HSU53874 | 3 | 376 | 13 |
| HSU53874 | 4 | 148 | 100 |
| HSUBA52G | 2 | 187 | |
| HSUBA52G | 2 | 400 | |
| HSUBA52G | 2 | 484 | |
| HSUBA52G | 2 | 918 | 48 |
| HSGGL2 | 2 | 507 | |
| HSGGL2 | 2 | 519 | |
| HSGGL2 | 2 | 785 | 136 |
| HUMFABP | 2 | 329 | |
| HUMFABP | 2 | 385 | |
| HUMFABP | 2 | 421 | |
| HUMFABP | 2 | 572 | |
| HUMFABP | 2 | 629 | |
| HUMFABP | 2 | 828 | |
| HUMFABP | 2 | 921 | 88 |
| HUMPROT2 | 1 | 127 | 36 |
| HSU20982 | 1 | 119 | |
| HSU20982 | 1 | 291 | |
| HSU20982 | 1 | 320 | |
| HSU20982 | 1 | 386 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSU20982 | 1 | 470 | 102 |
| HSU20982 | 2 | 136 | |
| HSU20982 | 2 | 253 | 139 |
| AF017178 | 1 | 205 | |
| AF017178 | 1 | 223 | |
| AF017178 | 1 | 294 | |
| AF017178 | 1 | 691 | |
| AF017178 | 1 | 907 | |
| AF017178 | 1 | 931 | |
| AF017178 | 1 | 1404 | 90 |
| AF017178 | 4 | 34 | |
| AF017178 | 5 | 252 | |
| AF017178 | 5 | 642 | 286 |
| AF017178 | 7 | 95 | |
| AF017178 | 9 | 185 | 145 |
| AF017178 | 11 | 94 | |
| AF017178 | 11 | 176 | |
| AF017178 | 11 | 265 | 13 |
| AF017178 | 25 | 10 | |
| AF017178 | 25 | 228 | 13 |
| AF017178 | 28 | 31 | 34 |
| AF017178 | 29 | 103 | |
| AF017178 | 29 | 181 | |
| AF017178 | 29 | 407 | 73 |
| AF017178 | 30 | 31 | 91 |
| AF017178 | 31 | 161 | 82 |
| AF017178 | 32 | 209 | 25 |
| AF017178 | 37 | 57 | 79 |
| AF017178 | 39 | 33 | |
| AF017178 | 45 | 157 | 121 |
| HSU32576 | 1 | 9 | |
| HSU32576 | 1 | 39 | |
| HSU32576 | 1 | 45 | |
| HSU32576 | 1 | 82 | |
| HSU32576 | 1 | 130 | |
| HSU32576 | 1 | 219 | |
| HSU32576 | 1 | 311 | |
| HSU32576 | 1 | 315 | |
| HSU32576 | 1 | 356 | |
| HSU32576 | 1 | 370 | |
| HSU32576 | 1 | 950 | |
| HSU32576 | 1 | 1154 | |
| HSU32576 | 1 | 1394 | |
| HSU32576 | 1 | 1470 | |
| HSU32576 | 1 | 1717 | |
| HSU32576 | 1 | 1882 | |
| HSU32576 | 1 | 1948 | |
| HSU32576 | 1 | 1966 | 48 |
| HSU70732 | 1 | 96 | |
| HSU70732 | 4 | 65 | 31 |
| HSU70732 | 5 | 83 | |
| HSU70732 | 5 | 125 | |
| HSU70732 | 5 | 167 | |
| HSU70732 | 5 | 209 | |
| HSU70732 | 8 | 26 | 34 |
| HSU70732 | 9 | 24 | 31 |
| HUMAK1 | 1 | 679 | |
| HUMAK1 | 1 | 773 | |
| HUMAK1 | 1 | 1212 | |
| HUMAK1 | 1 | 1484 | 48 |
| HUMAK1 | 3 | 18 | 313 |
| HUMAK1 | 4 | 90 | |
| HUMAK1 | 4 | 128 | |
| HUMAK1 | 4 | 1388 | |
| HUMAK1 | 4 | 1942 | |
| HUMAK1 | 4 | 1998 | |
| HUMAK1 | 4 | 2048 | |
| HUMAK1 | 4 | 2069 | |
| HUMAK1 | 4 | 2283 | |
| HUMAK1 | 4 | 2299 | |
| HUMAK1 | 4 | 2317 | |
| HUMAK1 | 4 | 2548 | |
| HUMAK1 | 4 | 2911 | |
| HUMAK1 | 4 | 2948 | 10 |
| HUMAK1 | 5 | 184 | |
| HUMAK1 | 5 | 208 | 187 |
| HSHOX3D | 1 | 266 | 9 |
| HSU40391 | 2 | 50 | |
| HSU40391 | 2 | 219 | 115 |
| HSU07807 | 1 | 282 | |
| HSU07807 | 1 | 880 | |
| HSU07807 | 1 | 1225 | |
| HSU07807 | 1 | 1233 | |
| HSU07807 | 1 | 1723 | |
| HSU07807 | 1 | 1810 | |
| HSU07807 | 1 | 1894 | |
| HSU07807 | 1 | 1978 | |
| HSU07807 | 1 | 2071 | |
| HSU07807 | 1 | 2115 | 6 |
| HSU07807 | 2 | 8 | |
| HSU07807 | 2 | 122 | |
| HSU07807 | 2 | 963 | 120 |
| AF032455 | 1 | 3 | |
| AF032455 | 1 | 417 | |
| AF032455 | 1 | 708 | |
| AF032455 | 1 | 1248 | |
| AF032455 | 1 | 1443 | |
| AF032455 | 1 | 1454 | |
| AF032455 | 1 | 1498 | |
| AF032455 | 1 | 1502 | |
| AF032455 | 1 | 1681 | |
| AF032455 | 1 | 1826 | |
| AF032455 | 1 | 1985 | |
| AF032455 | 1 | 2064 | |
| AF032455 | 1 | 2315 | |
| AF032455 | 1 | 2384 | |
| AF032455 | 1 | 2422 | |
| AF032455 | 1 | 2569 | |
| AF032455 | 1 | 2819 | |
| AF032455 | 1 | 3029 | |
| AF032455 | 1 | 3187 | |
| AF032455 | 1 | 3267 | |
| AF032455 | 1 | 3540 | |
| AF032455 | 1 | 3552 | |
| AF032455 | 1 | 3851 | |
| AF032455 | 1 | 3900 | |
| AF032455 | 1 | 3934 | |
| AF032455 | 1 | 3963 | |
| AF032455 | 1 | 4068 | |
| AF032455 | 1 | 4510 | |
| AF032455 | 1 | 5206 | |
| AF032455 | 1 | 5459 | |
| AF032455 | 1 | 5514 | |
| AF032455 | 1 | 5932 | |
| AF032455 | 1 | 6487 | |
| AF032455 | 1 | 6526 | 79 |
| AF032455 | 3 | 94 | |
| AF032455 | 3 | 435 | |
| AF032455 | 3 | 636 | |
| AF032455 | 3 | 701 | |
| AF032455 | 3 | 929 | 79 |
| AF032455 | 4 | 367 | 238 |
| AF032455 | 6 | 274 | 2 |
| AF032455 | 7 | 75 | |
| AF032455 | 7 | 218 | |
| AF032455 | 7 | 270 | 49 |
| AF032455 | 8 | 463 | |
| AF032455 | 8 | 583 | |
| AF032455 | 8 | 865 | |
| AF032455 | 8 | 1017 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| AF032455 | 8 | 1406 | 112 |
| AF032455 | 9 | 143 | |
| AF032455 | 9 | 240 | |
| AF032455 | 9 | 300 | |
| AF032455 | 9 | 310 | |
| AF032455 | 9 | 433 | |
| AF032455 | 9 | 599 | |
| AF032455 | 9 | 608 | |
| AF032455 | 9 | 1296 | |
| AF032455 | 9 | 1412 | |
| AF032455 | 9 | 1594 | |
| AF032455 | 9 | 2294 | 2 |
| HSU22027 | 2 | 17 | 87 |
| HSU22027 | 3 | 89 | 195 |
| HSU22027 | 4 | 298 | 199 |
| HSU22027 | 5 | 179 | |
| HSU22027 | 5 | 193 | |
| HSU22027 | 5 | 382 | |
| HSU22027 | 5 | 386 | |
| HSU22027 | 5 | 499 | |
| HSU22027 | 5 | 575 | |
| HSU22027 | 5 | 584 | 76 |
| HSU22027 | 6 | 101 | |
| HSU22027 | 6 | 196 | 141 |
| HSU22027 | 8 | 139 | |
| HSU22027 | 8 | 520 | 81 |
| HUMSOMI | 1 | 74 | |
| HUMSOMI | 1 | 219 | |
| HUMSOMI | 1 | 568 | |
| HUMSOMI | 1 | 689 | 97 |
| HUMMKXX | 3 | 182 | |
| HUMMKXX | 3 | 422 | |
| HUMMKXX | 3 | 443 | 87 |
| AC002366 | 1 | 23 | |
| AC002366 | 1 | 160 | |
| AC002366 | 1 | 462 | |
| AC002366 | 1 | 548 | |
| AC002366 | 1 | 660 | |
| AC002366 | 1 | 985 | |
| AC002366 | 1 | 1536 | 22 |
| AC002366 | 2 | 326 | |
| AC002366 | 2 | 337 | |
| AC002366 | 2 | 403 | |
| AC002366 | 2 | 685 | |
| AC002366 | 2 | 812 | |
| AC002366 | 2 | 857 | |
| AC002366 | 2 | 1148 | |
| AC002366 | 2 | 1197 | |
| AC002366 | 2 | 1317 | |
| AC002366 | 2 | 1343 | |
| AC002366 | 2 | 1366 | 40 |
| AC002366 | 4 | 185 | |
| AC002366 | 4 | 209 | |
| AC002366 | 4 | 630 | |
| AC002366 | 4 | 799 | |
| AC002366 | 4 | 1234 | 13 |
| HSCYTOK20 | 1 | 70 | |
| HSCYTOK20 | 1 | 417 | |
| HSCYTOK20 | 1 | 471 | |
| HSCYTOK20 | 1 | 1542 | |
| HSCYTOK20 | 1 | 1853 | 73 |
| HSCYTOK20 | 2 | 133 | |
| HSCYTOK20 | 2 | 203 | |
| HSCYTOK20 | 2 | 315 | |
| HSCYTOK20 | 2 | 384 | |
| HSCYTOK20 | 2 | 396 | |
| HSCYTOK20 | 2 | 450 | |
| HSCYTOK20 | 2 | 936 | |
| HSCYTOK20 | 2 | 1209 | |
| HSCYTOK20 | 2 | 1351 | |
| HSCYTOK20 | 2 | 1646 | 2 |
| HSCYTOK20 | 3 | 171 | 163 |
| HSCYTOK20 | 4 | 20 | 16 |
| HSCYTOK20 | 5 | 331 | |
| HSCYTOK20 | 5 | 556 | |
| HSCYTOK20 | 5 | 780 | |
| HSCYTOK20 | 5 | 859 | 13 |
| HSCYTOK20 | 6 | 517 | 2 |
| HSCYTOK20 | 7 | 77 | |
| HSCYTOK20 | 7 | 594 | 9 |
| AF005260 | 1 | 214 | |
| AF005260 | 1 | 358 | |
| AF005260 | 1 | 449 | |
| AF005260 | 1 | 969 | 168 |
| HSU50136 | 1 | 85 | |
| HSU50136 | 1 | 342 | |
| HSU50136 | 1 | 840 | |
| HSU50136 | 1 | 968 | |
| HSU50136 | 1 | 972 | |
| HSU50136 | 1 | 1285 | 18 |
| HSV698D2 | 1 | 597 | |
| HSV698D2 | 1 | 1054 | |
| HSV698D2 | 1 | 1146 | |
| HSV698D2 | 1 | 1411 | |
| HSV698D2 | 1 | 1715 | |
| HSV698D2 | 1 | 2138 | |
| HSV698D2 | 1 | 2354 | |
| HSV698D2 | 1 | 2358 | |
| HSV698D2 | 1 | 2751 | |
| HSV698D2 | 1 | 2948 | |
| HSV698D2 | 1 | 2990 | |
| HSV698D2 | 1 | 2994 | |
| HSV698D2 | 1 | 3270 | |
| HSV698D2 | 1 | 3910 | |
| HSV698D2 | 1 | 3923 | |
| HSV698D2 | 1 | 3941 | |
| HSV698D2 | 1 | 3975 | |
| HSV698D2 | 1 | 4307 | |
| HSV698D2 | 1 | 4359 | |
| HSV698D2 | 1 | 4518 | |
| HSV698D2 | 1 | 4739 | |
| HSV698D2 | 1 | 4837 | |
| HSV698D2 | 1 | 5434 | |
| HSV698D2 | 1 | 5504 | |
| HSV698D2 | 1 | 5697 | |
| HSV698D2 | 1 | 6198 | |
| HSV698D2 | 1 | 6232 | |
| HSV698D2 | 1 | 6521 | |
| HSV698D2 | 1 | 6646 | |
| HSV698D2 | 1 | 6749 | |
| HSV698D2 | 1 | 6796 | |
| HSV698D2 | 1 | 7279 | |
| HSV698D2 | 1 | 7890 | |
| HSV698D2 | 1 | 8055 | |
| HSV698D2 | 1 | 8405 | 18 |
| HSV698D2 | 2 | 256 | |
| HSV698D2 | 2 | 298 | |
| HSV698D2 | 2 | 400 | |
| HSV698D2 | 2 | 463 | |
| HSV698D2 | 2 | 472 | |
| HSV698D2 | 2 | 540 | |
| HSV698D2 | 2 | 564 | 2 |
| HSV698D2 | 3 | 145 | |
| HSV698D2 | 3 | 355 | |
| HSV698D2 | 3 | 424 | 28 |
| HSV698D2 | 4 | 84 | 75 |
| HSV698D2 | 5 | 168 | |
| HSV698D2 | 5 | 253 | |
| HSV698D2 | 5 | 404 | |
| HSV698D2 | 5 | 481 | 82 |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSV698D2 | 6 | 27 | |
| HSV698D2 | 6 | 222 | |
| HSV698D2 | 6 | 598 | |
| HSV698D2 | 6 | 693 | |
| HSV698D2 | 6 | 872 | 7 |
| HUMALIFA | 1 | 508 | |
| HUMALIFA | 1 | 909 | |
| HUMALIFA | 1 | 1066 | |
| HUMALIFA | 1 | 1277 | |
| HUMALIFA | 1 | 1320 | |
| HUMALIFA | 1 | 1609 | 507 |
| HUMALIFA | 2 | 224 | |
| HUMALIFA | 2 | 369 | 49 |
| HSU80184 | 1 | 783 | |
| HSU80184 | 1 | 787 | |
| HSU80184 | 1 | 1083 | |
| HSU80184 | 1 | 1177 | |
| HSU80184 | 1 | 1287 | |
| HSU80184 | 1 | 1503 | |
| HSU80184 | 1 | 1564 | 286 |
| HSU80184 | 2 | 46 | |
| HSU80184 | 2 | 150 | |
| HSU80184 | 2 | 169 | 40 |
| HSU80184 | 3 | 218 | |
| HSU80184 | 3 | 620 | |
| HSU80184 | 3 | 758 | |
| HSU80184 | 3 | 840 | |
| HSU80184 | 3 | 1142 | |
| HSU80184 | 3 | 1170 | 61 |
| HSU80184 | 4 | 140 | 34 |
| HSU80184 | 5 | 28 | |
| HSU80184 | 5 | 61 | |
| HSU80184 | 6 | 299 | 41 |
| HSU80184 | 7 | 197 | 156 |
| HSU80184 | 9 | 399 | 59 |
| HSU80184 | 10 | 123 | |
| HSU80184 | 10 | 192 | |
| HSU80184 | 10 | 266 | |
| HSU80184 | 10 | 279 | 85 |
| HSU80184 | 11 | 96 | 54 |
| HSU80184 | 12 | 128 | 67 |
| HSU80184 | 13 | 95 | |
| HSU80184 | 13 | 102 | 214 |
| HSU80184 | 14 | 79 | |
| HSU80184 | 14 | 92 | |
| HSU80184 | 14 | 165 | |
| HSU80184 | 14 | 391 | |
| HSU80184 | 14 | 632 | |
| HSU80184 | 14 | 677 | |
| HSU80184 | 14 | 936 | |
| HSU80184 | 14 | 1265 | 13 |
| HSU80184 | 15 | 5 | 2 |
| HSU80184 | 16 | 14 | |
| HSU80184 | 16 | 19 | |
| HSU80184 | 16 | 64 | 2 |
| HSU80184 | 18 | 462 | 145 |
| HSU80184 | 20 | 274 | |
| HSU80184 | 23 | 67 | |
| HSU80184 | 23 | 87 | 112 |
| HSU80184 | 29 | 25 | |
| HSRPII145 | 4 | 25 | |
| HSRPII145 | 4 | 30 | 2 |
| HSRPII145 | 5 | 68 | |
| HSRPII145 | 5 | 144 | 22 |
| HSU23143 | 1 | 270 | 64 |
| HSU23143 | 3 | 187 | 2 |
| HSU23143 | 5 | 42 | |
| HSU23143 | 5 | 50 | |
| HSU23143 | 6 | 230 | 122 |
| HSU23143 | 8 | 11 | |
| HSU23143 | 8 | 18 | 21 |
| HSU51243 | 1 | 172 | |
| HSU51243 | 1 | 550 | |
| HSU51243 | 1 | 1609 | |
| HSU51243 | 1 | 1851 | |
| HSU51243 | 1 | 1865 | 33 |
| HSU51243 | 2 | 73 | 2 |
| HSU51243 | 3 | 3 | |
| HSU51243 | 3 | 569 | |
| HSU51243 | 3 | 713 | |
| HSU51243 | 3 | 879 | |
| HSU51243 | 3 | 1406 | 262 |
| HSU51243 | 4 | 231 | |
| HSU51243 | 4 | 249 | |
| HSU51243 | 4 | 419 | 2 |
| HSU51243 | 5 | 254 | |
| HSU51243 | 5 | 271 | |
| HSU51243 | 5 | 458 | |
| HSU51243 | 5 | 482 | 22 |
| HSU51243 | 6 | 115 | |
| HSU51243 | 6 | 183 | |
| HSU51243 | 6 | 231 | |
| HSU51243 | 6 | 450 | 2 |
| H5U51243 | 7 | 107 | |
| HSU51243 | 7 | 619 | |
| HSU51243 | 7 | 741 | |
| HSU51243 | 7 | 915 | |
| HSU51243 | 7 | 1125 | |
| HSU51243 | 7 | 1254 | |
| HSU51243 | 7 | 1801 | |
| HSU51243 | 7 | 1875 | |
| HSU51243 | 7 | 2039 | |
| HSU51243 | 7 | 2098 | |
| HSU51243 | 7 | 2310 | |
| HSU51243 | 7 | 2453 | |
| HSU51243 | 7 | 2812 | |
| HSU51243 | 7 | 2866 | |
| HSU51243 | 7 | 2951 | |
| HSU51243 | 7 | 3004 | 13 |
| HSU51243 | 8 | 341 | |
| HSU51243 | 8 | 845 | |
| HSU51243 | 8 | 916 | |
| HSU51243 | 8 | 944 | |
| HSU51243 | 8 | 1065 | |
| HSU51243 | 8 | 1099 | |
| HSU51243 | 8 | 1106 | |
| HSU51243 | 8 | 1110 | |
| HSU51243 | 8 | 1251 | |
| HSU51243 | 8 | 1519 | |
| HSU51243 | 8 | 1578 | |
| HSU51243 | 8 | 1973 | |
| HSU51243 | 8 | 2347 | |
| HSU51243 | 8 | 2457 | 2 |
| HSU51243 | 9 | 99 | |
| HSU51243 | 9 | 1197 | |
| HSU51243 | 9 | 1833 | |
| HSU51243 | 9 | 1988 | 115 |
| HSU51243 | 10 | 323 | |
| HSU51243 | 10 | 680 | |
| HSU51243 | 10 | 807 | |
| HSU51243 | 10 | 1038 | 164 |
| HSU51243 | 11 | 317 | 79 |
| HSU51243 | 12 | 1109 | |
| HSU51243 | 12 | 1474 | 8 |
| HSU51243 | 13 | 228 | |
| HSU51243 | 13 | 508 | |
| HSU51243 | 13 | 756 | |
| HSU51243 | 13 | 900 | 22 |
| AF015812 | 1 | 33 | |
| AF015812 | 1 | 363 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| AF015812 | 1 | 376 | |
| AF015812 | 1 | 380 | |
| AF015812 | 1 | 964 | |
| AF015812 | 1 | 993 | |
| AF015812 | 1 | 1240 | 11 |
| AF015812 | 2 | 69 | |
| AF015812 | 2 | 130 | |
| AF015812 | 2 | 154 | |
| AF015812 | 2 | 228 | 97 |
| AF015812 | 4 | 52 | |
| AF015812 | 4 | 77 | 25 |
| AF015812 | 5 | 93 | |
| AF015812 | 5 | 194 | 46 |
| AF015812 | 8 | 68 | |
| AF015812 | 8 | 82 | |
| AF015812 | 8 | 286 | 2 |
| AF015812 | 9 | 177 | 8 |
| AF015812 | 11 | 214 | |
| AF015812 | 11 | 418 | |
| AF015812 | 11 | 534 | |
| AF015812 | 11 | 587 | |
| AF015812 | 11 | 679 | |
| AF015812 | 11 | 750 | 3 |
| AF015812 | 12 | 73 | 12 |
| D87675 | 1 | 1051 | |
| D87675 | 1 | 1345 | |
| D87675 | 1 | 1680 | |
| D87675 | 1 | 1968 | |
| D87675 | 1 | 2126 | |
| D87675 | 1 | 2169 | |
| D87675 | 1 | 2173 | |
| D87675 | 1 | 2237 | |
| D87675 | 1 | 2290 | |
| D87675 | 1 | 2384 | |
| D87675 | 1 | 2398 | |
| D87675 | 1 | 2400 | |
| D87675 | 1 | 3252 | |
| D87675 | 1 | 3329 | |
| D87675 | 1 | 3449 | |
| D87675 | 1 | 3768 | |
| D87675 | 1 | 4424 | |
| D87675 | 1 | 5028 | |
| D87675 | 1 | 5235 | |
| D87675 | 1 | 5331 | |
| D87675 | 1 | 6606 | |
| D87675 | 1 | 6876 | |
| D87675 | 1 | 6920 | |
| D87675 | 1 | 7290 | |
| D87675 | 1 | 7595 | |
| D87675 | 1 | 7626 | |
| D87675 | 1 | 7754 | |
| D87675 | 1 | 8495 | |
| D87675 | 1 | 9122 | |
| D87675 | 1 | 9146 | |
| D87675 | 1 | 9180 | |
| D87675 | 1 | 9246 | |
| D87675 | 1 | 9327 | |
| D87675 | 1 | 9364 | |
| D87675 | 1 | 9807 | |
| D87675 | 1 | 10080 | |
| D87675 | 1 | 10427 | |
| D87675 | 1 | 10446 | |
| D87675 | 1 | 11251 | |
| D87675 | 1 | 11595 | |
| D87675 | 1 | 11611 | |
| D87675 | 1 | 11772 | |
| D87675 | 1 | 12071 | |
| D87675 | 1 | 12148 | |
| D87675 | 1 | 12358 | |
| D87675 | 1 | 12812 | |
| D87675 | 1 | 12887 | |
| D87675 | 1 | 13245 | |
| D87675 | 1 | 13263 | |
| D87675 | 1 | 14188 | |
| D87675 | 1 | 14395 | |
| D87675 | 1 | 14976 | |
| D87675 | 1 | 15529 | |
| D87675 | 1 | 16194 | |
| D87675 | 1 | 16285 | |
| D87675 | 1 | 16495 | |
| D87675 | 1 | 16962 | |
| D87675 | 1 | 17002 | |
| D87675 | 1 | 17325 | |
| D87675 | 1 | 17420 | |
| D87675 | 1 | 17671 | |
| D87675 | 1 | 18137 | |
| D87675 | 1 | 18653 | |
| D87675 | 1 | 18770 | |
| D87675 | 1 | 18781 | |
| D87675 | 1 | 18785 | |
| D87675 | 1 | 18873 | |
| D87675 | 1 | 18881 | |
| D87675 | 1 | 19079 | |
| D87675 | 1 | 19197 | |
| D87675 | 1 | 19299 | |
| D87675 | 1 | 19546 | |
| D87675 | 1 | 19577 | |
| D87675 | 1 | 19612 | |
| D87675 | 1 | 19997 | |
| D87675 | 1 | 20394 | |
| D87675 | 1 | 20646 | |
| D87675 | 1 | 20778 | |
| D87675 | 1 | 21232 | |
| D87675 | 1 | 21396 | |
| D87675 | 1 | 21425 | |
| D87675 | 1 | 21674 | |
| D87675 | 1 | 22287 | |
| D87675 | 1 | 22378 | |
| D87675 | 1 | 22382 | |
| D87675 | 1 | 22445 | |
| D87675 | 1 | 22621 | |
| D87675 | 1 | 22770 | |
| D87675 | 1 | 23242 | |
| D87675 | 1 | 23431 | |
| D87675 | 1 | 23509 | |
| D87675 | 1 | 23657 | |
| D87675 | 1 | 23661 | |
| D87675 | 1 | 24309 | |
| D87675 | 1 | 24351 | |
| D87675 | 1 | 24816 | |
| D87675 | 1 | 24833 | |
| D87675 | 1 | 25039 | |
| D87675 | 1 | 25054 | |
| D87675 | 1 | 25316 | |
| D87675 | 1 | 25393 | |
| D87675 | 1 | 25591 | |
| D87675 | 1 | 25623 | |
| D87675 | 1 | 25816 | |
| D87675 | 1 | 26263 | |
| D87675 | 1 | 26403 | |
| D87675 | 1 | 26561 | |
| D87675 | 1 | 26687 | |
| D87675 | 1 | 26858 | |
| D87675 | 1 | 27010 | |
| D87675 | 1 | 27021 | |
| D87675 | 1 | 27380 | |
| D87675 | 1 | 27417 | |
| D87675 | 1 | 28189 | |
| D87675 | 1 | 28598 | |
| D87675 | 1 | 28613 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| D87675 | 1 | 28621 | |
| D87675 | 1 | 28923 | |
| D87675 | 1 | 29012 | |
| D87675 | 1 | 30207 | |
| D87675 | 1 | 30326 | |
| D87675 | 1 | 30409 | |
| D87675 | 1 | 30413 | |
| D87675 | 1 | 30455 | |
| D87675 | 1 | 30794 | |
| D87675 | 1 | 31215 | |
| D87675 | 1 | 31272 | |
| D87675 | 1 | 31702 | |
| D87675 | 1 | 32791 | |
| D87675 | 1 | 32795 | |
| D87675 | 1 | 33386 | |
| D87675 | 1 | 33860 | |
| D87675 | 1 | 33950 | |
| D87675 | 1 | 34267 | |
| D87675 | 1 | 34556 | |
| D87675 | 1 | 34689 | |
| D87675 | 1 | 34851 | |
| D87675 | 1 | 35061 | |
| D87675 | 1 | 35289 | |
| D87675 | 1 | 35578 | |
| D87675 | 1 | 35813 | |
| D87675 | 1 | 36103 | |
| D87675 | 1 | 36109 | |
| D87675 | 1 | 36166 | |
| D87675 | 1 | 37230 | |
| D87675 | 1 | 37662 | |
| D87675 | 1 | 37782 | |
| D87675 | 1 | 37884 | |
| D87675 | 1 | 38061 | |
| D87675 | 1 | 38293 | |
| D87675 | 1 | 38359 | |
| D87675 | 1 | 38430 | |
| D87675 | 1 | 38597 | |
| D87675 | 1 | 39080 | |
| D87675 | 1 | 39294 | |
| D87675 | 1 | 39339 | |
| D87675 | 1 | 39370 | |
| D87675 | 1 | 39479 | |
| D87675 | 1 | 40150 | |
| D87675 | 1 | 40587 | |
| D87675 | 1 | 40649 | |
| D87675 | 1 | 40945 | |
| D87675 | 1 | 40979 | |
| D87675 | 1 | 41105 | |
| D87675 | 1 | 41145 | |
| D87675 | 1 | 41900 | |
| D87675 | 1 | 42145 | |
| D87675 | 1 | 42537 | |
| D87675 | 1 | 42765 | |
| D87675 | 1 | 42836 | |
| D87675 | 1 | 42934 | |
| D87675 | 1 | 43037 | |
| D87675 | 1 | 43523 | |
| D87675 | 1 | 43882 | |
| D87675 | 1 | 43912 | |
| D87675 | 1 | 43967 | |
| D87675 | 1 | 44011 | |
| D87675 | 1 | 44106 | |
| D87675 | 1 | 44112 | |
| D87675 | 1 | 44153 | |
| D87675 | 1 | 44676 | |
| D87675 | 1 | 44763 | |
| D87675 | 1 | 45443 | |
| D87675 | 1 | 45742 | |
| D87675 | 1 | 45887 | |
| D87675 | 1 | 46235 | |
| D87675 | 1 | 46240 | |
| D87675 | 1 | 46741 | |
| D87675 | 1 | 47356 | |
| D87675 | 1 | 47423 | |
| D87675 | 1 | 47451 | |
| D87675 | 1 | 47455 | |
| D87675 | 1 | 47500 | |
| D87675 | 1 | 47657 | |
| D87675 | 1 | 47751 | |
| D87675 | 1 | 47981 | |
| D87675 | 1 | 48184 | |
| D87675 | 1 | 48201 | |
| D87675 | 1 | 48291 | |
| D87675 | 1 | 48433 | |
| D87675 | 1 | 48612 | |
| D87675 | 1 | 49018 | |
| D87675 | 1 | 49286 | |
| D87675 | 1 | 50571 | |
| D87675 | 1 | 50653 | |
| D87675 | 1 | 50839 | |
| D87675 | 1 | 50983 | |
| D87675 | 1 | 51195 | |
| D87675 | 1 | 51316 | |
| D87675 | 1 | 51327 | |
| D87675 | 1 | 51558 | |
| D87675 | 1 | 51569 | |
| D87675 | 1 | 51766 | |
| D87675 | 1 | 51810 | |
| D87675 | 1 | 52391 | |
| D87675 | 1 | 52479 | |
| D87675 | 1 | 53037 | |
| D87675 | 1 | 53144 | |
| D87675 | 1 | 53631 | |
| D87675 | 1 | 53662 | |
| D87675 | 1 | 54084 | |
| D87675 | 1 | 54374 | |
| D87675 | 1 | 54525 | |
| D87675 | 1 | 54688 | |
| D87675 | 1 | 54735 | 67 |
| D87675 | 2 | 712 | |
| D87675 | 2 | 1094 | |
| D87675 | 2 | 1422 | |
| D87675 | 2 | 2140 | |
| D87675 | 2 | 2409 | |
| D87675 | 2 | 2510 | |
| D87675 | 2 | 2963 | |
| D87675 | 2 | 3627 | |
| D87675 | 2 | 3740 | |
| D87675 | 2 | 4038 | |
| D87675 | 2 | 4454 | |
| D87675 | 2 | 4818 | |
| D87675 | 2 | 4850 | |
| D87675 | 2 | 5019 | |
| D87675 | 2 | 5060 | |
| D87675 | 2 | 5127 | |
| D87675 | 2 | 5138 | |
| D87675 | 2 | 5191 | |
| D87675 | 2 | 5313 | |
| D87675 | 2 | 5479 | |
| D87675 | 2 | 5545 | |
| D87675 | 2 | 5575 | |
| D87675 | 2 | 5720 | |
| D87675 | 2 | 6155 | |
| D87675 | 2 | 7071 | |
| D87675 | 2 | 7671 | |
| D87675 | 2 | 7785 | |
| D87675 | 2 | 7919 | |
| D87675 | 2 | 8206 | |
| D87675 | 2 | 8460 | |
| D87675 | 2 | 9171 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| D87675 | 2 | 9347 | |
| D87675 | 2 | 9656 | |
| D87675 | 2 | 9813 | |
| D87675 | 2 | 11007 | |
| D87675 | 2 | 11097 | |
| D87675 | 2 | 11716 | |
| D87675 | 2 | 13225 | |
| D87675 | 2 | 13715 | |
| D87675 | 2 | 14250 | |
| D87675 | 2 | 14254 | |
| D87675 | 2 | 14306 | |
| D87675 | 2 | 15737 | |
| D87675 | 2 | 15810 | |
| D87675 | 2 | 15874 | |
| D87675 | 2 | 16182 | |
| D87675 | 2 | 16244 | |
| D87675 | 2 | 16402 | |
| D87675 | 2 | 16443 | |
| D87675 | 2 | 16447 | |
| D87675 | 2 | 16901 | |
| D87675 | 2 | 17761 | |
| D87675 | 2 | 18122 | |
| D87675 | 2 | 18271 | |
| D87675 | 2 | 18545 | |
| D87675 | 2 | 18958 | |
| D87675 | 2 | 19667 | |
| D87675 | 2 | 19744 | |
| D87675 | 2 | 19749 | |
| D87675 | 2 | 20019 | |
| D87675 | 2 | 20168 | |
| D87675 | 2 | 20974 | |
| D87675 | 2 | 21150 | |
| D87675 | 2 | 21723 | 91 |
| D87675 | 3 | 919 | |
| D87675 | 3 | 1067 | |
| D87675 | 3 | 1084 | |
| D87675 | 3 | 1495 | |
| D87675 | 3 | 1514 | |
| D87675 | 3 | 1856 | |
| D87675 | 3 | 2431 | |
| D87675 | 3 | 2574 | |
| D87675 | 3 | 2888 | |
| D87675 | 3 | 3257 | |
| D87675 | 3 | 3591 | |
| D87675 | 3 | 3705 | |
| D87675 | 3 | 3954 | |
| D87675 | 3 | 4048 | |
| D87675 | 3 | 4260 | |
| D87675 | 3 | 4865 | |
| D87675 | 3 | 5332 | |
| D87675 | 3 | 5470 | |
| D87675 | 3 | 5728 | |
| D87675 | 3 | 6026 | |
| D87675 | 3 | 6216 | |
| D87675 | 3 | 6470 | |
| D87675 | 3 | 6650 | |
| D87675 | 3 | 7077 | |
| D87675 | 3 | 7138 | |
| D87675 | 3 | 7329 | |
| D87675 | 3 | 7361 | |
| D87675 | 3 | 7532 | |
| D87675 | 3 | 7917 | |
| D87675 | 3 | 7942 | |
| D87675 | 3 | 8661 | |
| D87675 | 3 | 8719 | |
| D87675 | 3 | 8810 | |
| D87675 | 3 | 9296 | |
| D87675 | 3 | 9648 | |
| D87675 | 3 | 9719 | |
| D87675 | 3 | 9859 | |
| D87675 | 3 | 9901 | |
| D87675 | 3 | 10036 | |
| D87675 | 3 | 10192 | |
| D87675 | 3 | 10647 | |
| D87675 | 3 | 10982 | |
| D87675 | 3 | 11116 | |
| D87675 | 3 | 12179 | |
| D87675 | 3 | 12692 | |
| D87675 | 3 | 13400 | |
| D87675 | 3 | 13586 | |
| D87675 | 3 | 13621 | |
| D87675 | 3 | 13799 | |
| D87675 | 3 | 13817 | |
| D87675 | 3 | 14665 | |
| D87675 | 3 | 15078 | |
| D87675 | 3 | 15560 | |
| D87675 | 3 | 15625 | |
| D87675 | 3 | 15654 | |
| D87675 | 3 | 15675 | |
| D87675 | 3 | 15755 | |
| D87675 | 3 | 16143 | |
| D87675 | 3 | 17310 | |
| D87675 | 3 | 17328 | |
| D87675 | 3 | 17524 | |
| D87675 | 3 | 17758 | |
| D87675 | 3 | 17976 | |
| D87675 | 3 | 18005 | |
| D87675 | 3 | 18182 | |
| D87675 | 3 | 18608 | |
| D87675 | 3 | 18898 | |
| D87675 | 3 | 19660 | |
| D87675 | 3 | 20231 | |
| D87675 | 3 | 20385 | |
| D87675 | 3 | 21014 | |
| D87675 | 3 | 21073 | |
| D87675 | 3 | 21709 | |
| D87675 | 3 | 21817 | |
| D87675 | 3 | 22177 | |
| D87675 | 3 | 22445 | |
| D87675 | 3 | 22625 | |
| D87675 | 3 | 22657 | |
| D87675 | 3 | 23426 | |
| D87675 | 3 | 23447 | |
| D87675 | 3 | 23468 | |
| D87675 | 3 | 23601 | |
| D87675 | 3 | 23605 | |
| D87675 | 3 | 23814 | |
| D87675 | 3 | 23913 | |
| D87675 | 3 | 23941 | |
| D87675 | 3 | 24005 | |
| D87675 | 3 | 24576 | |
| D87675 | 3 | 24666 | |
| D87675 | 3 | 24843 | |
| D87675 | 3 | 25956 | |
| D87675 | 3 | 25989 | |
| D87675 | 3 | 26122 | |
| D87675 | 3 | 26848 | |
| D87675 | 3 | 26933 | |
| D87675 | 3 | 27065 | |
| D87675 | 3 | 27497 | |
| D87675 | 3 | 27539 | |
| D87675 | 3 | 27613 | |
| D87675 | 3 | 27857 | |
| D87675 | 3 | 28055 | |
| D87675 | 3 | 28059 | |
| D87675 | 3 | 28063 | |
| D87675 | 3 | 28109 | |
| D87675 | 3 | 28615 | |
| D87675 | 3 | 28619 | |
| D87675 | 3 | 29119 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| D87675 | 3 | 29467 | |
| D87675 | 3 | 29710 | |
| D87675 | 3 | 29760 | |
| D87675 | 3 | 29771 | |
| D87675 | 3 | 30391 | |
| D87675 | 3 | 31175 | |
| D87675 | 3 | 31598 | |
| D87675 | 3 | 31907 | |
| D87675 | 3 | 32149 | |
| D87675 | 3 | 32275 | |
| D87675 | 3 | 32441 | |
| D87675 | 3 | 32468 | |
| D87675 | 3 | 32773 | |
| D87675 | 3 | 32873 | |
| D87675 | 3 | 33091 | |
| D87675 | 3 | 33389 | |
| D87675 | 3 | 33492 | |
| D87675 | 3 | 33790 | |
| D87675 | 3 | 33930 | |
| D87675 | 3 | 33938 | |
| D87675 | 3 | 33952 | |
| D87675 | 3 | 34283 | |
| D87675 | 3 | 34376 | |
| D87675 | 3 | 34685 | |
| D87675 | 3 | 34734 | |
| D87675 | 3 | 35904 | |
| D87675 | 3 | 36087 | |
| D87675 | 3 | 36284 | |
| D87675 | 3 | 36538 | 75 |
| D87675 | 4 | 615 | |
| D87675 | 4 | 671 | |
| D87675 | 4 | 693 | |
| D87675 | 4 | 704 | |
| D87675 | 4 | 1510 | |
| D87675 | 4 | 1619 | |
| D87675 | 4 | 1647 | 34 |
| D87675 | 5 | 258 | |
| D87675 | 5 | 367 | |
| D87675 | 5 | 807 | |
| D87675 | 5 | 1641 | |
| D87675 | 5 | 2017 | |
| D87675 | 5 | 2021 | |
| D87675 | 5 | 2243 | |
| D87675 | 5 | 2368 | |
| D87675 | 5 | 2408 | |
| D87675 | 5 | 2446 | |
| D87675 | 5 | 2644 | |
| D87675 | 5 | 2853 | |
| D87675 | 5 | 3014 | |
| D87675 | 5 | 3217 | |
| D87675 | 5 | 3420 | |
| D87675 | 5 | 3534 | |
| D87675 | 5 | 3850 | |
| D87675 | 5 | 3863 | |
| D87675 | 5 | 4096 | |
| D87675 | 5 | 4154 | |
| D87675 | 5 | 4387 | |
| D87675 | 5 | 4405 | |
| D87675 | 5 | 4782 | |
| D87675 | 5 | 4937 | |
| D87675 | 5 | 5021 | |
| D87675 | 5 | 5088 | |
| D87675 | 5 | 5134 | |
| D87675 | 5 | 5192 | |
| D87675 | 5 | 5214 | |
| D87675 | 5 | 5275 | |
| D87675 | 5 | 5563 | |
| D87675 | 5 | 6211 | |
| D87675 | 5 | 6659 | |
| D87675 | 5 | 6750 | |
| D87675 | 5 | 7154 | |
| D87675 | 5 | 7201 | |
| D87675 | 5 | 7334 | |
| D87675 | 5 | 7421 | |
| D87675 | 5 | 8068 | |
| D87675 | 5 | 8728 | |
| D87675 | 5 | 8896 | |
| D87675 | 5 | 8952 | |
| D87675 | 5 | 9196 | |
| D87675 | 5 | 9290 | |
| D87675 | 5 | 10049 | |
| D87675 | 5 | 10356 | |
| D87675 | 5 | 10817 | |
| D87675 | 5 | 10911 | |
| D87675 | 5 | 11348 | |
| D87675 | 5 | 11368 | |
| D87675 | 5 | 11968 | |
| D87675 | 5 | 11972 | |
| D87675 | 5 | 12454 | |
| D87675 | 5 | 12520 | |
| D87675 | 5 | 13082 | |
| D87675 | 5 | 13491 | |
| D87675 | 5 | 14068 | |
| D87675 | 5 | 14090 | |
| D87675 | 5 | 14324 | |
| D87675 | 5 | 14442 | |
| D87675 | 5 | 14579 | |
| D87675 | 5 | 14903 | |
| D87675 | 5 | 16467 | |
| D87675 | 5 | 16854 | |
| D87675 | 5 | 18380 | |
| D87675 | 5 | 18422 | |
| D87675 | 5 | 18631 | |
| D87675 | 5 | 19300 | |
| D87675 | 5 | 19452 | |
| D87675 | 5 | 19511 | |
| D87675 | 5 | 19549 | |
| D87675 | 5 | 20031 | |
| D87675 | 5 | 20312 | |
| D87675 | 5 | 20546 | |
| D87675 | 5 | 20913 | |
| D87675 | 5 | 21064 | |
| D87675 | 5 | 21571 | |
| D87675 | 5 | 21617 | |
| D87675 | 5 | 22305 | |
| D87675 | 5 | 22886 | |
| D87675 | 5 | 23161 | |
| D87675 | 5 | 23246 | |
| D87675 | 5 | 23255 | |
| D87675 | 5 | 23429 | |
| D87675 | 5 | 23840 | |
| D87675 | 5 | 24195 | |
| D87675 | 5 | 24393 | |
| D87675 | 5 | 24436 | |
| D87675 | 5 | 24508 | |
| D87675 | 5 | 24822 | |
| D87675 | 5 | 25215 | |
| D87675 | 5 | 25682 | |
| D87675 | 5 | 25701 | |
| D87675 | 5 | 25886 | |
| D87675 | 5 | 26060 | |
| D87675 | 5 | 26334 | |
| D87675 | 5 | 26928 | |
| D87675 | 5 | 27041 | |
| D87675 | 5 | 27752 | |
| D87675 | 5 | 27756 | |
| D87675 | 5 | 27784 | |
| D87675 | 5 | 27926 | |
| D87675 | 5 | 27948 | |
| D87675 | 5 | 27998 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| D87675 | 5 | 28020 | |
| D87675 | 5 | 28070 | |
| D87675 | 5 | 28092 | |
| D87675 | 5 | 28274 | |
| D87675 | 5 | 28460 | |
| D87675 | 5 | 28850 | 2 |
| D87675 | 6 | 300 | |
| D87675 | 6 | 325 | |
| D87675 | 6 | 382 | |
| D87675 | 6 | 450 | |
| D87675 | 6 | 798 | |
| D87675 | 6 | 838 | |
| D87675 | 6 | 898 | |
| D87675 | 6 | 1877 | |
| D87675 | 6 | 2124 | |
| D87675 | 6 | 2442 | |
| D87675 | 6 | 2449 | |
| D87675 | 6 | 2633 | |
| D87675 | 6 | 2731 | |
| D87675 | 6 | 2738 | |
| D87675 | 6 | 3236 | |
| D87675 | 6 | 3369 | |
| D87675 | 6 | 3415 | |
| D87675 | 6 | 3448 | |
| D87675 | 6 | 3483 | |
| D87675 | 6 | 3563 | |
| D87675 | 6 | 3825 | |
| D87675 | 6 | 3895 | |
| D87675 | 6 | 4401 | |
| D87675 | 6 | 4766 | |
| D87675 | 6 | 5037 | |
| D87675 | 6 | 5109 | |
| D87675 | 6 | 5558 | |
| D87675 | 6 | 5576 | |
| D87675 | 6 | 6074 | |
| D87675 | 6 | 6132 | |
| D87675 | 6 | 6225 | |
| D87675 | 6 | 6281 | |
| D87675 | 6 | 6314 | |
| D87675 | 6 | 6647 | |
| D87675 | 6 | 6900 | |
| D87675 | 6 | 7032 | |
| D87675 | 6 | 7431 | |
| D87675 | 6 | 7885 | |
| D87675 | 6 | 7936 | |
| D87675 | 6 | 8086 | |
| D87675 | 6 | 8606 | |
| D87675 | 6 | 8741 | |
| D87675 | 6 | 8783 | |
| D87675 | 6 | 8992 | |
| D87675 | 6 | 9084 | |
| D87675 | 6 | 9718 | |
| D87675 | 6 | 9741 | |
| D87675 | 6 | 9878 | |
| D87675 | 6 | 9892 | |
| D87675 | 6 | 10017 | |
| D87675 | 6 | 10138 | |
| D87675 | 6 | 10515 | |
| D87675 | 6 | 10938 | |
| D87675 | 6 | 11326 | |
| D87675 | 6 | 11455 | |
| D87675 | 6 | 11584 | |
| D87675 | 6 | 11677 | |
| D87675 | 6 | 11791 | |
| D87675 | 6 | 12002 | |
| D87675 | 6 | 12020 | |
| D87675 | 6 | 12951 | |
| D87675 | 6 | 13539 | |
| D87675 | 6 | 13594 | |
| D87675 | 6 | 13861 | |
| D87675 | 6 | 14582 | |
| D87675 | 6 | 15539 | |
| D87675 | 6 | 15623 | |
| D87675 | 6 | 15734 | |
| D87675 | 6 | 15784 | |
| D87675 | 6 | 16239 | |
| D87675 | 6 | 16361 | |
| D87675 | 6 | 16509 | |
| D87675 | 6 | 16539 | |
| D87675 | 6 | 16644 | |
| D87675 | 6 | 17072 | |
| D87675 | 6 | 17315 | |
| D87675 | 6 | 17389 | |
| D87675 | 6 | 17481 | |
| D87675 | 6 | 18029 | |
| D87675 | 6 | 18041 | |
| D87675 | 6 | 18178 | |
| D87675 | 6 | 18603 | |
| D87675 | 6 | 18821 | |
| D87675 | 6 | 18968 | |
| D87675 | 6 | 19077 | |
| D87675 | 6 | 19107 | |
| D87675 | 6 | 19406 | |
| D87675 | 6 | 19548 | |
| D87675 | 6 | 19835 | |
| D87675 | 6 | 19908 | |
| D87675 | 6 | 20096 | |
| D87675 | 6 | 20390 | |
| D87675 | 6 | 20652 | |
| D87675 | 6 | 20684 | |
| D87675 | 6 | 20753 | |
| D87675 | 6 | 20856 | |
| D87675 | 6 | 20951 | 51 |
| D87675 | 7 | 452 | |
| D87675 | 7 | 520 | |
| D87675 | 7 | 661 | |
| D87675 | 7 | 805 | |
| D87675 | 7 | 1117 | |
| D87675 | 7 | 1145 | |
| D87675 | 7 | 1264 | |
| D87675 | 7 | 1699 | |
| D87675 | 7 | 2141 | |
| D87675 | 7 | 2484 | 171 |
| D87675 | 8 | 399 | |
| D87675 | 8 | 530 | |
| D87675 | 8 | 588 | |
| D87675 | 8 | 644 | |
| D87675 | 8 | 674 | |
| D87675 | 8 | 682 | |
| D87675 | 8 | 908 | |
| D87675 | 8 | 992 | |
| D87675 | 8 | 1084 | |
| D87675 | 8 | 1088 | |
| D87675 | 8 | 1297 | |
| D87675 | 8 | 1482 | |
| D87675 | 8 | 1650 | |
| D87675 | 8 | 1663 | |
| D87675 | 8 | 1718 | |
| D87675 | 8 | 1959 | |
| D87675 | 8 | 2226 | |
| D87675 | 8 | 2611 | |
| D87675 | 8 | 2699 | |
| D87675 | 8 | 3353 | |
| D87675 | 8 | 3795 | |
| D87675 | 8 | 3863 | |
| D87675 | 8 | 4033 | |
| D87675 | 8 | 4460 | |
| D87675 | 8 | 4597 | |
| D87675 | 8 | 4618 | |
| D87675 | 8 | 5358 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| D87675 | 8 | 5482 | |
| D87675 | 8 | 5751 | |
| D87675 | 8 | 6441 | |
| D87675 | 8 | 6511 | |
| D87675 | 8 | 6604 | |
| D87675 | 8 | 6811 | |
| D87675 | 8 | 7064 | |
| D87675 | 8 | 7853 | |
| D87675 | 8 | 8194 | |
| D87675 | 8 | 8239 | |
| D87675 | 8 | 8513 | |
| D87675 | 8 | 8877 | |
| D87675 | 8 | 9441 | |
| D87675 | 8 | 9837 | |
| D87675 | 8 | 9898 | |
| D87675 | 8 | 10433 | |
| D87675 | 8 | 10476 | |
| D87675 | 8 | 10915 | |
| D87675 | 8 | 10978 | |
| D87675 | 8 | 11211 | |
| D87675 | 8 | 11952 | |
| D87675 | 8 | 11977 | |
| D87675 | 8 | 12393 | |
| D87675 | 8 | 12747 | |
| D87675 | 8 | 13521 | |
| D87675 | 8 | 13923 | 18 |
| D87675 | 9 | 261 | |
| D87675 | 9 | 936 | |
| D87675 | 9 | 963 | |
| D87675 | 9 | 2532 | |
| D87675 | 9 | 2810 | |
| D87675 | 9 | 4104 | |
| D87675 | 9 | 4162 | |
| D87675 | 9 | 4280 | |
| D87675 | 9 | 4296 | |
| D87675 | 9 | 4782 | |
| D87675 | 9 | 4864 | |
| D87675 | 9 | 5154 | |
| D87675 | 9 | 5187 | |
| D87675 | 9 | 5339 | |
| D87675 | 9 | 6185 | 118 |
| D87675 | 10 | 518 | |
| D87675 | 10 | 556 | 97 |
| D87675 | 11 | 791 | |
| D87675 | 11 | 1254 | |
| D87675 | 11 | 1344 | |
| D87675 | 11 | 1753 | |
| D87675 | 11 | 1954 | |
| D87675 | 11 | 2085 | |
| D87675 | 11 | 3117 | |
| D87675 | 11 | 3214 | |
| D87675 | 11 | 3383 | |
| D87675 | 11 | 3644 | |
| D87675 | 11 | 3729 | |
| D87675 | 11 | 3862 | |
| D87675 | 11 | 4070 | |
| D87675 | 11 | 4255 | |
| D87675 | 11 | 4604 | |
| D87675 | 11 | 4675 | |
| D87675 | 11 | 5924 | |
| D87675 | 11 | 6188 | |
| D87675 | 11 | 6659 | |
| D87675 | 11 | 6810 | |
| D87675 | 11 | 6812 | |
| D87675 | 11 | 7693 | |
| D87675 | 11 | 8058 | |
| D87675 | 11 | 8139 | |
| D87675 | 11 | 8150 | |
| D87675 | 11 | 8158 | |
| D87675 | 11 | 8248 | |
| D87675 | 11 | 8454 | |
| D87675 | 11 | 8464 | |
| D87675 | 11 | 8494 | |
| D87675 | 11 | 8633 | |
| D87675 | 11 | 8715 | |
| D87675 | 11 | 8939 | |
| D87675 | 11 | 9000 | |
| D87675 | 11 | 9462 | |
| D87675 | 11 | 9565 | |
| D87675 | 11 | 9959 | |
| D87675 | 11 | 10166 | |
| D87675 | 11 | 10475 | |
| D87675 | 11 | 10587 | |
| D87675 | 11 | 11211 | |
| D87675 | 11 | 11278 | |
| D87675 | 11 | 11568 | |
| D87675 | 11 | 11582 | |
| D87675 | 11 | 11806 | |
| D87675 | 11 | 11909 | |
| D87675 | 11 | 12009 | |
| D87675 | 11 | 12023 | |
| D87675 | 11 | 12090 | |
| D87675 | 11 | 12179 | |
| D87675 | 11 | 12334 | |
| D87675 | 11 | 12479 | |
| D87675 | 11 | 12493 | |
| D87675 | 11 | 12541 | |
| D87675 | 11 | 12742 | |
| D87675 | 11 | 12865 | |
| D87675 | 11 | 13889 | |
| D87675 | 11 | 13900 | |
| D87675 | 11 | 13962 | |
| D87675 | 11 | 14152 | |
| D87675 | 11 | 14806 | |
| D87675 | 11 | 15191 | |
| D87675 | 11 | 15688 | |
| D87675 | 11 | 15928 | |
| D87675 | 11 | 15998 | |
| D87675 | 11 | 16144 | |
| D87675 | 11 | 16363 | |
| D87675 | 11 | 16431 | |
| D87675 | 11 | 16468 | |
| D87675 | 11 | 16558 | |
| D87675 | 11 | 18166 | |
| D87675 | 11 | 18625 | |
| D87675 | 11 | 18690 | |
| D87675 | 11 | 19136 | |
| D87675 | 11 | 19194 | 91 |
| D87675 | 12 | 99 | |
| D87675 | 12 | 134 | |
| D87675 | 12 | 362 | |
| D87675 | 12 | 653 | |
| D87675 | 12 | 812 | 34 |
| D87675 | 13 | 3 | |
| D87675 | 13 | 65 | |
| D87675 | 13 | 494 | |
| D87675 | 13 | 510 | |
| D87675 | 13 | 707 | |
| D87675 | 13 | 902 | |
| D87675 | 13 | 1120 | |
| D87675 | 13 | 1407 | |
| D87675 | 13 | 1875 | |
| D87675 | 13 | 1899 | |
| D87675 | 13 | 2348 | |
| D87675 | 13 | 2363 | |
| D87675 | 13 | 2399 | |
| D87675 | 13 | 3260 | |
| D87675 | 13 | 3429 | |
| D87675 | 13 | 3976 | |
| D87675 | 13 | 4460 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| D87675 | 13 | 4470 | |
| D87675 | 13 | 5590 | |
| D87675 | 13 | 5844 | |
| D87675 | 13 | 6474 | |
| D87675 | 13 | 6666 | |
| D87675 | 13 | 6986 | |
| D87675 | 13 | 7282 | |
| D87675 | 13 | 7341 | |
| D87675 | 13 | 7553 | |
| D87675 | 13 | 7830 | |
| D87675 | 13 | 8657 | |
| D87675 | 13 | 9068 | |
| D87675 | 13 | 9344 | |
| D87675 | 13 | 9409 | |
| D87675 | 13 | 9465 | |
| D87675 | 13 | 10022 | |
| D87675 | 13 | 10100 | |
| D87675 | 13 | 10160 | |
| D87675 | 13 | 10174 | |
| D87675 | 13 | 10595 | |
| D87675 | 13 | 10778 | |
| D87675 | 13 | 11187 | |
| D87675 | 13 | 11205 | |
| D87675 | 13 | 11356 | |
| D87675 | 13 | 11559 | |
| D87675 | 13 | 12062 | |
| D87675 | 13 | 12231 | |
| D87675 | 13 | 12465 | |
| D87675 | 13 | 12469 | |
| D87675 | 13 | 12609 | |
| D87675 | 13 | 12773 | |
| D87675 | 13 | 12881 | |
| D87675 | 13 | 13120 | |
| D87675 | 13 | 13462 | |
| D87675 | 13 | 13560 | |
| D87675 | 13 | 13763 | |
| D87675 | 13 | 13839 | |
| D87675 | 13 | 13927 | |
| D87675 | 13 | 14036 | |
| D87675 | 13 | 14072 | |
| D87675 | 13 | 14144 | |
| D87675 | 13 | 14372 | |
| D87675 | 13 | 14490 | |
| D87675 | 13 | 14721 | |
| D87675 | 13 | 14899 | |
| D87675 | 13 | 15256 | |
| D87675 | 13 | 15280 | |
| D87675 | 13 | 15449 | |
| D87675 | 13 | 15552 | |
| D87675 | 13 | 15611 | |
| D87675 | 13 | 15778 | |
| D87675 | 13 | 16027 | |
| D87675 | 13 | 16282 | |
| D87675 | 13 | 16314 | |
| D87675 | 13 | 17232 | |
| D87675 | 13 | 17389 | |
| D87675 | 13 | 17656 | |
| D87675 | 13 | 17923 | |
| D87675 | 13 | 18014 | |
| D87675 | 13 | 18253 | |
| D87675 | 13 | 18686 | |
| D87675 | 13 | 19007 | |
| D87675 | 13 | 19076 | |
| D87675 | 13 | 19922 | |
| D87675 | 13 | 20111 | |
| D87675 | 13 | 20324 | |
| D87675 | 13 | 20594 | |
| D87675 | 13 | 20958 | |
| D87675 | 13 | 21003 | |
| D87675 | 13 | 21105 | |
| D87675 | 13 | 21238 | |
| D87675 | 13 | 21332 | |
| D87675 | 13 | 21377 | |
| D87675 | 13 | 21415 | |
| D87675 | 13 | 21680 | |
| D87675 | 13 | 21739 | |
| D87675 | 13 | 21933 | |
| D87675 | 13 | 22147 | |
| D87675 | 13 | 22224 | |
| D87675 | 13 | 22728 | |
| D87675 | 13 | 23029 | |
| D87675 | 13 | 23099 | |
| D87675 | 13 | 23161 | |
| D87675 | 13 | 23606 | |
| D87675 | 13 | 24570 | |
| D87675 | 13 | 25364 | |
| D87675 | 13 | 25430 | |
| D87675 | 13 | 25638 | |
| D87675 | 13 | 25919 | |
| D87675 | 13 | 26133 | |
| D87675 | 13 | 26636 | |
| D87675 | 13 | 26724 | |
| D87675 | 13 | 28002 | |
| D87675 | 13 | 28259 | |
| D87675 | 13 | 29015 | |
| D87675 | 13 | 29031 | |
| D87675 | 13 | 29406 | |
| D87675 | 13 | 29532 | |
| D87675 | 13 | 29566 | |
| D87675 | 13 | 29853 | |
| D87675 | 13 | 29937 | |
| D87675 | 13 | 30084 | |
| D87675 | 13 | 30317 | |
| D87675 | 13 | 30953 | |
| D87675 | 13 | 31484 | |
| D87675 | 13 | 31510 | |
| D87675 | 13 | 31922 | |
| D87675 | 13 | 31939 | |
| D87675 | 13 | 32250 | |
| D87675 | 13 | 33389 | |
| D87675 | 13 | 33642 | |
| D87675 | 13 | 33848 | |
| D87675 | 13 | 34255 | |
| D87675 | 13 | 34656 | |
| D87675 | 13 | 35239 | |
| D87675 | 13 | 35438 | |
| D87675 | 13 | 35632 | |
| D87675 | 13 | 35878 | |
| D87675 | 13 | 35963 | |
| D87675 | 13 | 36026 | |
| D87675 | 13 | 36769 | |
| D87675 | 13 | 37439 | |
| D87675 | 13 | 37443 | |
| D87675 | 13 | 37589 | |
| D87675 | 13 | 37636 | |
| D87675 | 13 | 37653 | |
| D87675 | 13 | 38186 | |
| D87675 | 13 | 38358 | |
| D87675 | 13 | 38504 | |
| D87675 | 13 | 38627 | |
| D87675 | 13 | 38980 | |
| D87675 | 13 | 39425 | |
| D87675 | 13 | 39448 | |
| D87675 | 13 | 39678 | |
| D87675 | 13 | 40331 | |
| D87675 | 13 | 40409 | |
| D87675 | 13 | 40681 | |
| D87675 | 13 | 40886 | |
| D87675 | 13 | 40962 | |
| D87675 | 13 | 41035 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| D87675 | 13 | 41677 | |
| D87675 | 13 | 41727 | |
| D87675 | 13 | 42553 | 6 |
| D87675 | 14 | 36 | |
| D87675 | 14 | 57 | |
| D87675 | 14 | 100 | |
| D87675 | 14 | 155 | |
| D87675 | 14 | 320 | |
| D87675 | 14 | 668 | |
| D87675 | 14 | 1042 | |
| D87675 | 14 | 1361 | |
| D87675 | 14 | 1377 | |
| D87675 | 14 | 1744 | |
| D87675 | 14 | 1969 | |
| D87675 | 14 | 2175 | |
| D87675 | 14 | 3022 | |
| D87675 | 14 | 4234 | |
| D87675 | 14 | 4287 | |
| D87675 | 14 | 4353 | |
| D87675 | 14 | 4641 | |
| D87675 | 14 | 4724 | |
| D87675 | 14 | 4750 | |
| D87675 | 14 | 4862 | |
| D87675 | 14 | 4874 | |
| D87675 | 14 | 4898 | |
| D87675 | 14 | 5276 | |
| D87675 | 14 | 5913 | |
| D87675 | 14 | 5924 | |
| D87675 | 14 | 6085 | |
| D87675 | 14 | 6414 | 96 |
| D87675 | 15 | 364 | |
| D87675 | 15 | 421 | |
| D87675 | 15 | 1246 | |
| D87675 | 15 | 1300 | |
| D87675 | 15 | 1374 | |
| D87675 | 15 | 1411 | |
| D87675 | 15 | 1487 | |
| D87675 | 15 | 1585 | |
| D87675 | 15 | 1874 | |
| D87675 | 15 | 2528 | |
| D87675 | 15 | 2549 | |
| D87675 | 15 | 2620 | |
| D87675 | 15 | 2975 | |
| D87675 | 15 | 3339 | |
| D87675 | 15 | 4159 | |
| D87675 | 15 | 4281 | |
| D87675 | 15 | 4934 | |
| D87675 | 15 | 4990 | |
| D87675 | 15 | 5058 | |
| D87675 | 15 | 5293 | |
| D87675 | 15 | 5404 | |
| D87675 | 15 | 5836 | |
| D87675 | 15 | 6181 | |
| D87675 | 15 | 6226 | |
| D87675 | 15 | 6915 | 15 |
| D87675 | 16 | 225 | |
| D87675 | 16 | 811 | |
| D87675 | 16 | 1073 | |
| D87675 | 16 | 1150 | |
| D87675 | 16 | 1448 | |
| D87675 | 16 | 1934 | |
| D87675 | 16 | 2163 | |
| D87675 | 16 | 2175 | |
| D87675 | 16 | 2615 | |
| D87675 | 16 | 2910 | |
| D87675 | 16 | 3152 | |
| D87675 | 16 | 3381 | |
| D87675 | 16 | 3389 | |
| D87675 | 16 | 3579 | |
| D87675 | 16 | 4212 | |
| D87675 | 16 | 5065 | |
| D87675 | 16 | 5101 | |
| D87675 | 16 | 5105 | |
| D87675 | 16 | 5498 | |
| D87675 | 16 | 5528 | 100 |
| D87675 | 17 | 3 | |
| D87675 | 17 | 448 | |
| D87675 | 17 | 463 | |
| D87675 | 17 | 1198 | |
| D87675 | 17 | 1294 | |
| D87675 | 17 | 2359 | |
| D87675 | 17 | 3376 | |
| D87675 | 17 | 4295 | |
| D87675 | 17 | 4751 | |
| D87675 | 17 | 4793 | |
| D87675 | 17 | 4935 | |
| D87675 | 17 | 5081 | |
| D87675 | 17 | 5127 | |
| D87675 | 17 | 5780 | |
| D87675 | 17 | 5947 | |
| D87675 | 17 | 6197 | |
| D87675 | 17 | 6201 | |
| D87675 | 17 | 6443 | |
| D87675 | 17 | 6688 | |
| D87675 | 17 | 7058 | |
| D87675 | 17 | 7235 | |
| D87675 | 17 | 7411 | |
| D87675 | 17 | 7529 | |
| D87675 | 17 | 7597 | |
| D87675 | 17 | 7615 | |
| D87675 | 17 | 8775 | |
| D87675 | 17 | 9118 | |
| D87675 | 17 | 9217 | 37 |
| HUMPIM1A | 3 | 41 | 31 |
| HUMPIM1A | 4 | 29 | |
| HUMPIM1A | 4 | 96 | |
| HUMPIM1A | 4 | 678 | |
| HUMPIM1A | 4 | 863 | |
| HUMPIM1A | 4 | 1120 | |
| HUMPIM1A | 4 | 1302 | |
| HUMPIM1A | 4 | 1337 | |
| HUMPIM1A | 4 | 1470 | 93 |
| HUMPIM1A | 5 | 131 | |
| HUMPIM1A | 5 | 197 | |
| HUMPIM1A | 5 | 405 | |
| HUMPIM1A | 5 | 413 | |
| HUMPIM1A | 5 | 417 | |
| HUMPIM1A | 5 | 489 | 6 |
| HSTCRT3D | 1 | 14 | |
| HSTCRT3D | 1 | 563 | |
| HSTCRT3D | 1 | 703 | |
| HSTCRT3D | 1 | 1620 | |
| HSTCRT3D | 1 | 1682 | 108 |
| HSTCRT3D | 2 | 48 | |
| HSTCRT3D | 2 | 104 | |
| HSTCRT3D | 2 | 109 | |
| HSTCRT3D | 2 | 218 | |
| HSTCRT3D | 2 | 315 | 36 |
| HSTCRT3D | 3 | 108 | 3 |
| HSTCRT3D | 4 | 37 | |
| HSTCRT3D | 4 | 127 | 40 |
| HSCYTOK17 | 2 | 241 | |
| HSCYTOK17 | 2 | 369 | 2 |
| HSCYTOK17 | 3 | 4 | |
| HSCYTOK17 | 3 | 277 | |
| HSCYTOK17 | 3 | 552 | 280 |
| HSCYTOK17 | 4 | 178 | |
| HSCYTOK17 | 4 | 190 | |
| HSCYTOK17 | 4 | 401 | 55 |
| HSCYTOK17 | 7 | 123 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSCYTOK17 | 7 | 694 | 99 |
| HUMTRPY1B | 1 | 45 | |
| HUMTRPY1B | 1 | 57 | 135 |
| HUMTRPY1B | 2 | 40 | 2 |
| HUMTRPY1B | 3 | 20 | |
| HUMTRPY1B | 3 | 73 | |
| AB005803 | 1 | 53 | |
| AB005803 | 1 | 327 | |
| AB005803 | 1 | 484 | |
| AB005803 | 1 | 639 | |
| AB005803 | 1 | 1019 | |
| AB005803 | 1 | 1071 | |
| AB005803 | 1 | 1211 | |
| AB005803 | 1 | 1339 | |
| AB005803 | 1 | 1442 | |
| AB005803 | 1 | 1457 | |
| AB005803 | 1 | 1484 | |
| AB005803 | 1 | 1536 | |
| AB005803 | 1 | 1579 | |
| AB005803 | 1 | 1610 | |
| AB005803 | 1 | 1841 | |
| AB005803 | 1 | 2080 | 25 |
| AB005803 | 2 | 196 | |
| AB005803 | 2 | 240 | |
| AB005803 | 2 | 296 | |
| AB005803 | 2 | 417 | |
| AB005803 | 2 | 501 | 115 |
| AB005803 | 3 | 260 | |
| AB005803 | 3 | 264 | |
| AB005803 | 3 | 753 | |
| AB005803 | 3 | 795 | |
| AB005803 | 3 | 1140 | 15 |
| AB005803 | 4 | 147 | |
| AB005803 | 4 | 511 | |
| AB005803 | 4 | 753 | |
| AB005803 | 4 | 832 | |
| AB005803 | 4 | 882 | 13 |
| AB005803 | 5 | 210 | |
| AB005803 | 5 | 446 | |
| AB005803 | 5 | 825 | |
| AB005803 | 5 | 1425 | |
| AB005803 | 5 | 1474 | |
| AB005803 | 5 | 1676 | 28 |
| AB005803 | 6 | 93 | |
| AB005803 | 6 | 465 | |
| AB005803 | 6 | 885 | |
| AB005803 | 6 | 910 | |
| AB005803 | 6 | 1473 | |
| AB005803 | 6 | 1548 | |
| AB005803 | 6 | 1658 | 88 |
| HSDNAAMHI | 1 | 89 | |
| HSDNAAMHI | 1 | 102 | 105 |
| HSDNAAMHI | 2 | 22 | 222 |
| HSDNAAMHI | 3 | 44 | |
| HSDNAAMHI | 3 | 134 | |
| HSDNAAMHI | 3 | 172 | |
| HSDNAAMHI | 3 | 223 | 48 |
| HSDNAAMHI | 6 | 21 | |
| HSDNAAMHI | 6 | 53 | |
| HSDNAAMHI | 6 | 179 | |
| HSDNAAMHI | 6 | 472 | |
| HSDNAAMHI | 6 | 681 | |
| HSDNAAMHI | 6 | 1040 | |
| HSDNAAMHI | 6 | 1319 | |
| HSDNAAMHI | 6 | 1362 | |
| HSDNAAMHI | 6 | 1895 | |
| HSDNAAMHI | 6 | 2013 | |
| HSDNAAMHI | 6 | 2211 | |
| HSDNAAMHI | 6 | 2474 | |
| HSDNAAMHI | 6 | 2571 | |
| HSDNAAMHI | 6 | 2761 | 115 |
| HSDNAAMHI | 7 | 3 | |
| HSDNAAMHI | 7 | 150 | |
| HSDNAAMHI | 7 | 166 | 6 |
| HSDNAAMHI | 8 | 19 | 22 |
| HSDNAAMHI | 10 | 456 | 274 |
| HSDNAMIA | 2 | 413 | |
| HSDNAMIA | 2 | 615 | |
| HSDNAMIA | 2 | 764 | 94 |
| HSDNAMIA | 3 | 97 | 178 |
| HSU75285 | 2 | 212 | |
| HSU75285 | 2 | 413 | |
| HSU75285 | 2 | 1244 | |
| HSU75285 | 2 | 1565 | 2 |
| HSU75285 | 3 | 198 | |
| HSU75285 | 3 | 224 | |
| HSU75285 | 3 | 494 | |
| HSU75285 | 3 | 556 | |
| HSU75285 | 3 | 629 | |
| HSU75285 | 3 | 671 | |
| HSU75285 | 3 | 992 | |
| HSU75285 | 3 | 1136 | |
| HSU75285 | 3 | 1408 | |
| HSU75285 | 3 | 1470 | |
| HSU75285 | 3 | 2098 | |
| HSU75285 | 3 | 2302 | |
| HSU75285 | 3 | 2541 | |
| HSU75285 | 3 | 2676 | |
| HSU75285 | 3 | 2859 | |
| HSU75285 | 3 | 3136 | |
| HSU75285 | 3 | 3335 | |
| HSU75285 | 3 | 3427 | |
| HSU75285 | 3 | 4076 | |
| HSU75285 | 3 | 4394 | |
| HSU75285 | 3 | 5020 | |
| HSU75285 | 3 | 5317 | |
| HSU75285 | 3 | 5554 | |
| HSU75285 | 3 | 5589 | |
| HSU75285 | 3 | 5820 | |
| HSU75285 | 3 | 5888 | |
| HSU75285 | 3 | 6019 | |
| HSU75285 | 3 | 6206 | |
| HSU75285 | 3 | 6531 | |
| HSU75285 | 3 | 6627 | 46 |
| HSCOSE | 1 | 825 | |
| HSCOSE | 1 | 1132 | 103 |
| HSLPAPGEN | 1 | 109 | |
| HSLPAPGEN | 1 | 818 | |
| HSLPAPGEN | 1 | 899 | |
| HSLPAPGEN | 1 | 936 | |
| HSLPAPGEN | 1 | 1028 | |
| HSLPAPGEN | 1 | 1054 | 55 |
| HSU56438 | 1 | 381 | |
| HSU56438 | 1 | 533 | |
| HSU56438 | 1 | 828 | |
| HSU56438 | 1 | 1015 | |
| HSU56438 | 1 | 1057 | |
| HSU56438 | 1 | 1205 | |
| HSU56438 | 1 | 1209 | |
| HSU56438 | 1 | 1409 | |
| HSU56438 | 1 | 1846 | |
| HSU56438 | 1 | 2064 | |
| HSU56438 | 1 | 2615 | 2 |
| HSU08198 | 1 | 92 | |
| HSU08198 | 1 | 123 | 64 |
| HSU08198 | 3 | 22 | 36 |
| HSU08198 | 4 | 75 | 78 |
| HSU08198 | 6 | 33 | 36 |
| HSCFOS | 1 | 212 | |
| HSCFOS | 1 | 404 | 82 |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSCFOS | 2 | 299 | |
| HSCFOS | 2 | 364 | |
| HSCFOS | 2 | 368 | |
| HSCFOS | 2 | 378 | 118 |
| D89501 | 1 | 252 | |
| D89501 | 1 | 285 | |
| D89501 | 1 | 1200 | |
| D89501 | 1 | 1251 | |
| D89501 | 1 | 1607 | |
| D89501 | 1 | 1919 | |
| D89501 | 1 | 1982 | |
| D89501 | 1 | 2103 | |
| D89501 | 1 | 2167 | |
| D89501 | 1 | 2611 | |
| D89501 | 1 | 2787 | |
| D89501 | 1 | 2812 | |
| D89501 | 1 | 3117 | |
| D89501 | 1 | 3283 | |
| D89501 | 1 | 4003 | |
| D89501 | 1 | 4039 | |
| D89501 | 1 | 4336 | 100 |
| HUMGARE | 1 | 656 | |
| HUMGARE | 1 | 714 | 57 |
| HUMGARE | 2 | 3 | |
| HUMGARE | 2 | 133 | 6 |
| HUMGARE | 3 | 207 | 2 |
| HUMGARE | 4 | 14 | |
| HUMGARE | 4 | 88 | |
| HUMGARE | 4 | 94 | |
| HUMGARE | 4 | 135 | |
| HUMGARE | 4 | 140 | |
| HUMCRPGA | 1 | 39 | |
| HUMCRPGA | 1 | 127 | |
| HUMCRPGA | 1 | 158 | |
| HUMCRPGA | 1 | 177 | |
| HUMCRPGA | 1 | 209 | |
| HUMCRPGA | 1 | 213 | 57 |
| HSNGALGEN | 1 | 65 | |
| HSNGALGEN | 1 | 253 | 268 |
| HSNGALGEN | 2 | 617 | |
| HSNGALGEN | 2 | 867 | 2 |
| HSNGALGEN | 3 | 15 | 9 |
| HSNGALGEN | 5 | 694 | 18 |
| HSU43415 | 1 | 206 | |
| HSU43415 | 1 | 437 | |
| HSU43415 | 1 | 657 | |
| HSU43415 | 1 | 1227 | |
| HSU43415 | 1 | 1499 | |
| HSU43415 | 1 | 2118 | 94 |
| HUMHMG14A | 2 | 26 | 40 |
| HUMHMG14A | 3 | 48 | |
| HUMHMG14A | 4 | 114 | |
| HUMHMG14A | 4 | 375 | |
| HUMHMG14A | 4 | 449 | |
| HUMHMG14A | 4 | 573 | |
| HUMHMG14A | 4 | 604 | |
| HUMHMG14A | 4 | 715 | |
| HUMHMG14A | 4 | 741 | |
| HUMHMG14A | 4 | 1040 | |
| HUMHMG14A | 4 | 1094 | |
| HUMHMG14A | 4 | 1331 | |
| HUMHMG14A | 4 | 1391 | |
| HUMHMG14A | 4 | 1410 | |
| HUMHMG14A | 4 | 1422 | |
| HUMHMG14A | 4 | 1453 | |
| HUMHMG14A | 4 | 1566 | |
| HUMHMG14A | 4 | 1898 | |
| HUMHMG14A | 4 | 1925 | |
| HUMHMG14A | 4 | 2114 | |
| HUMHMG14A | 4 | 2121 | |
| HUMHMG14A | 4 | 2296 | |
| HUMHMG14A | 4 | 2460 | |
| HUMHMG14A | 4 | 2475 | |
| HUMHMG14A | 4 | 2764 | |
| HUMHMG14A | 4 | 2964 | 79 |
| HUMHMG14A | 5 | 6 | |
| HUMHMG14A | 5 | 145 | |
| HUMHMG14A | 5 | 187 | |
| HUMHMG14A | 5 | 195 | |
| HUMHMG14A | 5 | 416 | |
| HUMHMG14A | 5 | 713 | |
| HUMHMG14A | 5 | 1119 | |
| HUMHMG14A | 5 | 1161 | |
| HUMHMG14A | 5 | 1436 | |
| HUMHMG14A | 5 | 1479 | |
| HUMHMG14A | 5 | 1841 | |
| HUMHMG14A | 5 | 1880 | |
| HUMHMG14A | 5 | 1884 | 67 |
| HUMPCNA | 1 | 349 | |
| HUMPCNA | 1 | 617 | 2 |
| HUMPCNA | 2 | 53 | 60 |
| HUMPCNA | 3 | 571 | |
| HUMPCNA | 3 | 653 | |
| HUMPCNA | 3 | 875 | 22 |
| HUMPCNA | 4 | 59 | |
| HUMPCNA | 4 | 100 | |
| HUMPCNA | 4 | 1011 | |
| HUMPCNA | 4 | 1262 | |
| HUMPCNA | 4 | 1472 | |
| HUMPCNA | 4 | 1497 | 13 |
| HUMHMGIY | 1 | 50 | |
| HUMHMGIY | 1 | 124 | |
| HUMHMGIY | 1 | 489 | |
| HUMHMGIY | 1 | 835 | |
| HUMHMGIY | 1 | 1061 | |
| HUMHMGIY | 1 | 1613 | |
| HUMHMGIY | 1 | 1673 | |
| HUMHMGIY | 1 | 1761 | 115 |
| HUMHMGIY | 2 | 142 | |
| HUMHMGIY | 2 | 231 | |
| HUMHMGIY | 2 | 471 | |
| HUMHMGIY | 2 | 557 | |
| HUMHMGIY | 2 | 588 | |
| HUMHMGIY | 2 | 621 | 34 |
| HUMHMGIY | 3 | 3 | |
| HUMHMGIY | 3 | 149 | |
| HUMHMGIY | 3 | 178 | |
| HUMHMGIY | 3 | 358 | |
| HUMHMGIY | 3 | 691 | |
| HUMHMGIY | 3 | 772 | |
| HUMHMGIY | 3 | 1090 | |
| HUMHMGIY | 3 | 1103 | 43 |
| HSHOX51 | 1 | 77 | |
| HSHOX51 | 1 | 148 | |
| HSHOX51 | 1 | 340 | |
| HSHOX51 | 1 | 344 | |
| HSHOX51 | 1 | 348 | |
| HSHOX51 | 1 | 362 | |
| HSHOX51 | 1 | 466 | 18 |
| HSSGK | 2 | 192 | 2 |
| HSSGK | 7 | 128 | 2 |
| HSSGK | 8 | 201 | |
| HSSGK | 8 | 205 | |
| HSSGK | 8 | 240 | |
| HSSGK | 8 | 274 | 109 |
| HSSGK | 9 | 293 | |
| HSSGK | 9 | 393 | 97 |
| HSSGK | 11 | 223 | |
| HSSGK | 11 | 227 | |
| HSSGK | 11 | 303 | 130 |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSU30787 | 1 | 516 | 2 |
| HSU30787 | 5 | 73 | 91 |
| HSU30787 | 6 | 195 | |
| HSU30787 | 6 | 218 | |
| HSU30787 | 6 | 297 | 43 |
| HSU30787 | 8 | 14 | |
| HSU30787 | 8 | 33 | 2 |
| HUMGLUT4B | 1 | 113 | |
| HUMGLUT4B | 1 | 645 | |
| HUMGLUT4B | 1 | 892 | |
| HUMGLUT4B | 1 | 954 | 154 |
| HUMGLUT4B | 2 | 48 | |
| HUMGLUT4B | 5 | 74 | 91 |
| HUMGLUT4B | 9 | 52 | 16 |
| HUMGLUT4B | 10 | 40 | |
| HUMGLUT4B | 10 | 112 | |
| HUMGLUT4B | 10 | 187 | 58 |
| HUMAPOE4 | 1 | 450 | |
| HUMAPOE4 | 1 | 696 | |
| HUMAPOE4 | 1 | 948 | |
| HUMAPOE4 | 1 | 1029 | 177 |
| HUMTRHYAL | 1 | 147 | |
| HUMTRHYAL | 1 | 208 | |
| HUMTRHYAL | 1 | 586 | |
| HUMTRHYAL | 1 | 694 | 43 |
| HSPPTII | 1 | 34 | 85 |
| HSPPTII | 2 | 213 | |
| HSPPTII | 2 | 315 | |
| HSPPTII | 2 | 380 | |
| HSPPTII | 2 | 430 | |
| HSPPTII | 2 | 711 | |
| HSPPTII | 2 | 1328 | |
| HSPPTII | 2 | 1366 | |
| HSPPTII | 2 | 1486 | |
| HSPPTII | 2 | 1501 | |
| HSPPTII | 2 | 1587 | |
| HSPPTII | 2 | 1797 | 53 |
| HSU51899 | 1 | 131 | |
| HSU51899 | 1 | 945 | |
| HSU51899 | 1 | 1618 | |
| HSU51899 | 1 | 1738 | |
| HSU51899 | 1 | 2074 | 7 |
| HSU51899 | 2 | 58 | |
| HSU51899 | 2 | 155 | |
| HSU51899 | 2 | 719 | |
| HSU51899 | 2 | 733 | |
| HSU51899 | 2 | 1050 | |
| HSU51899 | 2 | 1087 | 13 |
| HUMANT2X | 1 | 186 | |
| HUMANT2X | 1 | 683 | |
| HUMANT2X | 1 | 736 | 112 |
| HUMANT2X | 2 | 175 | 105 |
| HUMANT2X | 3 | 170 | |
| HUMANT2X | 3 | 287 | 33 |
| HUMCHYMASE | 1 | 427 | |
| HUMCHYMASE | 1 | 562 | 24 |
| HUMCHYMASE | 4 | 91 | |
| HUMCHYMASE | 4 | 99 | |
| HUMCHYMASE | 4 | 184 | |
| HUMCHYMASE | 4 | 251 | 49 |
| HSRING3GE | 1 | 26 | |
| HSRING3GE | 1 | 346 | |
| HSRING3GE | 1 | 386 | |
| HSRING3GE | 1 | 513 | 52 |
| HSRING3GE | 2 | 28 | |
| HSRING3GE | 2 | 113 | |
| HSRING3GE | 2 | 171 | |
| HSRING3GE | 2 | 195 | |
| HSRING3GE | 2 | 445 | 121 |
| HSRING3GE | 5 | 457 | 49 |
| HSRING3GE | 6 | 75 | |
| HSRING3GE | 6 | 133 | 22 |
| HSRING3GE | 7 | 30 | 16 |
| HSRING3GE | 8 | 1027 | |
| HSRING3GE | 8 | 1204 | |
| HSRING3GE | 8 | 1208 | |
| HSRING3GE | 8 | 1394 | 2 |
| AF027807 | 1 | 492 | |
| AF027807 | 1 | 535 | |
| AF027807 | 1 | 583 | |
| AF027807 | 1 | 764 | 61 |
| AF027807 | 2 | 129 | |
| AF027807 | 2 | 396 | |
| AF027807 | 2 | 496 | |
| AF027807 | 2 | 528 | |
| AF027807 | 2 | 547 | |
| AF027807 | 2 | 934 | 7 |
| AF027807 | 4 | 313 | |
| AF027807 | 4 | 333 | |
| AF027807 | 4 | 586 | |
| AF027807 | 4 | 774 | |
| AF027807 | 4 | 901 | 10 |
| AF027807 | 5 | 105 | |
| AF027807 | 5 | 160 | |
| AF027807 | 5 | 282 | |
| AF027807 | 5 | 327 | |
| AF027807 | 5 | 521 | |
| AF027807 | 5 | 738 | |
| AF027807 | 5 | 883 | 67 |
| HUMPCBD | 1 | 59 | |
| HUMPCBD | 1 | 862 | |
| HUMPCBD | 1 | 1426 | |
| HUMPCBD | 1 | 1740 | |
| HUMPCBD | 1 | 2270 | 181 |
| HUMPCBD | 3 | 357 | |
| HUMPCBD | 3 | 420 | |
| HUMPCBD | 3 | 436 | |
| HUMPCBD | 3 | 1067 | 58 |
| HSHAP1 | 1 | 69 | 72 |
| HSHAP1 | 2 | 368 | 13 |
| HUMTNFX | 1 | 226 | |
| HUMTNFX | 1 | 349 | |
| HUMTNFX | 1 | 473 | |
| HUMTNFX | 1 | 564 | 244 |
| HUMTNFX | 2 | 51 | |
| HUMTNFX | 2 | 117 | 120 |
| HUMTNFX | 3 | 89 | |
| HUMTNFX | 3 | 170 | 39 |
| HUMAGAL | 1 | 36 | |
| HUMAGAL | 1 | 76 | |
| HUMAGAL | 1 | 80 | |
| HUMAGAL | 1 | 324 | |
| HUMAGAL | 1 | 625 | |
| HUMAGAL | 1 | 962 | |
| HUMAGAL | 1 | 993 | |
| HUMAGAL | 1 | 998 | |
| HUMAGAL | 1 | 1422 | 33 |
| HUMAGAL | 2 | 92 | |
| HUMAGAL | 2 | 254 | |
| HUMAGAL | 2 | 448 | 2 |
| HUMAGAL | 3 | 77 | |
| HUMAGAL | 3 | 302 | |
| HUMAGAL | 3 | 320 | 37 |
| HUMAGAL | 4 | 180 | 78 |
| HUMAGAL | 5 | 123 | |
| HUMAGAL | 5 | 134 | |
| HUMAGAL | 5 | 172 | |
| HUMAGAL | 5 | 194 | |
| HUMAGAL | 5 | 362 | |
| HUMAGAL | 5 | 491 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMAGAL | 5 | 495 | 133 |
| HUMAGAL | 6 | 101 | |
| HUMAGAL | 6 | 501 | |
| HUMAGAL | 6 | 649 | |
| HUMAGAL | 6 | 870 | |
| HUMAGAL | 6 | 886 | |
| HUMAGAL | 6 | 1347 | |
| HUMAGAL | 6 | 1590 | |
| HUMAGAL | 6 | 1780 | |
| HUMAGAL | 6 | 1872 | |
| HUMAGAL | 6 | 2187 | |
| HUMAGAL | 6 | 2500 | 25 |
| HUMAGAL | 7 | 192 | |
| HUMAGAL | 7 | 270 | |
| HUMAGAL | 7 | 568 | |
| HUMAGAL | 7 | 733 | |
| HUMAGAL | 7 | 981 | |
| HUMAGAL | 7 | 997 | |
| HUMAGAL | 7 | 1579 | |
| HUMAGAL | 7 | 1700 | 34 |
| HUMFIXG | 1 | 133 | |
| HUMFIXG | 1 | 137 | |
| HUMFIXG | 1 | 258 | |
| HUMFIXG | 1 | 472 | |
| HUMFIXG | 1 | 484 | |
| HUMFIXG | 1 | 1044 | |
| HUMFIXG | 1 | 1180 | |
| HUMFIXG | 1 | 1358 | |
| HUMFIXG | 1 | 1495 | |
| HUMFIXG | 1 | 1542 | |
| HUMFIXG | 1 | 1742 | |
| HUMFIXG | 1 | 1956 | |
| HUMFIXG | 1 | 1961 | |
| HUMFIXG | 1 | 2003 | |
| HUMFIXG | 1 | 2012 | |
| HUMFIXG | 1 | 2378 | |
| HUMFIXG | 1 | 2559 | |
| HUMFIXG | 1 | 2706 | |
| HUMFIXG | 1 | 2751 | |
| HUMFIXG | 1 | 2868 | |
| HUMFIXG | 1 | 2914 | |
| HUMFIXG | 1 | 2992 | |
| HUMFIXG | 1 | 3227 | |
| HUMFIXG | 1 | 3268 | |
| HUMFIXG | 1 | 3612 | |
| HUMFIXG | 1 | 3984 | |
| HUMFIXG | 1 | 4008 | |
| HUMFIXG | 1 | 4060 | |
| HUMFIXG | 1 | 4283 | |
| HUMFIXG | 1 | 4315 | |
| HUMFIXG | 1 | 4554 | |
| HUMFIXG | 1 | 4906 | |
| HUMFIXG | 1 | 5101 | |
| HUMFIXG | 1 | 5302 | |
| HUMFIXG | 1 | 5591 | |
| HUMFIXG | 1 | 5950 | 84 |
| HUMFIXG | 2 | 101 | 16 |
| HUMFIXG | 3 | 51 | |
| HUMFIXG | 3 | 185 | |
| HUMFIXG | 3 | 987 | |
| HUMFIXG | 3 | 1278 | |
| HUMFIXG | 3 | 1354 | |
| HUMFIXG | 3 | 2062 | |
| HUMFIXG | 3 | 2929 | |
| HUMFIXG | 3 | 3570 | 27 |
| HUMFIXG | 4 | 3 | |
| HUMFIXG | 4 | 192 | |
| HUMFIXG | 4 | 258 | |
| HUMFIXG | 4 | 458 | |
| HUMFIXG | 4 | 1085 | |
| HUMFIXG | 4 | 1101 | |
| HUMFIXG | 4 | 1535 | |
| HUMFIXG | 4 | 1575 | |
| HUMFIXG | 4 | 2179 | |
| HUMFIXG | 4 | 3051 | |
| HUMFIXG | 4 | 3631 | |
| HUMFIXG | 4 | 3916 | |
| HUMFIXG | 4 | 3951 | |
| HUMFIXG | 4 | 4061 | |
| HUMFIXG | 4 | 4428 | |
| HUMFIXG | 4 | 4765 | |
| HUMFIXG | 4 | 4963 | |
| HUMFIXG | 4 | 5207 | |
| HUMFIXG | 4 | 5547 | |
| HUMFIXG | 4 | 6040 | |
| HUMFIXG | 4 | 6550 | |
| HUMFIXG | 4 | 6694 | |
| HUMFIXG | 4 | 6778 | 6 |
| HUMFIXG | 5 | 373 | |
| HUMFIXG | 5 | 1477 | |
| HUMFIXG | 5 | 1485 | |
| HUMFIXG | 5 | 1881 | |
| HUMFIXG | 5 | 1990 | |
| HUMFIXG | 5 | 2536 | 24 |
| HUMFIXG | 6 | 15 | |
| HUMFIXG | 6 | 56 | |
| HUMFIXG | 6 | 98 | |
| HUMFIXG | 6 | 135 | |
| HUMFIXG | 6 | 337 | |
| HUMFIXG | 6 | 607 | |
| HUMFIXG | 6 | 785 | |
| HUMFIXG | 6 | 830 | |
| HUMFIXG | 6 | 1268 | |
| HUMFIXG | 6 | 1543 | |
| HUMFIXG | 6 | 1622 | |
| HUMFIXG | 6 | 1721 | |
| HUMFIXG | 6 | 1755 | |
| HUMFIXG | 6 | 2606 | |
| HUMFIXG | 6 | 3688 | |
| HUMFIXG | 6 | 3714 | |
| HUMFIXG | 6 | 4291 | |
| HUMFIXG | 6 | 4336 | |
| HUMFIXG | 6 | 4852 | |
| HUMFIXG | 6 | 4933 | |
| HUMFIXG | 6 | 5501 | |
| HUMFIXG | 6 | 5648 | |
| HUMFIXG | 6 | 5652 | |
| HUMFIXG | 6 | 5689 | |
| HUMFIXG | 6 | 5713 | |
| HUMFIXG | 6 | 5733 | |
| HUMFIXG | 6 | 5786 | |
| HUMFIXG | 6 | 5811 | |
| HUMFIXG | 6 | 5836 | |
| HUMFIXG | 6 | 6379 | |
| HUMFIXG | 6 | 6870 | |
| HUMFIXG | 6 | 6963 | |
| HUMFIXG | 6 | 7159 | |
| HUMFIXG | 6 | 7405 | |
| HUMFIXG | 6 | 8341 | |
| HUMFIXG | 6 | 8611 | |
| HUMFIXG | 6 | 9060 | 67 |
| HUMFIXG | 7 | 372 | |
| HUMFIXG | 7 | 584 | 51 |
| AF009356 | 1 | 240 | |
| AF009356 | 1 | 403 | |
| AF009356 | 1 | 435 | 2 |
| AF009356 | 2 | 169 | |
| AF009356 | 2 | 177 | |
| AF009356 | 2 | 181 | 2 |
| AF009356 | 3 | 163 | 6 |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| AF009356 | 4 | 122 | |
| AF009356 | 4 | 305 | |
| AF009356 | 4 | 538 | |
| AF009356 | 4 | 562 | |
| AF009356 | 4 | 713 | |
| AF009356 | 4 | 734 | |
| AF009356 | 4 | 888 | 70 |
| HSMECDAG | 1 | 62 | |
| HSMECDAG | 1 | 411 | |
| HSMECDAG | 1 | 662 | |
| HSMECDAG | 1 | 755 | |
| HSMECDAG | 1 | 814 | 169 |
| HSMECDAG | 2 | 66 | |
| HSMECDAG | 2 | 70 | |
| HSMECDAG | 2 | 75 | |
| HSMECDAG | 2 | 79 | |
| HSMECDAG | 2 | 83 | |
| HSMECDAG | 2 | 98 | 73 |
| HSMECDAG | 4 | 65 | |
| HSMECDAG | 4 | 105 | |
| HSMECDAG | 4 | 123 | |
| HSMECDAG | 4 | 195 | |
| HSMECDAG | 4 | 203 | |
| HSMECDAG | 4 | 235 | |
| HSMECDAG | 4 | 386 | 121 |
| HSMECDAG | 6 | 133 | 61 |
| HSU12709 | 1 | 45 | 108 |
| HSU12709 | 3 | 174 | 14 |
| HUMANFA | 1 | 77 | 118 |
| HUMANFA | 2 | 333 | |
| HUMANFA | 2 | 450 | |
| HUMANFA | 2 | 554 | |
| HUMANFA | 2 | 645 | |
| HUMANFA | 2 | 991 | 157 |
| HSERPG | 1 | 82 | 198 |
| HSERPG | 3 | 90 | |
| HSERPG | 3 | 259 | 112 |
| HUMTPA | 1 | 504 | |
| HUMTPA | 1 | 522 | |
| HUMTPA | 1 | 692 | |
| HUMTPA | 1 | 860 | |
| HUMTPA | 1 | 1290 | |
| HUMTPA | 1 | 1596 | 205 |
| HUMTPA | 2 | 219 | |
| HUMTPA | 2 | 717 | |
| HUMTPA | 2 | 1113 | |
| HUMTPA | 2 | 1519 | |
| HUMTPA | 2 | 2066 | |
| HUMTPA | 2 | 2205 | 114 |
| HUMTPA | 3 | 59 | |
| HUMTPA | 3 | 156 | |
| HUMTPA | 3 | 458 | |
| HUMTPA | 3 | 542 | 9 |
| HUMTPA | 4 | 7 | |
| HUMTPA | 4 | 171 | |
| HUMTPA | 4 | 301 | 6 |
| HUMTPA | 5 | 149 | |
| HUMTPA | 5 | 185 | |
| HUMTPA | 5 | 271 | |
| HUMTPA | 5 | 548 | |
| HUMTPA | 5 | 600 | |
| HUMTPA | 5 | 612 | |
| HUMTPA | 5 | 715 | |
| HUMTPA | 5 | 960 | |
| HUMTPA | 5 | 1164 | |
| HUMTPA | 5 | 1440 | |
| HUMTPA | 5 | 1537 | |
| HUMTPA | 5 | 1893 | |
| HUMTPA | 6 | 108 | |
| HUMTPA | 6 | 317 | |
| HUMTPA | 6 | 490 | |
| HUMTPA | 6 | 941 | |
| HUMTPA | 6 | 981 | |
| HUMTPA | 6 | 1026 | |
| HUMTPA | 6 | 1139 | |
| HUMTPA | 6 | 1147 | |
| HUMTPA | 6 | 1380 | 69 |
| HUMTPA | 7 | 406 | 2 |
| HUMTPA | 8 | 153 | |
| HUMTPA | 8 | 240 | |
| HUMTPA | 8 | 466 | |
| HUMTPA | 8 | 578 | |
| HUMTPA | 8 | 582 | |
| HUMTPA | 8 | 657 | |
| HUMTPA | 8 | 772 | |
| HUMTPA | 8 | 819 | |
| HUMTPA | 8 | 879 | 141 |
| HUMTPA | 11 | 473 | |
| HUMTPA | 11 | 538 | |
| HUMTPA | 11 | 561 | 114 |
| HUMTPA | 12 | 376 | |
| HUMTPA | 12 | 394 | |
| HUMTPA | 12 | 729 | |
| HUMTPA | 12 | 993 | |
| HUMTPA | 12 | 1365 | |
| HUMTPA | 12 | 1387 | |
| HUMTPA | 12 | 1519 | |
| HUMTPA | 12 | 1575 | |
| HUMTPA | 12 | 1644 | |
| HUMTPA | 12 | 1706 | |
| HUMTPA | 12 | 1778 | |
| HUMTPA | 12 | 1786 | |
| HUMTPA | 12 | 1873 | |
| HUMTPA | 12 | 2031 | |
| HUMTPA | 12 | 2056 | |
| HUMTPA | 12 | 2130 | |
| HUMTPA | 12 | 2171 | 112 |
| AC004022 | 1 | 14 | |
| AC004022 | 1 | 228 | |
| AC004022 | 1 | 696 | |
| AC004022 | 1 | 1006 | |
| AC004022 | 1 | 1058 | |
| AC004022 | 1 | 1466 | |
| AC004022 | 1 | 1561 | |
| AC004022 | 1 | 1784 | |
| AC004022 | 1 | 2513 | |
| AC004022 | 1 | 2656 | |
| AC004022 | 1 | 2688 | |
| AC004022 | 1 | 2825 | |
| AC004022 | 1 | 2850 | |
| AC004022 | 1 | 2875 | |
| AC004022 | 1 | 3146 | |
| AC004022 | 1 | 3163 | |
| AC004022 | 1 | 3218 | |
| AC004022 | 1 | 3319 | |
| AC004022 | 1 | 3686 | |
| AC004022 | 1 | 3702 | |
| AC004022 | 1 | 3763 | |
| AC004022 | 1 | 3883 | |
| AC004022 | 1 | 4161 | |
| AC004022 | 1 | 4212 | |
| AC004022 | 1 | 4416 | |
| AC004022 | 1 | 4558 | |
| AC004022 | 1 | 4607 | |
| AC004022 | 1 | 5079 | |
| AC004022 | 1 | 5130 | |
| AC004022 | 1 | 5156 | |
| AC004022 | 1 | 5459 | |
| AC004022 | 1 | 5463 | 2 |
| AC004022 | 2 | 3 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| AC004022 | 2 | 7 | |
| AC004022 | 2 | 342 | |
| AC004022 | 2 | 528 | |
| AC004022 | 2 | 1453 | |
| AC004022 | 2 | 1458 | 66 |
| AC004022 | 3 | 248 | |
| AC004022 | 3 | 368 | |
| AC004022 | 3 | 725 | 31 |
| AC004022 | 4 | 1086 | |
| AC004022 | 4 | 1554 | |
| AC004022 | 4 | 1619 | |
| AC004022 | 4 | 1658 | |
| AC004022 | 4 | 1838 | |
| AC004022 | 4 | 2115 | |
| AC004022 | 4 | 2458 | |
| AC004022 | 4 | 2523 | |
| AC004022 | 4 | 2588 | |
| AC004022 | 4 | 3660 | 111 |
| AC004022 | 5 | 84 | |
| AC004022 | 5 | 769 | |
| AC004022 | 5 | 788 | |
| AC004022 | 5 | 1045 | |
| AC004022 | 5 | 1062 | |
| AC004022 | 5 | 1149 | |
| AC004022 | 5 | 2837 | |
| AC004022 | 5 | 2851 | |
| AC004022 | 5 | 3217 | 5 |
| AC004022 | 6 | 289 | |
| AC004022 | 6 | 330 | |
| AC004022 | 6 | 376 | |
| AC004022 | 6 | 428 | |
| AC004022 | 6 | 486 | |
| AC004022 | 6 | 663 | |
| AC004022 | 6 | 708 | |
| AC004022 | 6 | 989 | |
| AC004022 | 6 | 1386 | |
| AC004022 | 6 | 1510 | |
| AC004022 | 6 | 1521 | 77 |
| AC004022 | 7 | 17 | |
| AC004022 | 7 | 95 | |
| AC004022 | 7 | 99 | |
| AC004022 | 7 | 461 | |
| AC004022 | 7 | 1298 | |
| AC004022 | 7 | 1394 | |
| AC004022 | 7 | 1547 | |
| AC004022 | 7 | 1592 | |
| AC004022 | 7 | 1703 | |
| AC004022 | 7 | 2114 | |
| AC004022 | 7 | 2960 | |
| AC004022 | 7 | 3043 | |
| AC004022 | 7 | 3169 | |
| AC004022 | 7 | 3186 | |
| AC004022 | 7 | 3225 | |
| AC004022 | 7 | 3784 | |
| AC004022 | 7 | 3798 | 40 |
| AC004022 | 8 | 25 | |
| AC004022 | 8 | 476 | |
| AC004022 | 8 | 670 | |
| AC004022 | 8 | 999 | |
| AC004022 | 8 | 1028 | |
| AC004022 | 8 | 1354 | |
| AC004022 | 8 | 1726 | |
| AC004022 | 8 | 1922 | |
| AC004022 | 8 | 2647 | |
| AC004022 | 8 | 2955 | |
| AC004022 | 8 | 3058 | 28 |
| HSGLTH1 | 2 | 48 | 94 |
| HSGEBCMA | 1 | 92 | |
| HSGEBCMA | 1 | 158 | |
| HSGEBCMA | 1 | 280 | |
| HSGEBCMA | 1 | 428 | |
| HSGEBCMA | 1 | 529 | |
| HSGEBCMA | 1 | 686 | |
| HSGEBCMA | 1 | 690 | 6 |
| HSGEBCMA | 2 | 11 | |
| HSGEBCMA | 2 | 48 | |
| HSGEBCMA | 2 | 151 | |
| HSGEBCMA | 2 | 200 | |
| HSGEBCMA | 2 | 795 | 51 |
| AB005990 | 1 | 226 | 49 |
| AB005990 | 2 | 275 | 2 |
| AB005990 | 8 | 151 | |
| AB005990 | 8 | 155 | 61 |
| HUMAPOCIA | 1 | 50 | |
| HUMAPOCIA | 1 | 136 | |
| HUMAPOCIA | 1 | 264 | |
| HUMAPOCIA | 1 | 268 | |
| HUMAPOCIA | 1 | 296 | |
| HUMAPOCIA | 1 | 341 | |
| HUMAPOCIA | 1 | 804 | |
| HUMAPOCIA | 1 | 880 | 78 |
| HUMAPOCIA | 2 | 33 | |
| HUMAPOCIA | 2 | 260 | |
| HUMAPOCIA | 2 | 278 | |
| HUMAPOCIA | 2 | 425 | |
| HUMAPOCIA | 2 | 676 | |
| HUMAPOCIA | 2 | 1038 | |
| HUMAPOCIA | 2 | 1056 | |
| HUMAPOCIA | 2 | 1440 | |
| HUMAPOCIA | 2 | 1736 | |
| HUMAPOCIA | 2 | 1926 | |
| HUMAPOCIA | 2 | 2484 | |
| HUMAPOCIA | 2 | 2551 | |
| HUMAPOCIA | 2 | 2770 | |
| HUMAPOCIA | 2 | 2811 | 173 |
| HSGLA | 1 | 47 | |
| HSGLA | 1 | 447 | |
| HSGLA | 1 | 773 | |
| HSGLA | 1 | 869 | |
| HSGLA | 1 | 964 | |
| HSGLA | 1 | 1097 | |
| HSGLA | 1 | 1465 | |
| HSGLA | 1 | 2047 | |
| HSGLA | 1 | 2687 | |
| HSGLA | 1 | 2774 | |
| HSGLA | 1 | 2790 | |
| HSGLA | 1 | 2892 | |
| HSGLA | 1 | 3647 | |
| HSGLA | 1 | 3665 | 578 |
| HSGLA | 2 | 1129 | |
| HSGLA | 2 | 1436 | |
| HSGLA | 2 | 1688 | |
| HSGLA | 2 | 1713 | |
| HSGLA | 2 | 1971 | 10 |
| HSGLA | 3 | 398 | |
| HSGLA | 3 | 564 | 87 |
| HSGLA | 4 | 429 | |
| HSGLA | 4 | 921 | |
| HSGLA | 4 | 1454 | |
| HSGLA | 4 | 1507 | |
| HSGLA | 4 | 1675 | 7 |
| HSGLA | 5 | 65 | |
| HSGLA | 5 | 75 | |
| HSGLA | 5 | 101 | |
| HSGLA | 5 | 159 | 10 |
| HSU43901 | 1 | 34 | |
| HSU43901 | 1 | 67 | |
| HSU43901 | 1 | 78 | |
| HSU43901 | 1 | 189 | |
| HSU43901 | 1 | 288 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSU43901 | 1 | 332 | |
| HSU43901 | 1 | 339 | 3 |
| HSU43901 | 2 | 14 | |
| HSU43901 | 2 | 164 | |
| HSU43901 | 2 | 1075 | |
| HSU43901 | 2 | 1334 | |
| HSU43901 | 2 | 1674 | |
| HSU43901 | 2 | 1915 | |
| HSU43901 | 2 | 1939 | 76 |
| HSU43901 | 3 | 361 | |
| HSU43901 | 3 | 574 | |
| HSU43901 | 3 | 589 | 40 |
| HSU43901 | 4 | 83 | |
| HSU43901 | 5 | 17 | |
| HSU43901 | 5 | 150 | 30 |
| HUMCSPA | 1 | 3 | |
| HUMCSPA | 1 | 284 | |
| HUMCSPA | 1 | 900 | 6 |
| HUMCSPA | 2 | 200 | 2 |
| HUMCSPA | 3 | 96 | 88 |
| HUMCSPA | 4 | 298 | 49 |
| HUMSPERSYN | 1 | 375 | 32 |
| HUMSPERSYN | 2 | 46 | 163 |
| HUMSPERSYN | 3 | 89 | |
| HUMSPERSYN | 3 | 172 | |
| HUMSPERSYN | 3 | 455 | |
| HUMSPERSYN | 3 | 788 | |
| HUMSPERSYN | 3 | 1649 | |
| HUMSPERSYN | 3 | 1694 | |
| HUMSPERSYN | 3 | 1889 | 175 |
| HUMSPERSYN | 4 | 48 | |
| HUMSPERSYN | 4 | 330 | |
| HUMSPERSYN | 4 | 385 | 75 |
| HUMSPERSYN | 6 | 38 | |
| HUMSPERSYN | 6 | 131 | |
| HUMSPERSYN | 6 | 377 | |
| HUMSPERSYN | 6 | 422 | |
| HUMSPERSYN | 6 | 440 | 166 |
| HUMHLL4G | 1 | 275 | |
| HUMHLL4G | 1 | 575 | 88 |
| HUMHLL4G | 2 | 133 | |
| HUMHLL4G | 2 | 459 | |
| HUMHLL4G | 2 | 522 | |
| HUMHLL4G | 2 | 539 | |
| HUMHLL4G | 2 | 1308 | |
| HUMHLL4G | 2 | 1326 | |
| HUMHLL4G | 2 | 1361 | 2 |
| HUMHLL4G | 3 | 61 | |
| HUMHLL4G | 3 | 545 | |
| HUMHLL4G | 3 | 563 | 163 |
| HUMN79E2 | 1 | 84 | |
| HUMN79E2 | 1 | 113 | |
| HUMN79E2 | 1 | 217 | |
| HUMN79E2 | 1 | 627 | |
| HUMN79E2 | 1 | 802 | |
| HUMN79E2 | 1 | 1063 | |
| HUMN79E2 | 1 | 1144 | |
| HUMN79E2 | 1 | 1402 | |
| HUMN79E2 | 1 | 1543 | |
| HUMN79E2 | 1 | 1870 | |
| HUMN79E2 | 1 | 1972 | |
| HUMN79E2 | 1 | 2403 | |
| HUMN79E2 | 1 | 2472 | |
| HUMN79E2 | 1 | 2676 | |
| HUMN79E2 | 1 | 4386 | |
| HUMN79E2 | 1 | 4678 | |
| HUMN79E2 | 1 | 4763 | |
| HUMN79E2 | 1 | 4822 | |
| HUMN79E2 | 1 | 4879 | |
| HUMN79E2 | 1 | 5024 | |
| HUMN79E2 | 1 | 5151 | |
| HUMN79E2 | 1 | 5582 | |
| HUMN79E2 | 1 | 5620 | |
| HUMN79E2 | 1 | 5845 | |
| HUMN79E2 | 1 | 6124 | |
| HUMN79E2 | 1 | 6656 | |
| HUMN79E2 | 1 | 7106 | |
| HUMN79E2 | 1 | 7603 | |
| HUMN79E2 | 1 | 8007 | |
| HUMN79E2 | 1 | 8026 | |
| HUMN79E2 | 1 | 8383 | |
| HUMN79E2 | 1 | 8695 | |
| HUMN79E2 | 1 | 8828 | |
| HUMN79E2 | 1 | 9392 | |
| HUMN79E2 | 1 | 9856 | |
| HUMN79E2 | 1 | 10301 | |
| HUMN79E2 | 1 | 10395 | |
| HUMN79E2 | 1 | 10513 | |
| HUMN79E2 | 1 | 11148 | |
| HUMN79E2 | 1 | 11172 | |
| HUMN79E2 | 1 | 11362 | |
| HUMN79E2 | 1 | 11431 | |
| HUMN79E2 | 1 | 11563 | |
| HUMN79E2 | 1 | 11955 | |
| HUMN79E2 | 1 | 11972 | |
| HUMN79E2 | 1 | 11978 | |
| HUMN79E2 | 1 | 12183 | |
| HUMN79E2 | 1 | 12252 | |
| HUMN79E2 | 1 | 12500 | |
| HUMN79E2 | 1 | 12873 | |
| HUMN79E2 | 1 | 12915 | |
| HUMN79E2 | 1 | 13129 | |
| HUMN79E2 | 1 | 13362 | |
| HUMN79E2 | 1 | 13613 | |
| HUMN79E2 | 1 | 13657 | |
| HUMN79E2 | 1 | 13876 | |
| HUMN79E2 | 1 | 13925 | |
| HUMN79E2 | 1 | 14243 | |
| HUMN79E2 | 1 | 14337 | |
| HUMN79E2 | 1 | 14389 | |
| HUMN79E2 | 1 | 14552 | |
| HUMN79E2 | 1 | 14672 | |
| HUMN79E2 | 1 | 14895 | |
| HUMN79E2 | 1 | 15038 | |
| HUMN79E2 | 1 | 15328 | |
| HUMN79E2 | 1 | 15511 | |
| HUMN79E2 | 1 | 15637 | |
| HUMN79E2 | 1 | 15754 | |
| HUMN79E2 | 1 | 15900 | |
| HUMN79E2 | 1 | 15965 | |
| HUMN79E2 | 1 | 16106 | |
| HUMN79E2 | 1 | 16198 | |
| HUMN79E2 | 1 | 16227 | |
| HUMN79E2 | 1 | 16323 | |
| HUMN79E2 | 1 | 16441 | |
| HUMN79E2 | 1 | 16624 | |
| HUMN79E2 | 1 | 16839 | |
| HUMN79E2 | 1 | 16857 | |
| HUMN79E2 | 1 | 16975 | 133 |
| HSU96876 | 1 | 366 | |
| HSU96876 | 1 | 688 | |
| HSU96876 | 1 | 867 | |
| HSU96876 | 1 | 930 | |
| HSU96876 | 1 | 1169 | |
| HSU96876 | 1 | 1237 | |
| HSU96876 | 1 | 1285 | |
| HSU96876 | 1 | 1661 | |
| HSU96876 | 1 | 1798 | |
| HSU96876 | 1 | 1824 | 30 |
| HSU96876 | 2 | 375 | 40 |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSU96876 | 3 | 6 | |
| HSU96876 | 3 | 10 | |
| HSU96876 | 3 | 261 | 77 |
| HSU96876 | 4 | 1015 | |
| HSU96876 | 4 | 1535 | |
| HSU96876 | 4 | 1669 | |
| HSU96876 | 4 | 1721 | |
| HSU96876 | 4 | 1738 | |
| HSU96876 | 4 | 1777 | |
| HSU96876 | 4 | 1787 | |
| HSU96876 | 4 | 2337 | |
| HSU96876 | 4 | 2844 | |
| HSU96876 | 4 | 3508 | |
| HSU96876 | 4 | 3536 | |
| HSU96876 | 4 | 3645 | |
| HSU96876 | 4 | 3715 | |
| HSU96876 | 4 | 3894 | |
| HSU96876 | 4 | 3899 | |
| HSU96876 | 4 | 3934 | |
| HSU96876 | 4 | 4169 | |
| HSU96876 | 4 | 4330 | 49 |
| HUMHSP89KD | 2 | 26 | 150 |
| HUMHSP89KD | 3 | 11 | |
| HUMHSP89KD | 3 | 40 | |
| HUMHSP89KD | 3 | 49 | |
| HUMHSP89KD | 3 | 274 | 25 |
| HUMHSP89KD | 5 | 121 | |
| HUMHSP89KD | 5 | 252 | 12 |
| HUMHSP89KD | 7 | 59 | |
| HUMHSP89KD | 7 | 129 | |
| HUMHSP89KD | 7 | 157 | |
| HUMHSP89KD | 7 | 222 | 105 |
| HUMHSP89KD | 8 | 3 | |
| HUMHSP89KD | 8 | 40 | |
| HUMHSP89KD | 8 | 180 | 22 |
| HUMHSP89KD | 9 | 122 | |
| HUMHSP89KD | 9 | 143 | 18 |
| AF016898 | 1 | 350 | |
| AF016898 | 1 | 657 | |
| AF016898 | 1 | 1297 | |
| AF016898 | 1 | 1979 | |
| AF016898 | 1 | 2017 | |
| AF016898 | 1 | 2191 | 88 |
| AF016898 | 2 | 27 | |
| AF016898 | 2 | 111 | |
| AF016898 | 2 | 115 | |
| AF016898 | 2 | 126 | |
| AF016898 | 2 | 140 | |
| AF016898 | 2 | 145 | |
| AF016898 | 2 | 245 | |
| AF016898 | 2 | 259 | |
| AF016898 | 2 | 1301 | |
| AF016898 | 2 | 1305 | |
| AF016898 | 2 | 1766 | |
| AF016898 | 2 | 1793 | |
| AF016898 | 2 | 2830 | |
| AF016898 | 2 | 3053 | |
| AF016898 | 2 | 3301 | |
| AF016898 | 2 | 4168 | |
| AF016898 | 2 | 4218 | |
| AF016898 | 2 | 4474 | |
| AF016898 | 2 | 4615 | |
| AF016898 | 2 | 5017 | |
| AF016898 | 2 | 5557 | |
| AF016898 | 2 | 5960 | |
| AF016898 | 2 | 6127 | |
| AF016898 | 2 | 6261 | |
| AF016898 | 2 | 6326 | |
| AF016898 | 2 | 7032 | |
| AF016898 | 2 | 7240 | |
| AF016898 | 2 | 8190 | |
| AF016898 | 2 | 8611 | |
| AF016898 | 2 | 8629 | |
| AF016898 | 2 | 9028 | |
| AF016898 | 2 | 9621 | |
| AF016898 | 2 | 9637 | |
| AF016898 | 2 | 9744 | 37 |
| HSPEX | 1 | 31 | |
| HSPEX | 1 | 225 | |
| HSPEX | 1 | 231 | |
| HSPEX | 1 | 519 | |
| HSPEX | 1 | 618 | |
| HSPEX | 1 | 1160 | |
| HSPEX | 1 | 1171 | |
| HSPEX | 1 | 1723 | |
| HSPEX | 1 | 3171 | |
| HSPEX | 1 | 3758 | |
| HSPEX | 1 | 4650 | |
| HSPEX | 1 | 5165 | 66 |
| HSPEX | 2 | 531 | |
| HSPEX | 2 | 778 | |
| HSPEX | 2 | 991 | |
| HSPEX | 2 | 1426 | |
| HSPEX | 2 | 1497 | |
| HSPEX | 2 | 1695 | |
| HSPEX | 2 | 1772 | |
| HSPEX | 2 | 2053 | |
| HSPEX | 2 | 2113 | |
| HSPEX | 2 | 2190 | |
| HSPEX | 2 | 2234 | |
| HSPEX | 2 | 2395 | |
| HSPEX | 2 | 2404 | |
| HSPEX | 2 | 2427 | |
| HSPEX | 2 | 2609 | |
| HSPEX | 2 | 2666 | |
| HSPEX | 2 | 2833 | |
| HSPEX | 2 | 3083 | |
| HSPEX | 2 | 3106 | |
| HSPEX | 2 | 3489 | |
| HSPEX | 2 | 3526 | |
| HSPEX | 2 | 4369 | |
| HSPEX | 2 | 4439 | |
| HSPEX | 2 | 4647 | |
| HSPEX | 2 | 4795 | |
| HSPEX | 2 | 4935 | |
| HSPEX | 2 | 4974 | |
| HSPEX | 2 | 5102 | |
| HSPEX | 2 | 5224 | |
| HSPEX | 2 | 5522 | |
| HSPEX | 2 | 5561 | |
| HSPEX | 2 | 5589 | |
| HSPEX | 2 | 5683 | |
| HSPEX | 2 | 5885 | |
| HSPEX | 2 | 5942 | |
| HSPEX | 2 | 6235 | |
| HSPEX | 2 | 7044 | |
| HSPEX | 2 | 7294 | |
| HSPEX | 2 | 7800 | |
| HSPEX | 2 | 7860 | |
| HSPEX | 2 | 8130 | |
| HSPEX | 2 | 8367 | 96 |
| HSPEX | 3 | 195 | |
| HSPEX | 3 | 711 | |
| HSPEX | 3 | 771 | |
| HSPEX | 3 | 785 | |
| HSPEX | 3 | 1139 | |
| HSPEX | 3 | 1533 | |
| HSPEX | 3 | 1721 | |
| HSPEX | 3 | 1878 | |
| HSPEX | 3 | 2137 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSPEX | 3 | 2432 | |
| HSPEX | 3 | 2559 | |
| HSPEX | 3 | 2981 | |
| HSPEX | 3 | 3153 | |
| HSPEX | 3 | 3784 | |
| HSPEX | 3 | 4022 | |
| HSPEX | 3 | 4091 | |
| HSPEX | 3 | 4105 | |
| HSPEX | 3 | 4189 | |
| HSPEX | 3 | 4659 | |
| HSPEX | 3 | 4864 | |
| HSPEX | 3 | 5251 | |
| HSPEX | 3 | 5293 | |
| HSPEX | 3 | 5357 | |
| HSPEX | 3 | 5602 | |
| HSPEX | 3 | 6189 | |
| HSPEX | 3 | 6286 | |
| HSPEX | 3 | 6501 | |
| HSPEX | 3 | 7023 | |
| HSPEX | 3 | 7158 | |
| HSPEX | 3 | 7200 | |
| HSPEX | 3 | 7356 | |
| HSPEX | 3 | 7547 | |
| HSPEX | 3 | 7624 | |
| HSPEX | 3 | 7628 | |
| HSPEX | 3 | 7659 | |
| HSPEX | 3 | 7690 | |
| HSPEX | 3 | 8230 | |
| HSPEX | 3 | 8625 | |
| HSPEX | 3 | 8818 | |
| HSPEX | 3 | 8992 | |
| HSPEX | 3 | 9084 | |
| HSPEX | 3 | 9357 | |
| HSPEX | 3 | 9375 | |
| HSPEX | 3 | 9438 | |
| HSPEX | 3 | 9748 | |
| HSPEX | 3 | 9755 | |
| HSPEX | 3 | 9961 | |
| HSPEX | 3 | 10029 | |
| HSPEX | 3 | 10160 | |
| HSPEX | 3 | 10282 | |
| HSPEX | 3 | 10949 | |
| HSPEX | 3 | 11467 | |
| HSPEX | 3 | 11870 | |
| HSPEX | 3 | 11987 | |
| HSPEX | 3 | 12159 | |
| HSPEX | 3 | 12439 | |
| HSPEX | 3 | 12512 | |
| HSPEX | 3 | 12738 | |
| HSPEX | 3 | 12790 | |
| HSPEX | 3 | 12919 | |
| HSPEX | 3 | 13247 | |
| HSPEX | 3 | 13287 | |
| HSPEX | 3 | 13453 | |
| HSPEX | 3 | 13647 | |
| HSPEX | 3 | 13651 | |
| HSPEX | 3 | 13795 | |
| HSPEX | 3 | 14179 | |
| HSPEX | 3 | 14270 | |
| HSPEX | 3 | 14350 | |
| HSPEX | 3 | 14420 | |
| HSPEX | 3 | 14571 | |
| HSPEX | 3 | 14618 | |
| HSPEX | 3 | 14666 | |
| HSPEX | 3 | 14781 | |
| HSPEX | 3 | 15040 | |
| HSPEX | 3 | 15117 | |
| HSPEX | 3 | 15141 | |
| HSPEX | 3 | 15691 | |
| HSPEX | 3 | 15852 | |
| HSPEX | 3 | 15943 | |
| HSPEX | 3 | 16159 | |
| HSPEX | 3 | 16268 | |
| HSPEX | 3 | 16971 | |
| HSPEX | 3 | 16980 | |
| HSPEX | 3 | 16984 | |
| HSPEX | 3 | 17173 | |
| HSPEX | 3 | 17299 | |
| HSPEX | 3 | 17533 | |
| HSPEX | 3 | 17697 | |
| HSPEX | 3 | 17762 | |
| HSPEX | 3 | 17944 | |
| HSPEX | 3 | 18491 | |
| HSPEX | 3 | 18662 | |
| HSPEX | 3 | 19033 | |
| HSPEX | 3 | 19247 | |
| HSPEX | 3 | 19557 | |
| HSPEX | 3 | 19575 | |
| HSPEX | 3 | 19800 | |
| HSPEX | 3 | 20369 | |
| HSPEX | 3 | 20389 | |
| HSPEX | 3 | 20443 | |
| HSPEX | 3 | 20721 | |
| HSPEX | 3 | 20861 | |
| HSPEX | 3 | 20995 | |
| HSPEX | 3 | 21455 | |
| HSPEX | 3 | 21501 | |
| HSPEX | 3 | 21642 | |
| HSPEX | 3 | 21705 | |
| HSPEX | 3 | 21821 | |
| HSPEX | 3 | 22483 | |
| HSPEX | 3 | 22769 | |
| HSPEX | 3 | 22911 | |
| HSPEX | 3 | 23377 | |
| HSPEX | 3 | 23671 | |
| HSPEX | 3 | 23732 | |
| HSPEX | 3 | 24672 | |
| HSPEX | 3 | 25102 | |
| HSPEX | 3 | 25448 | |
| HSPEX | 3 | 25525 | |
| HSPEX | 3 | 25728 | |
| HSPEX | 3 | 25839 | |
| HSPEX | 3 | 25898 | |
| HSPEX | 3 | 26570 | |
| HSPEX | 3 | 26614 | |
| HSPEX | 3 | 26768 | |
| HSPEX | 3 | 26794 | |
| HSPEX | 3 | 27203 | |
| HSPEX | 3 | 27292 | |
| HSPEX | 3 | 27434 | |
| HSPEX | 3 | 27636 | |
| HSPEX | 3 | 27650 | |
| HSPEX | 3 | 28033 | |
| HSPEX | 3 | 28119 | |
| HSPEX | 3 | 28366 | |
| HSPEX | 3 | 28516 | |
| HSPEX | 3 | 28616 | |
| HSPEX | 3 | 29136 | 63 |
| HSPEX | 4 | 539 | |
| HSPEX | 4 | 575 | |
| HSPEX | 4 | 823 | 6 |
| HSPEX | 5 | 1061 | |
| HSPEX | 5 | 1112 | |
| HSPEX | 5 | 1264 | |
| HSPEX | 5 | 1411 | |
| HSPEX | 5 | 1723 | |
| HSPEX | 5 | 1946 | |
| HSPEX | 5 | 2235 | |
| HSPEX | 5 | 2546 | |
| HSPEX | 5 | 3156 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSPEX | 5 | 3882 | |
| HSPEX | 5 | 4057 | |
| HSPEX | 5 | 4092 | |
| HSPEX | 5 | 4182 | |
| HSPEX | 5 | 4442 | |
| HSPEX | 5 | 4502 | |
| HSPEX | 5 | 4760 | |
| HSPEX | 5 | 4793 | |
| HSPEX | 5 | 5082 | |
| HSPEX | 5 | 5498 | |
| HSPEX | 5 | 5590 | |
| HSPEX | 5 | 5595 | |
| HSPEX | 5 | 5898 | |
| HSPEX | 5 | 6294 | |
| HSPEX | 5 | 6390 | |
| HSPEX | 5 | 6561 | |
| HSPEX | 5 | 6684 | |
| HSPEX | 5 | 7026 | |
| HSPEX | 5 | 7644 | |
| HSPEX | 5 | 7658 | |
| HSPEX | 5 | 7775 | |
| HSPEX | 5 | 8100 | |
| HSPEX | 5 | 8288 | |
| HSPEX | 5 | 8488 | |
| HSPEX | 5 | 8680 | |
| HSPEX | 5 | 8925 | |
| HSPEX | 5 | 9346 | |
| HSPEX | 5 | 10433 | |
| HSPEX | 5 | 10612 | |
| HSPEX | 5 | 10652 | |
| HSPEX | 5 | 11015 | |
| HSPEX | 5 | 11272 | |
| HSPEX | 5 | 11279 | |
| HSPEX | 5 | 11419 | |
| HSPEX | 5 | 11461 | |
| HSPEX | 5 | 11995 | |
| HSPEX | 5 | 12579 | |
| HSPEX | 5 | 12672 | |
| HSPEX | 5 | 12676 | 4 |
| HSPEX | 6 | 448 | 41 |
| HSPEX | 6 | 487 | |
| HSPEX | 6 | 964 | |
| HSPEX | 6 | 1269 | |
| HSPEX | 6 | 1345 | |
| HSPEX | 6 | 1540 | |
| HSPEX | 6 | 1975 | |
| HSPEX | 6 | 2682 | |
| HSPEX | 6 | 2717 | |
| HSPEX | 6 | 2769 | |
| HSPEX | 6 | 2802 | |
| HSPEX | 6 | 2864 | |
| HSPEX | 6 | 3026 | |
| HSPEX | 6 | 3030 | 55 |
| HSPEX | 7 | 504 | |
| HSPEX | 7 | 517 | |
| HSPEX | 7 | 640 | |
| HSPEX | 7 | 984 | |
| HSPEX | 7 | 994 | |
| HSPEX | 7 | 1020 | |
| HSPEX | 7 | 1533 | |
| HSPEX | 7 | 1703 | |
| HSPEX | 7 | 1927 | |
| HSPEX | 7 | 2083 | |
| HSPEX | 7 | 2102 | |
| HSPEX | 7 | 2126 | |
| HSPEX | 7 | 2291 | |
| HSPEX | 7 | 2304 | |
| HSPEX | 7 | 2460 | |
| HSPEX | 7 | 2516 | 13 |
| HSPEX | 8 | 252 | |
| HSPEX | 8 | 430 | |
| HSPEX | 8 | 575 | |
| HSPEX | 8 | 681 | |
| HSPEX | 8 | 829 | |
| HSPEX | 8 | 996 | |
| HSPEX | 8 | 1128 | |
| HSPEX | 8 | 1461 | |
| HSPEX | 8 | 1516 | |
| HSPEX | 8 | 1629 | |
| HSPEX | 8 | 1694 | |
| HSPEX | 8 | 1860 | 136 |
| HSPEX | 9 | 416 | |
| HSPEX | 9 | 1005 | |
| HSPEX | 9 | 1009 | |
| HSPEX | 9 | 1240 | |
| HSPEX | 9 | 1337 | |
| HSPEX | 9 | 1391 | |
| HSPEX | 9 | 1430 | |
| HSPEX | 9 | 1548 | |
| HSPEX | 9 | 1788 | |
| HSPEX | 9 | 2552 | |
| HSPEX | 9 | 2871 | |
| HSPEX | 9 | 3156 | |
| HSPEX | 9 | 3190 | |
| HSPEX | 9 | 3463 | |
| HSPEX | 9 | 3508 | |
| HSPEX | 9 | 3535 | |
| HSPEX | 9 | 3787 | |
| HSPEX | 9 | 3885 | |
| HSPEX | 9 | 4223 | |
| HSPEX | 9 | 4386 | |
| HSPEX | 9 | 5129 | |
| HSPEX | 9 | 5216 | |
| HSPEX | 9 | 5307 | |
| HSPEX | 9 | 5493 | |
| HSPEX | 9 | 5652 | |
| HSPEX | 9 | 5788 | |
| HSPEX | 9 | 5846 | |
| HSPEX | 9 | 6285 | |
| HSPEX | 9 | 6498 | |
| HSPEX | 9 | 6619 | |
| HSPEX | 9 | 6651 | |
| HSPEX | 9 | 6842 | |
| HSPEX | 9 | 7011 | |
| HSPEX | 9 | 7607 | |
| HSPEX | 9 | 7886 | |
| HSPEX | 9 | 7924 | |
| HSPEX | 9 | 8023 | |
| HSPEX | 9 | 8266 | |
| HSPEX | 9 | 8273 | |
| HSPEX | 9 | 8717 | |
| HSPEX | 9 | 8972 | |
| HSPEX | 9 | 9447 | |
| HSPEX | 9 | 9576 | |
| HSPEX | 9 | 9731 | |
| HSPEX | 9 | 9939 | |
| HSPEX | 9 | 10342 | |
| HSPEX | 9 | 10466 | |
| HSPEX | 9 | 10499 | |
| HSPEX | 9 | 10609 | |
| HSPEX | 9 | 10799 | |
| HSPEX | 9 | 10851 | |
| HSPEX | 9 | 10877 | |
| HSPEX | 9 | 10987 | |
| HSPEX | 9 | 11187 | |
| HSPEX | 9 | 11227 | |
| HSPEX | 9 | 11353 | |
| HSPEX | 9 | 11425 | |
| HSPEX | 9 | 11584 | |
| HSPEX | 9 | 11628 | 2 |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSPEX | 10 | 187 | |
| HSPEX | 10 | 895 | |
| HSPEX | 10 | 902 | |
| HSPEX | 10 | 1128 | |
| HSPEX | 10 | 1436 | |
| HSPEX | 10 | 1606 | |
| HSPEX | 10 | 1611 | |
| HSPEX | 10 | 2067 | |
| HSPEX | 10 | 2624 | |
| HSPEX | 10 | 2668 | 37 |
| HSPEX | 11 | 194 | |
| HSPEX | 11 | 211 | |
| HSPEX | 11 | 293 | |
| HSPEX | 11 | 297 | |
| HSPEX | 11 | 527 | |
| HSPEX | 11 | 1088 | |
| HSPEX | 11 | 2423 | |
| HSPEX | 11 | 2581 | |
| HSPEX | 11 | 3055 | |
| HSPEX | 11 | 3169 | |
| HSPEX | 11 | 3528 | |
| HSPEX | 11 | 3562 | |
| HSPEX | 11 | 3672 | |
| HSPEX | 11 | 3784 | |
| HSPEX | 11 | 3862 | |
| HSPEX | 11 | 4088 | |
| HSPEX | 11 | 5148 | |
| HSPEX | 11 | 5289 | |
| HSPEX | 11 | 5352 | |
| HSPEX | 11 | 5365 | |
| HSPEX | 11 | 5392 | |
| HSPEX | 11 | 5651 | |
| HSPEX | 11 | 5690 | |
| HSPEX | 11 | 5899 | |
| HSPEX | 11 | 6083 | |
| HSPEX | 11 | 6250 | |
| HSPEX | 11 | 6476 | |
| HSPEX | 11 | 6695 | |
| HSPEX | 11 | 6789 | |
| HSPEX | 11 | 6816 | |
| HSPEX | 11 | 6896 | |
| HSPEX | 11 | 7037 | |
| HSPEX | 11 | 7344 | |
| HSPEX | 11 | 7509 | |
| HSPEX | 11 | 7730 | |
| HSPEX | 11 | 8172 | |
| HSPEX | 11 | 8281 | |
| HSPEX | 11 | 8544 | |
| HSPEX | 11 | 8679 | |
| HSPEX | 11 | 8831 | |
| HSPEX | 11 | 9043 | |
| HSPEX | 11 | 9124 | |
| HSPEX | 11 | 9386 | |
| HSPEX | 11 | 9544 | |
| HSPEX | 11 | 9674 | |
| HSPEX | 11 | 10415 | |
| HSPEX | 11 | 10496 | |
| HSPEX | 11 | 10779 | |
| HSPEX | 11 | 10854 | |
| HSPEX | 11 | 11312 | |
| HSPEX | 11 | 11482 | |
| HSPEX | 11 | 11490 | |
| HSPEX | 11 | 11982 | |
| HSPEX | 11 | 12091 | |
| HSPEX | 11 | 12519 | |
| HSPEX | 11 | 12561 | |
| HSPEX | 11 | 12797 | |
| HSPEX | 11 | 13141 | |
| HSPEX | 11 | 13218 | |
| HSPEX | 11 | 13243 | |
| HSPEX | 11 | 13261 | |
| HSPEX | 11 | 13353 | |
| HSPEX | 11 | 13710 | |
| HSPEX | 11 | 14449 | |
| HSPEX | 11 | 14544 | |
| HSPEX | 11 | 14555 | |
| HSPEX | 11 | 14594 | |
| HSPEX | 11 | 14735 | |
| HSPEX | 11 | 15022 | |
| HSPEX | 11 | 15675 | |
| HSPEX | 11 | 16053 | |
| HSPEX | 11 | 16730 | |
| HSPEX | 11 | 17799 | |
| HSPEX | 11 | 18181 | |
| HSPEX | 11 | 18209 | |
| HSPEX | 11 | 18734 | 139 |
| HSPEX | 12 | 170 | |
| HSPEX | 12 | 281 | |
| HSPEX | 12 | 738 | |
| HSPEX | 12 | 752 | |
| HSPEX | 12 | 909 | |
| HSPEX | 12 | 1034 | |
| HSPEX | 12 | 1104 | |
| HSPEX | 12 | 1243 | |
| HSPEX | 12 | 1503 | |
| HSPEX | 12 | 1724 | |
| HSPEX | 12 | 1818 | |
| HSPEX | 12 | 2379 | |
| HSPEX | 12 | 2407 | |
| HSPEX | 12 | 2749 | |
| HSPEX | 12 | 3112 | |
| HSPEX | 12 | 3196 | |
| HSPEX | 12 | 3439 | |
| HSPEX | 12 | 3822 | |
| HSPEX | 12 | 3854 | |
| HSPEX | 12 | 3951 | |
| HSPEX | 12 | 3999 | |
| HSPEX | 12 | 4115 | |
| HSPEX | 12 | 4819 | |
| HSPEX | 12 | 4876 | |
| HSPEX | 12 | 5388 | |
| HSPEX | 12 | 5405 | |
| HSPEX | 12 | 5679 | |
| HSPEX | 12 | 5816 | |
| HSPEX | 12 | 5993 | |
| HSPEX | 12 | 6040 | |
| HSPEX | 12 | 6288 | |
| HSPEX | 12 | 6316 | |
| HSPEX | 12 | 6506 | |
| HSPEX | 12 | 6571 | |
| HSPEX | 12 | 6620 | |
| HSPEX | 12 | 6633 | |
| HSPEX | 12 | 6957 | |
| HSPEX | 12 | 7284 | |
| HSPEX | 12 | 7288 | |
| HSPEX | 12 | 7589 | |
| HSPEX | 12 | 7631 | |
| HSPEX | 12 | 8412 | |
| HSPEX | 12 | 9038 | |
| HSPEX | 12 | 9511 | |
| HSPEX | 12 | 9751 | |
| HSPEX | 12 | 9820 | |
| HSPEX | 12 | 10313 | |
| HSPEX | 12 | 10555 | |
| HSPEX | 12 | 11187 | |
| HSPEX | 12 | 11754 | |
| HSPEX | 12 | 11772 | |
| HSPEX | 12 | 12687 | |
| HSPEX | 12 | 13342 | |
| HSPEX | 12 | 13346 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSPEX | 12 | 13496 | |
| HSPEX | 12 | 14244 | |
| HSPEX | 12 | 14571 | |
| HSPEX | 12 | 14783 | |
| HSPEX | 12 | 14855 | |
| HSPEX | 12 | 15036 | |
| HSPEX | 12 | 15094 | |
| HSPEX | 12 | 15522 | |
| HSPEX | 12 | 15556 | |
| HSPEX | 12 | 15645 | |
| HSPEX | 12 | 15915 | |
| HSPEX | 12 | 16161 | |
| HSPEX | 12 | 16217 | |
| HSPEX | 12 | 16497 | |
| HSPEX | 12 | 16539 | |
| HSPEX | 12 | 17111 | |
| HSPEX | 12 | 17137 | |
| HSPEX | 12 | 17392 | |
| HSPEX | 12 | 17726 | |
| HSPEX | 12 | 17754 | |
| HSPEX | 12 | 18520 | |
| HSPEX | 12 | 18563 | |
| HSPEX | 12 | 19055 | |
| HSPEX | 12 | 19189 | |
| HSPEX | 12 | 19355 | |
| HSPEX | 12 | 20337 | |
| HSPEX | 12 | 20632 | |
| HSPEX | 12 | 20723 | |
| HSPEX | 12 | 21037 | |
| HSPEX | 12 | 21656 | |
| HSPEX | 12 | 21775 | |
| HSPEX | 12 | 21807 | |
| HSPEX | 12 | 21893 | |
| HSPEX | 12 | 21947 | |
| HSPEX | 12 | 22655 | |
| HSPEX | 12 | 22665 | |
| HSPEX | 12 | 22701 | |
| HSPEX | 12 | 22970 | |
| HSPEX | 12 | 23384 | |
| HSPEX | 12 | 23535 | |
| HSPEX | 12 | 23635 | |
| HSPEX | 12 | 23755 | |
| HSPEX | 12 | 23785 | |
| HSPEX | 12 | 23813 | |
| HSPEX | 12 | 23922 | |
| HSPEX | 12 | 24880 | |
| HSPEX | 12 | 24954 | |
| HSPEX | 12 | 25013 | |
| HSPEX | 12 | 25201 | |
| HSPEX | 12 | 25207 | |
| HSPEX | 12 | 25419 | |
| HSPEX | 12 | 25637 | |
| HSPEX | 12 | 26163 | |
| HSPEX | 12 | 26505 | |
| HSPEX | 12 | 26696 | |
| HSPEX | 12 | 26710 | |
| HSPEX | 12 | 27147 | |
| HSPEX | 12 | 27295 | |
| HSPEX | 12 | 27617 | |
| HSPEX | 12 | 28030 | |
| HSPEX | 12 | 28517 | |
| HSPEX | 12 | 28796 | |
| HSPEX | 12 | 29345 | |
| HSPEX | 12 | 30110 | |
| HSPEX | 12 | 30207 | |
| HSPEX | 12 | 30308 | |
| HSPEX | 12 | 30756 | |
| HSPEX | 12 | 30773 | |
| HSPEX | 12 | 30876 | |
| HSPEX | 12 | 31190 | |
| HSPEX | 12 | 31444 | |
| HSPEX | 12 | 31542 | |
| HSPEX | 12 | 31651 | |
| HSPEX | 12 | 31655 | |
| HSPEX | 12 | 31903 | |
| HSPEX | 12 | 32312 | |
| HSPEX | 12 | 32963 | |
| HSPEX | 12 | 33007 | |
| HSPEX | 12 | 33438 | |
| HSPEX | 12 | 33725 | |
| HSPEX | 12 | 33993 | |
| HSPEX | 12 | 34192 | 43 |
| HSPEX | 13 | 496 | |
| HSPEX | 13 | 567 | |
| HSPEX | 13 | 635 | |
| HSPEX | 13 | 719 | |
| HSPEX | 13 | 835 | |
| HSPEX | 13 | 1135 | |
| HSPEX | 13 | 1424 | |
| HSPEX | 13 | 1742 | |
| HSPEX | 13 | 1881 | |
| HSPEX | 13 | 2033 | |
| HSPEX | 13 | 2647 | |
| HSPEX | 13 | 3292 | |
| HSPEX | 13 | 3644 | |
| HSPEX | 13 | 3686 | |
| HSPEX | 13 | 3815 | |
| HSPEX | 13 | 3892 | |
| HSPEX | 13 | 3954 | |
| HSPEX | 13 | 4086 | |
| HSPEX | 13 | 4392 | |
| HSPEX | 13 | 4507 | |
| HSPEX | 13 | 4572 | |
| HSPEX | 13 | 4587 | |
| HSPEX | 13 | 4689 | |
| HSPEX | 13 | 4850 | |
| HSPEX | 13 | 5114 | |
| HSPEX | 13 | 5126 | |
| HSPEX | 13 | 5193 | |
| HSPEX | 13 | 6451 | |
| HSPEX | 13 | 6638 | |
| HSPEX | 13 | 6699 | |
| HSPEX | 13 | 6899 | |
| HSPEX | 13 | 7061 | |
| HSPEX | 13 | 7645 | |
| HSPEX | 13 | 7765 | |
| HSPEX | 13 | 8036 | |
| HSPEX | 13 | 8324 | |
| HSPEX | 13 | 8486 | |
| HSPEX | 13 | 8763 | |
| HSPEX | 13 | 8786 | |
| HSPEX | 13 | 8790 | |
| HSPEX | 13 | 9019 | |
| HSPEX | 13 | 9077 | |
| HSPEX | 13 | 9339 | |
| HSPEX | 13 | 9606 | 85 |
| HSPEX | 14 | 40 | |
| HSPEX | 14 | 166 | |
| HSPEX | 14 | 382 | |
| HSPEX | 14 | 419 | |
| HSPEX | 14 | 589 | |
| HSPEX | 14 | 1015 | |
| HSPEX | 14 | 1649 | |
| HSPEX | 14 | 1691 | |
| HSPEX | 14 | 1806 | |
| HSPEX | 14 | 2123 | |
| HSPEX | 14 | 2151 | |
| HSPEX | 14 | 2466 | |
| HSPEX | 14 | 2731 | |
| HSPEX | 14 | 2766 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSPEX | 14 | 2927 | |
| HSPEX | 14 | 3134 | |
| HSPEX | 14 | 3438 | |
| HSPEX | 14 | 3646 | |
| HSPEX | 14 | 3859 | |
| HSPEX | 14 | 4869 | |
| HSPEX | 14 | 4966 | |
| HSPEX | 14 | 4983 | |
| HSPEX | 14 | 5387 | |
| HSPEX | 14 | 6225 | |
| HSPEX | 14 | 6315 | |
| HSPEX | 14 | 6519 | |
| HSPEX | 14 | 7614 | |
| HSPEX | 14 | 7808 | |
| HSPEX | 14 | 7891 | |
| HSPEX | 14 | 7986 | |
| HSPEX | 14 | 8317 | |
| HSPEX | 14 | 8327 | |
| HSPEX | 14 | 8919 | |
| HSPEX | 14 | 9289 | |
| HSPEX | 14 | 9299 | |
| HSPEX | 14 | 9632 | |
| HSPEX | 14 | 9646 | |
| HSPEX | 14 | 9732 | |
| HSPEX | 14 | 9834 | |
| HSPEX | 14 | 10177 | |
| HSPEX | 14 | 10252 | |
| HSPEX | 14 | 10620 | |
| HSPEX | 14 | 10638 | |
| HSPEX | 14 | 11128 | |
| HSPEX | 14 | 11146 | |
| HSPEX | 14 | 11495 | |
| HSPEX | 14 | 11499 | |
| HSPEX | 14 | 11661 | |
| HSPEX | 14 | 11823 | 2 |
| HSPEX | 15 | 73 | |
| HSPEX | 15 | 357 | |
| HSPEX | 15 | 398 | |
| HSPEX | 15 | 474 | |
| HSPEX | 15 | 480 | |
| HSPEX | 15 | 659 | |
| HSPEX | 15 | 1028 | |
| HSPEX | 15 | 1174 | |
| HSPEX | 15 | 1515 | |
| HSPEX | 15 | 2005 | |
| HSPEX | 15 | 2506 | |
| HSPEX | 15 | 3110 | |
| HSPEX | 15 | 3533 | |
| HSPEX | 15 | 3811 | |
| HSPEX | 15 | 3967 | |
| HSPEX | 15 | 4056 | |
| HSPEX | 15 | 4074 | |
| HSPEX | 15 | 4416 | |
| HSPEX | 15 | 4514 | |
| HSPEX | 15 | 5341 | |
| HSPEX | 15 | 5534 | |
| HSPEX | 15 | 5579 | |
| HSPEX | 15 | 6751 | |
| HSPEX | 15 | 7033 | |
| HSPEX | 15 | 7228 | |
| HSPEX | 15 | 7874 | |
| HSPEX | 15 | 7894 | |
| HSPEX | 15 | 8041 | |
| HSPEX | 15 | 8342 | |
| HSPEX | 15 | 8787 | |
| HSPEX | 15 | 9047 | |
| HSPEX | 15 | 9218 | |
| HSPEX | 15 | 9252 | |
| HSPEX | 15 | 9584 | |
| HSPEX | 15 | 9594 | |
| HSPEX | 15 | 9680 | |
| HSPEX | 15 | 9800 | |
| HSPEX | 15 | 9874 | |
| HSPEX | 15 | 10295 | |
| HSPEX | 15 | 10311 | |
| HSPEX | 15 | 10581 | |
| HSPEX | 15 | 10959 | |
| HSPEX | 15 | 11171 | |
| HSPEX | 15 | 11330 | |
| HSPEX | 15 | 11344 | |
| HSPEX | 15 | 11349 | |
| HSPEX | 15 | 11606 | |
| HSPEX | 15 | 12554 | |
| HSPEX | 15 | 12574 | |
| HSPEX | 15 | 12579 | |
| HSPEX | 15 | 12738 | |
| HSPEX | 15 | 13502 | |
| HSPEX | 15 | 13564 | |
| HSPEX | 15 | 13676 | |
| HSPEX | 15 | 13832 | |
| HSPEX | 15 | 14103 | |
| HSPEX | 15 | 14288 | |
| HSPEX | 15 | 14904 | |
| HSPEX | 15 | 15233 | |
| HSPEX | 15 | 15754 | |
| HSPEX | 15 | 15799 | |
| HSPEX | 15 | 16033 | |
| HSPEX | 15 | 16065 | |
| HSPEX | 15 | 16173 | |
| HSPEX | 15 | 16184 | |
| HSPEX | 15 | 16510 | |
| HSPEX | 15 | 16590 | |
| HSPEX | 15 | 16736 | |
| HSPEX | 15 | 17030 | |
| HSPEX | 15 | 17437 | |
| HSPEX | 15 | 17631 | |
| HSPEX | 15 | 17702 | |
| HSPEX | 15 | 17727 | |
| HSPEX | 15 | 17813 | |
| HSPEX | 15 | 18209 | |
| HSPEX | 15 | 18249 | |
| HSPEX | 15 | 18340 | |
| HSPEX | 15 | 18479 | |
| HSPEX | 15 | 18543 | |
| HSPEX | 15 | 18572 | |
| HSPEX | 15 | 18619 | |
| HSPEX | 15 | 18641 | |
| HSPEX | 15 | 18694 | |
| HSPEX | 15 | 19369 | |
| HSPEX | 15 | 19891 | |
| HSPEX | 15 | 20146 | |
| HSPEX | 15 | 20608 | |
| HSPEX | 15 | 20652 | |
| HSPEX | 15 | 20708 | |
| HSPEX | 15 | 20894 | |
| HSPEX | 15 | 20941 | |
| HSPEX | 15 | 21025 | |
| HSPEX | 15 | 21180 | |
| HSPEX | 15 | 21233 | |
| HSPEX | 15 | 21246 | |
| HSPEX | 15 | 21505 | |
| HSPEX | 15 | 21584 | 60 |
| HSPEX | 16 | 85 | |
| HSPEX | 16 | 147 | |
| HSPEX | 16 | 212 | |
| HSPEX | 16 | 519 | |
| HSPEX | 16 | 619 | |
| HSPEX | 16 | 651 | |
| HSPEX | 16 | 827 | |
| HSPEX | 16 | 929 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSPEX | 16 | 1038 | |
| HSPEX | 16 | 1123 | |
| HSPEX | 16 | 1524 | |
| HSPEX | 16 | 2176 | |
| HSPEX | 16 | 2204 | |
| HSPEX | 16 | 2589 | |
| HSPEX | 16 | 2617 | |
| HSPEX | 16 | 3661 | |
| HSPEX | 16 | 3796 | |
| HSPEX | 16 | 3996 | |
| HSPEX | 16 | 4507 | |
| HSPEX | 16 | 4590 | |
| HSPEX | 16 | 4685 | |
| HSPEX | 16 | 5072 | |
| HSPEX | 16 | 5242 | |
| HSPEX | 16 | 5481 | |
| HSPEX | 16 | 5558 | |
| HSPEX | 16 | 5914 | 2 |
| HSPEX | 17 | 615 | |
| HSPEX | 17 | 1599 | |
| HSPEX | 17 | 2213 | |
| HSPEX | 17 | 2437 | 21 |
| HSPEX | 18 | 291 | |
| HSPEX | 18 | 375 | |
| HSPEX | 18 | 760 | |
| HSPEX | 18 | 1151 | |
| HSPEX | 18 | 1668 | |
| HSPEX | 18 | 1729 | |
| HSPEX | 18 | 1769 | |
| HSPEX | 18 | 2241 | |
| HSPEX | 18 | 2339 | |
| HSPEX | 18 | 2516 | |
| HSPEX | 18 | 2541 | |
| HSPEX | 18 | 2729 | |
| HSPEX | 18 | 2763 | |
| HSPEX | 18 | 2910 | |
| HSPEX | 18 | 3074 | |
| HSPEX | 18 | 3105 | |
| HSPEX | 18 | 3137 | |
| HSPEX | 18 | 3653 | |
| HSPEX | 18 | 3912 | |
| HSPEX | 18 | 3971 | |
| HSPEX | 18 | 4244 | |
| HSPEX | 18 | 4290 | |
| HSPEX | 18 | 4337 | |
| HSPEX | 18 | 4458 | |
| HSPEX | 18 | 4462 | |
| HSPEX | 18 | 4473 | |
| HSPEX | 18 | 4579 | 70 |
| HSPEX | 19 | 133 | |
| HSPEX | 19 | 653 | |
| HSPEX | 19 | 842 | 43 |
| HSPEX | 20 | 138 | |
| HSPEX | 20 | 239 | |
| HSPEX | 20 | 508 | |
| HSPEX | 20 | 680 | |
| HSPEX | 20 | 805 | |
| HSPEX | 20 | 1236 | |
| HSPEX | 20 | 1294 | |
| HSPEX | 20 | 2416 | |
| HSPEX | 20 | 2887 | |
| HSPEX | 20 | 2904 | |
| HSPEX | 20 | 3215 | |
| HSPEX | 20 | 3950 | |
| HSPEX | 20 | 4172 | |
| HSPEX | 20 | 4470 | |
| HSPEX | 20 | 5030 | |
| HSPEX | 20 | 5069 | |
| HSPEX | 20 | 5087 | |
| HSPEX | 20 | 5190 | |
| HSPEX | 20 | 5652 | |
| HSPEX | 20 | 6050 | |
| HSPEX | 20 | 6277 | |
| HSPEX | 20 | 6628 | |
| HSPEX | 20 | 6863 | |
| HSPEX | 20 | 7025 | |
| HSPEX | 20 | 7501 | |
| HSPEX | 20 | 7506 | |
| HSPEX | 20 | 7792 | |
| HSPEX | 20 | 7873 | |
| HSPEX | 20 | 8415 | |
| HSPEX | 20 | 9469 | |
| HSPEX | 20 | 9629 | |
| HSPEX | 20 | 10274 | |
| HSPEX | 20 | 10278 | |
| HSPEX | 20 | 10451 | |
| HSPEX | 20 | 10593 | |
| HSPEX | 20 | 10671 | |
| HSPEX | 20 | 11150 | |
| HSPEX | 20 | 11287 | |
| HSPEX | 20 | 11640 | |
| HSPEX | 20 | 11833 | |
| HSPEX | 20 | 11886 | |
| HSPEX | 20 | 12057 | |
| HSPEX | 20 | 13413 | |
| HSPEX | 20 | 13568 | |
| HSPEX | 20 | 15246 | |
| HSPEX | 20 | 15692 | |
| HSPEX | 20 | 15996 | |
| HSPEX | 20 | 16371 | |
| HSPEX | 20 | 16771 | |
| HSPEX | 20 | 16876 | 31 |
| HSPEX | 21 | 88 | |
| HSPEX | 21 | 297 | |
| HSPEX | 21 | 663 | |
| HSPEX | 21 | 1303 | |
| HSPEX | 21 | 1413 | |
| HSPEX | 21 | 2129 | 2 |
| HUMTNP2SS | 1 | 14 | |
| HUMTNP2SS | 1 | 282 | |
| HUMTNP2SS | 1 | 421 | |
| HUMTNP2SS | 1 | 787 | 9 |
| HSU46165 | 1 | 620 | |
| HSU46165 | 1 | 696 | |
| HSU46165 | 1 | 706 | 54 |
| HSU46165 | 2 | 38 | |
| HSU46165 | 2 | 104 | |
| HSU46165 | 3 | 259 | |
| HSU46165 | 3 | 299 | |
| HSU46165 | 3 | 431 | |
| HSU46165 | 3 | 587 | 6 |
| HUMCP21OH | 1 | 46 | 33 |
| HUMCP21OH | 2 | 222 | 45 |
| HUMACCYBB | 2 | 198 | 193 |
| HUMACCYBB | 4 | 34 | |
| HUMACCYBB | 4 | 54 | 19 |
| HSMGSAG | 1 | 77 | 96 |
| HSMGSAG | 3 | 93 | |
| HSMGSAG | 3 | 229 | |
| HSMGSAG | 3 | 233 | 2 |
| HSDAO | 1 | 269 | 78 |
| HSDAO | 2 | 29 | |
| HSDAO | 2 | 116 | |
| HSDAO | 2 | 224 | |
| HSDAO | 2 | 334 | |
| HSDAO | 2 | 439 | |
| HSDAO | 2 | 897 | |
| HSDAO | 2 | 915 | 2 |
| HSDAO | 3 | 262 | 247 |
| HUMATP1A2 | 1 | 37 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMATP1A2 | 1 | 150 | |
| HUMATP1A2 | 1 | 361 | |
| HUMATP1A2 | 1 | 445 | |
| HUMATP1A2 | 1 | 663 | |
| HUMATP1A2 | 1 | 1091 | |
| HUMATP1A2 | 1 | 1280 | |
| HUMATP1A2 | 1 | 1683 | |
| HUMATP1A2 | 1 | 1688 | |
| HUMATP1A2 | 1 | 3092 | |
| HUMATP1A2 | 1 | 3237 | |
| HUMATP1A2 | 1 | 3622 | |
| HUMATP1A2 | 1 | 3630 | |
| HUMATP1A2 | 1 | 3778 | |
| HUMATP1A2 | 1 | 3899 | |
| HUMATP1A2 | 1 | 4043 | |
| HUMATP1A2 | 1 | 4307 | 40 |
| HUMATP1A2 | 2 | 157 | 160 |
| HUMATP1A2 | 3 | 666 | |
| HUMATP1A2 | 3 | 1259 | |
| HUMATP1A2 | 3 | 1375 | |
| HUMATP1A2 | 3 | 1648 | |
| HUMATP1A2 | 3 | 1846 | |
| HUMATP1A2 | 3 | 1903 | 82 |
| HUMATP1A2 | 4 | 245 | |
| HUMATP1A2 | 4 | 367 | |
| HUMATP1A2 | 4 | 493 | 16 |
| HUMATP1A2 | 6 | 205 | |
| HUMATP1A2 | 6 | 295 | |
| HUMATP1A2 | 6 | 374 | |
| HUMATP1A2 | 6 | 631 | 73 |
| HUMATP1A2 | 7 | 465 | |
| HUMATP1A2 | 7 | 587 | 24 |
| HUMATP1A2 | 8 | 176 | |
| HUMATP1A2 | 8 | 720 | |
| HUMATP1A2 | 8 | 767 | 16 |
| HUMATP1A2 | 9 | 63 | 66 |
| HUMATP1A2 | 10 | 23 | 148 |
| HUMATP1A2 | 11 | 46 | |
| HUMATP1A2 | 11 | 385 | |
| HUMATP1A2 | 11 | 510 | |
| HUMATP1A2 | 11 | 617 | 49 |
| HUMATP1A2 | 13 | 789 | |
| HUMATP1A2 | 13 | 805 | |
| HUMATP1A2 | 13 | 1102 | |
| HUMATP1A2 | 13 | 1269 | |
| HUMATP1A2 | 13 | 1273 | |
| HUMATP1A2 | 13 | 1303 | |
| HUMATP1A2 | 13 | 1375 | |
| HUMATP1A2 | 13 | 1967 | |
| HUMATP1A2 | 13 | 2023 | |
| HUMATP1A2 | 13 | 2458 | |
| HUMATP1A2 | 13 | 2945 | 112 |
| HUMATP1A2 | 14 | 272 | |
| HUMATP1A2 | 14 | 333 | |
| HUMATP1A2 | 14 | 374 | 2 |
| HUMATP1A2 | 19 | 38 | 16 |
| HUMATP1A2 | 20 | 420 | |
| HUMATP1A2 | 20 | 491 | |
| HUMATP1A2 | 20 | 567 | 2 |
| HUMATP1A2 | 22 | 329 | 150 |
| HUMDNL1L | 1 | 73 | |
| HUMDNL1L | 1 | 104 | |
| HUMDNL1L | 1 | 172 | |
| HUMDNL1L | 1 | 179 | 166 |
| HUMDNL1L | 3 | 52 | |
| HUMDNL1L | 3 | 57 | |
| HUMDNL1L | 3 | 1027 | 2 |
| HUMDNL1L | 4 | 22 | 87 |
| AB000381 | 1 | 296 | |
| AB000381 | 1 | 322 | 72 |
| AB000381 | 2 | 321 | |
| AB000381 | 2 | 455 | |
| AB000381 | 2 | 845 | |
| AB000381 | 2 | 1130 | |
| AB000381 | 2 | 1166 | |
| AB000381 | 2 | 1460 | |
| AB000381 | 2 | 1637 | |
| AB000381 | 2 | 1770 | |
| AB000381 | 2 | 2021 | |
| AB000381 | 2 | 2406 | |
| AB000381 | 2 | 2851 | |
| AB000381 | 2 | 3118 | |
| AB000381 | 2 | 3205 | |
| AB000381 | 2 | 3224 | |
| AB000381 | 2 | 3260 | |
| AB000381 | 2 | 3820 | |
| AB000381 | 2 | 3954 | |
| AB000381 | 2 | 4370 | |
| AB000381 | 2 | 4452 | |
| AB000381 | 2 | 4528 | |
| AB000381 | 2 | 4718 | |
| AB000381 | 2 | 5225 | |
| AB000381 | 2 | 5230 | 213 |
| HUMIL2RGA | 1 | 27 | 30 |
| HUMIL2RGA | 2 | 36 | |
| HUMIL2RGA | 2 | 104 | 68 |
| HUMIL2RGA | 3 | 103 | 78 |
| HUMIL2RGA | 4 | 15 | |
| HUMIL2RGA | 4 | 169 | |
| HUMIL2RGA | 4 | 307 | |
| HUMIL2RGA | 4 | 437 | |
| HUMIL2RGA | 4 | 503 | |
| HUMIL2RGA | 4 | 610 | |
| HUMIL2RGA | 4 | 685 | 10 |
| HUMIL2RGA | 5 | 280 | |
| HUMIL2RGA | 5 | 380 | |
| HUMIL2RGA | 5 | 391 | 87 |
| HUMIL2RGA | 6 | 94 | 2 |
| HSEDMDGEN | 4 | 287 | 40 |
| HUMGASTA | 1 | 87 | 12 |
| HUMEDN1B | 1 | 19 | |
| HUMEDN1B | 1 | 38 | |
| HUMEDN1B | 1 | 318 | |
| HUMEDN1B | 1 | 469 | |
| HUMEDN1B | 1 | 757 | |
| HUMEDN1B | 1 | 1026 | |
| HUMEDN1B | 1 | 1263 | |
| HUMEDN1B | 1 | 1390 | |
| HUMEDN1B | 1 | 1428 | |
| HUMEDN1B | 1 | 1463 | 15 |
| HUMEDN1B | 2 | 336 | |
| HUMEDN1B | 2 | 343 | |
| HUMEDN1B | 2 | 347 | |
| HUMEDN1B | 2 | 479 | |
| HUMEDN1B | 2 | 780 | |
| HUMEDN1B | 2 | 1018 | |
| HUMEDN1B | 2 | 1358 | 2 |
| HUMEDN1B | 4 | 24 | |
| HUMEDN1B | 4 | 102 | |
| HUMEDN1B | 4 | 250 | |
| HUMEDN1B | 4 | 601 | |
| HUMEDN1B | 4 | 1516 | 2 |
| HSTPI1G | 1 | 172 | |
| HSTPI1G | 1 | 225 | |
| HSTPI1G | 1 | 811 | |
| HSTPI1G | 1 | 874 | |
| HSTPI1G | 1 | 938 | |
| HSTPI1G | 1 | 1070 | 228 |
| HSTPI1G | 2 | 20 | 2 |
| HSTPI1G | 4 | 165 | 24 |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSTPI1G | 6 | 67 | 45 |
| AC002482 | 1 | 499 | |
| AC002482 | 1 | 752 | 96 |
| HSHHA2GEN | 1 | 11 | |
| HSHHA2GEN | 1 | 16 | |
| HSHHA2GEN | 1 | 356 | 19 |
| HSHHA2GEN | 3 | 401 | |
| HSHHA2GEN | 3 | 1013 | |
| HSHHA2GEN | 3 | 1109 | |
| HSHHA2GEN | 3 | 1273 | 160 |
| HSHHA2GEN | 5 | 201 | |
| HSHHA2GEN | 5 | 337 | |
| HSHHA2GEN | 5 | 455 | |
| HSHHA2GEN | 5 | 589 | |
| HSHHA2GEN | 5 | 902 | 49 |
| HSHHA2GEN | 6 | 335 | |
| HSHHA2GEN | 6 | 596 | |
| HSHHA2GEN | 6 | 854 | |
| HSHHA2GEN | 6 | 1112 | |
| HSHHA2GEN | 6 | 1533 | |
| HSHHA2GEN | 6 | 1546 | |
| HSHHA2GEN | 6 | 1551 | |
| HSHHA2GEN | 6 | 1680 | |
| HSHHA2GEN | 6 | 1741 | |
| HSHHA2GEN | 6 | 1745 | |
| HSHHA2GEN | 6 | 1839 | |
| HSHHA2GEN | 6 | 1879 | |
| HSHHA2GEN | 6 | 1897 | |
| HSHHA2GEN | 6 | 1995 | |
| HSHHA2GEN | 6 | 2055 | |
| HSHHA2GEN | 6 | 2425 | 23 |
| HSINSU | 1 | 577 | 126 |
| AF000573 | 1 | 178 | |
| AF000573 | 1 | 486 | |
| AF000573 | 1 | 629 | |
| AF000573 | 1 | 663 | |
| AF000573 | 1 | 968 | |
| AF000573 | 1 | 1241 | |
| AF000573 | 1 | 1270 | |
| AF000573 | 1 | 1451 | |
| AF000573 | 1 | 1575 | |
| AF000573 | 1 | 1726 | |
| AF000573 | 1 | 1890 | |
| AF000573 | 1 | 1954 | |
| AF000573 | 1 | 2131 | |
| AF000573 | 1 | 2219 | |
| AF000573 | 1 | 2570 | |
| AF000573 | 1 | 2696 | |
| AF000573 | 1 | 2801 | |
| AF000573 | 1 | 4000 | |
| AF000573 | 1 | 4225 | |
| AF000573 | 1 | 4575 | |
| AF000573 | 1 | 4686 | |
| AF000573 | 1 | 4770 | |
| AF000573 | 1 | 4802 | |
| AF000573 | 1 | 4835 | |
| AF000573 | 1 | 5957 | |
| AF000573 | 1 | 5977 | 94 |
| AF000573 | 2 | 297 | |
| AF000573 | 2 | 322 | |
| AF000573 | 2 | 492 | |
| AF000573 | 2 | 546 | |
| AF000573 | 2 | 750 | 4 |
| AF000573 | 3 | 174 | |
| AF000573 | 3 | 191 | |
| AF000573 | 3 | 411 | |
| AF000573 | 3 | 591 | |
| AF000573 | 3 | 666 | |
| AF000573 | 3 | 720 | |
| AF000573 | 3 | 843 | |
| AF000573 | 3 | 965 | |
| AF000573 | 3 | 1045 | |
| AF000573 | 3 | 1066 | |
| AF000573 | 3 | 1114 | |
| AF000573 | 3 | 1261 | |
| AF000573 | 3 | 1408 | |
| AF000573 | 3 | 1720 | |
| AF000573 | 3 | 2163 | |
| AF000573 | 3 | 2223 | |
| AF000573 | 3 | 2405 | |
| AF000573 | 3 | 2789 | |
| AF000573 | 3 | 2802 | |
| AF000573 | 3 | 3475 | |
| AF000573 | 3 | 3640 | |
| AF000573 | 3 | 4060 | |
| AF000573 | 3 | 4171 | 11 |
| AF000573 | 4 | 127 | |
| AF000573 | 4 | 205 | |
| AF000573 | 4 | 457 | |
| AF000573 | 4 | 496 | |
| AF000573 | 4 | 521 | |
| AF000573 | 4 | 1066 | |
| AF000573 | 4 | 1094 | |
| AF000573 | 4 | 1122 | |
| AF000573 | 4 | 1246 | |
| AF000573 | 4 | 1568 | |
| AF000573 | 4 | 1715 | |
| AF000573 | 4 | 1810 | |
| AF000573 | 4 | 2176 | |
| AF000573 | 4 | 2845 | |
| AF000573 | 4 | 3218 | |
| AF000573 | 4 | 3473 | |
| AF000573 | 4 | 3706 | |
| AF000573 | 4 | 3776 | |
| AF000573 | 4 | 3859 | |
| AF000573 | 4 | 4552 | |
| AF000573 | 4 | 5145 | |
| AF000573 | 4 | 5624 | |
| AF000573 | 4 | 5874 | |
| AF000573 | 4 | 5900 | |
| AF000573 | 4 | 5912 | |
| AF000573 | 4 | 6981 | |
| AF000573 | 4 | 7041 | |
| AF000573 | 4 | 7878 | |
| AF000573 | 4 | 7966 | |
| AF000573 | 4 | 8628 | |
| AF000573 | 4 | 9117 | |
| AF000573 | 4 | 9149 | |
| AF000573 | 4 | 9276 | |
| AF000573 | 4 | 9482 | |
| AF000573 | 4 | 9809 | |
| AF000573 | 4 | 10039 | |
| AF000573 | 4 | 10190 | |
| AF000573 | 4 | 10310 | |
| AF000573 | 4 | 10419 | |
| AF000573 | 4 | 10737 | |
| AF000573 | 4 | 11031 | |
| AF000573 | 4 | 11828 | |
| AF000573 | 4 | 12151 | |
| AF000573 | 4 | 12295 | |
| AF000573 | 4 | 12400 | |
| AF000573 | 4 | 12417 | |
| AF000573 | 4 | 12488 | |
| AF000573 | 4 | 12492 | |
| AF000573 | 4 | 12523 | |
| AF000573 | 4 | 12609 | |
| AF000573 | 4 | 12766 | |
| AF000573 | 4 | 12784 | |
| AF000573 | 4 | 13144 | |
| AF000573 | 4 | 13627 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| AF000573 | 4 | 14013 | |
| AF000573 | 4 | 14406 | |
| AF000573 | 4 | 14557 | |
| AF000573 | 4 | 14848 | |
| AF000573 | 4 | 15027 | |
| AF000573 | 4 | 15073 | |
| AF000573 | 4 | 15381 | |
| AF000573 | 4 | 15465 | |
| AF000573 | 4 | 15629 | |
| AF000573 | 4 | 15821 | |
| AF000573 | 4 | 16019 | |
| AF000573 | 4 | 16240 | |
| AF000573 | 4 | 16331 | |
| AF000573 | 4 | 16409 | |
| AF000573 | 4 | 17484 | |
| AF000573 | 4 | 17612 | |
| AF000573 | 4 | 17659 | 46 |
| AF000573 | 5 | 3 | |
| AF000573 | 5 | 48 | |
| AF000573 | 5 | 527 | |
| AF000573 | 5 | 667 | |
| AF000573 | 5 | 1471 | |
| AF000573 | 5 | 1532 | 55 |
| AF000573 | 6 | 422 | |
| AF000573 | 6 | 1390 | |
| AF000573 | 6 | 1406 | |
| AF000573 | 6 | 2090 | |
| AF000573 | 6 | 2124 | |
| AF000573 | 6 | 2804 | 2 |
| AF000573 | 7 | 296 | |
| AF000573 | 7 | 526 | 9 |
| AF000573 | 9 | 412 | |
| AF000573 | 9 | 455 | |
| AF000573 | 9 | 952 | |
| AF000573 | 9 | 1277 | 60 |
| AF000573 | 10 | 210 | |
| AF000573 | 10 | 303 | |
| AF000573 | 10 | 364 | |
| AF000573 | 10 | 702 | |
| AF000573 | 10 | 962 | |
| AF000573 | 10 | 1386 | |
| AF000573 | 10 | 1726 | |
| AF000573 | 10 | 2434 | |
| AF000573 | 10 | 2453 | 7 |
| AF000573 | 11 | 138 | |
| AF000573 | 11 | 833 | |
| AF000573 | 11 | 1789 | |
| AF000573 | 11 | 1826 | |
| AF000573 | 11 | 2948 | 31 |
| AF000573 | 12 | 1132 | |
| AF000573 | 12 | 1286 | |
| AF000573 | 12 | 1385 | |
| AF000573 | 12 | 1822 | |
| AF000573 | 12 | 1936 | |
| AF000573 | 12 | 2254 | |
| AF000573 | 12 | 2503 | |
| AF000573 | 12 | 2669 | |
| AF000573 | 12 | 2701 | |
| AF000573 | 12 | 2746 | |
| AF000573 | 12 | 2817 | |
| AF000573 | 12 | 3371 | |
| AF000573 | 12 | 3602 | |
| AF000573 | 12 | 3660 | |
| AF000573 | 12 | 3957 | |
| AF000573 | 12 | 4100 | |
| AF000573 | 12 | 4279 | |
| AF000573 | 12 | 4326 | 75 |
| AF000573 | 13 | 3 | |
| AF000573 | 13 | 128 | |
| AF000573 | 13 | 386 | |
| AF000573 | 13 | 767 | |
| AF000573 | 13 | 1602 | |
| AF000573 | 13 | 1666 | |
| AF000573 | 13 | 1959 | |
| AF000573 | 13 | 2142 | |
| AF000573 | 13 | 2309 | |
| AF000573 | 13 | 2673 | |
| AF000573 | 13 | 3101 | |
| AF000573 | 13 | 3408 | |
| AF000573 | 13 | 3503 | |
| AF000573 | 13 | 3749 | |
| AF000573 | 13 | 3826 | |
| AF000573 | 13 | 4249 | |
| AF000573 | 13 | 4356 | 127 |
| HUMGCB1 | 2 | 3 | |
| HUMGCB1 | 2 | 140 | |
| HUMGCB1 | 2 | 274 | |
| HUMGCB1 | 2 | 383 | |
| HUMGCB1 | 2 | 425 | |
| HUMGCB1 | 2 | 452 | 6 |
| HUMGCB1 | 3 | 48 | 45 |
| HUMGCB1 | 4 | 480 | |
| HUMGCB1 | 4 | 522 | 27 |
| HUMGCB1 | 5 | 62 | 136 |
| HUMGCB1 | 6 | 482 | 2 |
| HUMGCB1 | 7 | 181 | |
| HUMGCB1 | 7 | 238 | |
| HUMGCB1 | 7 | 324 | |
| HUMGCB1 | 7 | 399 | |
| HUMGCB1 | 7 | 503 | |
| HUMGCB1 | 7 | 507 | |
| HUMGCB1 | 7 | 676 | 103 |
| HUMGCB1 | 9 | 155 | |
| HUMGCB1 | 9 | 217 | |
| HUMGCB1 | 9 | 283 | |
| HUMGCB1 | 9 | 295 | |
| HUMGCB1 | 9 | 299 | 2 |
| HUMGCB1 | 10 | 11 | 2 |
| HUMATPSYB | 1 | 222 | |
| HUMATPSYB | 1 | 232 | 81 |
| HUMATPSYB | 3 | 64 | |
| HUMATPSYB | 3 | 252 | |
| HUMATPSYB | 3 | 294 | |
| HUMATPSYB | 3 | 387 | |
| HUMATPSYB | 3 | 538 | |
| HUMATPSYB | 3 | 687 | |
| HUMATPSYB | 3 | 701 | |
| HUMATPSYB | 3 | 721 | |
| HUMATPSYB | 3 | 786 | 2 |
| HUMATPSYB | 7 | 132 | |
| HUMATPSYB | 7 | 212 | |
| HUMATPSYB | 7 | 227 | |
| HUMATPSYB | 7 | 671 | |
| HUMATPSYB | 7 | 838 | |
| HUMATPSYB | 7 | 1173 | |
| HUMATPSYB | 7 | 1274 | |
| HUMATPSYB | 7 | 1308 | |
| HUMATPSYB | 7 | 1837 | |
| HUMATPSYB | 7 | 1889 | |
| HUMATPSYB | 7 | 1991 | 16 |
| HUMATPSYB | 8 | 334 | |
| HUMATPSYB | 8 | 468 | |
| HUMATPSYB | 8 | 598 | 127 |
| HUMATPSYB | 9 | 295 | |
| HUMATPSYB | 9 | 431 | |
| HUMATPSYB | 9 | 607 | 75 |
| HSPSAG | 1 | 424 | 603 |
| HSPSAG | 2 | 29 | |
| HSPSAG | 2 | 235 | |
| HSPSAG | 2 | 534 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSPSAG | 2 | 548 | |
| HSPSAG | 2 | 830 | 2 |
| HSPSAG | 3 | 101 | 48 |
| HSPSAG | 4 | 35 | |
| HSPSAG | 4 | 178 | |
| HSPSAG | 4 | 382 | |
| HSPSAG | 4 | 448 | |
| HSPSAG | 4 | 1006 | 109 |
| HUMEF1A | 1 | 61 | |
| HUMEF1A | 1 | 79 | |
| HUMEF1A | 1 | 142 | |
| HUMEF1A | 1 | 166 | 64 |
| HUMEF1A | 4 | 58 | 57 |
| HUMPSAP | 1 | 138 | 105 |
| HUMPSAP | 2 | 17 | |
| HUMPSAP | 2 | 52 | |
| HUMPSAP | 2 | 123 | |
| HUMPSAP | 2 | 157 | |
| HUMPSAP | 2 | 195 | |
| HUMPSAP | 2 | 248 | |
| HUMPSAP | 2 | 322 | |
| HUMPSAP | 2 | 401 | 126 |
| HUMPSAP | 3 | 272 | |
| HUMPSAP | 3 | 287 | |
| HUMPSAP | 3 | 317 | |
| HUMPSAP | 3 | 412 | |
| HUMPSAP | 3 | 421 | |
| HUMPSAP | 3 | 440 | 78 |
| HSFESFPS | 1 | 20 | |
| HSFESFPS | 2 | 96 | |
| HSFESFPS | 2 | 335 | 313 |
| HSFESFPS | 4 | 308 | |
| HSFESFPS | 4 | 389 | |
| HSFESFPS | 4 | 432 | |
| HSFESFPS | 4 | 536 | |
| HSFESFPS | 4 | 671 | |
| HSFESFPS | 4 | 835 | |
| HSFESFPS | 4 | 1185 | |
| HSFESFPS | 4 | 1210 | |
| HSFESFPS | 4 | 1817 | 2 |
| HSFESFPS | 9 | 456 | |
| HSFESFPS | 9 | 464 | 46 |
| HSFESFPS | 10 | 179 | 82 |
| HSFESFPS | 11 | 122 | |
| HSFESFPS | 11 | 201 | 76 |
| HSFESFPS | 12 | 476 | 97 |
| HSFESFPS | 14 | 24 | 27 |
| HSFESFPS | 15 | 52 | 2 |
| HSFESFPS | 17 | 298 | |
| HSFESFPS | 17 | 429 | |
| HSFESFPS | 17 | 610 | |
| HSFESFPS | 17 | 780 | 243 |
| HUNPIV | 1 | 92 | |
| HUNPIV | 1 | 160 | |
| HUNPIV | 1 | 197 | |
| HUNPIV | 1 | 350 | 141 |
| HUMIMPDH | 2 | 34 | 37 |
| HUMIMPDH | 4 | 48 | 46 |
| HUMIMPDH | 5 | 222 | |
| HUMIMPDH | 5 | 482 | 46 |
| HUMIMPDH | 7 | 16 | 57 |
| HUMIMPDH | 8 | 41 | |
| HUMIMPDH | 9 | 328 | |
| HUMIMPDH | 9 | 744 | |
| HUMIMPDH | 9 | 854 | |
| HUMIMPDH | 9 | 864 | 15 |
| HSU73002 | 1 | 234 | |
| HSU73002 | 1 | 378 | 237 |
| HSU73002 | 2 | 117 | |
| HSU73002 | 2 | 267 | 87 |
| HSU73002 | 3 | 415 | |
| HSU73002 | 3 | 432 | 25 |
| HSU73002 | 4 | 431 | 25 |
| HUMHIAPPA | 1 | 587 | |
| HUMHIAPPA | 1 | 682 | |
| HUMHIAPPA | 1 | 738 | |
| HUMHIAPPA | 1 | 1046 | |
| HUMHIAPPA | 1 | 1485 | |
| HUMHIAPPA | 1 | 1787 | |
| HUMHIAPPA | 1 | 2162 | |
| HUMHIAPPA | 1 | 2398 | |
| HUMHIAPPA | 1 | 2412 | |
| HUMHIAPPA | 1 | 2502 | |
| HUMHIAPPA | 1 | 2701 | |
| HUMHIAPPA | 1 | 2936 | |
| HUMHIAPPA | 1 | 3327 | |
| HUMHIAPPA | 1 | 3708 | |
| HUMHIAPPA | 1 | 3879 | |
| HUMHIAPPA | 1 | 4117 | |
| HUMHIAPPA | 1 | 4507 | |
| HUMHIAPPA | 1 | 4665 | 47 |
| HSU32323 | 2 | 163 | |
| HSU32323 | 2 | 237 | |
| HSU32323 | 2 | 333 | |
| HSU32323 | 2 | 735 | |
| HSU32323 | 2 | 815 | |
| HSU32323 | 2 | 880 | 2 |
| HSU32323 | 3 | 59 | 87 |
| HSU32323 | 4 | 52 | |
| HSU32323 | 4 | 73 | 83 |
| HSU32323 | 5 | 6 | 2 |
| HSU32323 | 6 | 431 | 99 |
| HSU32323 | 7 | 140 | |
| HSU32323 | 7 | 147 | |
| HSU32323 | 7 | 192 | |
| HSU32323 | 7 | 349 | |
| HSU32323 | 7 | 747 | |
| HSU32323 | 7 | 1033 | 46 |
| HSU32323 | 8 | 80 | |
| HSU32323 | 8 | 274 | 57 |
| HSU32323 | 10 | 3 | 2 |
| HSU32323 | 11 | 316 | 6 |
| HUMG0S19A | 1 | 187 | |
| HUMG0S19A | 1 | 305 | |
| HUMG0S19A | 1 | 465 | 75 |
| HUMG0S19A | 2 | 33 | |
| HUMG0S19A | 2 | 134 | 2 |
| HUMPGAMMG | 2 | 27 | |
| HUMPGAMMG | 2 | 224 | |
| HUMPGAMMG | 2 | 992 | |
| HUMPGAMMG | 2 | 1307 | |
| HUMPGAMMG | 2 | 1560 | 126 |
| HUMCYPBB | 2 | 71 | |
| HUMCYPBB | 2 | 121 | |
| HUMCYPBB | 2 | 327 | |
| HUMCYPBB | 2 | 489 | |
| HUMCYPBB | 2 | 501 | |
| HUMCYPBB | 2 | 541 | |
| HUMCYPBB | 2 | 606 | |
| HUMCYPBB | 2 | 754 | |
| HUMCYPBB | 2 | 978 | |
| HUMCYPBB | 2 | 987 | |
| HUMCYPBB | 2 | 1425 | |
| HUMCYPBB | 2 | 1430 | |
| HUMCYPBB | 2 | 1511 | 2 |
| HUMCYPBB | 5 | 179 | |
| HUMCYPBB | 5 | 535 | 34 |
| HUMCYPBB | 8 | 173 | |
| HUMCYPBB | 8 | 288 | 151 |
| HUMTSHB2 | 1 | 156 | |

TABLE 6-continued

Database of genes having putative latent splice sites
Each row includes the following information from left to right
<GENBANK Accession No.><Number of intron (IVS) which includes the latent site/s><The coordinate of the latent site/s in the intron (in nt, counted from the 5 end of the intron)><The position of the first stop codon (in nt, counted from the 5' end of the intron>.

| Accession No. | IVS No. | Latent Pos. | First Stop codon |
|---|---|---|---|
| HUMTSHB2 | 1 | 364 | 31 |
| HSIL1RECA | 1 | 24 | |
| HSIL1RECA | 1 | 240 | |
| HSIL1RECA | 1 | 673 | |
| HSIL1RECA | 1 | 855 | |
| HSIL1RECA | 1 | 996 | |
| HSIL1RECA | 1 | 1023 | |
| HSIL1RECA | 1 | 1031 | |
| HSIL1RECA | 1 | 1049 | |
| HSIL1RECA | 1 | 1153 | |
| HSIL1RECA | 1 | 1351 | |
| HSIL1RECA | 1 | 1439 | |
| HSIL1RECA | 1 | 1456 | |
| HSIL1RECA | 1 | 1592 | 2 |
| HSIL1RECA | 2 | 208 | |
| HSIL1RECA | 2 | 215 | |
| HSIL1RECA | 2 | 872 | |
| HSIL1RECA | 2 | 958 | |
| HSIL1RECA | 2 | 1044 | |
| HSIL1RECA | 2 | 1130 | 90 |
| HSIL1RECA | 3 | 707 | |
| HSIL1RECA | 3 | 764 | |
| HSIL1RECA | 3 | 952 | |
| HSIL1RECA | 3 | 1059 | |
| HSIL1RECA | 3 | 1075 | |
| HSIL1RECA | 3 | 1149 | 94 |
| HUMIL8A | 1 | 249 | |
| HUMIL8A | 1 | 257 | |
| HUMIL8A | 1 | 326 | 57 |
| HUMIL8A | 3 | 100 | |
| HUMIL8A | 3 | 142 | 2 |
| HSS100A2 | 1 | 33 | |
| HSS100A2 | 1 | 288 | |
| HSS100A2 | 1 | 601 | |
| HSS100A2 | 1 | 674 | |
| HSS100A2 | 1 | 1002 | |
| HSS100A2 | 1 | 1053 | |
| HSS100A2 | 1 | 1161 | |
| HSS100A2 | 1 | 1478 | |
| HSS100A2 | 1 | 1516 | 55 |
| HUMGFP40H | 3 | 404 | |
| HUMGFP40H | 3 | 574 | |
| HUMGFP40H | 3 | 672 | |
| HUMGFP40H | 3 | 769 | |
| HUMGFP40H | 3 | 1187 | 16 |
| HUMGFP40H | 4 | 34 | |
| HUMGFP40H | 4 | 45 | |
| HUMGFP40H | 4 | 158 | |
| HUMGFP40H | 4 | 187 | |
| HUMGFP40H | 4 | 490 | |
| HUMGFP40H | 4 | 532 | |
| HUMGFP40H | 4 | 625 | |
| HUMGFP40H | 4 | 667 | |
| HUMGFP40H | 4 | 701 | |
| HUMGFP40H | 4 | 832 | |
| HUMGFP40H | 4 | 1239 | |
| HUMGFP40H | 4 | 1431 | 37 |
| HSUBR | 1 | 310 | |
| HSUBR | 1 | 333 | 2 |
| HUMBLYM1 | 1 | 96 | 8 |
| HSCYP450 | 1 | 20 | |
| HSCYP450 | 1 | 65 | |
| HSCYP450 | 1 | 505 | 124 |
| HSCYP450 | 3 | 24 | 6 |
| HSCYP450 | 4 | 64 | 2 |
| HSZNGP1 | 1 | 46 | |
| HSZNGP1 | 1 | 623 | |
| HSZNGP1 | 1 | 788 | |
| HSZNGP1 | 1 | 2153 | |
| HSZNGP1 | 1 | 2751 | |
| HSZNGP1 | 1 | 3214 | |
| HSZNGP1 | 1 | 3482 | |
| HSZNGP1 | 1 | 3679 | 276 |
| HSZNGP1 | 2 | 58 | |
| HSZNGP1 | 2 | 1033 | |
| HSZNGP1 | 2 | 1086 | |
| HSZNGP1 | 2 | 1271 | |
| HSZNGP1 | 2 | 1628 | |
| HSZNGP1 | 2 | 1683 | |
| HSZNGP1 | 2 | 1716 | |
| HSZNGP1 | 2 | 1946 | |
| HSZNGP1 | 2 | 2556 | |
| HSZNGP1 | 2 | 2691 | 6 |
| HSZNGP1 | 3 | 274 | |
| HSZNGP1 | 3 | 283 | |
| HSZNGP1 | 3 | 672 | |
| HSZNGP1 | 3 | 677 | 78 |
| HSU09954 | 2 | 40 | |
| HSU09954 | 2 | 289 | |
| HSU09954 | 2 | 373 | |
| HSU09954 | 2 | 436 | |
| HSU09954 | 2 | 444 | 196 |
| HSU09954 | 3 | 66 | |
| HSU09954 | 3 | 512 | |
| HSU09954 | 3 | 762 | |
| HSU09954 | 3 | 916 | |
| HSU09954 | 3 | 942 | 112 |
| HSU09954 | 4 | 295 | |
| HSU09954 | 4 | 307 | |
| HSU09954 | 4 | 412 | |
| HSU09954 | 4 | 718 | |
| HSU09954 | 4 | 760 | |
| HSU09954 | 4 | 1315 | |
| HSU09954 | 4 | 1389 | 114 |
| HUMTFPB | 1 | 323 | |
| HUMTFPB | 1 | 964 | |
| HUMTFPB | 1 | 1065 | |
| HUMTFPB | 1 | 1087 | |
| HUMTFPB | 1 | 1095 | 156 |
| HUMTFPB | 2 | 394 | |
| HUMTFPB | 2 | 817 | |
| HUMTFPB | 2 | 905 | |
| HUMTFPB | 2 | 1104 | |
| HUMTFPB | 2 | 1108 | |
| HUMTFPB | 2 | 1284 | |
| HUMTFPB | 2 | 1468 | |
| HUMTFPB | 2 | 1569 | |
| HUMTFPB | 2 | 1599 | |
| HUMTFPB | 2 | 1663 | |
| HUMTFPB | 2 | 2830 | |
| HUMTFPB | 2 | 2968 | |
| HUMTFPB | 2 | 3830 | 2 |
| HUMTFPB | 3 | 119 | |
| HUMTFPB | 3 | 207 | |
| HUMTFPB | 3 | 267 | |
| HUMTFPB | 3 | 788 | |
| HUMTFPB | 3 | 827 | |
| HUMTFPB | 3 | 922 | |
| HUMTFPB | 3 | 977 | |
| HUMTFPB | 3 | 1040 | |
| HUMTFPB | 3 | 1750 | |
| HUMTFPB | 3 | 1867 | |
| HUMTFPB | 3 | 2456 | 18 |
| HUMTFPB | 4 | 108 | 13 |
| HUMTFPB | 5 | 45 | |
| HUMTFPB | 5 | 235 | |
| HUMTFPB | 5 | 407 | |
| HUMTFPB | 5 | 503 | |
| HUMTFPB | 5 | 522 | |
| HUMTFPB | 5 | 787 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMTFPB | 5 | 942 | |
| HUMTFPB | 5 | 1579 | 48 |
| HSCD1R3 | 1 | 91 | 21 |
| HSCD1R3 | 2 | 186 | 117 |
| HSCD1R3 | 3 | 123 | |
| HSCD1R3 | 3 | 390 | 126 |
| HSCD1R3 | 4 | 93 | |
| HSCD1R3 | 4 | 325 | 114 |
| HSU96846 | 1 | 60 | |
| HSU96846 | 1 | 303 | 36 |
| HSU96846 | 2 | 462 | 24 |
| HSU96846 | 3 | 27 | |
| HSU96846 | 3 | 384 | 54 |
| HSL7A | 1 | 140 | |
| HSL7A | 1 | 502 | 13 |
| HSL7A | 2 | 53 | |
| HSL7A | 2 | 343 | 6 |
| HSL7A | 3 | 200 | 123 |
| HSL7A | 4 | 170 | 159 |
| HSL7A | 5 | 72 | |
| HSL7A | 5 | 90 | |
| HSL7A | 5 | 94 | |
| HSL7A | 5 | 145 | 22 |
| HSL7A | 6 | 208 | 2 |
| HSUSF2 | 5 | 25 | 9 |
| HSUSF2 | 7 | 10 | |
| HSUSF2 | 7 | 148 | |
| HSUSF2 | 7 | 400 | |
| HSUSF2 | 7 | 404 | |
| HSUSF2 | 7 | 515 | |
| HSUSF2 | 7 | 808 | |
| HSUSF2 | 7 | 955 | |
| HSUSF2 | 7 | 1230 | |
| HSUSF2 | 7 | 1351 | |
| HSUSF2 | 7 | 1561 | |
| HSUSF2 | 7 | 1713 | |
| HSUSF2 | 7 | 1856 | |
| HSUSF2 | 7 | 2320 | |
| HSUSF2 | 7 | 2370 | |
| HSUSF2 | 7 | 2578 | |
| HSUSF2 | 7 | 2739 | |
| HSUSF2 | 7 | 2782 | |
| HSUSF2 | 7 | 3220 | |
| HSUSF2 | 7 | 3362 | |
| HSUSF2 | 7 | 4006 | |
| HSUSF2 | 7 | 4284 | |
| HSUSF2 | 7 | 4725 | |
| HSUSF2 | 7 | 4759 | |
| HSUSF2 | 7 | 4768 | |
| HSUSF2 | 7 | 5688 | |
| HSUSF2 | 7 | 5803 | |
| HSUSF2 | 7 | 5814 | |
| HSUSF2 | 7 | 6328 | |
| HSUSF2 | 7 | 6921 | 138 |
| HSFAU1 | 2 | 32 | |
| HSFAU1 | 2 | 43 | |
| HSFAU1 | 2 | 252 | 6 |
| HSFAU1 | 3 | 127 | 157 |
| HSCSRP2S2 | 1 | 512 | |
| HSCSRP2S2 | 1 | 683 | |
| HSCSRP2S2 | 1 | 1531 | |
| HSCSRP2S2 | 1 | 1580 | |
| HSCSRP2S2 | 1 | 1907 | |
| HSCSRP2S2 | 1 | 2235 | |
| HSCSRP2S2 | 1 | 2596 | |
| HSCSRP2S2 | 1 | 2675 | 6 |
| HSCSRP2S2 | 2 | 255 | |
| HSCSRP2S2 | 2 | 347 | |
| HSCSRP2S2 | 2 | 365 | |
| HSCSRP2S2 | 2 | 717 | |
| HSCSRP2S2 | 2 | 1417 | |
| HSCSRP2S2 | 2 | 1732 | |
| HSCSRP2S2 | 2 | 1736 | |
| HSCSRP2S2 | 2 | 2381 | |
| HSCSRP2S2 | 2 | 2426 | 2 |
| HSCSRP2S2 | 3 | 161 | |
| HSCSRP2S2 | 3 | 270 | 235 |
| HSCSRP2S2 | 4 | 239 | 111 |
| D49493 | 1 | 102 | |
| D49493 | 1 | 768 | |
| D49493 | 1 | 791 | |
| D49493 | 1 | 829 | |
| D49493 | 1 | 915 | |
| D49493 | 1 | 987 | |
| D49493 | 1 | 1079 | |
| D49493 | 1 | 1220 | |
| D49493 | 1 | 1517 | |
| D49493 | 1 | 1752 | |
| D49493 | 1 | 1948 | |
| D49493 | 1 | 1966 | |
| D49493 | 1 | 2014 | |
| D49493 | 1 | 2178 | |
| D49493 | 1 | 2281 | |
| D49493 | 1 | 2357 | |
| D49493 | 1 | 2588 | |
| D49493 | 1 | 2666 | |
| D49493 | 1 | 2734 | |
| D49493 | 1 | 2765 | |
| D49493 | 1 | 2777 | |
| D49493 | 1 | 2992 | |
| D49493 | 1 | 3158 | |
| D49493 | 1 | 3173 | |
| D49493 | 1 | 3681 | |
| D49493 | 1 | 3725 | |
| D49493 | 1 | 3775 | |
| D49493 | 1 | 3788 | |
| D49493 | 1 | 3998 | |
| D49493 | 1 | 4193 | |
| D49493 | 1 | 4217 | |
| D49493 | 1 | 4875 | |
| D49493 | 1 | 5555 | |
| D49493 | 1 | 5932 | |
| D49493 | 1 | 5950 | |
| D49493 | 1 | 5961 | |
| D49493 | 1 | 7386 | |
| D49493 | 1 | 7409 | |
| D49493 | 1 | 7629 | |
| D49493 | 1 | 8670 | |
| D49493 | 1 | 8735 | 6 |
| D49493 | 2 | 194 | |
| D49493 | 2 | 766 | |
| D49493 | 2 | 915 | |
| D49493 | 2 | 1216 | |
| D49493 | 2 | 1239 | |
| D49493 | 2 | 1314 | |
| D49493 | 2 | 1745 | |
| D49493 | 2 | 1821 | |
| D49493 | 2 | 1829 | |
| D49493 | 2 | 1833 | |
| D49493 | 2 | 1850 | 31 |
| HSU01882 | 1 | 20 | 133 |
| HSU01882 | 2 | 291 | |
| HSU01882 | 2 | 501 | |
| HSU01882 | 2 | 581 | |
| HSU01882 | 2 | 588 | |
| HSU01882 | 2 | 742 | |
| HSU01882 | 2 | 752 | |
| HSU01882 | 2 | 809 | |
| HSU01882 | 2 | 994 | 16 |
| HSU01882 | 3 | 366 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSU01882 | 3 | 657 | 43 |
| HSU01882 | 4 | 62 | |
| HSU01882 | 4 | 183 | |
| HSU01882 | 4 | 401 | |
| HSU01882 | 4 | 459 | 2 |
| HSU01882 | 5 | 93 | |
| HSU01882 | 5 | 120 | |
| HSU01882 | 5 | 144 | 123 |
| HSU96402 | 2 | 172 | 175 |
| HSACKI10 | 1 | 6 | |
| HSACKI10 | 1 | 510 | |
| HSACKI10 | 1 | 512 | |
| HSACKI10 | 1 | 692 | 64 |
| HSACKI10 | 2 | 146 | |
| HSACKI10 | 2 | 195 | 2 |
| HSACKI10 | 5 | 95 | 7 |
| HSU78190 | 1 | 228 | |
| HSU78190 | 1 | 232 | |
| HSU78190 | 1 | 579 | |
| HSU78190 | 1 | 770 | |
| HSU78190 | 1 | 933 | 376 |
| HSU78190 | 2 | 567 | |
| HSU78190 | 2 | 1198 | 2 |
| HUMCOX5B | 1 | 443 | 375 |
| HUMCOX5B | 2 | 127 | 55 |
| HUMCOX5B | 3 | 80 | |
| HUMCOX5B | 3 | 94 | |
| HUMCOX5B | 3 | 178 | |
| HUMCOX5B | 3 | 358 | |
| HUMCOX5B | 3 | 374 | 36 |
| HSHCF1 | 2 | 33 | 2 |
| HSHCF1 | 3 | 83 | |
| HSHCF1 | 3 | 88 | |
| HSHCF1 | 3 | 592 | 210 |
| HSHCF1 | 4 | 343 | |
| HSHCF1 | 4 | 385 | 2 |
| HSHCF1 | 5 | 290 | |
| HSHCF1 | 5 | 504 | |
| HSHCF1 | 5 | 857 | |
| HSHCF1 | 5 | 889 | |
| HSHCF1 | 5 | 1076 | 183 |
| HSHCF1 | 7 | 275 | 39 |
| HSHCF1 | 8 | 175 | |
| HSHCF1 | 8 | 374 | |
| HSHCF1 | 8 | 494 | |
| HSHCF1 | 8 | 516 | 67 |
| HSHCF1 | 9 | 120 | |
| HSHCF1 | 9 | 212 | 88 |
| HSHCF1 | 10 | 39 | 136 |
| HSHCF1 | 15 | 54 | |
| HSHCF1 | 15 | 249 | |
| HSHCF1 | 15 | 456 | |
| HSHCF1 | 15 | 477 | |
| HSHCF1 | 15 | 516 | 13 |
| HSHCF1 | 17 | 290 | |
| HSHCF1 | 17 | 431 | 127 |
| HSHCF1 | 18 | 322 | 153 |
| HSHCF1 | 19 | 50 | |
| HSHCF1 | 20 | 8 | 25 |
| HSHCF1 | 21 | 29 | |
| HSHCF1 | 21 | 33 | |
| HSHCF1 | 21 | 122 | 19 |
| HSHCF1 | 23 | 299 | |
| HSHCF1 | 23 | 388 | |
| HSHCF1 | 23 | 433 | |
| HSHCF1 | 23 | 475 | 213 |
| HSU25826 | 1 | 544 | |
| HSU25826 | 1 | 776 | |
| HSU25826 | 1 | 832 | |
| HSU25826 | 1 | 909 | |
| HSU25826 | 1 | 1094 | |
| HSU25826 | 1 | 1234 | |
| HSU25826 | 1 | 1610 | 9 |
| HSU25826 | 2 | 180 | 2 |
| HSRAS1 | 2 | 40 | 2 |
| HSRAS1 | 3 | 175 | 112 |
| D83657 | 1 | 3 | 46 |
| HSGROW2 | 1 | 116 | 12 |
| HSGROW2 | 2 | 44 | 82 |
| HUMI309 | 1 | 153 | |
| HUMI309 | 1 | 263 | |
| HUMI309 | 1 | 745 | |
| HUMI309 | 1 | 1030 | |
| HUMI309 | 1 | 1137 | 120 |
| HUMI309 | 2 | 176 | |
| HUMI309 | 2 | 378 | |
| HUMI309 | 2 | 575 | |
| HUMI309 | 2 | 763 | 2 |
| HSPAT133 | 1 | 218 | |
| HSPAT133 | 1 | 334 | 333 |
| HSU20758 | 2 | 129 | |
| HSU20758 | 2 | 189 | |
| HSU20758 | 2 | 205 | 25 |
| HSU20758 | 4 | 194 | 46 |
| HSU20758 | 5 | 172 | 37 |
| HSU82827 | 1 | 77 | |
| HSU82827 | 1 | 196 | |
| HSU82827 | 1 | 280 | |
| HSU82827 | 1 | 430 | |
| HSU82827 | 1 | 520 | 6 |
| HSU17969 | 1 | 340 | |
| HSU17969 | 1 | 429 | |
| HSU17969 | 1 | 950 | |
| HSU17969 | 1 | 1113 | |
| HSU17969 | 1 | 1141 | 94 |
| HUMCYP2DG | 1 | 66 | |
| HUMCYP2DG | 1 | 479 | |
| HUMCYP2DG | 1 | 540 | 73 |
| HUMCYP2DG | 2 | 32 | |
| HUMCYP2DG | 2 | 140 | |
| HUMCYP2DG | 2 | 217 | |
| HUMCYP2DG | 2 | 361 | |
| HUMCYP2DG | 2 | 395 | 287 |
| HUMCYP2DG | 4 | 180 | |
| HUMCYP2DG | 4 | 312 | |
| HUMCYP2DG | 4 | 317 | |
| HUMCYP2DG | 4 | 324 | |
| HUMCYP2DG | 4 | 383 | 91 |
| HUMCYP2DG | 5 | 33 | |
| HUMCYP2DG | 5 | 136 | 118 |
| HUMCYP2DG | 7 | 71 | |
| HUMCYP2DG | 7 | 277 | 46 |
| HUMPRCA | 1 | 102 | |
| HUMPRCA | 1 | 107 | |
| HUMPRCA | 1 | 152 | |
| HUMPRCA | 1 | 718 | |
| HUMPRCA | 1 | 979 | |
| HUMPRCA | 1 | 1236 | 105 |
| HUMPRCA | 2 | 71 | |
| HUMPRCA | 2 | 164 | |
| HUMPRCA | 2 | 224 | |
| HUMPRCA | 2 | 251 | |
| HUMPRCA | 2 | 363 | |
| HUMPRCA | 2 | 543 | |
| HUMPRCA | 2 | 1146 | 88 |
| HUMPRCA | 4 | 12 | |
| HUMPRCA | 5 | 1018 | |
| HUMPRCA | 5 | 1191 | |
| HUMPRCA | 5 | 1666 | |
| HUMPRCA | 5 | 1832 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMPRCA | 5 | 2236 | |
| HUMPRCA | 5 | 2408 | 60 |
| HUMPRCA | 6 | 127 | |
| HUMPRCA | 6 | 183 | |
| HUMPRCA | 6 | 187 | |
| HUMPRCA | 6 | 645 | 121 |
| HUMPRCA | 7 | 91 | |
| HUMPRCA | 7 | 127 | |
| HUMPRCA | 7 | 232 | |
| HUMPRCA | 7 | 667 | |
| HUMPRCA | 7 | 961 | 45 |
| AF041427 | 1 | 100 | |
| AF041427 | 1 | 200 | |
| AF041427 | 1 | 345 | 25 |
| AF041427 | 2 | 259 | |
| AF041427 | 2 | 713 | |
| AF041427 | 2 | 1085 | |
| AF041427 | 2 | 1202 | |
| AF041427 | 2 | 1440 | |
| AF041427 | 2 | 1757 | 43 |
| AF041427 | 3 | 205 | |
| AF041427 | 3 | 659 | |
| AF041427 | 3 | 669 | |
| AF041427 | 3 | 778 | |
| AF041427 | 3 | 1033 | |
| AF041427 | 3 | 1083 | 399 |
| AF041427 | 4 | 17 | |
| AF041427 | 4 | 45 | |
| AF041427 | 4 | 137 | |
| AF041427 | 4 | 203 | |
| AF041427 | 4 | 404 | |
| AF041427 | 4 | 652 | |
| AF041427 | 4 | 722 | |
| AF041427 | 4 | 726 | |
| AF041427 | 4 | 924 | |
| AF041427 | 4 | 1295 | |
| AF041427 | 4 | 1455 | |
| AF041427 | 4 | 1520 | |
| AF041427 | 4 | 1708 | |
| AF041427 | 4 | 1722 | |
| AF041427 | 4 | 1765 | |
| AF041427 | 4 | 1825 | |
| AF041427 | 4 | 1933 | |
| AF041427 | 4 | 2086 | |
| AF041427 | 4 | 2203 | |
| AF041427 | 4 | 2400 | |
| AF041427 | 4 | 2892 | |
| AF041427 | 4 | 3055 | |
| AF041427 | 4 | 3090 | |
| AF041427 | 4 | 3783 | |
| AF041427 | 4 | 3836 | |
| AF041427 | 4 | 3937 | |
| AF041427 | 4 | 4081 | |
| AF041427 | 4 | 4089 | |
| AF041427 | 4 | 4108 | |
| AF041427 | 4 | 4114 | |
| AF041427 | 4 | 4222 | |
| AF041427 | 4 | 4243 | |
| AF041427 | 4 | 4596 | |
| AF041427 | 4 | 4777 | |
| AF041427 | 4 | 4789 | |
| AF041427 | 4 | 4926 | |
| AF041427 | 4 | 5465 | |
| AF041427 | 4 | 5489 | |
| AF041427 | 4 | 5538 | |
| AF041427 | 4 | 5893 | |
| AF041427 | 4 | 6026 | |
| AF041427 | 4 | 6656 | |
| AF041427 | 4 | 6854 | |
| AF041427 | 4 | 6913 | |
| AF041427 | 4 | 7753 | |
| AF041427 | 4 | 7946 | |
| AF041427 | 4 | 8218 | |
| AF041427 | 4 | 8321 | |
| AF041427 | 4 | 8589 | |
| AF041427 | 4 | 8791 | 76 |
| AF041427 | 5 | 191 | |
| AF041427 | 5 | 336 | |
| AF041427 | 5 | 549 | |
| AF041427 | 5 | 1253 | |
| AF041427 | 5 | 1310 | |
| AF041427 | 5 | 1314 | |
| AF041427 | 5 | 1493 | |
| AF041427 | 5 | 1509 | |
| AF041427 | 5 | 1924 | |
| AF041427 | 5 | 2005 | |
| AF041427 | 5 | 2047 | |
| AF041427 | 5 | 2878 | |
| AF041427 | 5 | 2985 | |
| AF041427 | 5 | 3058 | |
| AF041427 | 5 | 3327 | |
| AF041427 | 5 | 3331 | |
| AF041427 | 5 | 3517 | |
| AF041427 | 5 | 3752 | |
| AF041427 | 5 | 3815 | |
| AF041427 | 5 | 3992 | |
| AF041427 | 5 | 4005 | |
| AF041427 | 5 | 4478 | |
| AF041427 | 5 | 4918 | |
| AF041427 | 5 | 6547 | |
| AF041427 | 5 | 7077 | |
| AF041427 | 5 | 7215 | |
| AF041427 | 5 | 7424 | |
| AF041427 | 5 | 7757 | |
| AF041427 | 5 | 7771 | |
| AF041427 | 5 | 8070 | |
| AF041427 | 5 | 8120 | |
| AF041427 | 5 | 8758 | |
| AF041427 | 5 | 8850 | |
| AF041427 | 5 | 9037 | |
| AF041427 | 5 | 9063 | |
| AF041427 | 5 | 9517 | |
| AF041427 | 5 | 9579 | |
| AF041427 | 5 | 10225 | 102 |
| AF041427 | 6 | 292 | |
| AF041427 | 6 | 335 | |
| AF041427 | 6 | 339 | |
| AF041427 | 6 | 426 | |
| AF041427 | 6 | 1155 | |
| AF041427 | 6 | 1237 | |
| AF041427 | 6 | 1459 | |
| AF041427 | 6 | 1470 | 106 |
| HUMG0S8PP | 1 | 130 | |
| HUMG0S8PP | 1 | 143 | |
| HUMG0S8PP | 1 | 353 | |
| HUMG0S8PP | 1 | 487 | |
| HUMG0S8PP | 1 | 832 | |
| HUMG0S8PP | 1 | 894 | 2 |
| HUMG0S8PP | 2 | 67 | 2 |
| HUMG0S8PP | 3 | 180 | |
| HUMG0S8PP | 3 | 466 | 66 |
| HUMMIS | 1 | 45 | |
| HUMMIS | 1 | 154 | 63 |
| HUMMIS | 2 | 130 | 85 |
| HSU49742 | 1 | 1051 | |
| HSU49742 | 1 | 1088 | |
| HSU49742 | 1 | 1189 | 84 |
| HSU49742 | 2 | 480 | |
| HSU49742 | 2 | 1029 | 2 |
| HSU49742 | 4 | 228 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSU49742 | 4 | 249 | |
| HSU49742 | 4 | 403 | |
| HSU49742 | 4 | 659 | 442 |
| HSPXFGEN | 1 | 275 | |
| HSPXFGEN | 1 | 688 | |
| HSPXFGEN | 1 | 716 | |
| HSPXFGEN | 1 | 793 | |
| HSPXFGEN | 1 | 917 | |
| HSPXFGEN | 1 | 1016 | |
| HSPXFGEN | 1 | 1222 | |
| HSPXFGEN | 1 | 1268 | 12 |
| HSPXFGEN | 2 | 116 | |
| HSPXFGEN | 2 | 321 | |
| HSPXFGEN | 2 | 383 | 4 |
| HSPXFGEN | 3 | 164 | 120 |
| HSPXFGEN | 4 | 161 | 13 |
| HSPXFGEN | 5 | 190 | |
| HSPXFGEN | 5 | 404 | |
| HSPXFGEN | 5 | 854 | |
| HSPXFGEN | 5 | 1078 | |
| HSPXFGEN | 5 | 1082 | |
| HSPXFGEN | 5 | 1086 | |
| HSPXFGEN | 5 | 1181 | |
| HSPXFGEN | 5 | 1402 | |
| HSPXFGEN | 5 | 1442 | |
| HSPXFGEN | 5 | 1624 | 52 |
| HSPXFGEN | 7 | 80 | 28 |
| HUMVIPAA | 1 | 138 | |
| HUMVIPAA | 1 | 322 | |
| HUMVIPAA | 1 | 498 | |
| HUMVIPAA | 1 | 776 | |
| HUMVIPAA | 1 | 1119 | |
| HUMVIPAA | 1 | 1357 | |
| HUMVIPAA | 1 | 1437 | 2 |
| HUMVIPAA | 2 | 449 | |
| HUMVIPAA | 2 | 472 | |
| HUMVIPAA | 2 | 808 | 2 |
| HUMVIPAA | 3 | 306 | |
| HUMVIPAA | 3 | 429 | |
| HUMVIPAA | 3 | 700 | 2 |
| HUMVIPAA | 4 | 445 | |
| HUMVIPAA | 4 | 489 | 2 |
| HUMOP18A | 1 | 3 | 6 |
| HUMOP18A | 2 | 277 | |
| HUMOP18A | 2 | 498 | |
| HUMOP18A | 2 | 643 | |
| HUMOP18A | 2 | 749 | |
| HUMOP18A | 2 | 763 | |
| HUMOP18A | 2 | 768 | |
| HUMOP18A | 2 | 872 | |
| HUMOP18A | 2 | 1074 | |
| HUMOP18A | 2 | 1132 | |
| HUMOP18A | 2 | 1142 | |
| HUMOP18A | 2 | 1426 | |
| HUMOP18A | 2 | 1740 | |
| HUMOP18A | 2 | 1800 | 151 |
| HUMOP18A | 3 | 82 | |
| HUMOP18A | 3 | 135 | |
| HUMOP18A | 3 | 320 | 40 |
| HSCBMYHC | 1 | 16 | 19 |
| HSCBMYHC | 7 | 123 | |
| HSCBMYHC | 7 | 207 | 48 |
| HSCBMYHC | 9 | 167 | |
| HSCBMYHC | 9 | 326 | |
| HSCBMYHC | 9 | 344 | |
| HSCBMYHC | 9 | 390 | |
| HSCBMYHC | 9 | 394 | 10 |
| HSCBMYHC | 10 | 181 | |
| HSCBMYHC | 10 | 292 | 93 |
| HSCBMYHC | 13 | 358 | 55 |
| HSCBMYHC | 14 | 63 | 57 |
| HSCBMYHC | 17 | 73 | |
| HSCBMYHC | 17 | 121 | 8 |
| HSCBMYHC | 18 | 207 | 16 |
| HSCBMYHC | 19 | 207 | 2 |
| HSCBMYHC | 22 | 552 | |
| HSCBMYHC | 22 | 844 | |
| HSCBMYHC | 22 | 1111 | 202 |
| HSCBMYHC | 23 | 175 | |
| HSCBMYHC | 23 | 764 | 44 |
| HSCBMYHC | 24 | 163 | 202 |
| HSCBMYHC | 26 | 143 | 165 |
| HSCBMYHC | 28 | 206 | 2 |
| HSCBMYHC | 29 | 86 | 157 |
| HSCBMYHC | 32 | 86 | |
| HSCBMYHC | 32 | 109 | 85 |
| HSCBMYHC | 34 | 60 | 67 |
| HSCBMYHC | 35 | 11 | |
| HSCBMYHC | 35 | 168 | |
| HSCBMYHC | 35 | 398 | |
| HSCBMYHC | 35 | 496 | |
| HSCBMYHC | 35 | 734 | 40 |
| HSCBMYHC | 37 | 128 | 25 |
| HUMIBP3 | 1 | 15 | |
| HUMIBP3 | 1 | 142 | |
| HUMIBP3 | 1 | 403 | |
| HUMIBP3 | 1 | 493 | |
| HUMIBP3 | 1 | 569 | |
| HUMIBP3 | 1 | 700 | |
| HUMIBP3 | 1 | 707 | |
| HUMIBP3 | 1 | 914 | |
| HUMIBP3 | 1 | 1482 | |
| HUMIBP3 | 1 | 1511 | |
| HUMIBP3 | 1 | 1542 | |
| HUMIBP3 | 1 | 1805 | |
| HUMIBP3 | 1 | 1862 | |
| HUMIBP3 | 1 | 1916 | |
| HUMIBP3 | 1 | 1964 | |
| HUMIBP3 | 1 | 2034 | |
| HUMIBP3 | 1 | 2482 | |
| HUMIBP3 | 1 | 2680 | |
| HUMIBP3 | 1 | 3111 | |
| HUMIBP3 | 1 | 3144 | 264 |
| HUMIBP3 | 2 | 421 | 106 |
| HUMIBP3 | 3 | 146 | |
| HUMIBP3 | 3 | 519 | |
| HUMIBP3 | 3 | 566 | |
| HUMIBP3 | 3 | 631 | |
| HUMIBP3 | 3 | 759 | |
| HUMIBP3 | 3 | 1069 | |
| HUMIBP3 | 3 | 1224 | |
| HUMIBP3 | 3 | 1307 | 88 |
| S45332 | 1 | 178 | |
| S45332 | 1 | 627 | 72 |
| S45332 | 2 | 248 | |
| S45332 | 2 | 652 | |
| S45332 | 2 | 777 | 2 |
| S45332 | 6 | 381 | |
| S45332 | 6 | 408 | |
| S45332 | 6 | 742 | |
| S45332 | 6 | 829 | |
| S45332 | 6 | 1104 | |
| S45332 | 6 | 1198 | |
| S45332 | 6 | 1202 | |
| S45332 | 6 | 1236 | |
| S45332 | 6 | 1388 | |
| S45332 | 6 | 1516 | |
| S45332 | 6 | 1619 | |
| S45332 | 6 | 1870 | |
| S45332 | 6 | 2048 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| S45332 | 6 | 2074 | 2 |
| S45332 | 7 | 75 | 70 |
| HUMMRP14A | 1 | 245 | |
| HUMMRP14A | 1 | 390 | |
| HUMMRP14A | 1 | 430 | |
| HUMMRP14A | 1 | 811 | |
| HUMMRP14A | 1 | 851 | |
| HUMMRP14A | 1 | 1147 | |
| HUMMRP14A | 1 | 1243 | |
| HUMMRP14A | 1 | 1563 | |
| HUMMRP14A | 1 | 1690 | 301 |
| L29472 | 1 | 70 | |
| L29472 | 1 | 145 | |
| L29472 | 1 | 497 | |
| L29472 | 1 | 579 | |
| L29472 | 1 | 606 | |
| L29472 | 1 | 675 | |
| L29472 | 1 | 953 | |
| L29472 | 1 | 999 | |
| L29472 | 1 | 1295 | |
| L29472 | 1 | 1475 | 207 |
| L29472 | 3 | 321 | 9 |
| L29472 | 5 | 147 | 25 |
| HUMIRBPG | 1 | 39 | |
| HUMIRBPG | 1 | 218 | |
| HUMIRBPG | 1 | 368 | |
| HUMIRBPG | 1 | 679 | |
| HUMIRBPG | 1 | 1139 | |
| HUMIRBPG | 1 | 1366 | |
| HUMIRBPG | 1 | 1417 | |
| HUMIRBPG | 1 | 1430 | |
| HUMIRBPG | 1 | 1490 | |
| HUMIRBPG | 1 | 1504 | |
| HUMIRBPG | 1 | 1554 | |
| HUMIRBPG | 1 | 1678 | 88 |
| HUMIRBPG | 2 | 13 | |
| HUMIRBPG | 2 | 182 | |
| HUMIRBPG | 2 | 398 | |
| HUMIRBPG | 2 | 410 | |
| HUMIRBPG | 2 | 417 | |
| HUMIRBPG | 2 | 687 | |
| HUMIRBPG | 2 | 917 | |
| HUMIRBPG | 2 | 1179 | |
| HUMIRBPG | 2 | 1434 | 344 |
| HUMIRBPG | 3 | 77 | |
| HUMIRBPG | 3 | 100 | |
| HUMIRBPG | 3 | 268 | |
| HUMIRBPG | 3 | 787 | |
| HUMIRBPG | 3 | 1279 | 153 |
| HSMED | 1 | 237 | |
| HSMED | 1 | 419 | 147 |
| HSMED | 2 | 54 | 2 |
| HSMED | 3 | 838 | |
| HSMED | 3 | 1583 | |
| HSMED | 3 | 2039 | 427 |
| HSMED | 4 | 116 | 79 |
| HSU57623 | 1 | 141 | |
| HSU57623 | 1 | 253 | |
| HSU57623 | 1 | 264 | |
| HSU57623 | 1 | 491 | |
| HSU57623 | 1 | 868 | |
| HSU57623 | 1 | 1454 | |
| HSU57623 | 1 | 1917 | |
| HSU57623 | 1 | 2077 | 93 |
| HSU57623 | 2 | 176 | |
| HSU57623 | 2 | 314 | |
| HSU57623 | 2 | 432 | |
| HSU57623 | 2 | 851 | |
| HSU57623 | 2 | 909 | |
| HSU57623 | 2 | 1067 | |
| HSU57623 | 2 | 1253 | |
| HSU57623 | 2 | 1713 | 46 |
| HSU57623 | 3 | 141 | |
| HSU57623 | 3 | 884 | |
| HSU57623 | 3 | 946 | |
| HSU57623 | 3 | 1283 | |
| HSU57623 | 3 | 1337 | 160 |
| HSU10307 | 1 | 42 | |
| HSU10307 | 1 | 46 | |
| HSU10307 | 1 | 102 | |
| HSU10307 | 1 | 197 | |
| HSU10307 | 1 | 531 | |
| HSU10307 | 1 | 555 | 13 |
| HSU10307 | 3 | 88 | 211 |
| HUMPRPH1 | 1 | 711 | |
| HUMPRPH1 | 1 | 727 | |
| HUMPRPH1 | 1 | 1015 | 27 |
| HUMPRPH1 | 2 | 260 | |
| HUMPRPH1 | 2 | 301 | 12 |
| AC002132 | 1 | 55 | 9 |
| AC002132 | 2 | 325 | |
| AC002132 | 2 | 3166 | |
| AC002132 | 2 | 3500 | 120 |
| AC002132 | 4 | 294 | |
| AC002132 | 4 | 467 | |
| AC002132 | 4 | 515 | |
| AC002132 | 4 | 1396 | |
| AC002132 | 4 | 1438 | |
| AC002132 | 4 | 1811 | 108 |
| AC002132 | 5 | 880 | |
| AC002132 | 5 | 1408 | |
| AC002132 | 5 | 2108 | |
| AC002132 | 5 | 2174 | |
| AC002132 | 5 | 2248 | |
| AC002132 | 5 | 2739 | |
| AC002132 | 5 | 4006 | |
| AC002132 | 5 | 4087 | |
| AC002132 | 5 | 4249 | |
| AC002132 | 5 | 4643 | |
| AC002132 | 5 | 4648 | |
| AC002132 | 5 | 4652 | |
| AC002132 | 5 | 4678 | |
| AC002132 | 5 | 4682 | |
| AC002132 | 5 | 4692 | |
| AC002132 | 5 | 5091 | |
| AC002132 | 5 | 5146 | |
| AC002132 | 5 | 5391 | |
| AC002132 | 5 | 5395 | |
| AC002132 | 5 | 5413 | |
| AC002132 | 5 | 6043 | |
| AC002132 | 5 | 6296 | |
| AC002132 | 5 | 6365 | |
| AC002132 | 5 | 6374 | |
| AC002132 | 5 | 6566 | |
| AC002132 | 5 | 6942 | 159 |
| AC002132 | 7 | 796 | |
| AC002132 | 7 | 1031 | |
| AC002132 | 7 | 1068 | |
| AC002132 | 7 | 1102 | 2 |
| AC002132 | 8 | 307 | |
| AC002132 | 8 | 628 | |
| AC002132 | 8 | 666 | |
| AC002132 | 8 | 806 | |
| AC002132 | 8 | 891 | 184 |
| AF008303 | 1 | 830 | |
| AF008303 | 1 | 929 | |
| AF008303 | 1 | 1081 | |
| AF008303 | 1 | 1721 | 6 |
| HSSLIPG | 1 | 41 | |
| HSSLIPG | 1 | 63 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSSLIPG | 1 | 151 | |
| HSSLIPG | 1 | 616 | 87 |
| HSSLIPG | 2 | 102 | |
| HSSLIPG | 2 | 165 | |
| HSSLIPG | 2 | 293 | 102 |
| HSSLIPG | 3 | 327 | |
| HSSLIPG | 3 | 350 | 24 |
| D67013 | 1 | 54 | |
| D67013 | 1 | 1274 | |
| D67013 | 1 | 1574 | 31 |
| D67013 | 2 | 186 | |
| D67013 | 2 | 628 | 85 |
| D67013 | 3 | 97 | |
| D67013 | 3 | 214 | 63 |
| D67013 | 4 | 254 | |
| D67013 | 4 | 611 | |
| D67013 | 4 | 1142 | 109 |
| D67013 | 5 | 66 | |
| D67013 | 5 | 229 | |
| D67013 | 5 | 443 | |
| D67013 | 5 | 525 | 70 |
| D67013 | 6 | 258 | |
| D67013 | 6 | 364 | |
| D67013 | 6 | 375 | |
| D67013 | 6 | 403 | |
| D67013 | 6 | 407 | |
| D67013 | 6 | 503 | |
| D67013 | 6 | 548 | 13 |
| HUMPREELAS | 1 | 11 | |
| HUMPREELAS | 1 | 229 | |
| HUMPREELAS | 1 | 473 | 6 |
| HSRPS7 | 2 | 160 | 118 |
| HSRPS7 | 3 | 220 | |
| HSRPS7 | 3 | 274 | |
| HSRPS7 | 3 | 489 | |
| HSRPS7 | 3 | 907 | 46 |
| HSRPS7 | 4 | 25 | |
| HSRPS7 | 4 | 205 | |
| HSRPS7 | 4 | 389 | |
| HSRPS7 | 4 | 399 | |
| HSRPS7 | 4 | 403 | |
| HSRPS7 | 4 | 833 | |
| HSRPS7 | 4 | 845 | |
| HSRPS7 | 4 | 1154 | |
| HSRPS7 | 4 | 1481 | |
| HSRPS7 | 4 | 1657 | |
| HSRPS7 | 4 | 1682 | |
| HSRPS7 | 4 | 1809 | |
| HSRPS7 | 4 | 1813 | |
| HSRPS7 | 4 | 1882 | |
| HSRPS7 | 4 | 1969 | |
| HSRPS7 | 4 | 2070 | |
| HSRPS7 | 4 | 2153 | |
| HSRPS7 | 4 | 2174 | |
| HSRPS7 | 4 | 2299 | 2 |
| HSRPS7 | 5 | 268 | |
| HSRPS7 | 5 | 310 | |
| HSRPS7 | 5 | 314 | 109 |
| HSHFE | 1 | 554 | |
| HSHFE | 1 | 663 | |
| HSHFE | 1 | 773 | |
| HSHFE | 1 | 843 | |
| HSHFE | 1 | 1579 | |
| HSHFE | 1 | 1818 | |
| HSHFE | 1 | 1822 | |
| HSHFE | 1 | 2386 | |
| HSHFE | 1 | 2485 | |
| HSHFE | 1 | 2540 | |
| HSHFE | 1 | 2601 | |
| HSHFE | 1 | 2697 | |
| HSHFE | 1 | 2711 | |
| HSHFE | 1 | 2828 | |
| HSHFE | 1 | 3257 | 87 |
| HSHFE | 3 | 88 | |
| HSHFE | 3 | 372 | |
| HSHFE | 3 | 654 | |
| HSHFE | 3 | 784 | |
| HSHFE | 3 | 884 | 162 |
| HSHFE | 4 | 3 | |
| HSHFE | 4 | 65 | 6 |
| HSHFE | 5 | 307 | |
| HSHFE | 5 | 450 | |
| HSHFE | 5 | 743 | |
| HSHFE | 5 | 774 | |
| HSHFE | 5 | 866 | |
| HSHFE | 5 | 913 | 6 |
| HUMMGPA | 1 | 231 | |
| HUMMGPA | 1 | 976 | 168 |
| HUMMGPA | 2 | 3 | |
| HUMMGPA | 2 | 125 | 6 |
| HUMLHDC | 1 | 59 | |
| HUMLHDC | 1 | 462 | |
| HUMLHDC | 1 | 533 | |
| HUMLHDC | 1 | 537 | |
| HUMLHDC | 1 | 784 | |
| HUMLHDC | 1 | 929 | |
| HUMLHDC | 1 | 1312 | |
| HUMLHDC | 1 | 1474 | |
| HUMLHDC | 1 | 1478 | |
| HUMLHDC | 1 | 1576 | |
| HUMLHDC | 1 | 1976 | 117 |
| HUMLHDC | 2 | 49 | |
| HUMLHDC | 2 | 557 | |
| HUMLHDC | 2 | 738 | |
| HUMLHDC | 2 | 1021 | |
| HUMLHDC | 2 | 1279 | |
| HUMLHDC | 2 | 1409 | |
| HUMLHDC | 2 | 1447 | |
| HUMLHDC | 2 | 2000 | |
| HUMLHDC | 2 | 2023 | |
| HUMLHDC | 2 | 2478 | |
| HUMLHDC | 2 | 2580 | |
| HUMLHDC | 2 | 2584 | |
| HUMLHDC | 2 | 2982 | |
| HUMLHDC | 2 | 3243 | |
| HUMLHDC | 2 | 3275 | |
| HUMLHDC | 2 | 3313 | |
| HUMLHDC | 2 | 3408 | |
| HUMLHDC | 2 | 3994 | |
| HUMLHDC | 2 | 4395 | |
| HUMLHDC | 2 | 4414 | 169 |
| HUMLHDC | 3 | 205 | |
| HUMLHDC | 3 | 485 | |
| HUMLHDC | 3 | 493 | 40 |
| HUMLHDC | 4 | 544 | |
| HUMLHDC | 4 | 655 | |
| HUMLHDC | 4 | 824 | |
| HUMLHDC | 4 | 992 | |
| HUMLHDC | 4 | 1189 | |
| HUMLHDC | 4 | 1652 | |
| HUMLHDC | 4 | 1778 | |
| HUMLHDC | 4 | 1955 | |
| HUMLHDC | 4 | 1996 | 64 |
| HUMLHDC | 5 | 81 | 139 |
| HUMLHDC | 6 | 44 | |
| HUMLHDC | 6 | 72 | |
| HUMLHDC | 6 | 149 | 31 |
| HUMLHDC | 7 | 608 | |
| HUMLHDC | 7 | 638 | |
| HUMLHDC | 7 | 762 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMLHDC | 7 | 805 | 57 |
| HUMLHDC | 9 | 1178 | |
| HUMLHDC | 9 | 1251 | |
| HUMLHDC | 9 | 1563 | |
| HUMLHDC | 9 | 1607 | |
| HUMLHDC | 9 | 1657 | |
| HUMLHDC | 9 | 2176 | |
| HUMLHDC | 9 | 2258 | |
| HUMLHDC | 9 | 2445 | |
| HUMLHDC | 9 | 2980 | |
| HUMLHDC | 9 | 3117 | |
| HUMLHDC | 9 | 3218 | |
| HUMLHDC | 9 | 3603 | |
| HUMLHDC | 9 | 3874 | 124 |
| HUMLHDC | 10 | 100 | |
| HUMLHDC | 10 | 113 | |
| HUMLHDC | 10 | 303 | |
| HUMLHDC | 10 | 318 | |
| HUMLHDC | 10 | 566 | |
| HUMLHDC | 10 | 738 | |
| HUMLHDC | 10 | 821 | |
| HUMLHDC | 10 | 896 | |
| HUMLHDC | 10 | 947 | |
| HUMLHDC | 10 | 1018 | |
| HUMLHDC | 10 | 1317 | |
| HUMLHDC | 10 | 1469 | |
| HUMLHDC | 10 | 2437 | |
| HUMLHDC | 10 | 3032 | |
| HUMLHDC | 10 | 3367 | |
| HUMLHDC | 10 | 3400 | |
| HUMLHDC | 10 | 3524 | |
| HUMLHDC | 10 | 3826 | |
| HUMLHDC | 10 | 3832 | |
| HUMLHDC | 10 | 4004 | |
| HUMLHDC | 10 | 4484 | |
| HUMLHDC | 10 | 4789 | 160 |
| HSSSPN1AG | 1 | 40 | |
| HSSSPN1AG | 1 | 63 | 175 |
| HSSSPN1AG | 3 | 43 | |
| HSSSPN1AG | 3 | 256 | |
| HSSSPN1AG | 3 | 470 | |
| HSSSPN1AG | 3 | 520 | |
| HSSSPN1AG | 3 | 1086 | |
| HSSSPN1AG | 3 | 1095 | |
| HSSSPN1AG | 3 | 1218 | |
| HSSSPN1AG | 3 | 1349 | 159 |
| HSSSPN1AG | 5 | 26 | 73 |
| HSHLAA1 | 3 | 329 | |
| HSHLAA1 | 3 | 380 | |
| HSHLAA1 | 3 | 432 | 27 |
| HSHLAA1 | 7 | 21 | |
| HSHLAA1 | 7 | 112 | 90 |
| HSSAA1A | 1 | 798 | 65 |
| HSSAA1A | 2 | 209 | |
| HSSAA1A | 2 | 356 | |
| HSSAA1A | 2 | 784 | |
| HSSAA1A | 2 | 1331 | |
| HSSAA1A | 2 | 1619 | |
| HSSAA1A | 2 | 2063 | |
| HSSAA1A | 2 | 2157 | |
| HSSAA1A | 2 | 2245 | |
| HSSAA1A | 2 | 2386 | 93 |
| HSSAA1A | 3 | 71 | |
| HSSAA1A | 3 | 217 | |
| HSSAA1A | 3 | 240 | 2 |
| HSENO2 | 1 | 165 | |
| HSENO2 | 1 | 169 | 168 |
| HSENO2 | 3 | 180 | |
| HSENO2 | 3 | 222 | 25 |
| HSENO2 | 4 | 257 | 63 |
| HSENO2 | 5 | 81 | |
| HSENO2 | 5 | 95 | |
| HSENO2 | 5 | 116 | 70 |
| HSENO2 | 6 | 607 | |
| HSENO2 | 6 | 639 | |
| HSENO2 | 6 | 762 | |
| HSENO2 | 6 | 1200 | 105 |
| HSENO2 | 7 | 92 | |
| HSENO2 | 7 | 378 | |
| HSENO2 | 7 | 870 | |
| HSENO2 | 7 | 1317 | 117 |
| HSENO2 | 9 | 16 | |
| HSENO2 | 9 | 81 | |
| HSENO2 | 9 | 133 | 19 |
| HSATPCP1 | 1 | 34 | |
| HSATPCP1 | 1 | 113 | |
| HSATPCP1 | 1 | 135 | |
| HSATPCP1 | 1 | 534 | |
| HSATPCP1 | 1 | 544 | 70 |
| HSATPCP1 | 2 | 447 | |
| HSATPCP1 | 2 | 460 | |
| HSATPCP1 | 2 | 477 | |
| HSATPCP1 | 2 | 482 | |
| HSATPCP1 | 2 | 616 | 13 |
| HSU26425 | 1 | 406 | |
| HSU26425 | 1 | 920 | |
| HSU26425 | 1 | 929 | |
| HSU26425 | 1 | 1147 | |
| HSU26425 | 1 | 1443 | |
| HSU26425 | 1 | 1672 | |
| HSU26425 | 1 | 1791 | |
| HSU26425 | 1 | 2133 | |
| HSU26425 | 1 | 2138 | |
| HSU26425 | 1 | 2341 | |
| HSU26425 | 1 | 2421 | |
| HSU26425 | 1 | 2450 | |
| HSU26425 | 1 | 2474 | |
| HSU26425 | 1 | 2478 | 349 |
| HSU26425 | 4 | 45 | 85 |
| HSU26425 | 7 | 30 | |
| HSU26425 | 8 | 264 | 2 |
| HSU26425 | 9 | 19 | |
| HSU26425 | 9 | 33 | 48 |
| HSU26425 | 10 | 496 | |
| HSU26425 | 10 | 600 | |
| HSU26425 | 10 | 772 | |
| HSU26425 | 10 | 777 | |
| HSU26425 | 10 | 816 | |
| HSU26425 | 10 | 951 | |
| HSU26425 | 10 | 1061 | |
| HSU26425 | 10 | 1197 | |
| HSU26425 | 10 | 1473 | |
| HSU26425 | 10 | 1498 | |
| HSU26425 | 10 | 1552 | |
| HSU26425 | 10 | 1604 | |
| HSU26425 | 10 | 1663 | |
| HSU26425 | 10 | 1677 | 42 |
| HSU26425 | 14 | 115 | |
| HSU26425 | 14 | 125 | |
| HSU26425 | 14 | 197 | |
| HSU26425 | 14 | 253 | |
| HSU26425 | 14 | 328 | |
| HSU26425 | 14 | 795 | |
| HSU26425 | 14 | 835 | |
| HSU26425 | 14 | 1102 | 118 |
| HSU26425 | 15 | 9 | 57 |
| HSU26425 | 19 | 64 | |
| HSU26425 | 19 | 178 | |
| HSU26425 | 19 | 191 | |
| HSU26425 | 19 | 199 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSU26425 | 19 | 373 | |
| HSU26425 | 19 | 555 | |
| HSU26425 | 19 | 565 | |
| HSU26425 | 19 | 573 | 181 |
| HSU26425 | 23 | 22 | |
| HSU26425 | 28 | 49 | 2 |
| HSU26425 | 29 | 476 | |
| HSU26425 | 29 | 520 | 250 |
| HSU26425 | 30 | 19 | |
| HUMKALLIST | 1 | 90 | |
| HUMKALLIST | 1 | 143 | |
| HUMKALLIST | 1 | 313 | |
| HUMKALLIST | 1 | 867 | |
| HUMKALLIST | 1 | 919 | |
| HUMKALLIST | 1 | 1021 | |
| HUMKALLIST | 1 | 1369 | |
| HUMKALLIST | 1 | 1487 | 27 |
| HUMKALLIST | 2 | 47 | |
| HUMKALLIST | 2 | 272 | 2 |
| HUMKALLIST | 3 | 294 | |
| HUMKALLIST | 3 | 352 | |
| HUMKALLIST | 3 | 476 | |
| HUMKALLIST | 3 | 559 | |
| HUMKALLIST | 3 | 627 | |
| HUMKALLIST | 3 | 642 | 106 |
| HSY09781 | 1 | 3 | |
| HSY09781 | 1 | 245 | |
| HSY09781 | 1 | 665 | |
| HSY09781 | 1 | 703 | |
| HSY09781 | 1 | 3159 | |
| HSY09781 | 1 | 3241 | |
| HSY09781 | 1 | 3501 | |
| HSY09781 | 1 | 4002 | |
| HSY09781 | 1 | 4433 | 232 |
| HSY09781 | 2 | 713 | |
| HSY09781 | 2 | 774 | |
| HSY09781 | 2 | 1193 | |
| HSY09781 | 2 | 1578 | |
| HSY09781 | 2 | 1908 | |
| HSY09781 | 2 | 2027 | |
| HSY09781 | 2 | 2031 | |
| HSY09781 | 2 | 2049 | |
| HSY09781 | 2 | 2053 | |
| HSY09781 | 2 | 2057 | |
| HSY09781 | 2 | 2061 | |
| HSY09781 | 2 | 2065 | |
| HSY09781 | 2 | 2069 | |
| HSY09781 | 2 | 2683 | |
| HSY09781 | 2 | 3259 | 70 |
| HSY09781 | 3 | 277 | |
| HSY09781 | 3 | 300 | |
| HSY09781 | 3 | 352 | |
| HSY09781 | 3 | 632 | 19 |
| HSY09781 | 5 | 126 | |
| HSY09781 | 5 | 197 | |
| HSY09781 | 5 | 406 | |
| HSY09781 | 5 | 609 | |
| HSY09781 | 5 | 654 | |
| HSY09781 | 5 | 971 | |
| HSY09781 | 5 | 1321 | |
| HSY09781 | 5 | 1476 | |
| HSY09781 | 5 | 3548 | |
| HSY09781 | 5 | 3767 | 22 |
| HUMA1GLY2 | 1 | 270 | |
| HUMA1GLY2 | 3 | 58 | 105 |
| HUMA1GLY2 | 5 | 947 | 148 |
| HSALDOA | 2 | 20 | |
| HSALDOA | 2 | 57 | |
| HSALDOA | 2 | 235 | |
| HSALDOA | 2 | 393 | |
| HSALDOA | 2 | 700 | |
| HSALDOA | 2 | 882 | |
| HSALDOA | 2 | 941 | 34 |
| HSALDOA | 4 | 163 | |
| HSALDOA | 4 | 267 | |
| HSALDOA | 4 | 271 | 202 |
| HSALDOA | 5 | 29 | 55 |
| HSALDOA | 7 | 16 | 85 |
| HUMPAP | 1 | 79 | |
| HUMPAP | 1 | 84 | |
| HUMPAP | 1 | 265 | 36 |
| HUMPAP | 2 | 25 | 10 |
| HUMPAP | 4 | 98 | |
| HUMPAP | 4 | 174 | 87 |
| HSPNMTB | 1 | 238 | |
| HSPNMTB | 1 | 305 | |
| HSPNMTB | 1 | 342 | |
| HSPNMTB | 1 | 680 | |
| HSPNMTB | 1 | 887 | 48 |
| HSPNMTB | 2 | 13 | 2 |
| HSU05259 | 1 | 31 | |
| HSU05259 | 1 | 168 | |
| HSU05259 | 1 | 394 | |
| HSU05259 | 1 | 1268 | |
| HSU05259 | 1 | 1308 | |
| HSU05259 | 1 | 1390 | 114 |
| HSU05259 | 2 | 88 | |
| HSU05259 | 2 | 173 | 60 |
| HSU05259 | 3 | 341 | |
| HSU05259 | 3 | 626 | 127 |
| AF017257 | 1 | 121 | |
| AF017257 | 1 | 190 | |
| AF017257 | 1 | 261 | |
| AF017257 | 1 | 726 | |
| AF017257 | 1 | 772 | |
| AF017257 | 1 | 856 | |
| AF017257 | 1 | 1565 | |
| AF017257 | 1 | 1587 | |
| AF017257 | 1 | 1707 | |
| AF017257 | 1 | 2231 | |
| AF017257 | 1 | 2369 | |
| AF017257 | 1 | 2460 | |
| AF017257 | 1 | 2837 | 94 |
| AF017257 | 2 | 78 | |
| AF017257 | 2 | 167 | |
| AF017257 | 2 | 575 | |
| AF017257 | 2 | 714 | |
| AF017257 | 2 | 792 | 81 |
| AF017257 | 3 | 29 | 168 |
| AF017257 | 4 | 71 | |
| AF017257 | 4 | 142 | |
| AF017257 | 4 | 189 | |
| AF017257 | 4 | 512 | |
| AF017257 | 4 | 674 | |
| AF017257 | 4 | 737 | |
| AF017257 | 4 | 901 | |
| AF017257 | 4 | 1401 | |
| AF017257 | 4 | 1458 | 9 |
| AF017257 | 5 | 122 | |
| AF017257 | 5 | 151 | |
| AF017257 | 5 | 403 | |
| AF017257 | 5 | 457 | |
| AF017257 | 5 | 1273 | 12 |
| AF017257 | 6 | 347 | |
| AF017257 | 6 | 755 | |
| AF017257 | 6 | 830 | 192 |
| AF017257 | 7 | 436 | |
| AF017257 | 7 | 487 | |
| AF017257 | 7 | 783 | 156 |
| AF017257 | 8 | 118 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| AF017257 | 8 | 454 | |
| AF017257 | 8 | 650 | 121 |
| HSIL1AG | 1 | 432 | |
| HSIL1AG | 1 | 740 | |
| HSIL1AG | 1 | 862 | 2 |
| HSIL1AG | 2 | 140 | |
| HSIL1AG | 2 | 258 | |
| HSIL1AG | 2 | 303 | |
| HSIL1AG | 2 | 360 | |
| HSIL1AG | 2 | 415 | |
| HSIL1AG | 2 | 723 | 10 |
| HSIL1AG | 3 | 120 | |
| HSIL1AG | 3 | 520 | |
| HSIL1AG | 3 | 991 | |
| HSIL1AG | 3 | 1016 | |
| HSIL1AG | 3 | 1253 | |
| HSIL1AG | 3 | 1789 | 93 |
| HSIL1AG | 4 | 950 | |
| HSIL1AG | 4 | 1028 | |
| HSIL1AG | 4 | 1170 | |
| HSIL1AG | 4 | 1232 | |
| HSIL1AG | 4 | 1247 | 186 |
| HSIL1AG | 5 | 84 | |
| HSIL1AG | 5 | 569 | |
| HSIL1AG | 5 | 573 | |
| HSIL1AG | 5 | 585 | |
| HSIL1AG | 5 | 1495 | |
| HSIL1AG | 5 | 1838 | |
| HSIL1AG | 5 | 1852 | |
| HSIL1AG | 5 | 1934 | 52 |
| HUMPP14B | 1 | 183 | 4 |
| HUMPP14B | 2 | 67 | |
| HUMPP14B | 2 | 239 | 17 |
| HUMPP14B | 3 | 224 | |
| HUMPP14B | 3 | 258 | |
| HUMPP14B | 3 | 319 | |
| HUMPP14B | 3 | 327 | |
| HUMPP14B | 3 | 335 | |
| HUMPP14B | 3 | 339 | |
| HUMPP14B | 3 | 343 | |
| HUMPP14B | 3 | 347 | |
| HUMPP14B | 3 | 351 | |
| HUMPP14B | 3 | 378 | |
| HUMPP14B | 3 | 382 | |
| HUMPP14B | 3 | 390 | |
| HUMPP14B | 3 | 394 | |
| HUMPP14B | 3 | 398 | |
| HUMPP14B | 3 | 406 | |
| HUMPP14B | 3 | 414 | |
| HUMPP14B | 3 | 418 | |
| HUMPP14B | 3 | 430 | |
| HUMPP14B | 3 | 438 | |
| HUMPP14B | 3 | 446 | |
| HUMPP14B | 3 | 454 | |
| HUMPP14B | 3 | 462 | |
| HUMPP14B | 3 | 470 | |
| HUMPP14B | 3 | 478 | |
| HUMPP14B | 3 | 486 | |
| HUMPP14B | 3 | 494 | |
| HUMPP14B | 3 | 502 | |
| HUMPP14B | 3 | 506 | |
| HUMPP14B | 3 | 510 | |
| HUMPP14B | 3 | 514 | |
| HUMPP14B | 3 | 534 | |
| HUMPP14B | 3 | 538 | |
| HUMPP14B | 3 | 550 | |
| HUMPP14B | 3 | 558 | |
| HUMPP14B | 3 | 574 | |
| HUMPP14B | 3 | 578 | |
| HUMPP14B | 3 | 598 | |
| HUMPP14B | 3 | 610 | |
| HUMPP14B | 3 | 614 | |
| HUMPP14B | 3 | 622 | |
| HUMPP14B | 3 | 626 | |
| HUMPP14B | 3 | 630 | |
| HUMPP14B | 3 | 634 | |
| HUMPP14B | 3 | 638 | |
| HUMPP14B | 3 | 646 | |
| HUMPP14B | 3 | 654 | |
| HUMPP14B | 3 | 662 | |
| HUMPP14B | 3 | 670 | |
| HUMPP14B | 3 | 1081 | 45 |
| HUMPP14B | 4 | 26 | |
| HUMPP14B | 4 | 30 | |
| HUMPP14B | 4 | 696 | |
| HUMPP14B | 4 | 727 | 18 |
| HUMPP14B | 5 | 90 | |
| HUMPP14B | 5 | 154 | 57 |
| HSTUBAG | 1 | 300 | |
| HSTUBAG | 1 | 365 | |
| HSTUBAG | 1 | 1375 | 109 |
| HSTUBAG | 2 | 22 | |
| HSTUBAG | 2 | 49 | |
| HSTUBAG | 3 | 22 | 25 |
| HSGCSFG | 2 | 3 | 97 |
| HUMLYTOXBB | 1 | 215 | |
| HUMLYTOXBB | 1 | 272 | 160 |
| HSMOGG | 1 | 658 | |
| HSMOGG | 1 | 1202 | |
| HSMOGG | 1 | 1599 | |
| HSMOGG | 1 | 1679 | |
| HSMOGG | 1 | 1683 | 114 |
| HSMOGG | 2 | 220 | |
| HSMOGG | 2 | 623 | |
| HSMOGG | 2 | 639 | |
| HSMOGG | 2 | 950 | |
| HSMOGG | 2 | 1142 | |
| HSMOGG | 2 | 1252 | |
| HSMOGG | 2 | 1277 | |
| HSMOGG | 2 | 1376 | |
| HSMOGG | 2 | 1431 | |
| HSMOGG | 2 | 1584 | |
| HSMOGG | 2 | 2300 | |
| HSMOGG | 2 | 2755 | |
| HSMOGG | 2 | 2961 | |
| HSMOGG | 2 | 4116 | |
| HSMOGG | 2 | 4146 | |
| HSMOGG | 2 | 4815 | |
| HSMOGG | 2 | 5098 | |
| HSMOGG | 2 | 5704 | |
| HSMOGG | 2 | 6209 | |
| HSMOGG | 2 | 6465 | 6 |
| HSMOGG | 3 | 13 | |
| HSMOGG | 3 | 81 | 39 |
| HSMOGG | 4 | 131 | |
| HSMOGG | 4 | 158 | 165 |
| HSMOGG | 5 | 290 | |
| HSMOGG | 5 | 334 | |
| HSMOGG | 5 | 674 | |
| HSMOGG | 5 | 1231 | |
| HSMOGG | 5 | 1601 | |
| HSMOGG | 5 | 1763 | |
| HSMOGG | 5 | 1795 | |
| HSMOGG | 5 | 2296 | 18 |
| HSARYLA | 4 | 90 | |
| HSARYLA | 4 | 236 | 86 |
| HSARYLA | 6 | 57 | |
| HSARYLA | 6 | 195 | 229 |
| HUMPCI | 1 | 156 | |
| HUMPCI | 1 | 640 | |

TABLE 6-continued

Database of genes having putative latent splice sites
Each row includes the following information from left to right
<GENBANK Accession No.><Number of intron (IVS) which includes the latent site/s><The coordinate of the latent site/s in the intron (in nt, counted from the 5 end of the intron)><The position of the first stop codon (in nt, counted from the 5' end of the intron>.

| Accession No. | IVS No. | Latent Pos. | First Stop codon |
|---|---|---|---|
| HUMPCI | 1 | 1034 | |
| HUMPCI | 1 | 1251 | |
| HUMPCI | 1 | 1395 | |
| HUMPCI | 1 | 1570 | 84 |
| HUMPCI | 2 | 376 | 29 |
| HSCST3G | 1 | 581 | |
| HSCST3G | 1 | 591 | |
| HSCST3G | 1 | 905 | |
| HSCST3G | 1 | 1013 | |
| HSCST3G | 1 | 1735 | |
| HSCST3G | 1 | 1826 | |
| HSCST3G | 1 | 1830 | |
| HSCST3G | 1 | 2094 | |
| HSCST3G | 1 | 2114 | |
| HSCST3G | 1 | 2139 | 175 |
| HSCST3G | 2 | 45 | |
| HSCST3G | 2 | 88 | |
| HSCST3G | 2 | 150 | |
| HSCST3G | 2 | 170 | |
| HSCST3G | 2 | 184 | |
| HSCST3G | 2 | 188 | |
| HSCST3G | 2 | 233 | |
| HSCST3G | 2 | 239 | |
| HSCST3G | 2 | 243 | |
| HSCST3G | 2 | 253 | |
| HSCST3G | 2 | 368 | |
| HSCST3G | 2 | 428 | |
| HSCST3G | 2 | 434 | |
| HSCST3G | 2 | 456 | |
| HSCST3G | 2 | 1118 | 70 |
| HUMGSTM4A | 2 | 132 | |
| HUMGSTM4A | 2 | 395 | 135 |
| HUMGSTM4A | 3 | 212 | 49 |
| HUMGSTM4A | 4 | 73 | |
| HUMGSTM4A | 5 | 347 | |
| HUMGSTM4A | 5 | 699 | |
| HUMGSTM4A | 5 | 797 | 97 |
| HUMGSTM4A | 7 | 236 | |
| HUMGSTM4A | 7 | 585 | |
| HUMGSTM4A | 7 | 847 | |
| HUMGSTM4A | 7 | 961 | |
| HUMGSTM4A | 7 | 1102 | |
| HUMGSTM4A | 7 | 1296 | |
| HUMGSTM4A | 7 | 1334 | |
| HUMGSTM4A | 7 | 1449 | |
| HUMGSTM4A | 7 | 1527 | 163 |
| HUMIL4A | 2 | 1183 | |
| HUMIL4A | 2 | 1342 | |
| HUMIL4A | 2 | 1370 | |
| HUMIL4A | 2 | 1390 | |
| HUMIL4A | 2 | 1418 | |
| HUMIL4A | 2 | 1607 | |
| HUMIL4A | 2 | 1627 | |
| HUMIL4A | 2 | 1741 | |
| HUMIL4A | 2 | 1753 | |
| HUMIL4A | 2 | 2250 | |
| HUMIL4A | 2 | 2410 | |
| HUMIL4A | 2 | 2838 | |
| HUMIL4A | 2 | 3203 | |
| HUMIL4A | 2 | 3370 | |
| HUMIL4A | 2 | 3467 | |
| HUMIL4A | 2 | 4007 | |
| HUMIL4A | 2 | 5075 | 58 |
| HUMIL4A | 3 | 429 | |
| HUMIL4A | 3 | 510 | |
| HUMIL4A | 3 | 629 | |
| HUMIL4A | 3 | 642 | |
| HUMIL4A | 3 | 662 | |
| HUMIL4A | 3 | 911 | |
| HUMIL4A | 3 | 977 | |
| HUMIL4A | 3 | 1037 | |
| HUMIL4A | 3 | 1131 | |
| HUMIL4A | 3 | 1136 | |
| HUMIL4A | 3 | 1204 | |
| HUMIL4A | 3 | 1312 | |
| HUMIL4A | 3 | 1403 | |
| HUMIL4A | 3 | 1457 | |
| HUMIL4A | 3 | 1462 | |
| HUMIL4A | 3 | 1508 | |
| HUMIL4A | 3 | 1519 | |
| HUMIL4A | 3 | 2365 | |
| HUMIL4A | 3 | 2396 | |
| HUMIL4A | 3 | 2497 | 76 |
| HUMTHY1A | 1 | 93 | |
| HUMTHY1A | 1 | 164 | |
| HUMTHY1A | 1 | 420 | 96 |
| HUMTHY1A | 2 | 25 | 15 |
| HUMRIGBCHA | 1 | 549 | |
| HUMRIGBCHA | 1 | 699 | |
| HUMRIGBCHA | 1 | 735 | 2 |
| HUMRIGBCHA | 3 | 124 | |
| HUMRIGBCHA | 3 | 187 | |
| HUMRIGBCHA | 3 | 452 | |
| HUMRIGBCHA | 3 | 466 | |
| HUMRIGBCHA | 3 | 744 | |
| HUMRIGBCHA | 3 | 856 | |
| HUMRIGBCHA | 3 | 993 | |
| HUMRIGBCHA | 3 | 1140 | |
| HUMRIGBCHA | 3 | 1385 | |
| HUMRIGBCHA | 3 | 1736 | |
| HUMRIGBCHA | 3 | 1921 | |
| HUMRIGBCHA | 3 | 1963 | |
| HUMRIGBCHA | 3 | 2056 | |
| HUMRIGBCHA | 3 | 2191 | |
| HUMRIGBCHA | 3 | 2204 | 16 |
| HUMRIGBCHA | 5 | 46 | |
| HUMRIGBCHA | 5 | 50 | |
| HUMRIGBCHA | 5 | 124 | |
| HUMRIGBCHA | 5 | 363 | 49 |
| HUMRIGBCHA | 6 | 242 | |
| HUMRIGBCHA | 6 | 296 | |
| HUMRIGBCHA | 6 | 813 | |
| HUMRIGBCHA | 6 | 976 | |
| HUMRIGBCHA | 6 | 1409 | |
| HUMRIGBCHA | 6 | 1451 | 19 |
| HSMICAGEN | 1 | 61 | |
| HSMICAGEN | 1 | 1728 | |
| HSMICAGEN | 1 | 1813 | |
| HSMICAGEN | 1 | 2096 | |
| HSMICAGEN | 1 | 3118 | |
| HSMICAGEN | 1 | 3279 | |
| HSMICAGEN | 1 | 3767 | |
| HSMICAGEN | 1 | 4273 | |
| HSMICAGEN | 1 | 4308 | |
| HSMICAGEN | 1 | 4747 | |
| HSMICAGEN | 1 | 4860 | |
| HSMICAGEN | 1 | 4940 | |
| HSMICAGEN | 1 | 5072 | |
| HSMICAGEN | 1 | 5410 | |
| HSMICAGEN | 1 | 5621 | |
| HSMICAGEN | 1 | 5633 | 288 |
| HSMICAGEN | 2 | 105 | |
| HSMICAGEN | 2 | 118 | |
| HSMICAGEN | 2 | 140 | |
| HSMICAGEN | 2 | 229 | 24 |
| HSMICAGEN | 3 | 241 | |
| HSMICAGEN | 3 | 470 | 129 |
| HSMICAGEN | 5 | 28 | |
| HSMICAGEN | 5 | 222 | |
| HSMICAGEN | 5 | 311 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSMICAGEN | 5 | 316 | |
| HSMICAGEN | 5 | 965 | |
| HSMICAGEN | 5 | 1112 | |
| HSMICAGEN | 5 | 1199 | |
| HSMICAGEN | 5 | 1264 | |
| HSMICAGEN | 5 | 1355 | |
| HSMICAGEN | 5 | 1966 | |
| HSMICAGEN | 5 | 1985 | |
| HSMICAGEN | 5 | 2153 | |
| HSMICAGEN | 5 | 2161 | 51 |
| HSU04636 | 1 | 116 | |
| HSU04636 | 1 | 305 | |
| HSU04636 | 1 | 430 | 144 |
| HSU04636 | 3 | 226 | |
| HSU04636 | 3 | 361 | 57 |
| HSU04636 | 5 | 285 | |
| HSU04636 | 5 | 356 | 7 |
| HSU04636 | 7 | 90 | |
| HSU04636 | 7 | 128 | 48 |
| HSU04636 | 8 | 359 | |
| HSU04636 | 8 | 363 | 133 |
| AF037372 | 1 | 95 | |
| AF037372 | 1 | 601 | 52 |
| AF037372 | 3 | 56 | |
| AF037372 | 3 | 197 | 129 |
| HSASML | 1 | 195 | |
| HSASML | 1 | 329 | 64 |
| HSASML | 2 | 39 | |
| HSASML | 2 | 948 | 98 |
| HSASML | 4 | 33 | 2 |
| D83195 | 2 | 28 | 23 |
| D83195 | 3 | 91 | |
| D83195 | 3 | 169 | |
| D83195 | 3 | 225 | |
| D83195 | 3 | 281 | 11 |
| D83195 | 4 | 189 | 174 |
| D83195 | 7 | 50 | 28 |
| AB002059 | 1 | 45 | |
| AB002059 | 1 | 363 | |
| AB002059 | 1 | 383 | |
| AB002059 | 1 | 475 | 2 |
| AB002059 | 2 | 277 | |
| AB002059 | 2 | 1065 | 55 |
| AB002059 | 3 | 86 | |
| AB002059 | 3 | 357 | |
| AB002059 | 3 | 518 | |
| AB002059 | 3 | 1486 | |
| AB002059 | 3 | 1613 | |
| AB002059 | 3 | 2483 | |
| AB002059 | 3 | 2656 | |
| AB002059 | 3 | 2660 | |
| AB002059 | 3 | 2765 | |
| AB002059 | 3 | 2807 | |
| AB002059 | 3 | 2839 | |
| AB002059 | 3 | 2853 | |
| AB002059 | 3 | 2861 | |
| AB002059 | 3 | 2903 | |
| AB002059 | 3 | 2930 | |
| AB002059 | 3 | 2935 | |
| AB002059 | 3 | 3001 | |
| AB002059 | 3 | 3321 | |
| AB002059 | 3 | 3434 | |
| AB002059 | 3 | 3919 | |
| AB002059 | 3 | 4029 | |
| AB002059 | 3 | 4069 | |
| AB002059 | 3 | 4178 | |
| AB002059 | 3 | 4215 | |
| AB002059 | 3 | 4488 | |
| AB002059 | 3 | 4503 | |
| AB002059 | 3 | 4588 | 232 |
| AB002059 | 8 | 105 | |
| AB002059 | 8 | 572 | |
| AB002059 | 8 | 1049 | |
| AB002059 | 8 | 1091 | |
| AB002059 | 8 | 1184 | |
| AB002059 | 8 | 1500 | |
| AB002059 | 8 | 1542 | |
| AB002059 | 8 | 1889 | 2 |
| AB002059 | 9 | 9 | 85 |
| AB002059 | 10 | 34 | |
| AB002059 | 10 | 53 | 37 |
| HUMCAPG | 1 | 283 | |
| HUMCAPG | 1 | 519 | 6 |
| HUMCAPG | 2 | 113 | 2 |
| HUMCAPG | 3 | 59 | |
| HUMCAPG | 4 | 208 | 181 |
| HSU16720 | 1 | 165 | |
| HSU16720 | 1 | 223 | |
| HSU16720 | 1 | 325 | |
| HSU16720 | 1 | 581 | 46 |
| HSU16720 | 2 | 185 | 40 |
| HSU16720 | 3 | 230 | |
| HSU16720 | 3 | 825 | 274 |
| HSU16720 | 4 | 239 | |
| HSU16720 | 4 | 490 | |
| HSU16720 | 4 | 502 | |
| HSU16720 | 4 | 661 | |
| HSU16720 | 4 | 801 | |
| HSU16720 | 4 | 909 | 187 |
| HSCLN3 | 1 | 120 | |
| HSCLN3 | 2 | 489 | |
| HSCLN3 | 2 | 514 | |
| HSCLN3 | 2 | 518 | |
| HSCLN3 | 2 | 530 | |
| HSCLN3 | 2 | 974 | |
| HSCLN3 | 2 | 1155 | |
| HSCLN3 | 2 | 1249 | |
| HSCLN3 | 2 | 1673 | |
| HSCLN3 | 2 | 2005 | 2 |
| HSCLN3 | 3 | 3 | |
| HSCLN3 | 3 | 28 | |
| HSCLN3 | 3 | 64 | |
| HSCLN3 | 3 | 509 | 49 |
| HSCLN3 | 4 | 166 | 52 |
| HSCLN3 | 5 | 5 | 8 |
| HSCLN3 | 6 | 218 | |
| HSCLN3 | 6 | 766 | 111 |
| HSCLN3 | 8 | 123 | |
| HSCLN3 | 8 | 189 | |
| HSCLN3 | 8 | 438 | |
| HSCLN3 | 8 | 440 | |
| HSCLN3 | 8 | 555 | |
| HSCLN3 | 8 | 595 | |
| HSCLN3 | 8 | 1172 | |
| HSCLN3 | 8 | 1246 | |
| HSCLN3 | 8 | 1459 | |
| HSCLN3 | 8 | 1548 | |
| HSCLN3 | 8 | 1656 | 2 |
| HSCLN3 | 9 | 24 | |
| HSCLN3 | 9 | 93 | |
| HSCLN3 | 9 | 613 | |
| HSCLN3 | 9 | 831 | |
| HSCLN3 | 9 | 975 | |
| HSCLN3 | 9 | 1110 | |
| HSCLN3 | 9 | 1214 | 69 |
| HSCLN3 | 10 | 17 | |
| HSCLN3 | 11 | 3 | 16 |
| HSCLN3 | 13 | 200 | |
| HSCLN3 | 13 | 330 | |
| HSCLN3 | 13 | 724 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSCLN3 | 13 | 768 | |
| HSCLN3 | 13 | 889 | |
| HSCLN3 | 13 | 1061 | |
| HSCLN3 | 13 | 1171 | |
| HSCLN3 | 13 | 1198 | |
| HSCLN3 | 13 | 1340 | |
| HSCLN3 | 13 | 1460 | |
| HSCLN3 | 13 | 1474 | |
| HSCLN3 | 13 | 1907 | |
| HSCLN3 | 13 | 2111 | |
| HSCLN3 | 13 | 2165 | |
| HSCLN3 | 13 | 2469 | |
| HSCLN3 | 13 | 2745 | |
| HSCLN3 | 13 | 2787 | |
| HSCLN3 | 13 | 2813 | |
| HSCLN3 | 13 | 2876 | |
| HSCLN3 | 13 | 2989 | |
| HSCLN3 | 13 | 3036 | |
| HSCLN3 | 13 | 3083 | |
| HSCLN3 | 13 | 3613 | |
| HSCLN3 | 13 | 3882 | |
| HSCLN3 | 13 | 4024 | |
| HSCLN3 | 13 | 4066 | 229 |
| HSU66711 | 1 | 301 | 156 |
| HSCDIR2 | 2 | 366 | 21 |
| HSCDIR2 | 3 | 148 | 42 |
| HUMEPOHYDD | 1 | 43 | |
| HUMEPOHYDD | 1 | 340 | |
| HUMEPOHYDD | 1 | 458 | |
| HUMEPOHYDD | 1 | 620 | |
| HUMEPOHYDD | 1 | 632 | |
| HUMEPOHYDD | 1 | 765 | |
| HUMEPOHYDD | 1 | 880 | |
| HUMEPOHYDD | 1 | 885 | |
| HUMEPOHYDD | 1 | 942 | |
| HUMEPOHYDD | 1 | 1407 | |
| HUMEPOHYDD | 1 | 2303 | |
| HUMEPOHYDD | 1 | 2560 | 325 |
| HUMEPOHYDD | 2 | 31 | |
| HUMEPOHYDD | 2 | 62 | |
| HUMEPOHYDD | 2 | 110 | |
| HUMEPOHYDD | 2 | 348 | |
| HUMEPOHYDD | 2 | 435 | |
| HUMEPOHYDD | 2 | 631 | |
| HUMEPOHYDD | 2 | 1345 | |
| HUMEPOHYDD | 2 | 1610 | |
| HUMEPOHYDD | 2 | 1622 | |
| HUMEPOHYDD | 2 | 1695 | |
| HUMEPOHYDD | 2 | 1778 | |
| HUMEPOHYDD | 2 | 1924 | |
| HUMEPOHYDD | 2 | 2585 | |
| HUMEPOHYDD | 2 | 3075 | |
| HUMEPOHYDD | 2 | 3135 | |
| HUMEPOHYDD | 2 | 3408 | |
| HUMEPOHYDD | 2 | 3712 | |
| HUMEPOHYDD | 2 | 3871 | |
| HUMEPOHYDD | 2 | 4122 | |
| HUMEPOHYDD | 2 | 4227 | |
| HUMEPOHYDD | 2 | 4231 | |
| HUMEPOHYDD | 2 | 4406 | |
| HUMEPOHYDD | 2 | 4544 | |
| HUMEPOHYDD | 2 | 4719 | |
| HUMEPOHYDD | 2 | 5107 | |
| HUMEPOHYDD | 2 | 5118 | |
| HUMEPOHYDD | 2 | 5227 | |
| HUMEPOHYDD | 2 | 5471 | |
| HUMEPOHYDD | 2 | 5723 | |
| HUMEPOHYDD | 2 | 5798 | |
| HUMEPOHYDD | 2 | 5909 | |
| HUMEPOHYDD | 2 | 6530 | 117 |
| HUMEPOHYDD | 3 | 84 | 24 |
| HUMEPOHYDD | 4 | 4 | |
| HUMEPOHYDD | 4 | 19 | |
| HUMEPOHYDD | 4 | 238 | 2 |
| HUMEPOHYDD | 5 | 299 | |
| HUMEPOHYDD | 5 | 304 | |
| HUMEPOHYDD | 5 | 462 | |
| HUMEPOHYDD | 5 | 713 | |
| HUMEPOHYDD | 5 | 735 | |
| HUMEPOHYDD | 5 | 1013 | |
| HUMEPOHYDD | 5 | 1034 | |
| HUMEPOHYDD | 5 | 1478 | |
| HUMEPOHYDD | 5 | 1520 | |
| HUMEPOHYDD | 5 | 1797 | |
| HUMEPOHYDD | 5 | 1950 | |
| HUMEPOHYDD | 5 | 2168 | 156 |
| HUMEPOHYDD | 6 | 168 | |
| HUMEPOHYDD | 6 | 366 | |
| HUMEPOHYDD | 6 | 493 | |
| HUMEPOHYDD | 6 | 1113 | |
| HUMEPOHYDD | 6 | 1340 | |
| HUMEPOHYDD | 6 | 1478 | |
| HUMEPOHYDD | 6 | 1515 | |
| HUMEPOHYDD | 6 | 1652 | |
| HUMEPOHYDD | 6 | 1678 | |
| HUMEPOHYDD | 6 | 1749 | |
| HUMEPOHYDD | 6 | 1774 | |
| HUMEPOHYDD | 6 | 1789 | 2 |
| HUMEPOHYDD | 7 | 152 | |
| HUMEPOHYDD | 7 | 184 | |
| HUMEPOHYDD | 7 | 293 | 2 |
| HSRPS3AGE | 1 | 244 | 2 |
| HSRPS3AGE | 3 | 296 | |
| HSRPS3AGE | 3 | 445 | |
| HSRPS3AGE | 3 | 849 | |
| HSRPS3AGE | 3 | 1083 | |
| HSRPS3AGE | 3 | 1426 | |
| HSRPS3AGE | 3 | 1518 | |
| HSRPS3AGE | 3 | 1532 | |
| HSRPS3AGE | 3 | 1540 | 19 |
| HSRPS3AGE | 4 | 81 | |
| HSRPS3AGE | 4 | 87 | |
| HSRPS3AGE | 4 | 411 | |
| HSRPS3AGE | 4 | 907 | |
| HSRPS3AGE | 4 | 941 | |
| HSRPS3AGE | 4 | 989 | 2 |
| HSRPS3AGE | 5 | 3 | 6 |
| HUMBETGLOA | 2 | 291 | |
| HUMBETGLOA | 2 | 480 | |
| HUMBETGLOA | 2 | 704 | 19 |
| HSEOTAX | 1 | 27 | |
| HSEOTAX | 1 | 32 | |
| HSEOTAX | 1 | 55 | |
| HSEOTAX | 1 | 418 | |
| HSEOTAX | 1 | 929 | 30 |
| HSEOTAX | 2 | 3 | |
| HSEOTAX | 2 | 136 | 2 |
| HSRPS8 | 2 | 156 | 76 |
| HSRPS8 | 3 | 133 | |
| HSRPS8 | 3 | 265 | |
| HSRPS8 | 3 | 397 | |
| HSRPS8 | 3 | 575 | |
| HSRPS8 | 3 | 674 | 6 |
| HSRPS8 | 5 | 22 | |
| HSRPS8 | 5 | 298 | |
| HSRPS8 | 5 | 313 | 42 |
| HUMHIS102 | 1 | 154 | |
| HUMHIS102 | 1 | 747 | 91 |
| HUMHIS102 | 3 | 350 | |
| HUMHIS102 | 3 | 644 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMHIS102 | 3 | 748 | 139 |
| HSU91522 | 1 | 241 | 10 |
| HSU91522 | 2 | 216 | |
| HSU91522 | 2 | 264 | |
| HSU91522 | 2 | 329 | |
| HSU91522 | 2 | 333 | |
| HSU91522 | 2 | 524 | |
| HSU91522 | 2 | 682 | |
| HSU91522 | 2 | 769 | 2 |
| HSE48ATGN | 1 | 702 | 78 |
| HSE48ATGN | 2 | 80 | |
| HSE48ATGN | 2 | 93 | 6 |
| HUMPHOSA | 1 | 78 | |
| HUMPHOSA | 1 | 191 | 2 |
| HUMPHOSA | 2 | 68 | |
| HUMPHOSA | 2 | 401 | 27 |
| HUMPHOSA | 3 | 60 | 63 |
| HUMPHOSA | 7 | 253 | |
| HUMPHOSA | 7 | 290 | 60 |
| HUMCFVII | 1 | 356 | |
| HUMCFVII | 1 | 366 | |
| HUMCFVII | 1 | 537 | |
| HUMCFVII | 1 | 542 | |
| HUMCFVII | 1 | 552 | |
| HUMCFVII | 1 | 617 | |
| HUMCFVII | 1 | 631 | |
| HUMCFVII | 1 | 732 | |
| HUMCFVII | 1 | 766 | |
| HUMCFVII | 1 | 890 | 153 |
| HUMCFVII | 2 | 992 | |
| HUMCFVII | 2 | 1077 | |
| HUMCFVII | 2 | 1244 | 1080 |
| HUMCFVII | 3 | 159 | |
| HUMCFVII | 3 | 371 | |
| HUMCFVII | 3 | 1481 | |
| HUMCFVII | 3 | 1854 | |
| HUMCFVII | 3 | 1891 | 274 |
| HUMCFVII | 5 | 97 | |
| HUMCFVII | 5 | 146 | |
| HUMCFVII | 5 | 841 | 156 |
| HUMCFVII | 6 | 132 | |
| HUMCFVII | 6 | 675 | |
| HUMCFVII | 6 | 699 | 30 |
| HUMCFVII | 7 | 90 | |
| HUMCFVII | 7 | 276 | |
| HUMCFVII | 7 | 344 | |
| HUMCFVII | 7 | 562 | 199 |
| HUMCFVII | 8 | 36 | |
| HUMCFVII | 8 | 73 | |
| HUMCFVII | 8 | 110 | |
| HUMCFVII | 8 | 147 | |
| HUMCFVII | 8 | 184 | |
| HUMCFVII | 8 | 484 | |
| HUMCFVII | 8 | 765 | 366 |
| HSU19765 | 2 | 46 | 69 |
| HSU19765 | 3 | 133 | |
| HSU19765 | 3 | 237 | |
| HSU19765 | 3 | 341 | |
| HSU19765 | 3 | 438 | 2 |
| HUMMHDC3B | 1 | 170 | |
| HUMMHDC3B | 1 | 273 | |
| HUMMHDC3B | 1 | 780 | |
| HUMMHDC3B | 1 | 840 | |
| HUMMHDC3B | 1 | 900 | |
| HUMMHDC3B | 1 | 930 | |
| HUMMHDC3B | 1 | 954 | |
| HUMMHDC3B | 1 | 1406 | 162 |
| HUMMHDC3B | 2 | 155 | |
| HUMMHDC3B | 2 | 581 | |
| HUMMHDC3B | 2 | 629 | |
| HUMMHDC3B | 2 | 719 | |
| HUMMHDC3B | 2 | 1038 | |
| HUMMHDC3B | 2 | 1185 | |
| HUMMHDC3B | 2 | 1686 | |
| HUMMHDC3B | 2 | 2291 | |
| HUMMHDC3B | 2 | 2480 | |
| HUMMHDC3B | 2 | 2703 | 87 |
| HUMMHDC3B | 3 | 261 | 90 |
| HUMMHDC3B | 4 | 427 | |
| HUMMHDC3B | 4 | 505 | |
| HUMMHDC3B | 4 | 989 | 72 |
| HSHLADMBG | 1 | 49 | |
| HSHLADMBG | 1 | 148 | |
| HSHLADMBG | 1 | 292 | |
| HSHLADMBG | 1 | 377 | |
| HSHLADMBG | 1 | 547 | |
| HSHLADMBG | 1 | 931 | 120 |
| HSHLADMBG | 2 | 165 | |
| HSHLADMBG | 2 | 174 | |
| HSHLADMBG | 2 | 203 | |
| HSHLADMBG | 2 | 508 | |
| HSHLADMBG | 2 | 746 | |
| HSHLADMBG | 2 | 781 | |
| HSHLADMBG | 2 | 1121 | 93 |
| HSHLADMBG | 3 | 174 | |
| HSHLADMBG | 3 | 186 | |
| HSHLADMBG | 3 | 313 | |
| HSHLADMBG | 3 | 348 | |
| HSHLADMBG | 3 | 1106 | |
| HSHLADMBG | 3 | 1144 | |
| HSHLADMBG | 3 | 1225 | |
| HSHLADMBG | 3 | 1444 | |
| HSHLADMBG | 3 | 1474 | |
| HSHLADMBG | 3 | 1497 | 27 |
| HSHLADMBG | 5 | 59 | |
| HSHLADMBG | 5 | 97 | |
| HSHLADMBG | 5 | 217 | 54 |
| HUMHPARS1 | 1 | 253 | |
| HUMHPARS1 | 1 | 582 | |
| HUMHPARS1 | 1 | 608 | |
| HUMHPARS1 | 1 | 914 | |
| HUMHPARS1 | 1 | 958 | |
| HUMHPARS1 | 1 | 1301 | |
| HUMHPARS1 | 1 | 1315 | |
| HUMHPARS1 | 1 | 1402 | |
| HUMHPARS1 | 1 | 1428 | 83 |
| HUMHPARS1 | 3 | 75 | |
| HUMHPARS1 | 3 | 237 | |
| HUMHPARS1 | 3 | 316 | 60 |
| HUMHPARS1 | 4 | 159 | 9 |
| HUMHPARS1 | 5 | 75 | |
| HUMHPARS1 | 5 | 237 | |
| HUMHPARS1 | 5 | 316 | 60 |
| HUMHPARS1 | 6 | 152 | |
| HUMHPARS1 | 6 | 795 | 9 |
| HSIFNAR | 1 | 38 | |
| HSIFNAR | 1 | 359 | |
| HSIFNAR | 1 | 525 | |
| HSIFNAR | 1 | 573 | |
| HSIFNAR | 1 | 709 | |
| HSIFNAR | 1 | 766 | |
| HSIFNAR | 1 | 1334 | |
| HSIFNAR | 1 | 1781 | |
| HSIFNAR | 1 | 1865 | |
| HSIFNAR | 1 | 1976 | |
| HSIFNAR | 1 | 2147 | |
| HSIFNAR | 1 | 2325 | |
| HSIFNAR | 1 | 2748 | |
| HSIFNAR | 1 | 2772 | |
| HSIFNAR | 1 | 3272 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HSIFNAR | 1 | 3352 | |
| HSIFNAR | 1 | 3650 | |
| HSIFNAR | 1 | 3781 | |
| HSIFNAR | 1 | 4555 | |
| HSIFNAR | 1 | 4817 | |
| HSIFNAR | 1 | 4881 | |
| HSIFNAR | 1 | 5012 | |
| HSIFNAR | 1 | 6867 | |
| HSIFNAR | 1 | 7145 | |
| HSIFNAR | 1 | 7281 | |
| HSIFNAR | 1 | 7351 | |
| HSIFNAR | 1 | 7738 | |
| HSIFNAR | 1 | 7763 | |
| HSIFNAR | 1 | 8388 | |
| HSIFNAR | 1 | 8421 | |
| HSIFNAR | 1 | 8936 | |
| HSIFNAR | 1 | 9030 | |
| HSIFNAR | 1 | 9197 | |
| HSIFNAR | 1 | 9439 | |
| HSIFNAR | 1 | 9592 | |
| HSIFNAR | 1 | 9846 | |
| HSIFNAR | 1 | 9969 | |
| HSIFNAR | 1 | 10195 | |
| HSIFNAR | 1 | 10296 | 276 |
| HSIFNAR | 2 | 3 | |
| HSIFNAR | 2 | 329 | |
| HSIFNAR | 2 | 338 | |
| HSIFNAR | 2 | 397 | |
| HSIFNAR | 2 | 2502 | |
| HSIFNAR | 2 | 2558 | |
| HSIFNAR | 2 | 2680 | |
| HSIFNAR | 2 | 2724 | |
| HSIFNAR | 2 | 2846 | |
| HSIFNAR | 2 | 3110 | |
| HSIFNAR | 2 | 3467 | |
| HSIFNAR | 2 | 3732 | |
| HSIFNAR | 2 | 3833 | |
| HSIFNAR | 2 | 4061 | |
| HSIFNAR | 2 | 4138 | |
| HSIFNAR | 2 | 4156 | |
| HSIFNAR | 2 | 4736 | |
| HSIFNAR | 2 | 4758 | 32 |
| HSIFNAR | 3 | 603 | |
| HSIFNAR | 3 | 736 | |
| HSIFNAR | 3 | 997 | |
| HSIFNAR | 3 | 1449 | 81 |
| HSIFNAR | 4 | 31 | 25 |
| HSIFNAR | 5 | 91 | |
| HSIFNAR | 5 | 247 | |
| HSIFNAR | 5 | 556 | |
| HSIFNAR | 5 | 593 | |
| HSIFNAR | 5 | 645 | |
| HSIFNAR | 5 | 903 | |
| HSIFNAR | 5 | 1352 | |
| HSIFNAR | 5 | 1394 | 21 |
| HSIFNAR | 6 | 106 | |
| HSIFNAR | 6 | 128 | |
| HSIFNAR | 6 | 997 | |
| HSIFNAR | 6 | 1050 | |
| HSIFNAR | 6 | 1167 | |
| HSIFNAR | 6 | 1205 | |
| HSIFNAR | 6 | 1405 | |
| HSIFNAR | 6 | 1453 | |
| HSIFNAR | 6 | 1511 | |
| HSIFNAR | 6 | 1586 | |
| HSIFNAR | 6 | 1868 | |
| HSIFNAR | 6 | 1910 | |
| HSIFNAR | 6 | 2003 | |
| HSIFNAR | 6 | 2236 | |
| HSIFNAR | 6 | 2633 | |
| HSIFNAR | 6 | 2650 | |
| HSIFNAR | 6 | 3208 | |
| HSIFNAR | 6 | 3212 | |
| HSIFNAR | 6 | 3226 | |
| HSIFNAR | 6 | 3609 | 2 |
| HSIFNAR | 8 | 53 | |
| HSIFNAR | 8 | 392 | |
| HSIFNAR | 8 | 462 | |
| HSIFNAR | 8 | 970 | |
| HSIFNAR | 8 | 1135 | |
| HSIFNAR | 8 | 1577 | |
| HSIFNAR | 8 | 1647 | |
| HSIFNAR | 8 | 1686 | |
| HSIFNAR | 8 | 1921 | |
| HSIFNAR | 8 | 2429 | |
| HSIFNAR | 8 | 2565 | |
| HSIFNAR | 8 | 2637 | |
| HSIFNAR | 8 | 2827 | |
| HSIFNAR | 8 | 2957 | |
| HSIFNAR | 8 | 3174 | 28 |
| HSIFNAR | 9 | 49 | |
| HSIFNAR | 9 | 338 | |
| HSIFNAR | 9 | 552 | 33 |
| HSIFNAR | 10 | 330 | |
| HSIFNAR | 10 | 344 | |
| HSIFNAR | 10 | 563 | |
| HSIFNAR | 10 | 581 | |
| HSIFNAR | 10 | 648 | |
| HSIFNAR | 10 | 659 | |
| HSIFNAR | 10 | 897 | |
| HSIFNAR | 10 | 934 | |
| HSIFNAR | 10 | 1394 | |
| HSIFNAR | 10 | 1443 | 34 |
| HUMPDHAL | 1 | 184 | |
| HUMPDHAL | 1 | 269 | |
| HUMPDHAL | 1 | 692 | |
| HUMPDHAL | 1 | 782 | |
| HUMPDHAL | 1 | 848 | |
| HUMPDHAL | 1 | 1144 | |
| HUMPDHAL | 1 | 1152 | |
| HUMPDHAL | 1 | 1250 | |
| HUMPDHAL | 1 | 1265 | |
| HUMPDHAL | 1 | 1591 | |
| HUMPDHAL | 1 | 1725 | |
| HUMPDHAL | 1 | 1740 | |
| HUMPDHAL | 1 | 2525 | |
| HUMPDHAL | 1 | 2762 | |
| HUMPDHAL | 1 | 2766 | |
| HUMPDHAL | 1 | 2935 | |
| HUMPDHAL | 1 | 3074 | |
| HUMPDHAL | 1 | 3754 | |
| HUMPDHAL | 1 | 3868 | |
| HUMPDHAL | 1 | 3963 | |
| HUMPDHAL | 1 | 3968 | |
| HUMPDHAL | 1 | 4019 | |
| HUMPDHAL | 1 | 4626 | |
| HUMPDHAL | 1 | 4640 | 193 |
| HUMPDHAL | 2 | 158 | 46 |
| HUMPDHAL | 3 | 6 | |
| HUMPDHAL | 3 | 10 | |
| HUMPDHAL | 3 | 108 | |
| HUMPDHAL | 3 | 162 | 97 |
| HUMPDHAL | 4 | 192 | |
| HUMPDHAL | 4 | 209 | |
| HUMPDHAL | 4 | 282 | |
| HUMPDHAL | 4 | 316 | |
| HUMPDHAL | 4 | 482 | |
| HUMPDHAL | 4 | 617 | |
| HUMPDHAL | 4 | 1055 | |
| HUMPDHAL | 4 | 1445 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMPDHAL | 4 | 1535 | 30 |
| HUMPDHAL | 5 | 327 | |
| HUMPDHAL | 5 | 352 | |
| HUMPDHAL | 5 | 519 | |
| HUMPDHAL | 5 | 543 | |
| HUMPDHAL | 5 | 561 | |
| HUMPDHAL | 5 | 825 | |
| HUMPDHAL | 5 | 1089 | |
| HUMPDHAL | 5 | 1160 | 31 |
| HUMPDHAL | 6 | 95 | 79 |
| HUMPDHAL | 7 | 48 | 124 |
| HUMPDHAL | 8 | 102 | |
| HUMPDHAL | 8 | 268 | |
| HUMPDHAL | 8 | 384 | |
| HUMPDHAL | 8 | 487 | |
| HUMPDHAL | 8 | 627 | |
| HUMPDHAL | 8 | 645 | |
| HUMPDHAL | 8 | 702 | |
| HUMPDHAL | 8 | 1265 | |
| HUMPDHAL | 8 | 1446 | 10 |
| HUMPDHAL | 9 | 405 | |
| HUMPDHAL | 9 | 927 | 41 |
| HUMPPPA | 1 | 181 | |
| HUMPPPA | 1 | 197 | 104 |
| HUMPDHBET | 2 | 410 | |
| HUMPDHBET | 2 | 1192 | |
| HUMPDHBET | 2 | 1228 | |
| HUMPDHBET | 2 | 1569 | 259 |
| HUMPDHBET | 3 | 34 | |
| HUMPDHBET | 5 | 384 | |
| HUMPDHBET | 5 | 388 | 19 |
| HUMPDHBET | 6 | 189 | |
| HUMPDHBET | 6 | 379 | 36 |
| HUMPDHBET | 7 | 160 | |
| HUMPDHBET | 7 | 164 | 33 |
| HUMPDHBET | 8 | 77 | |
| HUMPDHBET | 8 | 178 | |
| HUMPDHBET | 8 | 621 | |
| HUMPDHBET | 8 | 739 | 73 |
| HUMPDHBET | 9 | 120 | 123 |
| HSU52427 | 2 | 245 | 2 |
| HSU52427 | 3 | 206 | |
| HSU52427 | 3 | 683 | |
| HSU52427 | 3 | 716 | |
| HSU52427 | 3 | 952 | |
| HSU52427 | 3 | 1164 | |
| HSU52427 | 3 | 1204 | |
| HSU52427 | 3 | 1306 | |
| HSU52427 | 3 | 1438 | |
| HSU52427 | 3 | 1446 | |
| HSU52427 | 3 | 1674 | 31 |
| HSU52427 | 5 | 182 | |
| HSU52427 | 5 | 193 | 196 |
| HSU52427 | 6 | 339 | |
| HSU52427 | 6 | 464 | 163 |
| AF006501 | 1 | 289 | |
| AF006501 | 1 | 356 | |
| AF006501 | 1 | 372 | |
| AF006501 | 1 | 408 | |
| AF006501 | 1 | 818 | |
| AF006501 | 1 | 855 | |
| AF006501 | 1 | 927 | |
| AF006501 | 1 | 994 | |
| AF006501 | 1 | 1085 | |
| AF006501 | 1 | 1104 | |
| AF006501 | 1 | 1125 | |
| AF006501 | 1 | 2157 | |
| AF006501 | 1 | 2191 | |
| AF006501 | 1 | 2383 | |
| AF006501 | 1 | 2939 | 2 |
| AF006501 | 2 | 58 | |
| AF006501 | 2 | 299 | |
| AF006501 | 2 | 343 | |
| AF006501 | 2 | 496 | |
| AF006501 | 2 | 537 | |
| AF006501 | 2 | 569 | |
| AF006501 | 2 | 594 | |
| AF006501 | 2 | 642 | |
| AF006501 | 2 | 1610 | |
| AF006501 | 2 | 1804 | |
| AF006501 | 2 | 1846 | |
| AF006501 | 2 | 2007 | |
| AF006501 | 2 | 2011 | |
| AF006501 | 2 | 2121 | |
| AF006501 | 2 | 2261 | |
| AF006501 | 2 | 2315 | 61 |
| AF006501 | 3 | 294 | |
| AF006501 | 3 | 426 | |
| AF006501 | 3 | 452 | |
| AF006501 | 3 | 600 | |
| AF006501 | 3 | 1200 | |
| AF006501 | 3 | 1725 | |
| AF006501 | 3 | 1812 | |
| AF006501 | 3 | 1886 | |
| AF006501 | 3 | 1898 | |
| AF006501 | 3 | 2301 | |
| AF006501 | 3 | 2414 | |
| AF006501 | 3 | 2536 | |
| AF006501 | 3 | 3620 | |
| AF006501 | 3 | 3759 | |
| AF006501 | 3 | 3949 | |
| AF006501 | 3 | 4097 | |
| AF006501 | 3 | 4403 | |
| AF006501 | 3 | 4421 | |
| AF006501 | 3 | 4680 | |
| AF006501 | 3 | 4781 | |
| AF006501 | 3 | 4828 | |
| AF006501 | 3 | 4971 | |
| AF006501 | 3 | 5342 | |
| AF006501 | 3 | 5551 | |
| AF006501 | 3 | 5776 | |
| AF006501 | 3 | 5858 | |
| AF006501 | 3 | 6031 | |
| AF006501 | 3 | 6097 | |
| AF006501 | 3 | 6546 | |
| AF006501 | 3 | 6923 | |
| AF006501 | 3 | 6949 | |
| AF006501 | 3 | 7540 | 2 |
| HSMTS1G | 1 | 18 | |
| HSMTS1G | 1 | 199 | |
| HSMTS1G | 1 | 247 | |
| HSMTS1G | 1 | 263 | |
| HSMTS1G | 1 | 511 | 10 |
| HSU43572 | 1 | 606 | |
| HSU43572 | 1 | 663 | 425 |
| HSU43572 | 2 | 52 | 199 |
| HSU43572 | 4 | 152 | |
| HSU43572 | 4 | 307 | |
| HSU43572 | 4 | 992 | |
| HSU43572 | 4 | 1723 | 2 |
| HSU43572 | 5 | 61 | |
| HSU43572 | 5 | 179 | |
| HSU43572 | 5 | 412 | |
| HSU43572 | 5 | 1058 | |
| HSU43572 | 5 | 1134 | |
| HSU43572 | 5 | 1226 | |
| HSU43572 | 5 | 1387 | |
| HSU43572 | 5 | 1564 | |
| HSU43572 | 5 | 1616 | 105 |
| HUMGALT54X | 1 | 235 | |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMGALT54X | 1 | 239 | 57 |
| HSU20325 | 1 | 247 | |
| HSU20325 | 1 | 413 | 352 |
| HSU20325 | 2 | 4 | |
| HSU20325 | 2 | 98 | |
| HSU20325 | 2 | 142 | |
| HSU20325 | 2 | 183 | |
| HSU20325 | 2 | 334 | 88 |
| HUMGRP78 | 2 | 34 | |
| HUMGRP78 | 2 | 110 | 181 |
| HUMGRP78 | 6 | 189 | 27 |
| HUMGRP78 | 7 | 123 | |
| HUMGRP78 | 7 | 388 | |
| HUMGRP78 | 7 | 955 | 21 |
| HS370M22 | 1 | 3 | |
| HS370M22 | 1 | 209 | |
| HS370M22 | 1 | 288 | |
| HS370M22 | 1 | 300 | |
| HS370M22 | 1 | 368 | |
| HS370M22 | 1 | 915 | |
| HS370M22 | 1 | 944 | |
| HS370M22 | 1 | 1225 | |
| HS370M22 | 1 | 2029 | |
| HS370M22 | 1 | 2182 | |
| HS370M22 | 1 | 2554 | |
| HS370M22 | 1 | 3399 | |
| HS370M22 | 1 | 3558 | |
| HS370M22 | 1 | 3616 | |
| HS370M22 | 1 | 3649 | |
| HS370M22 | 1 | 4806 | |
| HS370M22 | 1 | 4826 | |
| HS370M22 | 1 | 5077 | |
| HS370M22 | 1 | 5168 | |
| HS370M22 | 1 | 5718 | |
| HS370M22 | 1 | 6567 | |
| HS370M22 | 1 | 7562 | |
| HS370M22 | 1 | 7610 | |
| HS370M22 | 1 | 7946 | |
| HS370M22 | 1 | 8453 | |
| HS370M22 | 1 | 8483 | 79 |
| HS370M22 | 2 | 302 | |
| HS370M22 | 2 | 700 | |
| HS370M22 | 2 | 793 | |
| HS370M22 | 2 | 835 | |
| HS370M22 | 2 | 1268 | |
| HS370M22 | 2 | 1383 | |
| HS370M22 | 2 | 1740 | |
| HS370M22 | 2 | 2532 | |
| HS370M22 | 2 | 2553 | |
| HS370M22 | 2 | 2714 | |
| HS370M22 | 2 | 2884 | |
| HS370M22 | 2 | 3032 | |
| HS370M22 | 2 | 3320 | |
| HS370M22 | 2 | 3615 | |
| HS370M22 | 2 | 3838 | |
| HS370M22 | 2 | 3941 | 2 |
| HS370M22 | 3 | 198 | |
| HS370M22 | 3 | 249 | |
| HS370M22 | 3 | 328 | |
| HS370M22 | 3 | 670 | |
| HS370M22 | 3 | 731 | |
| HS370M22 | 3 | 744 | |
| HS370M22 | 3 | 1403 | |
| HS370M22 | 3 | 1727 | |
| HS370M22 | 3 | 2394 | |
| HS370M22 | 3 | 2825 | |
| HS370M22 | 3 | 3386 | |
| HS370M22 | 3 | 3611 | |
| HS370M22 | 3 | 3627 | |
| HS370M22 | 3 | 3868 | |
| HS370M22 | 3 | 3963 | |
| HS370M22 | 3 | 4114 | |
| HS370M22 | 3 | 4882 | |
| HS370M22 | 3 | 4987 | |
| HS370M22 | 3 | 5064 | |
| HS370M22 | 3 | 5543 | |
| HS370M22 | 3 | 5597 | |
| HS370M22 | 3 | 5692 | |
| HS370M22 | 3 | 5746 | 5 |
| HS370M22 | 4 | 132 | |
| HS370M22 | 4 | 814 | |
| HS370M22 | 4 | 954 | |
| HS370M22 | 4 | 2113 | |
| HS370M22 | 4 | 3009 | |
| HS370M22 | 4 | 3013 | |
| HS370M22 | 4 | 3083 | |
| HS370M22 | 4 | 3136 | |
| HS370M22 | 4 | 3426 | |
| HS370M22 | 4 | 3527 | |
| HS370M22 | 4 | 3541 | |
| HS370M22 | 4 | 3804 | |
| HS370M22 | 4 | 4091 | |
| HS370M22 | 4 | 4415 | |
| HS370M22 | 4 | 4453 | 130 |
| S63697 | 1 | 11 | |
| S63697 | 1 | 154 | |
| S63697 | 1 | 223 | 34 |
| S63697 | 2 | 64 | 6 |
| HUMMCHEMP | 1 | 115 | |
| HUMMCHEMP | 1 | 137 | |
| HUMMCHEMP | 1 | 309 | |
| HUMMCHEMP | 1 | 313 | |
| HUMMCHEMP | 1 | 390 | |
| HUMMCHEMP | 1 | 402 | 24 |
| HSU12421 | 1 | 3 | |
| HSU12421 | 1 | 271 | |
| HSU12421 | 1 | 903 | |
| HSU12421 | 1 | 1088 | |
| HSU12421 | 1 | 1394 | |
| HSU12421 | 1 | 1570 | 2 |
| HSU12421 | 2 | 77 | |
| HSU12421 | 2 | 174 | |
| HSU12421 | 2 | 210 | |
| HSU12421 | 2 | 353 | |
| HSU12421 | 2 | 395 | |
| HSU12421 | 2 | 543 | |
| HSU12421 | 2 | 857 | |
| HSU12421 | 2 | 1135 | |
| HSU12421 | 2 | 1161 | |
| HSU12421 | 2 | 1268 | |
| HSU12421 | 2 | 1470 | |
| HSU12421 | 2 | 1492 | 70 |
| HUMIL1B | 1 | 124 | |
| HUMIL1B | 1 | 332 | |
| HUMIL1B | 1 | 435 | 29 |
| HUMIL1B | 2 | 760 | |
| HUMIL1B | 2 | 1251 | |
| HUMIL1B | 2 | 1354 | 16 |
| HUMIL1B | 3 | 256 | 6 |
| HUMIL1B | 4 | 434 | 81 |
| HUMIL1B | 5 | 3 | |
| HUMIL1B | 5 | 129 | |
| HUMIL1B | 5 | 440 | 127 |
| HUMV2R | 1 | 95 | |
| HUMV2R | 1 | 213 | |
| HUMV2R | 1 | 269 | 69 |
| HUMHMG2A | 1 | 35 | |
| HUMHMG2A | 1 | 240 | 70 |
| HUMHMG2A | 3 | 44 | |
| HUMHMG2A | 3 | 146 | 19 |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| HUMSPBAA | 1 | 239 | |
| HUMSPBAA | 1 | 261 | 48 |
| HUMSPBAA | 3 | 271 | 67 |
| HUMSPBAA | 5 | 100 | 103 |
| HUMSPBAA | 6 | 179 | |
| HUMSPBAA | 6 | 553 | |
| HUMSPBAA | 6 | 574 | |
| HUMSPBAA | 6 | 669 | |
| HUMSPBAA | 6 | 845 | |
| HUMSPBAA | 6 | 896 | |
| HUMSPBAA | 6 | 957 | |
| HUMSPBAA | 6 | 1151 | |
| HUMSPBAA | 6 | 1165 | |
| HUMSPBAA | 6 | 1213 | |
| HUMSPBAA | 6 | 1251 | 115 |
| HUMSPBAA | 8 | 150 | |
| HUMSPBAA | 8 | 379 | 55 |
| HUMSPBAA | 9 | 288 | |
| HUMSPBAA | 9 | 409 | 160 |
| HUMCEL | 1 | 207 | |
| HUMCEL | 1 | 295 | |
| HUMCEL | 1 | 313 | |
| HUMCEL | 1 | 393 | |
| HUMCEL | 1 | 468 | |
| HUMCEL | 1 | 593 | |
| HUMCEL | 1 | 630 | |
| HUMCEL | 1 | 1572 | |
| HUMCEL | 1 | 1715 | |
| HUMCEL | 1 | 1719 | |
| HUMCEL | 1 | 1870 | 145 |
| HUMCEL | 2 | 40 | |
| HUMCEL | 4 | 20 | |
| HUMCEL | 4 | 233 | |
| HUMCEL | 4 | 373 | |
| HUMCEL | 4 | 391 | |
| HUMCEL | 4 | 544 | |
| HUMCEL | 4 | 943 | 18 |
| HUMCEL | 7 | 36 | |
| HUMCEL | 7 | 267 | 6 |
| HUMCEL | 8 | 134 | 2 |
| HUMCEL | 9 | 86 | |
| HUMCEL | 9 | 481 | |
| HUMCEL | 9 | 499 | |
| HUMCEL | 9 | 723 | |
| HUMCEL | 9 | 967 | |
| HUMCEL | 9 | 990 | |
| HUMCEL | 9 | 1088 | 2 |
| HUMCEL | 10 | 6 | |
| HUMCEL | 10 | 131 | 2 |
| HSCEATG | 1 | 539 | |
| HSCEATG | 1 | 544 | |
| HSCEATG | 1 | 587 | |
| HSCEATG | 1 | 656 | 81 |
| HSQC8B6 | 1 | 1346 | |
| HSQC8B6 | 1 | 1887 | |
| HSQC8B6 | 1 | 1904 | |
| HSQC8B6 | 1 | 2110 | |
| HSQC8B6 | 1 | 2513 | |
| HSQC8B6 | 1 | 2604 | |
| HSQC8B6 | 1 | 3017 | |
| HSQC8B6 | 1 | 3308 | |
| HSQC8B6 | 1 | 3450 | |
| HSQC8B6 | 1 | 3602 | |
| HSQC8B6 | 1 | 3969 | |
| HSQC8B6 | 1 | 4462 | |
| HSQC8B6 | 1 | 4593 | |
| HSQC8B6 | 1 | 4917 | |
| HSQC8B6 | 1 | 4997 | |
| HSQC8B6 | 1 | 5795 | |
| HSQC8B6 | 1 | 5804 | |
| HSQC8B6 | 1 | 5831 | |
| HSQC8B6 | 1 | 5935 | |
| HSQC8B6 | 1 | 5942 | |
| HSQC8B6 | 1 | 5983 | |
| HSQC8B6 | 1 | 6184 | 138 |
| HSQC8B6 | 2 | 471 | |
| HSQC8B6 | 2 | 677 | |
| HSQC8B6 | 2 | 923 | |
| HSQC8B6 | 2 | 1093 | |
| HSQC8B6 | 2 | 1354 | |
| HSQC8B6 | 2 | 1584 | |
| HSQC8B6 | 2 | 1834 | 96 |
| HSQC8B6 | 3 | 585 | |
| HSQC8B6 | 3 | 647 | |
| HSQC8B6 | 3 | 727 | |
| HSQC8B6 | 3 | 1301 | 2 |
| HSQC8B6 | 4 | 160 | |
| HSQC8B6 | 4 | 281 | |
| HSQC8B6 | 4 | 1067 | |
| HSQC8B6 | 4 | 1300 | 64 |
| HSQC8B6 | 5 | 198 | |
| HSQC8B6 | 5 | 348 | |
| HSQC8B6 | 5 | 359 | |
| HSQC8B6 | 5 | 374 | |
| HSQC8B6 | 5 | 527 | |
| HSQC8B6 | 5 | 670 | |
| HSQC8B6 | 5 | 693 | |
| HSQC8B6 | 5 | 855 | |
| HSQC8B6 | 5 | 869 | |
| HSQC8B6 | 5 | 1570 | |
| HSQC8B6 | 5 | 1923 | 46 |
| HSNCAMX1 | 1 | 184 | |
| HSNCAMX1 | 1 | 501 | |
| HSNCAMX1 | 1 | 635 | |
| HSNCAMX1 | 1 | 740 | |
| HSNCAMX1 | 1 | 763 | |
| HSNCAMX1 | 1 | 771 | |
| HSNCAMX1 | 1 | 817 | |
| HSNCAMX1 | 1 | 860 | |
| HSNCAMX1 | 1 | 876 | |
| HSNCAMX1 | 1 | 927 | |
| HSNCAMX1 | 1 | 1198 | |
| HSNCAMX1 | 1 | 1288 | |
| HSNCAMX1 | 1 | 1394 | |
| HSNCAMX1 | 1 | 2045 | |
| HSNCAMX1 | 1 | 2138 | 6 |
| HSNCAMX1 | 2 | 14 | |
| HSNCAMX1 | 2 | 47 | 66 |
| HSNCAMX1 | 7 | 92 | 2 |
| HSNCAMX1 | 9 | 70 | |
| HSNCAMX1 | 10 | 180 | |
| HSNCAMX1 | 10 | 318 | 27 |
| HSNCAMX1 | 11 | 22 | 2 |
| HSNCAMX1 | 18 | 239 | |
| HSNCAMX1 | 18 | 526 | |
| HSNCAMX1 | 18 | 786 | 33 |
| HSNCAMX1 | 19 | 42 | |
| HSNCAMX1 | 19 | 58 | 40 |
| HSNCAMX1 | 25 | 196 | 9 |
| HSNCAMX1 | 26 | 86 | 2 |
| HUMREGB | 2 | 182 | 88 |
| HUMREGB | 3 | 43 | |
| HUMREGB | 3 | 478 | 46 |
| HUMREGB | 4 | 83 | 75 |
| AF042084 | 2 | 221 | |
| AF042084 | 2 | 270 | 39 |
| AF042084 | 3 | 158 | 64 |
| AF042084 | 4 | 124 | 43 |
| AF042084 | 5 | 41 | |
| AF042084 | 5 | 85 | 10 |

TABLE 6-continued

Database of genes having putative latent splice sites
Each row includes the following information from left to right
<GENBANK Accession No.><Number of intron (IVS) which includes
the latent site/s><The coordinate of the latent site/s in the intron
(in nt, counted from the 5 end of the intron)><The position of the
first stop codon (in nt, counted from the 5' end of the intron>.

| Accession No. | IVS No. | Latent Pos. | First Stop codon |
|---|---|---|---|
| AF042084 | 6 | 290 | |
| AF042084 | 6 | 334 | |
| AF042084 | 6 | 453 | 73 |
| AF042084 | 7 | 81 | 84 |
| HUMHSP90B | 1 | 249 | |
| HUMHSP90B | 1 | 574 | 97 |
| HUMHSP90B | 3 | 23 | 123 |
| HUMHSP90B | 5 | 122 | 4 |
| HUMHSP90B | 6 | 74 | 24 |
| HUMHSP90B | 9 | 43 | 178 |
| HSAPOAIA | 2 | 364 | 2 |
| HSLWBGTPT | 1 | 29 | |
| HSLWBGTPT | 1 | 52 | 66 |
| D63861 | 1 | 91 | |
| D63861 | 1 | 490 | |
| D63861 | 1 | 601 | |
| D63861 | 1 | 918 | |
| D63861 | 1 | 1127 | |
| D63861 | 1 | 1168 | |
| D63861 | 1 | 1618 | 159 |
| D63861 | 2 | 146 | |
| D63861 | 2 | 291 | |
| D63861 | 2 | 383 | |
| D63861 | 2 | 395 | |
| D63861 | 2 | 885 | |
| D63861 | 2 | 1158 | |
| D63861 | 2 | 1341 | |
| D63861 | 2 | 1976 | 18 |
| D63861 | 3 | 232 | |
| D63861 | 3 | 304 | |
| D63861 | 3 | 464 | |
| D63861 | 3 | 508 | |
| D63861 | 3 | 809 | |
| D63861 | 3 | 959 | |
| D63861 | 3 | 1050 | |
| D63861 | 3 | 1383 | |
| D63861 | 3 | 1471 | |
| D63861 | 3 | 1652 | |
| D63861 | 3 | 1659 | |
| D63861 | 3 | 1754 | |
| D63861 | 3 | 1812 | 7 |
| D63861 | 4 | 374 | |
| D63861 | 4 | 577 | |
| D63861 | 4 | 836 | |
| D63861 | 4 | 971 | |
| D63861 | 4 | 1007 | |
| D63861 | 4 | 1148 | 19 |
| D63861 | 5 | 37 | 28 |
| D63861 | 6 | 106 | |
| D63861 | 6 | 852 | |
| D63861 | 6 | 911 | |
| D63861 | 6 | 1623 | 2 |
| D63861 | 7 | 310 | |
| D63861 | 7 | 444 | |
| D63861 | 7 | 579 | |
| D63861 | 7 | 621 | |
| D63861 | 7 | 666 | |
| D63861 | 7 | 761 | |
| D63861 | 7 | 781 | |
| D63861 | 7 | 841 | |
| D63861 | 7 | 868 | |
| D63861 | 7 | 1461 | |
| D63861 | 7 | 1580 | |
| D63861 | 7 | 1778 | 31 |
| D63861 | 9 | 316 | |
| D63861 | 9 | 361 | 42 |
| HUMRPS17A | 1 | 3 | |
| HUMRPS17A | 1 | 262 | 169 |
| HUMRPS17A | 2 | 685 | |
| HUMRPS17A | 2 | 868 | |
| HUMRPS17A | 2 | 942 | 2 |
| HUMRPS17A | 3 | 325 | |
| HUMRPS17A | 3 | 454 | 31 |
| HUMRPS17A | 4 | 82 | |
| HUMRPS17A | 4 | 380 | |
| HUMRPS17A | 4 | 402 | |
| HUMRPS17A | 4 | 502 | |
| HUMRPS17A | 4 | 1205 | 82 |
| HUMCBRG | 1 | 136 | 72 |
| HUMTHROMA | 2 | 39 | 82 |
| HUMTHROMA | 3 | 187 | |
| HUMTHROMA | 3 | 399 | |
| HUMTHROMA | 3 | 1504 | |
| HUMTHROMA | 3 | 1644 | |
| HUMTHROMA | 3 | 1676 | 145 |
| HUMG0S24B | 1 | 169 | |
| HUMG0S24B | 1 | 180 | |
| HUMG0S24B | 1 | 632 | |
| HUMG0S24B | 1 | 783 | 172 |
| HUMP45C17 | 1 | 225 | |
| HUMP45C17 | 1 | 317 | |
| HUMP45C17 | 1 | 352 | |
| HUMP45C17 | 1 | 690 | |
| HUMP45C17 | 1 | 1202 | |
| HUMP45C17 | 1 | 1563 | 73 |
| HUMP45C17 | 2 | 76 | |
| HUMP45C17 | 2 | 185 | 87 |
| HUMP45C17 | 3 | 291 | |
| HUMP45C17 | 3 | 318 | |
| HUMP45C17 | 3 | 539 | 109 |
| HUMP45C17 | 4 | 3 | |
| HUMP45C17 | 4 | 192 | |
| HUMP45C17 | 4 | 469 | 31 |
| HUMP45C17 | 6 | 98 | |
| HUMP45C17 | 6 | 177 | |
| HUMP45C17 | 6 | 198 | |
| HUMP45C17 | 6 | 773 | 26 |
| HUMP45C17 | 7 | 288 | 129 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A computer program product, comprising at least one non-transitory computer readable medium having a computer readable program code embodied therein, said computer readable program code adapted to be executed to implement a method of identifying a gene having a latent splice site, the method comprising:
   identifying an in-frame stop codon in an intron sequence of the gene, and in said intron sequence, identifying a 5' splice site downstream of said in-frame stop codon, said 5' splice site being a latent splice site capable of transcribing an RNA to thereby identify the gene having the latent splice site; and
   providing data on said gene having the latent splice site in a user readable format.

2. The method of claim 1, wherein said identifying a latent splice site is effected on a large scale.

3. A method of identifying a gene having a latent splice site, the method comprising:
   identifying, using a computing processor, an in-frame stop codon in an intron sequence of the gene, and in said intron sequence, identifying, using said computing processor, a 5' splice site downstream of said in-frame stop codon, said 5' splice site being a latent splice site capable of transcribing an RNA to thereby identify the gene having the latent splice site; and
   providing data on said gene having the latent splice site in a user readable format.

* * * * *

SEQUENCE LISTING

<160> NUMBER OF SEQ ID NOS: 38

<210> SEQ ID NO 1
<211> LENGTH: 8
<212> TYPE: DNA
<213> ORGANISM: Artificial sequence
<220> FEATURE:
<223> OTHER INFORMATION: mRNA splice junction consensus sequence
<220> FEATURE:
<221> NAME/KEY: misc_feature
<222> LOCATION: (2)..(2)
<223> OTHER INFORMATION: splice junction

<400> SEQUENCE: 1 aggtragt                                                                  8

<210> SEQ ID NO 2
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 2
atcaagtgca ccaaactctt cgtggaggtg gcacag                                  36

<210> SEQ ID NO 3
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 3
atcaagtgca ccaaactctt cgtggaggtg ggacag                                  36

<210> SEQ ID NO 4
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 4
cacaaagctc caccgctagc tcagcccttca tacg                                   34

<210> SEQ ID NO 5
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 5
cacaaagctc caccgctagc tgagcccttca tacg                                   34

<210> SEQ ID NO 6
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 6
gcctgctctc cagcgccccg ctc                                                23

```
<210> SEQ ID NO 7
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 7
acgaagagtt tggtgcactt gatg                                              24

<210> SEQ ID NO 8
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 8 gggggatga gcgtgcatgc tggggttggg ag                                      32

<210> SEQ ID NO 9
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 9
ctcccaaccc cagcatgcac gctcatcccc cc                                     32

<210> SEQ ID NO 10
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 10
gcagcgtata agggctaggc tagcggtgga gct                                    33

<210> SEQ ID NO 11
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 11
agctccaccg ctagcctagc ccttatacgc tgc                                    33

<210> SEQ ID NO 12
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 12
gcagcgtata agggctaagc tagcggtgga gct                                    33

<210> SEQ ID NO 13
<211> LENGTH: 33
<212> TYPE: DNA
<213> ORGANISM: Artificial sequence
<220> FEATURE:
<223> OTHER INFORMATION: Single strand DNA oligonucleotide
```

<400> SEQUENCE: 13
agctccaccg ctagcttagc ccttatacgc tgc                                   33

<210> SEQ ID NO 14
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 14
gcagcgtata agggctgggc tagcggtgga gct                                   33

<210> SEQ ID NO 15
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 15
agctccaccg ctagcccagc ccttatacgc tgc                                   33

<210> SEQ ID NO 16
<211> LENGTH: 52
<212> TYPE: DNA
<213> ORGANISM: Artificial sequence
<220> FEATURE:
<223> OTHER INFORMATION: Single strand DNA oligonucleotide

<400> SEQUENCE: 16
cgggtgcagg agtgtacagc tgtgaagggg ggaagagcgt gcgctggggt tg              52

<210> SEQ ID NO 17
<211> LENGTH: 52
<212> TYPE: DNA
<213> ORGANISM: Artificial sequence
<220> FEATURE:
<223> OTHER INFORMATION: Single strand DNA oligonucleotide

<400> SEQUENCE: 17
caaccccagc gcacgctctt ccccccttca cagctgtaca ctcctgcacc cg              52

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
ctcagatcct ggtcgacggc                                                  20

<210> SEQ ID NO 19
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 19
ctcagatcct gggtcgacgg c                                                21

<210> SEQ ID NO 20
<211> LENGTH: 20
<212> TYPE: DNA

```
<213> ORGANISM: Artificial sequence
<220> FEATURE:
<223> OTHER INFORMATION: Single strand DNA oligonucleotide

<400> SEQUENCE: 20
cagggagccg caccagtttc                                                    20

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
ccgggtgcag gagtgacagc                                                    20

<210> SEQ ID NO 22
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 22
ccgggtgcag gagtgtacag c                                                  21

<210> SEQ ID NO 23
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 23
cctgaagttc tcaggatcc                                                     19

<210> SEQ ID NO 24
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 24
aggagaagtc tgccgttac                                                     19

<210> SEQ ID NO 25
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 25
agagggccct ctagatgcat gctggtggtg acaagctcca gcagc                        45

<210> SEQ ID NO 26
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 26
cgagcacgcg tggccatgcg t                                                  21
```

```
<210> SEQ ID NO 27
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 27
aggacgtact ggtcagcctg g                                              21

<210> SEQ ID NO 28
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 28
actgtgagag cttcagagac c                                              21

<210> SEQ ID NO 29
<211> LENGTH: 8
<212> TYPE: DNA
<213> ORGANISM: Artificial sequence
<220> FEATURE:
<223> OTHER INFORMATION: mRNA splice junction consensus sequence
<220> FEATURE:
<221> NAME/KEY: misc_feature
<222> LOCATION: (2)..(2)
<223> OTHER INFORMATION: splice junction

<400> SEQUENCE: 29 aggtragt                                                              8

<210> SEQ ID NO 30
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 30
ctctagcatt taggtgacac tatagaatag ggcc                                34

<210> SEQ ID NO 31
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 31
ccgctagctc agcccctta                                                 18

<210> SEQ ID NO 32
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 32
tacgactcac tatagggaga cccaagct                                       28

<210> SEQ ID NO 33
<211> LENGTH: 50
<212> TYPE: DNA
```

-continued

<213> ORGANISM: Artificial sequence
<220> FEATURE:
<223> OTHER INFORMATION: Single strand DNA oligonucleotide

<400> SEQUENCE: 33
cctgggctcc ggtccactgc ggccgccggg cacctaccta ccctcttacc        50

<210> SEQ ID NO 34
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 34
cctgggctcc ggtccactgc ggccgccggg cacctacctc ccctcttacc        50

<210> SEQ ID NO 35
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 35
aagcaggcag aggcccatca t                                       21

<210> SEQ ID NO 36
<211> LENGTH: 15
<212> TYPE: DNA
<213> ORGANISM: Artificial sequence
<220> FEATURE:
<223> OTHER INFORMATION: Single strand DNA oligonucleotide

<400> SEQUENCE: 36
atggtaagag ggcag                                              15

<210> SEQ ID NO 37
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 37
agaagagcag gtttagcacg g                                       21

<210> SEQ ID NO 38
<211> LENGTH: 21
<212> TYPE: DNA
<213> ORGANISM: Artificial sequence
<220> FEATURE:
<223> OTHER INFORMATION: HTH mini gene construct alternative splice site

<400> SEQUENCE: 38
atggtaagag ggcaggtagg t                                       21